US012643881B2

(12) United States Patent
Li et al.

(10) Patent No.: US 12,643,881 B2
(45) Date of Patent: Jun. 2, 2026

(54) BICYCLIC AMINE CDK12 INHIBITORS

(71) Applicant: Incyte Corporation, Wilmington, DE (US)

(72) Inventors: Xin Li, Claymont, DE (US); Michael Liang, Wilmington, DE (US); Evan Styduhar, Claymont, DE (US); Robert Swyka, Wilmington, DE (US); Oleg Vechorkin, Wilmington, DE (US); Anlai Wang, Wilmington, DE (US); Lin You, West Chester, PA (US); Peng Zhao, Newark, DE (US); Ke Zhang, Wilmington, DE (US); Minh Nguyen, Claymont, DE (US)

(73) Assignee: Incyte Corporation, Wilmington, DE (US)

( * ) Notice: Subject to any disclaimer, the term of this patent is extended or adjusted under 35 U.S.C. 154(b) by 239 days.

(21) Appl. No.: 18/073,782

(22) Filed: Dec. 2, 2022

(65) Prior Publication Data

US 2023/0203010 A1 Jun. 29, 2023

Related U.S. Application Data

(60) Provisional application No. 63/340,259, filed on May 10, 2022, provisional application No. 63/285,806, filed on Dec. 3, 2021.

(51) Int. Cl.
| | |
|---|---|
| *C07D 401/14* | (2006.01) |
| *C07D 405/14* | (2006.01) |
| *C07D 409/14* | (2006.01) |
| *C07D 487/04* | (2006.01) |

(52) U.S. Cl.
CPC ......... *C07D 401/14* (2013.01); *C07D 405/14* (2013.01); *C07D 409/14* (2013.01); *C07D 487/04* (2013.01)

(58) Field of Classification Search
CPC ...................................................... A61P 35/00
See application file for complete search history.

(56) References Cited

U.S. PATENT DOCUMENTS

| | | | |
|---|---|---|---|
| 4,820,710 | A | 4/1989 | Manoury et al. |
| 4,912,219 | A | 3/1990 | Manoury et al. |
| 5,521,184 | A | 5/1996 | Zimmermann |
| 6,143,749 | A | 11/2000 | Bhagwat et al. |
| 7,488,802 | B2 | 2/2009 | Collins et al. |
| 7,745,437 | B2 | 6/2010 | Ren et al. |
| 7,759,336 | B2 | 7/2010 | Habashita et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 9,670,202 | B2 | 6/2017 | Schirok et al. |
| 9,828,373 | B2 | 11/2017 | Zhang et al. |
| 10,059,690 | B2 | 8/2018 | Ciblat et al. |

| | | | |
|---|---|---|---|
| 10,106,526 | B2 | 10/2018 | Sprott et al. |
| 10,111,875 | B2 | 10/2018 | Su et al. |
| 10,519,135 | B2 | 12/2019 | Sprott et al. |
| 10,550,121 | B2 | 2/2020 | Gray et al. |
| 10,618,916 | B2 | 4/2020 | Wu et al. |
| 10,669,271 | B2 | 6/2020 | Wu et al. |
| 10,696,677 | B2 | 6/2020 | Maitra et al. |
| 10,851,082 | B2 | 12/2020 | Schiltz et al. |
| 10,894,788 | B2 | 1/2021 | Kanouni et al. |
| 10,906,920 | B2 | 2/2021 | Wu et al. |
| 11,248,001 | B2 | 2/2022 | Serrano-Wu et al. |
| 11,325,910 | B2 | 5/2022 | Gray et al. |
| 11,414,433 | B2 | 8/2022 | Wu et al. |
| 11,596,631 | B2 | 3/2023 | Hayes et al. |
| 11,746,151 | B2 | 9/2023 | Chinnaiyan et al. |
| 2004/0224967 | A1 | 11/2004 | Chen |
| 2005/0209284 | A1 | 9/2005 | Bentzien et al. |
| 2005/0228031 | A1 | 10/2005 | Bilodeau et al. |
| 2005/0277655 | A1 | 12/2005 | Ding et al. |
| 2009/0143302 | A1 | 6/2009 | Yen et al. |
| 2011/0306588 | A1 | 12/2011 | Allen et al. |
| 2013/0225552 | A1 | 8/2013 | Allen et al. |
| 2013/0303507 | A1 | 11/2013 | Antonios-McCrea et al. |
| 2018/0177784 | A1 | 6/2018 | Wu et al. |
| 2018/0177870 | A1 | 6/2018 | Liu et al. |
| 2018/0179179 | A1 | 6/2018 | Wu et al. |
| 2018/0179197 | A1 | 6/2018 | Wu et al. |
| 2018/0179201 | A1 | 6/2018 | Wu et al. |
| 2018/0179202 | A1 | 6/2018 | Wu et al. |
| 2018/0334461 | A1 | 11/2018 | Hu et al. |

(Continued)

FOREIGN PATENT DOCUMENTS

| | | |
|---|---|---|
| CN | 103864792 | 6/2014 |
| CN | 105294737 | 2/2016 |

(Continued)

OTHER PUBLICATIONS

Ajakane et al., "Identification of 6-amino-1 H-pyrazolo [3, 4-d] pyrimidines with in vivo efficacy against visceral leishmaniasis," RSC medicinal chemistry, Aug. 2020, 11(10):1168-77.

Amato et al., "Functionalized 6-(piperidin-1-yl)-8, 9-diphenyl purines as inverse agonists of the CB1 receptor-SAR efforts towards selectivity and peripheralization," Bioorganic & medicinal chemistry, Aug. 2019, 27(16):3632-49.

Cindrić et al., "Novel amidino substituted benzimidazole and benzothiazole benzo [b] thieno-2-carboxamides exert strong antiproliferative and DNA binding properties," European journal of medicinal chemistry, Aug. 2017, 136:468-79.

Grädler et al., "Biochemical, cellular and structural characterization of novel and selective ERK3 inhibitors," Bioorganic & Medicinal Chemistry Letters, Nov. 2020, 30(22):127551.

(Continued)

*Primary Examiner* — Jeffrey S Lundgren
*Assistant Examiner* — Eric Tran
(74) *Attorney, Agent, or Firm* — Fish & Richardson P.C.

(57) ABSTRACT

The present application provides bicyclic amines that are inhibitors of cyclin-dependent kinase 12 (CDK12), as well as pharmaceutical compositions thereof, and methods of treating cancer using the same.

53 Claims, No Drawings

Specification includes a Sequence Listing.

(56)                References Cited

U.S. PATENT DOCUMENTS

| | | |
|---|---|---|
| 2020/0248271 A1 | 8/2020 | Kong et al. |
| 2021/0128565 A1 | 5/2021 | Alexander et al. |
| 2023/0183251 A1 | 6/2023 | Nguyen et al. |

FOREIGN PATENT DOCUMENTS

| | | |
|---|---|---|
| CN | 105384695 | 3/2016 |
| CN | 105712998 | 6/2016 |
| CN | 106336398 | 1/2017 |
| CN | 106831605 | 6/2017 |
| CN | 107625766 | 1/2018 |
| CN | 110003171 | 7/2019 |
| CN | 110835320 | 2/2020 |
| CN | 111269217 | 6/2020 |
| CN | 111393415 | 7/2020 |
| EP | 2489663 | 8/2012 |
| EP | 3126352 | 2/2017 |
| JP | 6594949 | 10/2019 |
| KR | 20120018236 | 3/2012 |
| KR | 20160020616 | 2/2016 |
| KR | 20200029949 | 3/2020 |
| WO | WO 2000009495 | 2/2000 |
| WO | WO 2000053595 | 9/2000 |
| WO | WO 2001014402 | 3/2001 |
| WO | WO 2001019817 | 3/2001 |
| WO | WO 2001055143 | 8/2001 |
| WO | WO 2001064655 | 9/2001 |
| WO | WO 2002000196 | 1/2002 |
| WO | WO 2002046172 | 6/2002 |
| WO | WO 2002081443 | 10/2002 |
| WO | WO 2002094831 | 11/2002 |
| WO | WO 2002096905 | 12/2002 |
| WO | WO 2003024967 | 3/2003 |
| WO | WO 2003037347 | 5/2003 |
| WO | WO 2003042402 | 5/2003 |
| WO | WO 2003051886 | 6/2003 |
| WO | WO 2003055489 | 7/2003 |
| WO | WO 2003062236 | 7/2003 |
| WO | WO 2003082855 | 10/2003 |
| WO | WO 2003091245 | 11/2003 |
| WO | WO 2003099771 | 12/2003 |
| WO | WO 2004002964 | 1/2004 |
| WO | WO 2004005281 | 1/2004 |
| WO | WO 2004032882 | 4/2004 |
| WO | WO 2004037814 | 5/2004 |
| WO | WO 2004041813 | 5/2004 |
| WO | WO 2004043913 | 5/2004 |
| WO | WO 2004043962 | 5/2004 |
| WO | WO 2004046120 | 6/2004 |
| WO | WO 2004052862 | 6/2004 |
| WO | WO 2004056786 | 7/2004 |
| WO | WO 2004065378 | 8/2004 |
| WO | WO 2004080980 | 9/2004 |
| WO | WO 2004085425 | 10/2004 |
| WO | WO 2004089913 | 10/2004 |
| WO | WO 2004110350 | 12/2004 |
| WO | WO 2005009443 | 2/2005 |
| WO | WO 2005009978 | 2/2005 |
| WO | WO 2005013996 | 2/2005 |
| WO | WO 2005016894 | 2/2005 |
| WO | WO 2005028444 | 3/2005 |
| WO | WO 2005042497 | 5/2005 |
| WO | WO 2005042518 | 5/2005 |
| WO | WO 2005042525 | 5/2005 |
| WO | WO 2005060970 | 7/2005 |
| WO | WO 2005076854 | 8/2005 |
| WO | WO 2005080346 | 9/2005 |
| WO | WO 2005080393 | 9/2005 |
| WO | WO 2005105790 | 11/2005 |
| WO | WO 2005107760 | 11/2005 |
| WO | WO 2005118544 | 12/2005 |
| WO | WO 2005121121 | 12/2005 |
| WO | WO 2006004702 | 1/2006 |
| WO | WO 2006034341 | 3/2006 |
| WO | WO 2006037117 | 4/2006 |
| WO | WO 2006038001 | 4/2006 |
| WO | WO 2006044869 | 4/2006 |
| WO | WO 2006050076 | 5/2006 |
| WO | WO 2006056399 | 6/2006 |
| WO | WO 2006067614 | 6/2006 |
| WO | WO 2006069258 | 6/2006 |
| WO | WO 2006074057 | 7/2006 |
| WO | WO 2006076595 | 7/2006 |
| WO | WO 2006082371 | 8/2006 |
| WO | WO 2006082373 | 8/2006 |
| WO | WO 2006091737 | 8/2006 |
| WO | WO 2006097260 | 9/2006 |
| WO | WO 2006099941 | 9/2006 |
| WO | WO 2006099943 | 9/2006 |
| WO | WO 2006101977 | 9/2006 |
| WO | WO 2006103449 | 10/2006 |
| WO | WO 2006105222 | 10/2006 |
| WO | WO 2006128129 | 11/2006 |
| WO | WO 2006128172 | 11/2006 |
| WO | WO 2006138304 | 12/2006 |
| WO | WO 2007003934 | 1/2007 |
| WO | WO 2007024680 | 3/2007 |
| WO | WO 2007030438 | 3/2007 |
| WO | WO 2007039285 | 4/2007 |
| WO | WO 2007042784 | 4/2007 |
| WO | WO 2007056221 | 5/2007 |
| WO | WO 2007059299 | 5/2007 |
| WO | WO 2007095124 | 8/2007 |
| WO | WO 2007104053 | 9/2007 |
| WO | WO 2007109045 | 9/2007 |
| WO | WO 2007110344 | 10/2007 |
| WO | WO 2007114827 | 10/2007 |
| WO | WO 2007121918 | 11/2007 |
| WO | WO 2007123892 | 11/2007 |
| WO | WO 2007129044 | 11/2007 |
| WO | WO 2007138277 | 12/2007 |
| WO | WO 2008002245 | 1/2008 |
| WO | WO 2008003766 | 1/2008 |
| WO | WO 2008036967 | 3/2008 |
| WO | WO 2008040778 | 4/2008 |
| WO | WO 2008057280 | 5/2008 |
| WO | WO 2008068171 | 6/2008 |
| WO | WO 2008071587 | 6/2008 |
| WO | WO 2008077057 | 6/2008 |
| WO | WO 2008079346 | 7/2008 |
| WO | WO 2008092199 | 8/2008 |
| WO | WO 2008094575 | 8/2008 |
| WO | WO 2008094602 | 8/2008 |
| WO | WO 2008113469 | 9/2008 |
| WO | WO 2008126898 | 10/2008 |
| WO | WO 2008129380 | 10/2008 |
| WO | WO 2008135232 | 11/2008 |
| WO | WO 2008156712 | 12/2008 |
| WO | WO 2009017838 | 2/2009 |
| WO | WO 2009022171 | 2/2009 |
| WO | WO 2009028629 | 3/2009 |
| WO | WO 2009029622 | 3/2009 |
| WO | WO 2009032861 | 3/2009 |
| WO | WO 2009054332 | 4/2009 |
| WO | WO 2009062059 | 5/2009 |
| WO | WO 2009071701 | 6/2009 |
| WO | WO 2009085185 | 7/2009 |
| WO | WO 2009127321 | 10/2009 |
| WO | WO 2009127822 | 10/2009 |
| WO | WO 2009131687 | 10/2009 |
| WO | WO 2009158571 | 12/2009 |
| WO | WO 2009158587 | 12/2009 |
| WO | WO 2010011756 | 1/2010 |
| WO | WO 2010020432 | 2/2010 |
| WO | WO 2010027005 | 3/2010 |
| WO | WO 2010036959 | 4/2010 |
| WO | WO 2010048012 | 4/2010 |
| WO | WO 2010058032 | 5/2010 |
| WO | WO 2010075074 | 7/2010 |
| WO | WO 2010088050 | 8/2010 |
| WO | WO 2010089411 | 8/2010 |
| WO | WO 2010100431 | 9/2010 |
| WO | WO 2010129053 | 11/2010 |
| WO | WO 2010138575 | 12/2010 |

(56) References Cited

FOREIGN PATENT DOCUMENTS

| | | |
|---|---|---|
| WO | WO 2010138576 | 12/2010 |
| WO | WO 2011016472 | 2/2011 |
| WO | WO 2011029915 | 3/2011 |
| WO | WO 2011032050 | 3/2011 |
| WO | WO 2011034907 | 3/2011 |
| WO | WO 2011039344 | 4/2011 |
| WO | WO 2011066342 | 6/2011 |
| WO | WO 2011082400 | 7/2011 |
| WO | WO 2011101409 | 8/2011 |
| WO | WO 2011106168 | 9/2011 |
| WO | WO 2011119465 | 9/2011 |
| WO | WO 2011133750 | 10/2011 |
| WO | WO 2011133888 | 10/2011 |
| WO | WO 2011134831 | 11/2011 |
| WO | WO 2011143495 | 11/2011 |
| WO | WO 2011156698 | 12/2011 |
| WO | WO 2011159877 | 12/2011 |
| WO | WO 2011161699 | 12/2011 |
| WO | WO 2012009649 | 1/2012 |
| WO | WO 2012016217 | 2/2012 |
| WO | WO 2012022045 | 2/2012 |
| WO | WO 2012022265 | 2/2012 |
| WO | WO 2012061057 | 5/2012 |
| WO | WO 2012061156 | 5/2012 |
| WO | WO 2012062704 | 5/2012 |
| WO | WO 2012066070 | 5/2012 |
| WO | WO 2012083121 | 6/2012 |
| WO | WO 2012083122 | 6/2012 |
| WO | WO 2012086735 | 6/2012 |
| WO | WO 2012101065 | 8/2012 |
| WO | WO 2012101066 | 8/2012 |
| WO | WO 2012104388 | 8/2012 |
| WO | WO 2012129344 | 9/2012 |
| WO | WO 2012142498 | 10/2012 |
| WO | WO 2012151561 | 11/2012 |
| WO | WO 2013017480 | 2/2013 |
| WO | WO 2013041605 | 3/2013 |
| WO | WO 2013130890 | 9/2013 |
| WO | WO 2013151938 | 10/2013 |
| WO | WO 2013155262 | 10/2013 |
| WO | WO-2013192128 A1 * | 12/2013 ........... C07D 401/14 |
| WO | WO 2014048865 | 4/2014 |
| WO | WO 2014109858 | 7/2014 |
| WO | WO 2014113303 | 7/2014 |
| WO | WO 2014124230 | 8/2014 |
| WO | WO 2014128486 | 8/2014 |
| WO | WO 2014130856 | 8/2014 |
| WO | WO 2014135244 | 9/2014 |
| WO | WO 2014135245 | 9/2014 |
| WO | WO 2014152716 | 9/2014 |
| WO | WO 2014159690 | 10/2014 |
| WO | WO 2014196793 | 12/2014 |
| WO | WO 2014202827 | 12/2014 |
| WO | WO 2014207260 | 12/2014 |
| WO | WO 2015004024 | 1/2015 |
| WO | WO 2015006875 | 1/2015 |
| WO | WO 2015030847 | 3/2015 |
| WO | WO 2015048662 | 4/2015 |
| WO | WO 2015054572 | 4/2015 |
| WO | WO 2015056782 | 4/2015 |
| WO | WO 2015058126 | 4/2015 |
| WO | WO 2015058140 | 4/2015 |
| WO | WO 2015058163 | 4/2015 |
| WO | WO 2015104677 | 7/2015 |
| WO | WO 2015115673 | 8/2015 |
| WO | WO 2015144605 | 10/2015 |
| WO | WO 2015154022 | 10/2015 |
| WO | WO 2015154039 | 10/2015 |
| WO | WO-2015154039 A2 * | 10/2015 ........... A61K 31/506 |
| WO | WO 2015158310 | 10/2015 |
| WO | WO 2015164614 | 10/2015 |
| WO | WO 2015180642 | 12/2015 |
| WO | WO 2015196072 | 12/2015 |
| WO | WO 2016016421 | 2/2016 |
| WO | WO 2016058544 | 4/2016 |
| WO | WO 2016065461 | 5/2016 |
| WO | WO 2016084816 | 6/2016 |
| WO | WO 2016113273 | 7/2016 |
| WO | WO 2016142855 | 9/2016 |
| WO | WO 2016160617 | 10/2016 |
| WO | WO 2016169504 | 10/2016 |
| WO | WO 2016173557 | 11/2016 |
| WO | WO 2016193939 | 12/2016 |
| WO | WO 2016195776 | 12/2016 |
| WO | WO 2016201370 | 12/2016 |
| WO | WO 2016210291 | 12/2016 |
| WO | WO 2016210296 | 12/2016 |
| WO | WO 2017044858 | 3/2017 |
| WO | WO 2017049068 | 3/2017 |
| WO | WO 2017163076 | 9/2017 |
| WO | WO 2017181177 | 10/2017 |
| WO | WO 2017184662 | 10/2017 |
| WO | WO 2017185023 | 10/2017 |
| WO | WO 2017220431 | 12/2017 |
| WO | WO 2018005533 | 1/2018 |
| WO | WO 2018013867 | 1/2018 |
| WO | WO 2018040885 | 3/2018 |
| WO | WO 2018081167 | 5/2018 |
| WO | WO 2018086593 | 5/2018 |
| WO | WO 2018089499 | 5/2018 |
| WO | WO 2018098361 | 5/2018 |
| WO | WO 2018098561 | 6/2018 |
| WO | WO 2018106818 | 6/2018 |
| WO | WO 2018141002 | 8/2018 |
| WO | WO 2018154133 | 8/2018 |
| WO | WO 2018183923 | 10/2018 |
| WO | WO 2018195450 | 10/2018 |
| WO | WO 2018203691 | 11/2018 |
| WO | WO 2018208132 | 11/2018 |
| WO | WO 2018232094 | 12/2018 |
| WO | WO 2019001572 | 1/2019 |
| WO | WO 2019037678 | 2/2019 |
| WO | WO 2019037860 | 2/2019 |
| WO | WO 2019057825 | 3/2019 |
| WO | WO 2019058132 | 3/2019 |
| WO | WO 2019060365 | 3/2019 |
| WO | WO 2019079596 | 4/2019 |
| WO | WO 2019079607 | 4/2019 |
| WO | WO 2019090076 | 5/2019 |
| WO | WO 2019096322 | 5/2019 |
| WO | WO 2019133445 | 7/2019 |
| WO | WO 2019143730 | 7/2019 |
| WO | WO 2019162323 | 8/2019 |
| WO | WO 2019165315 | 8/2019 |
| WO | WO 2019169065 | 9/2019 |
| WO | WO 2019193509 | 10/2019 |
| WO | WO 2019212256 | 11/2019 |
| WO | WO 2019213403 | 11/2019 |
| WO | WO 2019236631 | 12/2019 |
| WO | WO 2020006497 | 1/2020 |
| WO | WO 2020007273 | 1/2020 |
| WO | WO 2020022787 | 1/2020 |
| WO | WO 2020023782 | 1/2020 |
| WO | WO 2020033413 | 2/2020 |
| WO | WO 2020123925 | 6/2020 |
| WO | WO 2020140052 | 7/2020 |
| WO | WO 2020140054 | 7/2020 |
| WO | WO 2020140098 | 7/2020 |
| WO | WO 2020150474 | 7/2020 |
| WO | WO 2020180959 | 9/2020 |
| WO | WO 2020202001 | 10/2020 |
| WO | WO 2020206034 | 10/2020 |
| WO | WO 2020210320 | 10/2020 |
| WO | WO 2020210381 | 10/2020 |
| WO | WO 2020219650 | 10/2020 |
| WO | WO 2020219926 | 10/2020 |
| WO | WO 2020224568 | 11/2020 |
| WO | WO 2020227563 | 11/2020 |
| WO | WO 2020233669 | 11/2020 |
| WO | WO 2020238900 | 12/2020 |
| WO | WO 2020254494 | 12/2020 |
| WO | WO 2020254552 | 12/2020 |
| WO | WO 2021003314 | 1/2021 |
| WO | WO 2021011796 | 1/2021 |

(56) References Cited

FOREIGN PATENT DOCUMENTS

| | | |
|---|---|---|
| WO | WO 2021016388 | 1/2021 |
| WO | WO 2021028362 | 2/2021 |
| WO | WO 2021057696 | 4/2021 |
| WO | WO 2021062036 | 4/2021 |
| WO | WO 2021073593 | 4/2021 |
| WO | WO 2021092240 | 5/2021 |
| WO | WO 2021104305 | 6/2021 |
| WO | WO 2021116178 | 6/2021 |
| WO | WO 2021122745 | 6/2021 |
| WO | WO 2021127045 | 6/2021 |
| WO | WO 2021133915 | 7/2021 |
| WO | WO 2021138215 | 7/2021 |
| WO | WO 2021176045 | 9/2021 |
| WO | WO 2021176049 | 9/2021 |
| WO | WO 2022093742 | 5/2022 |
| WO | WO 2022130304 | 6/2022 |
| WO | WO 2022243346 | 11/2022 |
| WO | WO 2022263604 | 12/2022 |
| WO | WO 2021072232 | 4/2023 |
| WO | WO 2023091726 | 5/2023 |
| WO | WO-2023091726 A1 * | 5/2023 |
| WO | WO 2023102184 | 6/2023 |
| WO | WO 2023107705 | 6/2023 |
| WO | WO 2023250430 | 12/2023 |
| WO | WO 2024032561 | 2/2024 |

OTHER PUBLICATIONS

Perales et al., "SAR of 2-amino and 2, 4-diamino pyrimidines with in vivo efficacy against Trypanosoma brucei," Bioorganic & medicinal chemistry letters, May 2011, 21(10):2816-9.

Sović et al., "Synthesis, antitumor activity and DNA binding features of benzothiazolyl and benzimidazolyl substituted isoindolines," Bioorganic & Medicinal Chemistry, May 2018, 26(8):1950-60.

International Preliminary Report on Patentability in International Application No. PT/US2022/051658, dated Jun. 13, 2024, 10 pages.

International Preliminary Report on Patentability in International Application No. PT/US2022/052426, dated Jun. 20, 2024, 6 pages.

Atzrodt et al., "The Renaissance of H/D Exchange," Angew. Chem. Int. Ed., 2007, 46:7744-7765.

Bajrami et al., "Genome-wide Profiling of Genetic Synthetic Lethality Identifies CDK12 as a Novel Determinant of PARP1/2 Inhibitor Sensitivity," Cancer Res., 2014, 74(1): 287-297.

Bartkowiak et al., "CDK12 is a transcription elongation-associated CTD kinase, the metazoan ortholog of yeast Ctk1," Genes & Dev., 2010, 24(20):2303-2316.

Bayles et al., "Ex vivo screen identifies CDK12 as a metastatic vulnerability in osteosarcoma," JCI, 2019, 129(10):4377-4392.

Blazek et al., "The Cyclin K/Cdk12 complex maintains genomic stability via regulation of expression of DNA damage response genes," Genes & Dev., 2011, 25(20):2158-2172.

Blom et al., "Optimizing Preparative LC-MS Configurations and Methods for Parallel Synthesis Purification," J. Combi. Chem., 2003, 5:670-683.

Blom et al., "Preparative LC-MS Purification: Improved Compound Specific Method Optimization," J. Combi. Chem., 2004, 6:874-883.

Blom, "Two-Pump at-Column Dilution Configuration for Preparative LC-MS," J. Combi. Chem., 2002, 4:295-301.

Choi et al., "Gene expression regulation by CDK12: a versatile kinase in cancer with functions beyond CTD phosphorylation," Exp. & Mol. Med., 2020, 52(5):762-771.

Dias et al., "Understanding and overcoming resistance to PARP inhibitors in cancer therapy," Nat. Rev. Clin. Oncol., 2021, 18(12):773-791.

Dieter et al., "Degradation of CCNK/CDK12 is a druggable vulnerability of colorectal cancer," Cell Rep., 2021, 36(109394):1-15.

Dubbury et al., "Cdk12 regulates DNA repair genes by suppressing intronic polyadenylation," Nature, 2018, 564(7734):141-145.

Ekumi et al., "Ovarian carcinoma CDK12 mutations misregulate expression of DNA repair genes via deficient formation and function of the Cdk12/CycK complex," Nucleic Acids Res., 2015, 43(5): 2575-2589.

Farmer et al., "Targeting the DNA repair defect in BRCA mutant cells as a therapeutic strategy," Nature, 2005, 434(7035): 917-921.

Iniguez et al., "EWS/FLI Confers Tumor Cell Synthetic Lethality to CDK12 Inhibition in Ewing Sarcoma," Cancer Cell, 2018, 33(2):202-216.

International Search Report and Written Opinion in International Application No. PCT/US2022/051658, mailed on Feb. 28, 2023, 17 pages.

International Search Report and Written Opinion in International Application No. PCT/US2022/052426, mailed on Mar. 15, 2023, 13 pages.

International Search Report and Written Opinion in International Application No. PCT/US2023/068895, mailed on Nov. 27, 2023, 21 pages.

Jiang et al., "Discovery and Resistance Mechanism of a Selective CDK12 Degrader," Nat. Chem. Biol., 2021, 17(6):675-683.

Jiang et al., "Structure-activity relationship study of THZ531 derivatives enables the discovery of BSJ-01-175 as a dual CDK12/13 covalent inhibitor with efficacy in Ewing sarcoma, " European Journal of Medicinal Chemistry, 2021, 221(11348):1-16.

Johnson et al., "CDK12 Inhibition Reverses De Novo and Acquired PARP Inhibitor Resistance In BRCA Wild-Type And Mutated Models of Triple-Negative Breast Cancer," Cell Rep., 2016, 17(9):2367-2381.

Kerekes et al., "Aurora kinase inhibitors based on the imidazo[1,2-a]pyrazine core: fluorine and deuterium incorporation improve oral absorption and exposure," J. Med. Chem., 2011, 54:201-210.

Knijnenburg et al., "Genomic and Molecular Landscape of DNA Damage Repair Deficiency across The Cancer Genome Atlas," Cell Rep., 2018, 23(1):239-254.

Kohoutek et al., "Cyclin K goes with Cdk12 and Cdk13," Cell Div., 2012, 7(12):1-10.

Liu et al., "Discovery of MFH290: A Potent and Highly Selective Covalent Inhibitor for Cyclin-Dependent Kinase 12/13," Journal of Medicinal Chemistry, 2020, 63(13):6708-6726.

Malumbres et al., "Cell cycle, CDKs and cancer: a changing paradigm," Nat. Rev. Cancer., 2009, 9(3):153-166.

Noordermeer et al., "PARP Inhibitor Resistance: A Tug-of-War in BRCA-Mutated Cells," Trends Cell Biol., 2019, 29(10):820-834.

Peturssion et al., "Protecting Groups in Carbohydrate Chemistry," J. Chem. Educ., 1997, 74(11):1297-1303.

Remington's Pharmaceutical Sciences, 17th ed., Gennaro (ed)., 1985, p. 1418.

Wang et al., "CDK12 inhibition mediates DNA damage and is synergistic with sorafenib treatment in hepatocellular carcinoma," Gut, 2020, 69(4):727-736.

Wu et al., "Inactiviation of CDK12 delineates a distinct immunogenic class of advanced prostate cancer," Cell, 2018, 173(7):1770-1782.

Xu et al., "Design, synthesis and biological evaluation of deuterated nintedanib for improving pharmacokinetic properties," J. Label Compd. Radiopharm., 2015, 58:308-312.

International Preliminary Report on Patentability in International Application No. PCT/US2023/068895, dated Jan. 2, 2025, 11 pages.

* cited by examiner

BICYCLIC AMINE CDK12 INHIBITORS

SEQUENCE LISTING

The instant application contains a Sequence Listing which has been submitted electronically as an XML filed named "20443-0751001_SL_ST26.xml". The XML file, created on Dec. 1, 2022, is 3 kilobytes in size. The material in the XML file is hereby incorporated by reference in its entirety.

TECHNICAL FIELD

This application is directed to bicyclic amines which inhibit cyclin-dependent kinase 12 (CDK12) and are useful for treating cancer.

BACKGROUND

CDK12 belongs to a family of serine/threonine kinases collectively known as cyclin-dependent kinases (Seung, H. C., et al., *Exp. Mol. Med.,* 2020, 52(5): 762-771). Collectively, CDK's are unique in that they require the binding of specific cyclin proteins for proper functionality (Malumbres, M., et al., *Nat. Rev. Cancer.,* 2009, 9(3): 153-66). Specifically, CDK12 (as well as CDK13) requires the binding of cyclin K in the cyclin binding domain for activation (Kohoutek, J., et al., *Cell Div.,* 2012, 7(12)). Mechanistically, CDK12 and CDK13 phosphorylate serine 2 (pser2) on the C-terminal tail of RNA polymerase II (RNA Pol II), which is required for transcriptional elongation (Bartkowiak, B., et al., *Genes Dev,* 2010, 24(20): 2303-2316). Therefore, inhibition of CDK12/13 can impact the expression of multiple genes.

Interestingly, CDK12 appears unique among the CDK's in that its inhibition can lead to a selective loss of expression of multiple genes involved in DNA damage repair (Blazek, D., et al., *Genes Dev,* 2011, 25(20): 2158-2172). Mechanistically, this is attributed to a role of CDK12 in maintaining proper mRNA splicing. Indeed, inhibition or genetic depletion of CDK12 leads to a decrease in proper exon splicing, which in turn increases intronic polyadenylation (IPA) and a subsequent loss of full length mRNA and translated protein (Dubbury, S. J., et al., *Nature,* 2018, 564(7734): 141-145). Many DNA repair genes are large genes with multiple IPA sites, which explains the selective loss of expression of these repair genes following CDK12 inhibition. Of note, multiple genes involved in the homologous recombination (HR) DNA repair pathway, such as BRCA1 and BRCA2, are especially sensitive to CDK12 inhibition, and indeed inactivating mutations in CDK12 are known to cause a "BRCAness" phenotype in certain cancers (Ekumi, K. M., et al., *Nucleic Acids Res,* 2015, 43(5): 2575-2589; Wu, Y. M., et al., *Cell,* 2018, 173(7): 1770-1782).

It is well known that many cancers exhibit defects in various DNA repair pathways; which can confer a selective advantage due to an increased mutation rate (Knijnenburg, T. A., et al., *Cell Rep,* 2018, 23(1): 239-254). However, these alterations can render cancer cells more susceptible to DNA-damage inducing chemotherapies, or targeted therapies that inhibit additional DNA repair pathways. A well-known example of this paradigm is the increased dependence on the DNA repair enzyme PARP in cancers with defects in HR signaling (i.e. cancers with a "BRCAness" phenotype) (Farmer, H., et al., *Nature,* 2005, 434(7035): 917-921). Indeed, preliminary studies have demonstrated that cancers with defective HR exhibit increased sensitivity to pharmacologic or genetic inhibition of CDK12 (Johnson, S. F., et al., *Cell Rep.,* 2016, 17(9): 2367-2381). This therapeutic effect is a consequence of the loss of expression of CDK12-dependent DNA repair genes; which leads to a lethal increase in DNA damage and loss of cell viability (Blazek, D., et al., *Genes Dev.,* 2011, 25(20): 2158-2172).

Despite the clinical emergence of PARP inhibitors as a therapy for patients with HR deficient cancers, de novo resistance or rapid relapse remain an unmet clinical need (Dias, M. P., et al., *Nat. Rev. Clin. Oncol.,* 2021). In the clinic, resistance to PARP inhibitors is most commonly attributed to a reversion to an HR restored tumor, or reliance on additional compensatory DNA repair pathways (Noordermeer, S. M., et al., *Trends Cell Biol.,* 2019, 29(10): 820-834). Similar to a PARP inhibitor, a CDK12 inhibitor is expected to yield the same synthetic lethal interaction in HR deficient tumors. However, given that CDK12 inhibition prevents the expression of HR genes (e.g., BRCA1, BRCA2) it is likely that a CDK12 inhibitor could avoid or overcome the HR-restoration mediate mechanism of resistance observed for PARP inhibitors. Therefore, a CDK12 inhibitor may help fill this unmet clinical need by preventing or overcoming HR restoration during or after PARP inhibitor therapy.

SUMMARY

The present invention relates to, inter alia, compounds of Formula (I):

(I)

or pharmaceutically acceptable salts thereof, wherein the constituent members are defined herein.

The present invention further provides pharmaceutical compositions comprising a compound described herein, or a pharmaceutically acceptable salt thereof, and a pharmaceutically acceptable carrier.

The present invention further provides methods of inhibiting CDK12, comprising contacting the CDK12 with a compound described herein, or a pharmaceutically acceptable salt thereof.

The present invention further provides methods of inhibiting CDK12 in a patient, comprising administering to the patient a compound described herein, or a pharmaceutically acceptable salt thereof.

The present invention further provides methods of treating a disease or disorder associated with CDK12 in a patient, comprising administering to the patient a compound described herein, or a pharmaceutically acceptable salt thereof.

The present invention further provides compounds described herein, or a pharmaceutically acceptable salt thereof, for use in any of the methods described herein.

The present invention further provides uses of a compound described herein, or a pharmaceutically acceptable salt thereof, for the preparation of a medicament for use in any of the methods described herein.

DETAILED DESCRIPTION

-continued

The present application provides, inter alia, a compound of Formula (I):

(I)

or a pharmaceutically acceptable salt thereof, wherein:
   each ═══ is independently a single or a double bond;
   k is 1 or 2;
   n is 0, 1, or 2;
   p is 0, 1, 2, 3, 4, 5, 6, 7, 8, 9, or 10;
   X is CH or N;
   Y is $CR^4$ or N; and W is $CR^2$; or
   Y is $NR^{4y}$, O or S; and W is absent;
   Ring A is a monocyclic 5-6 membered heteroaryl ring;
   Ring B and Ring C together form a fused bicycle;
   Ring B is phenyl, 6-membered heteroaryl, or 6-membered heterocycloalkyl, each of
   which is optionally substituted with 1, 2, or 3 independently selected $R^5$ substituents; and Ring C is 5-membered heteroaryl, each of which is optionally substituted with 1 or 2 independently selected $R^6$ substituents; or
   Ring B is 5-membered heteroaryl or 5-membered heterocycloalkyl, each of which is optionally substituted with 1, 2, 3, or 4 independently selected $R^5$ substituents; and Ring C is phenyl or a 6-membered heteroaryl, each of which is optionally substituted with 1, 2, or 3 independently selected $R^6$ substituents; or
   Ring B is cyclopentyl, which is optionally substituted with 1, 2, 3, or 4 independently selected $R^5$ substituents; and Ring C is 6-membered heteroaryl, each of which is optionally substituted with 1, 2, or 3 independently selected $R^6$ substituents;
   each $R^W$, attached to the B ring or the C ring, is independently:

5

-continued each L¹ is independently -L-C(O)—, -L-NR⁹C(O)—, -L-OC(O)—, -L-S(O)—, -L-S(O)₂—, -L-NR⁹S(O)—, -L-OS(O)—, -L-NR⁹S(O)₂—, or -L-OS(O)₂—, wherein L¹ is attached to Ring C through the L linking group;

each L² is independently -L-, -L-O—, -L-NR⁹—, -L-S—, -L-C(O)—, -L-NR⁹C(O)—, -L-OC(O)—, -L-S(O)—, -L-S(O)₂—, -L-NR⁹S(O)—, -L-OS(O)—, -L-NR⁹S(O)NR⁹—, -L-NR⁹S(O)O—, -L-OS(O)NR⁹—, -L-NR⁹S(O)₂—, -L-OS(O)₂—, -L-NR⁹S(O)₂NR⁹—, -L-NR⁹S(O)₂O—, -L-S(O)(NR⁹)—, -L-S(O)₂(NR⁹)—, or -L-OS(O)₂NR⁹—, wherein L² is attached to Ring C through the L linking group;

each L³ is independently -L-, -L-C(O)—, -L-NR⁹C(O)—, -L-OC(O)—, -L-S(O)—, -L-S(O)₂—, -L-NR⁹S(O)—, -L-OS(O)—, -L-NR⁹S(O)₂—, or -L-OS(O)₂—, wherein L³ is attached to Ring C through the L linking group;

each L⁴ is independently -L-, -L-O—, L-S—, -L-NR⁹—, wherein L⁴ is attached to Ring C through the L linking group;

each L⁵ is independently -L-O-Lˣ-, -L-NR⁹-Lˣ-, -L-S-Lˣ-, -L-C(O)-Lˣ-, -L-NR⁹C(O)-Lˣ-, -L-OC(O)-Lˣ-, -L-S

6

(O)-Lˣ-, -L-S(O)₂-Lˣ-, -L-NR⁹S(O)-Lˣ-, -L-OS(O)-Lˣ-, -L-NR⁹S(O)NR⁹-Lˣ-, -L-NR⁹S(O)O-Lˣ-, -L-OS(O)NR⁹-Lˣ-, -L-NR⁹S(O)₂-Lˣ-, -L-OS(O)₂-Lˣ-, -L-NR⁹S(O)₂NR⁹-Lˣ-, -L-NR⁹S(O)₂O-Lˣ-, -L-S(O)(NR⁹)-Lˣ-, -L-S(O)₂(NR⁹)-Lˣ-, or -L-OS(O)₂NR⁹-Lˣ-, wherein L⁵ is attached to Ring C through the L linking group;

each L⁶ is independently -L-, -L-O—, -L-NR⁹—, -L-S—, -L-C(O)—, -L-NR⁹C(O)—, -L-OC(O)—, -L-S(O)—, -L-S(O)₂—, -L-NR⁹S(O)—, -L-OS(O)—, -L-NR⁹S(O)NR⁹—, -L-NR⁹S(O)O—, -L-OS(O)NR⁹—, -L-NR⁹S(O)₂—, -L-OS(O)₂—, -L-NR⁹S(O)₂NR⁹—, -L-NR⁹S(O)₂O—, -L-S(O)(NR⁹)—, -L-S(O)₂(NR⁹)—, or -L-OS(O)₂NR⁹—;

each L is independently is a bond or C₁₋₆ alkylene, wherein said C₁₋₆ alkylene is optionally substituted by 1, 2, 3 or 4 independently selected R^G substituents; or each L is —O—C₁₋₆ alkyl or —N(R^N)—C₁₋₆ alkyl, wherein L is attached to Ring B or Ring C via the oxygen of the —O—C₁₋₆ alkyl or the nitrogen atom of the —N(R^N)—C₁₋₆ alkyl group;

each R^N is independently H or C₁₋₆ alkyl;

each Lˣ is independently is a C₁₋₆ alkylene, wherein said C₁₋₆ alkylene is optionally substituted by 1, 2, 3 or 4 independently selected R^G substituents;

each Ring D is independently a 4-12 membered heterocycloalkyl, C₃₋₁₂ cycloalkyl, C₆₋₁₀ aryl, or a 5-10 membered heteroaryl, each of which is optionally substituted with 1, 2, 3, or 4 independently selected C₁₋₆ alkyl groups;

each X¹ independently is O or NR⁹;

each q is independently 0, 1, 2, or 3;

each t is independently 0, 1, 2, or 3;

each u is, independently, 0, 1, 2, or 3;

each Ar is independently C₆₋₁₀ aryl or 5-10 membered heteroaryl, which are each optionally substituted with 1, 2, 3, or 4 independently selected R^9A substituents;

each R⁸¹, R⁸², and R⁸³ are independently selected from H, D, halo, NO₂, CN, C₁₋₆ alkyl, C₂₋₆ alkenyl, C₂₋₆ alkynyl, C₁₋₆ haloalkyl, C₃₋₁₀ cycloalkyl, 6-10 membered aryl, 4-10 membered heterocycloalkyl, 5-10 membered heteroaryl, C₃₋₁₀ cycloalkyl-C₁₋₄ alkyl, 6-10 membered aryl-C₁₋₄ alkyl, 4-10 membered heterocycloalkyl-C₁₋₄ alkyl, 5-10 membered heteroaryl-C₁₋₄ alkyl, OR^a8, SR^a8, NHOR^a8, C(O)R^b8, C(O)NR^c8R^d8, C(O)NR^c8(OR^a8), C(O)OR^a8, OC(O)R^b8, OC(O)NR^c8R^d8, NR^c8R^d8, NR^c8NR^c8R^d8, NR^c8C(O)R^b8, NR^c8C(O)OR^a8, NR^c8C(O)NR^c8R^d8, C(=NR^e8)R^b8, C(=NR^e8)NR^c8R^d8, NR^c8C(=NR^e8)NR^c8R^d8, NR^c8C(=NR^e8)R^b8, NR^c8S(O)NR^c8R^d8, NR^c8S(O)R^b8, NR^c8S(O)₂R^b8, NR^c8S(O)(=NR^e8)R^b8, NR^c8S(O)₂NR^c8R^d8, S(O)R^b8, S(O)NR^c8R^d8, S(O)₂R^b8, S(O)₂NR^c8R^d8, OS(O)(=NR^e8)R^b8, OS(O)₂R^b8, S(O)(=NR^e8)R^b8, SF₅, P(O)R^f8R^g8, OP(O)(OR^h8)(OR^i8), P(O)(OR^h8)(OR^i8), and BR^j8R^k8; wherein said C₁₋₆ alkyl, C₂₋₆ alkenyl, C₂₋₆ alkynyl, C₁₋₆ haloalkyl, C₃₋₁₀ cycloalkyl, 6-10 membered aryl, 4-10 membered heterocycloalkyl, 5-10 membered heteroaryl, C₃₋₁₀ cycloalkyl-C₁₋₄ alkyl, 6-10 membered aryl-C₁₋₄ alkyl, 4-10 membered heterocycloalkyl-C₁₋₄ alkyl, and 5-10 membered heteroaryl-C₁₋₄ alkyl are each optionally substituted by 1, 2, 3, or 4 independently selected R^G substituents;

each R^a8, R^c8, and R^d8 is independently selected from H, C₁₋₆ alkyl, C₁₋₆ haloalkyl, C₂₋₆ alkenyl, C₂₋₆ alkynyl, C₃₋₁₀ cycloalkyl, 6-10 membered aryl, 4-10 membered heterocycloalkyl, 5-10 membered heteroaryl, C₃₋₁₀ cycloalkyl-C₁₋₄ alkyl, 6-10 membered aryl-C₁₋₄ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^G$ substituents;

or, any $R^{c8}$ and $R^{d8}$ attached to the same N atom, together with the N atom to which they are attached, form a 4-10 membered heterocycloalkyl group, which is optionally substituted with 1, 2, 3, or 4 independently selected $R^G$ substituents;

each $R^{b8}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^G$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f8}$ and $R^{g8}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h8}$ and $R^{i8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j8}$ and $R^{k8}$ is independently selected from OH, $C_{1-6}$ alkoxy, and $C_{1-6}$ haloalkoxy;

or any $R^{j8}$ and $R^{k8}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

or any two $R^{81}$ and $R^{82}$ together with the atoms to which they are attached, form $C_{3-7}$ cycloalkyl, 4-7 membered heterocycloalkyl, phenyl, or 5-6-membered heteroaryl ring, each of which is optionally substituted with 1, 2, 3, or 4 independently selected $R^G$ substitutents;

each $R^{84}$ is independently H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, or 5-10 membered heteroaryl-$C_{1-4}$ alkyl, wherein said $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, or 5-10 membered heteroaryl-$C_{1-4}$ alkyl are optionally substituted by 1, 2, 3, or 4 independently selected $R^G$ substituents;

each $R^{85}$ is independently H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, or $C_{3-10}$ cycloalkyl-$C_{1-4}$ alkyl, wherein said $C_{1-6}$ alkyl, $C_{1-6}$ haloalkyl, $C_{3-10}$cycloalkyl, 4-10 membered heterocycloalkyl, and $C_{3-10}$ cycloalkyl-$C_{1-4}$ alkyl are each optionally substituted by 1, 2, 3, or 4 independently selected $R^G$ substituents;

each $R^9$ is independently selected from H, halo, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{b9}$, $OC(O)NR^{c9}R^{d9}$, $NR^{c9}C(O)R^{b9}$, $NR^{c9}C(O)OR^{a9}$, $NR^{c9}C(O)NR^{c9}R^{d9}$, $C(=NR^{e9})R^{b9}$, $C(=NR^{e9})NR^{c9}R^{d9}$, $NR^{c9}C(=NR^{e9})NR^{c9}R^{d9}$, $NR^{c9}C(=NR^{e9})R^{b9}$, $NR^{c9}S(O)NR^{c9}R^{d9}$, $NR^{c9}S(O)R^{b9}$, $NR^{c9}S(O)_2R^{b9}$, $NR^{c9}S(O)(=NR^{e9})R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $OS(O)(=NR^{e9})R^{b9}$, $OS(O)_2R^{b9}$, and $S(O)(=NR^{e9})R^{b9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

or, any $R^{c9}$ and $R^{d9}$ attached to the same N atom, together with the N atom to which they are attached, form a 4-10 membered heterocycloalkyl group, which is optionally substituted with 1, 2, 3, or 4 independently selected $R^{9A}$ substituents;

each $R^{b9}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{9A}$ substituents;

each $R^{e9}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, $NR^{c91}C(O)NR^{c91}R^{d91}$, $C(=NR^{e91})R^{b91}$, $C(=NR^{e91})NR^{c91}R^{d91}$, $NR^{c91}C(=NR^{e91})NR^{c91}R^{d91}$, $NR^{c91}C(=NR^{e91})R^{b91}$, $NR^{c91}S(O)NR^{c91}R^{d91}$, $NR^{c91}S(O)R^{b91}$, $NR^{c91}S(O)_2 R^{b91}$, $NR^{c91}S(O)(=NR^{e91})R^{b91}$, $NR^{c91}S(O)_2 NR^{c91}R^{d91}$, $S(O)R^{b91}$, $S(O)NR^{c91}R^{d91}$, $S(O)_2 R^{b91}$, $S(O)_2 NR^{c91}R^{d91}$, $OS(O)(=NR^{e91})R^{b91}$, $OS(O)_2 R^{b91}$, $S(O)(=NR^{e91})R^{b91}$, $SF_5$, $P(O)R^{f91}R^{g91}$, $OP(O)(OR^{h91})(OR^{i91})$, $P(O)(OR^{h91})(OR^{i91})$, and $BR^{j91}R^{k91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

or, any $R^{c91}$ and $R^{d91}$ attached to the same N atom, together with the N atom to which they are attached, form a 4-7 membered heterocycloalkyl group, which is optionally substituted with 1, 2, 3, or 4 independently selected $R^{9B}$ substituents;

each $R^{b91}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f91}$ and $R^{g91}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h91}$ and $R^{i91}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j91}$ and $R^{k91}$ is independently selected from OH, $C_{1-6}$ alkoxy, and $C_{1-6}$ haloalkoxy;

or any $R^{j91}$ and $R^{k91}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, $NR^{c92}C(O)NR^{c92}R^{d92}$, $C(=NR^{e92})R^{b92}$, $C(=NR^{e92})NR^{c92}R^{d92}$, $NR^{c92}C(=NR^{e92})NR^{c92}R^{d92}$, $NR^{c92}C(=NR^{e92})R^{b92}$, $NR^{c92}S(O)NR^{c92}R^{d92}$, $NR^{c92}S(O)R^{b92}$, $NR^{c92}S(O)_2 R^{b92}$, $NR^{c92}S(O)(=NR^{e92})R^{b92}$, $NR^{c92}S(O)_2 NR^{c92}R^{d92}$, $S(O)R^{b92}$, $S(O)NR^{c92}R^{d92}$, $S(O)_2 R^{b92}$, $S(O)_2 NR^{c92}R^{d92}$, $OS(O)(=NR^{e92})R^{b92}$, $OS(O)_2 R^{b92}$, $S(O)(=NR^{e92})R^{b92}$, $SF_5$, $P(O)R^{f92}R^{g92}$, $OP(O)(OR^{h92})(OR^{i92})$, $P(O)(OR^{h92})(OR^{i12})$, and $BR^{j92}R^{k92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c92}$ and $R^{d92}$ attached to the same N atom, together with the N atom to which they are attached, form a 4-7 membered heterocycloalkyl group, which is optionally substituted with 1, 2, 3, or 4 independently selected $R^G$ substituents;

each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e92}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f92}$ and $R^{g92}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h92}$ and $R^{i92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j92}$ and $R^{k92}$ is independently selected from OH, $C_{1-6}$ alkoxy, and $C_{1-6}$ haloalkoxy;

or any $R^{j92}$ and $R^{k92}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, 4-10 membered heterocycloalkyl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, are each optionally substituted with 1, 2, 3, or 4 independently selected $R^{1A}$ substituents;

or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, which are each optionally substituted with 1, 2, 3, or 4 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{f1}$ and $R^{g1}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)NR^{c11}R^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, $OS(O)_2R^{b11}$, $S(O)(=NR^{e11})R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

or, any $R^{c11}$ and $R^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f11}$ and $R^{g11}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)NR^{c12}R^{d12}$, $NR^{c12}S(O)R^{b12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, $OS(O)_2R^{b12}$, $S(O)(=NR^{e12})R^{b12}$, $SF_5$, $P(O)R^{f12}R^{g12}$, $OP(O)(OR^{h12})(OR^{i12})$, $P(O)(OR^{h12})(OR^{i12})$ and $BR^{j12}R^{k12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected Ric substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1C}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f12}$ and $R^{g12}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h12}$ and $R^{i12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j12}$ and $R^{k12}$ is independently selected from OH, $C_{1-6}$ alkoxy, and $C_{1-6}$ haloalkoxy;

or any $R^{j12}$ and $R^{k12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1C}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a13}$, $SR^{a13}$, $NHOR^{a13}$, $C(O)R^{b13}$, $C(O)NR^{c13}R^{d13}$, $C(O)NR^{c13}(OR^{a13})$, $C(O)OR^{a13}$, $OC(O)R^{b13}$, $OC(O)NR^{c13}R^{d13}$, $NR^{c13}R^{d13}$, $NR^{c13}NR^{c13}R^{d13}$, $NR^{c13}C(O)R^{b13}$, $NR^{c13}C(O)OR^{a13}$, $NR^{c13}C(O)$ $NR^{c13}R^{d13}$, $C(=NR^{e13})R^{b13}$, $C(=NR^{e13})NR^{c13}R^{d13}$, $NR^{c13}C(=NR^{e13})NR^{c13}R^{d13}$, $NR^{c13}C(=NR^{e13})R^{b13}$, $NR^{c13}S(O)NR^{c13}R^{d13}$, $NR^{c13}S(O)R^{b13}$, $NR^{c13}S(O)_2R^{b13}$, $NR^{c13}S(O)(=NR^{e13})R^{b13}$, $NR^{c13}S(O)_2NR^{c13}R^{d13}$, $S(O)R^{b13}$, $S(O)NR^{c13}R^{d13}$, $S(O)_2R^{b13}$, $S(O)_2NR^{c13}R^{d13}$, $OS(O)(=NR^{e13})R^{b13}$, $OS(O)_2R^{b13}$, $S(O)(=NR^{e13})R^{b13}$, $SF_5$, $P(O)R^{f13}R^{g13}$, $OP(O)$ $(OR^{h13})(OR^{i13})$, $P(O)(OR^{h13})(OR^{i13})$ and $BR^{j13}R^{k13}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a13}$, $R^{c13}$, and $R^{d13}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c13}$ and $R^{d13}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b13}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e13}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f13}$ and $R^{g13}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h13}$ and $R^{i13}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j13}$ and $R^{k13}$ is independently selected from OH, $C_{1-6}$ alkoxy, and $C_{1-6}$ haloalkoxy;

or any $R^{j13}$ and $R^{k13}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^2$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $S(O)(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f2}$ and $R^{g2}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, $OS(O)_2R^{b21}$, $S(O)(=NR^{e21})R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c21}$ and $R^{d21}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b21}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f21}$ and $R^{g21}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^3$ is H, D, $CH_3$, or $CD_3$;

$R^4$ is H, D, halo, CN, $C_{1-6}$ alkyl, $C_{1-6}$ haloalkyl, $C_{1-3}$ alkoxy, $C_{1-3}$ haloalkoxy, cyano-$C_{1-6}$ alkyl, HO—$C_{1-6}$ alkyl, $C_{1-3}$ alkoxy-$C_{1-6}$ alkyl, or $C_{3-6}$ cycloalkyl;

$R^{4y}$ is H, $C_{1-4}$ alkyl, $C_{1-4}$ haloalkyl, cyano-$C_{1-4}$ alkyl, HO—$C_{1-4}$ alkyl, $C_{1-3}$ alkoxy-$C_{1-4}$ alkyl, or $C_{3-4}$ cycloalkyl;

each $R^5$ is independently selected from oxo, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)NR^{c5}R^{d5}$, $NR^{c5}S(O)R^{b5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $S(O)(=NR^{e5})R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f5}$ and $R^{g5}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)NR^{c51}$($OR^{a51}$), $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})$ $R^{b51}$, $C(=NR^{e51})NR^{c51}R^{d51}$, $NR^{c51}C(=NR^{e51})$ $NR^{c51}R^{d51}$, $NR^{c51}C(=NR^{e51})R^{b51}$, $NR^{c51}S(O)$ $NR^{c51}R^{d51}$, $NR^{c51}S(O)R^{b51}$, $NR^{c51}S(O)_2R^{b51}$, $NR^{c51}S$ $(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)$ $(=NR^{e51})R^{b51}$, $OS(O)_2R^{b51}$, $S(O)(=NR^{e51})R^{b51}$, $SF_5$, $P(O)R^{f51}R^{g51}$, $OP(O)(OR^{h51})(OR^{i51})$, $P(O)(OR^{h51})$ $(OR^{i51})$, and $BR^{j51}R^{k51}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

or, any $R^{c51}$ and $R^{d51}$ attached to the same N atom, together with the N atom to which they are attached, form a 4-7 membered heterocycloalkyl group, which is optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f51}$ and $R^{g51}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h51}$ and $R^{i51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j51}$ and $R^{k51}$ is independently selected from OH, $C_{1-6}$ alkoxy, and $C_{1-6}$ haloalkoxy;

or any $R^{j51}$ and $R^{k51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{c52}C(=NR^{e52})NR^{c52}R^{d52}$, $NR^{c52}C(=NR^{e52})R^{b52}$, $NR^{c52}S(O)NR^{c52}R^{d52}$, $NR^{c52}S(O)R^{b52}$, $NR^{c52}S(O)_2R^{b52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, $OS(O)_2R^{b52}$, $S(O)(=NR^{e52})R^{b52}$, $SF_5$, $P(O)R^{f52}R^{g52}$, $OP(O)(OR^{h52})(OR^{i52})$, $P(O)(OR^{h52})(OR^{i52})$, and $BR^{j52}R^{k52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c52}$ and $R^{d52}$ attached to the same N atom, together with the N atom to which they are attached, form a 4-7 membered heterocycloalkyl group, which is optionally substituted with 1, 2, 3, or 4 independently selected $R^G$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e52}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f52}$ and $R^{g52}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h52}$ and $R^{i52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j52}$ and $R^{k52}$ is independently selected from OH, $C_{1-6}$ alkoxy, and $C_{1-6}$ haloalkoxy;

or any $R^{j52}$ and $R^{k52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^6$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NR^{e6})NR^{c6}R^{d6}$, $NR^{c6}C(=NR^{e6})NR^{b6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $S(O)(=NR^{e6})R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6A}$ substituents;

or, any $R^{c6}$ and $R^{d6}$ attached to the same N atom, together with the N atom to which they are attached, form a 4-10 membered heterocycloalkyl group, which is optionally substituted with 1, 2, 3, or 4 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f6}$ and $R^{g6}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)NR^{c61}$ $(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NR^{e61})$ $R^{b61}$, $C(=NR^{e61})NR^{c61}R^{d61}$, $NR^{c61}C(=NR^{e61})$ $NR^{c61}R^{d61}$, $NR^{c61}C(=NR^{e61})R^{b61}$, $NR^{c61}S(O)$ $NR^{c61}R^{d61}$, $NR^{c61}S(O)R^{b61}$, $NR^{c61}S(O)_2R^{b61}$, $NR^{c61}S$ $(O)(=NR^{e61})R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $OS(O)$ $(=NR^{e61})R^{b61}$, $OS(O)_2R^{b61}$, $S(O)(=NR^{e61})R^{b61}$, $SF_5$, $P(O)R^{f61}R^{g61}$, $OP(O)(OR^{h61})(OR^{i61})$, $P(O)(OR^{h61})$ $(OR^{i61})$, and $BR^{j61}R^{k61}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6B}$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6B}$ substituents;

or, any $R^{c61}$ and $R^{d61}$ attached to the same N atom, together with the N atom to which they are attached, form a 4-7 membered heterocycloalkyl group, which is optionally substituted with 1, 2, 3, or 4 independently selected $R^{6B}$ substituents;

each $R^{b61}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{6B}$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f61}$ and $R^{g61}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h61}$ and $R^{i61}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j61}$ and $R^{k61}$ is independently selected from OH, $C_{1-6}$ alkoxy, and $C_{1-6}$ haloalkoxy;

or any $R^{j61}$ and $R^{k61}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{6B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a62}$, $SR^{a62}$, $NHOR^{a62}$, $C(O)R^{b62}$, $C(O)$ $NR^{c62}R^{d62}$, $C(O)NR^{c62}(OR^{a62})$, $C(O)OR^{a62}$, $OC(O)$ $R^{b62}$, $OC(O)NR^{c62}R^{d62}$, $NR^{c62}R^{d62}$, $NR^{c62}NR^{c62}R^{d62}$, $NR^{c62}C(O)R^{b62}$, $NR^{c62}C(O)OR^{a62}$, $NR^{c62}C(O)$ $NR^{c62}R^{c62}$, $C(=NR^{e62})R^{b62}$, $C(=NR^{e62})NR^{c62}R^{d62}$, $NR^{c62}C(=NR^{e62})NR^{c62}R^{d62}$, $NR^{c62}C(=NR^{e62})R^{b62}$, $NR^{c62}S(O)NR^{c62}R^{d62}$, $NR^{c62}S(O)R^{b62}$, $NR^{c62}S(O)_2$ $R^{b62}$, $NR^{c62}S(O)(=NR^{e62})R^{b62}$, $NR^{c62}S(O)_2$ $NR^{c62}R^{d62}$, $S(O)R^{b62}$, $S(O)NR^{c62}R^{d62}$, $S(O)_2R^{b62}$, $S(O)_2NR^{c62}R^{b62}$, $OS(O)(=NR^{e62})R^{b62}$, $OS(O)_2R^{b62}$, $S(O)(=NR^{e62})R^{b62}$, $SF_5$, $P(O)R^{f62}R^{g62}$, $OP(O)$ $(OR^{h62})(OR^{i62})$, $P(O)(OR^{h62})(OR^{i62})$, and $BR^{j62}R^{k62}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a62}$, $R^{c62}$, and $R^{d62}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c62}$ and $R^{d62}$ attached to the same N atom, together with the N atom to which they are attached, form a 4-7 membered heterocycloalkyl group, which is optionally substituted with 1, 2, 3, or 4 independently selected $R^G$ substituents;

each $R^{b62}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e62}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f62}$ and $R^{g62}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h62}$ and $R^{i62}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j62}$ and $R^{k62}$ is independently selected from OH, $C_{1-6}$ alkoxy, and $C_{1-6}$ haloalkoxy;

or any $R^{j62}$ and $R^{k62}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)NR^{c7}R^{d7}$, $NR^{c7}S(O)R^{b7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $S(O)(=NR^{e7})R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$;

wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{74}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{74}$ substituents;

or, any $R^{c7}$ and $R^{d7}$ attached to the same N atom, together with the N atom to which they are attached, form a 4-10 membered heterocycloalkyl group, which is optionally substituted with 1, 2, 3, or 4 independently selected $R^{74}$ substituents;

each $R^{b7}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{74}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f7}$ and $R^{g7}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j7}$ and $R^{k7}$ is independently selected from OH, $C_{1-6}$ alkoxy, and $C_{1-6}$ haloalkoxy;

or any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a71}$, $SR^{a71}$, $NHOR^{a71}$, $C(O)R^{b71}$, $C(O)NR^{c71}R^{d71}$, $C(O)NR^{c71}(OR^{a71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a71}$, $NR^{c71}C(O)NR^{c71}R^{d71}$, $C(=NR^{e71})R^{b71}$, $C(=NR^{e71})NR^{c71}R^{d71}$, $NR^{c71}C(=NR^{e71})NR^{c71}R^{d71}$, $NR^{c71}C(=NR^{e71})R^{b71}$, $NR^{c71}S(O)NR^{c71}R^{d71}$, $NR^{c71}S(O)R^{b71}$, $NR^{c71}S(O)_2R^{b71}$, $NR^{c71}S(O)(=NR^{e71})R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, $OS(O)_2R^{b71}$, $S(O)(=NR^{e71})R^{b71}$, $SF_5$, $P(O)R^{f71}R^{g71}$, $OP(O)(OR^{h71})(OR^{i71})$, $P(O)(OR^{h71})(OR^{i71})$, and $BR^{j71}R^{k71}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7B}$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7B}$ substituents;

or, any $R^{c71}$ and $R^{d71}$ attached to the same N atom, together with the N atom to which they are attached, form a 4-7 membered heterocycloalkyl group, which is optionally substituted with 1, 2, 3, or 4 independently selected $R^{7B}$ substituents;

each $R^{b71}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{7B}$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f71}$ and $R^{g71}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h71}$ and $R^{i71}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j71}$ and $R^{k71}$ is independently selected from OH, $C_{1-6}$ alkoxy, and $C_{1-6}$ haloalkoxy;

or any $R^{j71}$ and $R^{k71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a72}$, $SR^{a72}$, $NHOR^{a72}$, $C(O)R^{b72}$, $C(O)NR^{c72}R^{d72}$, $C(O)NR^{c72}(OR^{a72})$, $C(O)OR^{a72}$, $OC(O)R^{b72}$, $OC(O)NR^{c72}R^{d72}$, $NR^{c72}R^{d72}$, $NR^{c72}NR^{c72}R^{d72}$, $NR^{c72}C(O)R^{b72}$, $NR^{c72}C(O)OR^{a72}$, $NR^{c72}C(O)NR^{c72}R^{d72}$, $C(=NR^{e72})R^{b72}$, $C(=NR^{e72})NR^{c72}R^{d72}$, $NR^{c72}C(=NR^{e72})NR^{c72}R^{d72}$, $NR^{c72}C(=NR^{e72})R^{b72}$, $NR^{c72}S(O)NR^{c72}R^{d72}$, $NR^{c72}S(O)R^{b72}$, $NR^{c72}S(O)_2R^{b72}$, $NR^{c72}S(O)(=NR^{e72})R^{b72}$, $NR^{c72}S(O)_2NR^{c72}R^{d72}$, $S(O)R^{b72}$, $S(O)NR^{c72}R^{d72}$, $S(O)_2R^{b72}$, $S(O)_2NR^{c72}R^{d72}$, $OS(O)(=NR^{e72})R^{b72}$, $OS(O)_2R^{b72}$, $S(O)(=NR^{e72})R^{b72}$, $SF_5$, $P(O)R^{f72}R^{g72}$, $OP(O)(OR^{h72})(OR^{i72})$, $P(O)(OR^{h72})(OR^{i12})$, and $BR^{j72}R^{k72}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c72}$ and $R^{d72}$ attached to the same N atom, together with the N atom to which they are attached, form a 4-7 membered heterocycloalkyl group, which is optionally substituted with 1, 2, 3, or 4 independently selected $R^G$ substituents;

each $R^{b72}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e72}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f72}$ and $R^{g72}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h72}$ and $R^{i72}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j72}$ and $R^{k72}$ is independently selected from OH, $C_{1-6}$ alkoxy, and $C_{1-6}$ haloalkoxy;

or any $R^{j72}$ and $R^{k72}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^G$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments:

each $\equiv$ is independently a single or a double bond;

k is 1 or 2;

n is 0, 1, or 2;

p is 0, 1, 2, 3, 4, 5, 6, 7, 8, 9, or 10;

X is CH or N;

Y is $CR^4$ or N; and W is $CR^2$; or

Y is $NR^{4y}$, O or S; and W is absent;

Ring A is a monocyclic 5-6 membered heteroaryl ring;

Ring B and Ring C together form a fused bicycle;

Ring B is phenyl, 6-membered heteroaryl, or 6-membered heterocycloalkyl, each of which is optionally substituted with 1, 2, or 3 independently selected $R^5$ substituents; and Ring C is 5-membered heteroaryl, each of which is optionally substituted with 1 or 2 independently selected $R^6$ substituents; or Ring B is 5-membered heteroaryl or 5-membered heterocycloalkyl, each of which is optionally substituted with 1, 2, 3, or 4 independently selected $R^5$ substituents; and Ring C is phenyl or a 6-membered heteroaryl, each of which is optionally substituted with 1, 2, or 3 independently selected $R^6$ substituents; or Ring B is cyclopentyl, which is optionally substituted with 1, 2, 3, or 4 independently selected $R^5$ substituents; and Ring C is 6-membered heteroaryl, each of which is optionally substituted with 1, 2, or 3 independently selected $R^6$ substituents;

each $R^W$, attached to the C ring, is independently:

-continued

-continued each $L^1$ is independently -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$—, or -L-OS(O)$_2$—, wherein $L^1$ is attached to Ring C through the L linking group;

each $L^2$ is independently -L-, -L-O—, -L-NR$^9$—, -L-S—, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)NR$^9$—, -L-NR$^9$S(O)O—, -L-OS(O)NR$^9$—, -L-NR$^9$S(O)$_2$—, -L-OS(O)$_2$—, -L-NR$^9$S(O)$_2$NR$^9$—, -L-NR$^9$S(O)$_2$O—, -L-S(O)(NR$^9$)—, -L-S(O)$_2$(NR$^9$)—, or -L-OS(O)$_2$NR$^9$—, wherein $L^2$ is attached to Ring C through the L linking group;

each $L^3$ is independently -L-, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$—, or -L-OS(O)$_2$—, wherein $L^3$ is attached to Ring C through the L linking group;

each $L^4$ is independently -L-, -L-O—, L-S—, -L-NR$^9$—, wherein $L^4$ is attached to Ring C through the L linking group;

each $L^5$ is independently -L-O-L$^x$-, -L-NR$^9$-L$^x$-, -L-S-L$^x$-, -L-C(O)-L$^x$-, -L-NR$^9$C(O)-L$^x$-, -L-OC(O)-L$^x$-, -L-S(O)-L$^x$-, -L-S(O)$_2$-L$^x$-, -L-NR$^9$S(O)-L$^x$-, -L-OS(O)-L$^x$-, -L-NR$^9$S(O)NR$^9$-L$^x$-, -L-NR$^9$S(O)O-L$^x$-, -L-OS(O)NR$^9$-L$^x$-, -L-NR$^9$S(O)$_2$-L$^x$-, -L-OS(O)$_2$-L$^x$-, -L-NR$^9$S(O)$_2$NR$^9$-L$^x$-, -L-NR$^9$S(O)$_2$O-L$^x$-, -L-S(O)(NR$^9$)-L$^x$-, -L-S(O)$_2$(NR$^9$)-L$^x$-, or -L-OS(O)$_2$NR$^9$-L$^x$-, wherein $L^5$ is attached to Ring C through the L linking group;

each L is independently is a bond or $C_{1-6}$ alkylene, wherein said $C_{1-6}$ alkylene is optionally substituted by 1, 2, 3 or 4 independently selected $R^G$ substituents;

each $L^x$ is independently is a $C_{1-6}$ alkylene, wherein said $C_{1-6}$ alkylene is optionally substituted by 1, 2, 3 or 4 independently selected $R^G$ substituents;

each $X^1$ independently is O or NR$^9$;

each q is independently 0, 1, 2, or 3;

each t is independently 0, 1, 2, or 3;

each u is, independently, 0, 1, 2, or 3;

each Ar is independently $C_{6-10}$ aryl or 5-10 membered heteroaryl, which are each optionally substituted with 1, 2, 3, or 4 independently selected $R^{9A}$ substituents;

each $R^{81}$, $R^{82}$, and $R^{83}$ are independently selected from H, D, halo, NO$_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, OR$^{a8}$, SR$^{a8}$, NHOR$^{a8}$, C(O)R$^{b8}$, C(O)NR$^{c8}$R$^{d8}$, C(O)NR$^{c8}$(OR$^{a8}$), C(O)OR$^{a8}$, OC(O)R$^{b8}$, OC(O)NR$^{c8}$R$^{d8}$, NR$^{c8}$R$^{d8}$, NR$^{c8}$NR$^{c8}$R$^{d8}$, NR$^{c8}$C(O)R$^{b8}$, NR$^{c8}$C(O)OR$^{a8}$, NR$^{c8}$C(O)NR$^{c8}$R$^{d8}$, C(=NR$^{e8}$)R$^{b8}$, C(=NR$^{e8}$)

$NR^{c8}R^{d8}$, $NR^{c8}C(=NR^{e8})NR^{c8}R^{d8}$, $NR^{c8}C(=NR^{e8})R^{b8}$, $NR^{c8}S(O)NR^{c8}R^{d8}$, $NR^{c8}S(O)R^{b8}$, $NR^{c8}S(O)_2R^{b8}$, $NR^{c8}S(O)(=NR^{e8})R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$, $OS(O)(=NR^{e8})R^{b8}$, $OS(O)_2R^{b8}$, $S(O)(=NR^{e8})R^{b8}$, $SF_5$, $P(O)R^{f8}R^{g8}$, $OP(O)(OR^{h8})(OR^{i8})$, $P(O)(OR^{h8})(OR^{i8})$, and $BR^{j8}R^{k8}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ substituents;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^G$ substituents;

or, any $R^{c8}$ and $R^{d8}$ attached to the same N atom, together with the N atom to which they are attached, form a 4-10 membered heterocycloalkyl group, which is optionally substituted with 1, 2, 3, or 4 independently selected $R^G$ substituents;

each $R^{b8}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^G$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f8}$ and $R^{g8}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h8}$ and $R^{i8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j8}$ and $R^{k8}$ is independently selected from OH, $C_{1-6}$ alkoxy, and $C_{1-6}$ haloalkoxy;

or any $R^{j8}$ and $R^{k8}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

or any two $R^{81}$ and $R^{82}$ together with the atoms to which they are attached, form $C_{3-7}$ cycloalkyl, 4-7 membered heterocycloalkyl, phenyl, or 5-6-membered heteroaryl ring, each of which is optionally substituted with 1, 2, 3, or 4 independently selected $R^G$ substitutents;

each $R^{84}$ is independently H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, or 5-10 membered heteroaryl-$C_{1-4}$ alkyl, wherein said $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, or 5-10 membered heteroaryl-$C_{1-4}$ alkyl are optionally substituted by 1, 2, 3, or 4 independently selected $R^G$ substituents;

each $R^{85}$ is independently H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, or $C_{3-10}$ cycloalkyl-$C_{1-4}$ alkyl, wherein said $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl are each optionally substituted by 1, 2, 3, or 4 independently selected $R^G$ substituents;

each $R^9$ is independently selected from H, halo, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $C(=NR^{e9})R^{b9}$, $C(=NR^{e9})NR^{c9}R^{d9}$, $NR^{c9}C(=NR^{e9})NR^{c9}R^{d9}$, $NR^{c9}C(=NR^{e9})R^{b9}$, $NR^{c9}S(O)NR^{c9}R^{d9}$, $NR^{c9}S(O)R^{b9}$, $NR^{c9}S(O)_2R^{b9}$, $NR^{c9}S(O)(=NR^{e9})R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $OS(O)(=NR^{e9})R^{b9}$, $OS(O)_2R^{b9}$, and $S(O)(=NR^{e9})R^{b9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

or, any $R^{c9}$ and $R^{d9}$ attached to the same N atom, together with the N atom to which they are attached, form a 4-10 membered heterocycloalkyl group, which is optionally substituted with 1, 2, 3, or 4 independently selected $R^{9A}$ substituents;

each $R^{b9}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{9A}$ substituents;

each $R^{e9}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, $NR^{c91}C(O)NR^{c91}R^{d91}$, $C(=NR^{e91})R^{b91}$, $C(=NR^{e91})NR^{c91}R^{d91}$, $NR^{c91}C(=NR^{e91})NR^{c91}R^{d91}$, $NR^{c91}C(=NR^{e91})R^{b91}$, $NR^{c91}S(O)NR^{c91}R^{d91}$, $NR^{c91}S(O)R^{b91}$, $NR^{c91}S(O)_2R^{b91}$, $NR^{c91}S(O)(=NR^{e91})R^{b91}$, $NR^{c91}S(O)_2NR^{c91}R^{d91}$, $S(O)R^{b91}$, $S(O)NR^{c91}R^{d91}$, $S(O)_2R^{b91}$, $S(O)_2NR^{c91}R^{d91}$, $OS(O)(=NR^{e91})R^{b91}$, $OS(O)_2R^{b91}$, $S(O)(=NR^{e91})R^{b91}$, $SF_5$, $P(O)R^{f91}R^{g91}$, $OP(O)(OR^{h91})(OR^{i91})$, $P(O)(OR^{h91})(OR^{i91})$, and $BR^{j91}R^{k91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

or, any $R^{c91}$ and $R^{d91}$ attached to the same N atom, together with the N atom to which they are attached, form a 4-7 membered heterocycloalkyl group, which is optionally substituted with 1, 2, 3, or 4 independently selected $R^{9B}$ substituents;

each $R^{b91}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f91}$ and $R^{g91}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h91}$ and $R^{i91}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j91}$ and $R^{k91}$ is independently selected from OH, $C_{1-6}$ alkoxy, and $C_{1-6}$ haloalkoxy;

or any $R^{j91}$ and $R^{k91}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, $NR^{c92}C(O)NR^{c92}R^{d92}$, $C(=NR^{e92})R^{b92}$, $C(=NR^{e92})NR^{c92}R^{d92}$, $NR^{c92}C(=NR^{e92})NR^{c92}R^{d92}$, $NR^{c92}C(=NR^{e92})R^{b92}$, $NR^{c92}S(O)NR^{c92}R^{d92}$, $NR^{c92}S(O)R^{b92}$, $NR^{c92}S(O)_2R^{b92}$, $NR^{c92}S(O)(=NR^{e92})R^{b92}$, $NR^{c92}S(O)_2NR^{c92}R^{d92}$, $S(O)R^{b92}$, $S(O)NR^{c92}R^{d92}$, $S(O)_2R^{b92}$, $S(O)_2NR^{c92}R^{d92}$, $OS(O)(=NR^{e92})R^{b92}$, $OS(O)_2R^{b92}$, $S(O)(=NR^{e92})R^{b92}$, $SF_5$, $P(O)R^{f92}R^{g92}$, $OP(O)(OR^{h92})(OR^{i92})$, $P(O)(OR^{h92})(OR^{i12})$, and $BR^{j92}R^{k92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{e92}$ and $R^{d92}$ attached to the same N atom, together with the N atom to which they are attached, form a 4-7 membered heterocycloalkyl group, which is optionally substituted with 1, 2, 3, or 4 independently selected $R^G$ substituents;

each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e92}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f92}$ and $R^{g92}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h92}$ and $R^{i92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j92}$ and $R^{k92}$ is independently selected from OH, $C_{1-6}$ alkoxy, and $C_{1-6}$ haloalkoxy;

or any $R^{j92}$ and $R^{k92}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, 4-10 membered heterocycloalkyl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl- $C_{1-4}$ alkyl, and 4-10 membered heterocycloalkyl-$C_{1-4}$ alkyl are each optionally substituted with 1, 2, 3, or 4 independently selected $R^{14}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, are each optionally substituted with 1, 2, 3, or 4 independently selected $R^{14}$ substituents;

or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{14}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, which are each optionally substituted with 1, 2, 3, or 4 independently selected $R^{14}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{f1}$ and $R^{g1}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{14}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)NR^{c11}R^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, $OS(O)_2R^{b11}$, $S(O)(=NR^{e11})R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

or, any $R^{c11}$ and $R^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f11}$ and $R^{g11}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)$ $R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)$ $NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)NR^{c12}R^{d12}$, $NR^{c12}S(O)R^{b12}$, $NR^{c12}S(O)_2$ $R^{b12}$, $NR^{c12}S(O)(=NR^{e12})R^{b12}$, $NR^{c12}S(O)_2$ $NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, $OS(O)_2R^{b12}$, $S(O)(=NR^{e12})R^{b12}$, $SF_5$, $P(O)R^{f12}R^{g12}$, $OP(O)$ $(OR^{h12})(OR^{i12})$, $P(O)(OR^{h12})(OR^{i12})$ and $BR^{j12}R^{k12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected Ric substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1C}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f12}$ and $R^{g12}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h12}$ and $R^{i12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j12}$ and $R^{k12}$ is independently selected from OH, $C_{1-6}$ alkoxy, and $C_{1-6}$ haloalkoxy;

or any $R^{j12}$ and $R^{k12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1C}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a13}$, $SR^{a13}$, $NHOR^{a13}$, $C(O)R^{b13}$, $C(O)NR^{c13}R^{d13}$, $C(O)NR^{c13}(OR^{a13})$, $C(O)OR^{a13}$, $OC(O)R^{b13}$, $OC(O)NR^{c13}R^{d13}$, $NR^{c13}R^{d13}$, $NR^{c13}NR^{c13}R^{d13}$, $NR^{c13}C(O)R^{b13}$, $NR^{c13}C(O)OR^{a13}$, $NR^{c13}C(O)NR^{c13}R^{d13}$, $C(=NR^{e13})R^{b13}$, $C(=NR^{e13})NR^{c13}R^{d13}$, $NR^{c13}C(=NR^{e13})NR^{c13}R^{d13}$, $NR^{c13}C(=NR^{e13})R^{b13}$, $NR^{c13}S(O)NR^{c13}R^{d13}$, $NR^{c13}S(O)R^{b13}$, $NR^{c13}S(O)_2R^{b13}$, $NR^{c13}S(O)(=NR^{e13})R^{b13}$, $NR^{c13}S(O)_2NR^{c13}R^{d13}$, $S(O)R^{b13}$, $S(O)NR^{c13}R^{d13}$, $S(O)_2R^{b13}$, $S(O)_2NR^{c13}R^{d13}$, $OS(O)(=NR^{e13})R^{b13}$, $OS(O)_2R^{b13}$, $S(O)(=NR^{e13})R^{b13}$, $SF_5$, $P(O)R^{f13}R^{g13}$, $OP(O)(OR^{h13})(OR^{i13})$, $P(O)(OR^{h13})(OR^{i13})$ and $BR^{j13}R^{k13}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a13}$, $R^{c13}$, and $R^{d13}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c13}$ and $R^{d13}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b13}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e13}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f13}$ and $R^{g13}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h13}$ and $R^{i13}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j13}$ and $R^{k13}$ is independently selected from OH, $C_{1-6}$ alkoxy, and $C_{1-6}$ haloalkoxy;

or any $R^{j13}$ and $R^{k13}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^2$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2 NR^{c2}R^{d2}$, $OS(O)(=NR^{e2})R^{b2}$, $OS(O)_2R^{b2}$, $S(O)(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f2}$ and $R^{g2}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, $OS(O)_2R^{b21}$, $S(O)(=NR^{e21})R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c21}$ and $R^{d21}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b21}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f21}$ and $R^{g21}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^3$ is H, D, $CH_3$, or $CD_3$;

$R^4$ is H, D, halo, CN, $C_{1-6}$ alkyl, $C_{1-6}$ haloalkyl, $C_{1-3}$ alkoxy, $C_{1-3}$ haloalkoxy, cyano-$C_{1-6}$ alkyl, HO—$C_{1-6}$ alkyl, $C_{1-3}$ alkoxy-$C_{1-6}$ alkyl, or $C_{3-6}$ cycloalkyl;

$R^{4y}$ is H, $C_{1-4}$ alkyl, $C_{1-4}$ haloalkyl, cyano-$C_{1-4}$ alkyl, HO—$C_{1-4}$ alkyl, $C_{1-3}$ alkoxy-$C_{1-4}$ alkyl, or $C_{3-4}$ cycloalkyl;

each $R^5$ is independently selected from oxo, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)NR^{c5}R^{d5}$, $NR^{c5}S(O)R^{b5}$, $NR^{c5}S(O)_2R^{b5}$, $NR^{c5}S(O)$ $(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $S(O)(=NR^{e5})R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f5}$ and $R^{g5}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}C(=NR^{e51})R^{b51}$, $NR^{c51}S(O)NR^{c51}R^{d51}$, $NR^{c51}S(O)R^{b51}$, $NR^{c51}S(O)_2R^{b51}$, $NR^{c51}S(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)(=NR^{e51})R^{b51}$, $OS(O)_2R^{b51}$, $S(O)(=NR^{e51})R^{b51}$, $SF_5$, $P(O)R^{f51}R^{g51}$, $OP(O)(OR^{h51})(OR^{i51})$, $P(O)(OR^{h51})(OR^{i51})$, and $BR^{j51}R^{k51}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

or, any $R^{c51}$ and $R^{d51}$ attached to the same N atom, together with the N atom to which they are attached, form a 4-7 membered heterocycloalkyl group, which is optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f51}$ and $R^{g51}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h51}$ and $R^{i51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j51}$ and $R^{k51}$ is independently selected from OH, $C_{1-6}$ alkoxy, and $C_{1-6}$ haloalkoxy;

or any $R^{j51}$ and $R^{k51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{c52}C(=NR^{e52})NR^{c52}R^{d52}$, $NR^{c52}C(=NR^{e52})R^{b52}$, $NR^{c52}S(O)NR^{c52}R^{d52}$, $NR^{c52}S(O)R^{b52}$, $NR^{c52}S(O)_2R^{b52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, $OS(O)_2R^{b52}$, $S(O)(=NR^{e52})R^{b52}$, $SF_5$, $P(O)R^{f52}R^{g52}$, $OP(O)(OR^{h52})(OR^{i52})$, $P(O)(OR^{h52})(OR^{i52})$, and $BR^{j52}R^{k52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c52}$ and $R^{d52}$ attached to the same N atom, together with the N atom to which they are attached, form a 4-7 membered heterocycloalkyl group, which is optionally substituted with 1, 2, 3, or 4 independently selected $R^G$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e52}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f52}$ and $R^{g52}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h52}$ and $R^{i52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j52}$ and $R^{k52}$ is independently selected from OH, $C_{1-6}$ alkoxy, and $C_{1-6}$ haloalkoxy;

or any $R^{j52}$ and $R^{k52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^6$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6C}(O)R^{b6}$, $NR^{c6C}(O)OR^{a6}$, $NR^{c6C}(O)NR^{c6}R^{d6}$, $C(=NR^{e6})R^{b6}$, $C(=NR^{e6})NR^{c6}R^{d6}$, $NR^{c6C}(=NR^{e6})NR^{c6}R^{d6}$, $NR^{c6C}(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $S(O)(=NR^{e6})R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6A}$ substituents;

or, any $R^{c6}$ and $R^{d6}$ attached to the same N atom, together with the N atom to which they are attached, form a 4-10 membered heterocycloalkyl group, which is optionally substituted with 1, 2, 3, or 4 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f6}$ and $R^{g6}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j6}$ and $R^{k6}$ is independently selected from OH, $C_{1-6}$ alkoxy, and $C_{1-6}$ haloalkoxy;

or any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)NR^{c61}(OR^{a61})$, $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NR^{e61})R^{b61}$, $C(=NR^{e61})NR^{c61}R^{d61}$, $NR^{c61}C(=NR^{e61})NR^{c61}R^{d61}$, $NR^{c61}C(=NR^{e61})R^{b61}$, $NR^{c61}S(O)NR^{c61}R^{d61}$, $NR^{c61}S(O)R^{b61}$, $NR^{c61}S(O)_2R^{b61}$, $NR^{c61}S(O)(=NR^{e61})R^{b61}$, $NR^{c61}S(O)_2NR^{c61}R^{d61}$, $S(O)R^{b61}$, $S(O)NR^{c61}R^{d61}$, $S(O)_2R^{b61}$, $S(O)_2NR^{c61}R^{d61}$, $OS(O)(=NR^{e61})R^{b61}$, $OS(O)_2R^{b61}$, $S(O)(=NR^{e61})R^{b61}$, $SF_5$, $P(O)R^{f61}R^{g61}$, $OP(O)(OR^{h61})(OR^{i61})$, $P(O)(OR^{h61})(OR^{i61})$, and $BR^{j61}R^{k61}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6B}$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6B}$ substituents;

or, any $R^{c61}$ and $R^{d61}$ attached to the same N atom, together with the N atom to which they are attached, form a 4-7 membered heterocycloalkyl group, which is optionally substituted with 1, 2, 3, or 4 independently selected $R^{6B}$ substituents;

each $R^{b61}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{6B}$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f61}$ and $R^{g61}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h61}$ and $R^{i61}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j61}$ and $R^{k61}$ is independently selected from OH, $C_{1-6}$ alkoxy, and $C_{1-6}$ haloalkoxy;

or any $R^{j61}$ and $R^{k61}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{6B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl- $C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a62}$, $SR^{a62}$, $NHOR^{a62}$, $C(O)R^{b62}$, $C(O)NR^{c62}R^{d62}$, $C(O)NR^{c62}(OR^{a62})$, $C(O)OR^{a62}$, $OC(O)R^{b62}$, $OC(O)NR^{c62}R^{d62}$, $NR^{c62}R^{d62}$, $NR^{c62}NR^{c62}R^{d62}$, $NR^{c62}C(O)R^{b62}$, $NR^{c62}C(O)OR^{a62}$, $NR^{c62}C(O)NR^{c62}R^{d62}$, $C(=NR^{e62})R^{b62}$, $C(=NR^{e62})NR^{c62}R^{d62}$, $NR^{c62}C(=NR^{e62})NR^{c62}R^{d62}$, $NR^{c62}C(=NR^{e62})R^{b62}$, $NR^{c62}S(O)NR^{c62}R^{d62}$, $NR^{c62}S(O)R^{b62}$, $NR^{c62}S(O)_2R^{b62}$, $NR^{c62}S(O)(=NR^{e62})R^{b62}$, $NR^{c62}S(O)_2NR^{c62}R^{d62}$, $S(O)R^{b62}$, $S(O)NR^{c62}R^{d62}$, $S(O)_2R^{b62}$, $S(O)_2NR^{c62}R^{d62}$, $OS(O)(=NR^{e62})R^{b62}$, $OS(O)_2R^{b62}$, $S(O)(=NR^{e62})R^{b62}$, $SF_5$, $P(O)R^{f62}R^{g62}$, $OP(O)(OR^{h62})(OR^{i62})$, $P(O)(OR^{h62})(OR^{i62})$, and $BR^{j62}R^{k62}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a62}$, $R^{c62}$, and $R^{d62}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c62}$ and $R^{d62}$ attached to the same N atom, together with the N atom to which they are attached, form a 4-7 membered heterocycloalkyl group, which is optionally substituted with 1, 2, 3, or 4 independently selected $R^G$ substituents;

each $R^{b62}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e62}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f62}$ and $R^{g62}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h62}$ and $R^{i62}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j62}$ and $R^{k62}$ is independently selected from OH, $C_{1-6}$ alkoxy, and $C_{1-6}$ haloalkoxy;

or any $R^{j62}$ and $R^{k62}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)NR^{c7}R^{d7}$, $NR^{c7}S(O)R^{b7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $OS(O)(=NR^{e7})R^{b7}$, $S(O)_2R^{b7}$, $S(O)_2NR^{c7}R^{d7}$, $OS(O)_2R^{b7}$, $S(O)(=NR^{e7})R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7A}$ substituents;

or, any $R^{c7}$ and $R^{d7}$ attached to the same N atom, together with the N atom to which they are attached, form a 4-10 membered heterocycloalkyl group, which is optionally substituted with 1, 2, 3, or 4 independently selected $R^{7A}$ substituents;

each $R^{b7}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{7A}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f7}$ and $R^{g7}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j7}$ and $R^{k7}$ is independently selected from OH, $C_{1-6}$ alkoxy, and $C_{1-6}$ haloalkoxy;

or any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a71}$, $SR^{a71}$, $NHOR^{a71}$, $C(O)R^{b71}$, $C(O)NR^{c71}R^{d71}$, $C(O)NR^{c71}(OR^{a71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a71}$, $NR^{c71}C(O)NR^{c71}R^{d71}$, $C(=NR^{e71})R^{b71}$, $C(=NR^{e71})NR^{c71}R^{d71}$, $NR^{c71}C(=NR^{e71})NR^{c71}R^{d71}$, $NR^{c71}C(=NR^{e71})R^{b71}$, $NR^{c71}S(O)NR^{c71}R^{d71}$, $NR^{c71}S(O)R^{b71}$, $NR^{c71}S(O)_2R^{b71}$, $NR^{c71}S(O)(=NR^{e71})R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)(=NR^{e71})R^{b71}$, $OS(O)_2R^{b71}$, $S(O)(=NR^{e71})R^{b71}$, $SF_5$, $P(O)R^{f71}R^{g71}$, $OP(O)(OR^{h71})(OR^{i71})$, $P(O)(OR^{h71})(OR^{i71})$, and $BR^{j71}R^{k71}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7B}$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7B}$ substituents;

or, any $R^{c71}$ and $R^{d71}$ attached to the same N atom, together with the N atom to which they are attached, form a 4-7 membered heterocycloalkyl group, which is optionally substituted with 1, 2, 3, or 4 independently selected $R^{7B}$ substituents;

each $R^{b71}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{7B}$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f71}$ and $R^{g71}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h71}$ and $R^{i71}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j71}$ and $R^{k71}$ is independently selected from OH, $C_{1-6}$ alkoxy, and $C_{1-6}$ haloalkoxy;

or any $R^{j71}$ and $R^{k71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a72}$, $SR^{a72}$, $NHOR^{a72}$, $C(O)R^{b72}$, $C(O)NR^{c72}R^{d72}$, $C(O)NR^{c72}(OR^{a72})$, $C(O)OR^{a72}$, $OC(O)R^{b72}$, $OC(O)NR^{c72}R^{d72}$, $NR^{c72}R^{d72}$, $NR^{c72}NR^{c72}R^{d72}$, $NR^{c72}C(O)R^{b72}$, $NR^{c72}C(O)OR^{a72}$, $NR^{c72}C(O)NR^{c72}R^{d72}$, $C(=NR^{e72})R^{b72}$, $C(=NR^{e72})NR^{c72}R^{d72}$, $NR^{c72}C(=NR^{e72})NR^{c72}R^{d72}$, $NR^{c72}C(=NR^{e72})R^{b72}$, $NR^{c72}S(O)NR^{c72}R^{d72}$, $NR^{c72}S(O)R^{b72}$, $NR^{c72}S(O)_2R^{b72}$, $NR^{c72}S(O)(=NR^{e72})R^{b72}$, $NR^{c72}S(O)_2NR^{c72}R^{d72}$, $S(O)R^{b72}$, $S(O)NR^{c72}R^{d72}$, $S(O)_2R^{b72}$, $S(O)_2NR^{c72}R^{d72}$, $OS(O)(=NR^{e72})R^{b72}$, $OS(O)_2R^{b72}$, $S(O)(=NR^{e72})R^{b72}$, $SF_5$, $P(O)R^{f72}R^{g72}$, $OP(O)(OR^{h72})(OR^{i72})$, $P(O)(OR^{h72})(OR^{i12})$, and $BR^{j72}R^{k72}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents;

each $R^{a72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c72}$ and $R^{d72}$ attached to the same N atom, together with the N atom to which they are attached, form a 4-7 membered heterocycloalkyl group, which is optionally substituted with 1, 2, 3, or 4 independently selected $R^G$ substituents;

each $R^{b72}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e72}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f72}$ and $R^{g72}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h72}$ and $R^{i72}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j72}$ and $R^{k72}$ is independently selected from OH, $C_{1-6}$ alkoxy, and $C_{1-6}$ haloalkoxy;

or any $R^{j72}$ and $R^{k72}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^G$ is independently selected from D, OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, W is $CR^2$.

In some embodiments, $R^2$ is selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, and $OS(O)_2R^{b2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{2A}$ substituents; and each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents.

In some embodiments, $R^2$ is selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$ $S(O)NR^{c2}R^{d2}$, $S(O)_2R^{b2}$, $S(O)_2NR^{b2}R^{d2}$, and $OS(O)_2R^{b2}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{2A}$ substituents; and each $R^{b2}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2A}$ substituents.

In some embodiments, $R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl, 4-6 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, and 5-6 membered heteroaryl are each optionally substituted with 1, 2, 3, or 4 independently selected $R^{2A}$ substituents.

In some embodiments, $R^2$ is Br, Cl, CN, $CH_3$, ethyl, isopropyl, vinyl, ethynyl, $CF_3$, $OCHF_2$, cyclopropyl, phenyl, or pyrazolyl, wherein said $CH_3$, ethyl, isopropyl, vinyl, ethynyl, cyclopropyl, phenyl, or pyrazolyl are each optionally substituted with 1, 2, 3, or 4 independently selected $R^{2A}$ substitutents.

In some embodiments, each $R^{2A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b21}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

In some embodiments, each $R^{2A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$;

each $R^{a21}$, $R^{c21}$, and $R^{d21}$ is independently selected from H, $C_{1-6}$ alkyl, and $C_{1-6}$ haloalkyl; and each $R^{b21}$ is independently selected from $C_{1-6}$ alkyl and $C_{1-6}$ haloalkyl.

In some embodiments, each $R^{2A}$ is independently selected from $CH_3$ and $OCH_3$.

In some embodiments, $R^2$ is Br, Cl, CN, $CH_3$, ethyl, isopropyl, vinyl, ethynyl, $CF_3$, $OCHF_2$, cyclopropyl, phenyl, or pyrazolyl, wherein said $CH_3$, ethyl, isopropyl, vinyl, ethynyl, cyclopropyl, phenyl, or pyrazolyl are each optionally substituted with 1, 2, 3, or 4 independently selected $R^{2A}$ substitutents;

wherein each $R^{2A}$ is independently selected from $C_{1-6}$ alkyl and $C_{1-6}$ alkoxy.

In some embodiments, $R^2$ is Br, Cl, CN, $CH_3$, ethyl, isopropyl, vinyl, ethynyl, $CF_3$, $OCHF_2$, cyclopropyl, phenyl, or pyrazolyl, wherein said $CH_3$, ethyl, isopropyl, vinyl, ethynyl, cyclopropyl, phenyl, or pyrazolyl are each optionally substituted with 1 or 2 independently selected $R^{2A}$ substituents;

wherein $R^{2A}$ is independently selected from $C_{1-6}$ alkyl and $C_{1-6}$ alkoxy.

In some embodiments, $R^2$ is Br, Cl, CN, $CH_3$, ethyl, isopropyl, vinyl, ethynyl, $CF_3$, $OCHF_2$, cyclopropyl, phenyl, or pyrazolyl, wherein said $CH_3$, ethyl, isopropyl, vinyl, ethynyl, cyclopropyl, phenyl, or pyrazolyl are each optionally substituted with 1, 2, 3, or 4 independently selected $R^{2A}$ substituents;

wherein $R^{2A}$ is independently selected from $CH_3$ and $OCH_3$.

In some embodiments, $R^2$ is Br, Cl, CN, $CH_3$, ethyl, isopropyl, vinyl, ethynyl, $CF_3$, $OCHF_2$, cyclopropyl, phenyl, or pyrazolyl, wherein said $CH_3$, ethyl, isopropyl, vinyl, ethynyl, cyclopropyl, phenyl, or pyrazolyl are each optionally substituted with 1 or 2 independently selected $R^{2A}$ substituents;

wherein $R^{2A}$ is independently selected from $CH_3$ and $OCH_3$.

In some embodiments, Y is N.

In some embodiments, Y is $CR^4$.

In some embodiments, $R^4$ is H, D, halo, CN, or $C_{1-6}$ alkyl.

In some embodiments, $R^4$ is H.

In some embodiments, W is absent.

In some embodiments, Y is S.

In some embodiments, Y is O.

In some embodiments, Y is $NR^{4y}$.

In some embodiments, $R^{4y}$ is H, $C_{1-4}$ alkyl, or $C_{1-4}$ haloalkyl.

In some embodiments, $R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, 4-10 membered heterocycloalkyl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R$, $S(O)_2NR^{c1}R^{d1}$, and $OS(O)_2Rb$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, are each optionally substituted with 1, 2, 3, or 4 independently selected $R^{1A}$ substituents;

or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{1A}$ substituents; and each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, which are each optionally substituted with 1, 2, 3, or 4 independently selected $R^{1A}$ substituents.

In some embodiments, $R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $C_{3-7}$ cycloalkyl-$C_{1-4}$ alkyl, 4-7 membered heterocycloalkyl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, and $OS(O)_2R^{b1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $C_{3-7}$ cycloalkyl-$C_{1-4}$ alkyl, and 4-7 membered heterocycloalkyl-$C_{1-4}$ alkyl, are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, $C_{3-7}$ cycloalkyl-$C_{1-4}$ alkyl, and 4-7 membered heterocycloalkyl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $C_{3-7}$ cycloalkyl-$C_{1-4}$ alkyl, and 4-7 membered heterocycloalkyl-$C_{1-4}$ alkyl, are each optionally substituted with 1, 2, 3, or 4 independently selected $R^{1A}$ substituents;

or, any $R^{c1}$ and $R^{d1}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1A}$ substituents; and each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, $C_{3-7}$ cycloalkyl-$C_{1-4}$ alkyl, and 4-7 membered heterocycloalkyl-$C_{1-4}$ alkyl, which are each optionally substituted with 1, 2, 3, or 4 independently selected $R^{1A}$ substituents.

In some embodiments, $R^1$ is selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $OR^{a1}$, and $NR^{c1}R^{d1}$, wherein said $C_{1-6}$ alkyl, $C_{2-6}$ alkenyl, $C_{2-6}$ alkynyl, $C_{1-6}$ haloalkyl, $C_{3-7}$cycloalkyl, and 4-7 membered heterocycloalkyl are each optionally substituted with 1, 2, 3, or 4 independently selected $R^{1A}$ substituents; and each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{1A}$ substituents.

In some embodiments, $R^1$ is selected from H, D, halo, CN, $C_{1-6}$ alkyl, $C_{1-6}$ haloalkyl, 4-7 membered heterocycloalkyl, $OR^{a1}$, and $NR^{c1}R^{d1}$, wherein said $C_{1-6}$ alkyl, $C_{1-6}$ haloalkyl, and 4-7 membered heterocycloalkyl are each optionally substituted with 1, 2, 3, or 4 independently selected $R^{1A}$ substituents; and each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{1A}$ substituents.

In some embodiments, each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2$ $R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents; and each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1C}$ substituents; and each $R^{1C}$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2$ $R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$;

each $R^{a12}$, $R^{c12}$, and $R^{d12}$ is independently selected from H, $C_{1-6}$ alkyl, $C_{1-6}$ haloalkyl, $C_{2-6}$ alkenyl, and $C_{2-6}$ alkynyl; and each $R^{b12}$ is independently selected from $C_{1-6}$ alkyl, $C_{1-6}$ haloalkyl, $C_{2-6}$ alkenyl, and $C_{2-6}$ alkynyl.

In some embodiments, each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)N^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2 R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{b11}$, and $R^{d11}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $C_{1-6}$ alkyl, $C_{2-6}$ alkenyl, $C_{2-6}$ alkynyl, $C_{1-6}$ haloalkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$;

each $R^{a12}$, $R^{c12}$, and $R^{d12}$ is independently selected from H, $C_{1-6}$ alkyl, $C_{1-6}$ haloalkyl, $C_{2-6}$ alkenyl, and $C_{2-6}$ alkynyl; and each $R^{b12}$ is independently selected from $C_{1-6}$ alkyl, $C_{1-6}$ haloalkyl, $C_{2-6}$ alkenyl, and $C_{2-6}$ alkynyl.

In some embodiments, each $R^{1A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2 NR^{c11}R^{d11}$;

each $R^{a11}$, $R^{c11}$, and $R^{d11}$ is independently selected from H, $C_{1-6}$ alkyl, and $C_{1-6}$ haloalkyl; and each $R^{b11}$ is independently selected from $C_{1-6}$ alkyl and $C_{1-6}$ haloalkyl.

In some embodiments, each $R^{1A}$ is independently selected from D, halo, CN, $C_{1-6}$ alkyl, $C_{2-6}$ alkenyl, $C_{2-6}$ alkynyl, $C_{1-6}$ haloalkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)_2R^{b11}$, and $S(O)_2NR^{c11}R^{d11}$;

each $R^{a11}$, $R^{c11}$, and $R^{d11}$ is independently selected from H, $C_{1-6}$ alkyl, and $C_{1-6}$ haloalkyl; and each $R^{b11}$ is independently selected from $C_{1-6}$ alkyl and $C_{1-6}$ haloalkyl.

In some embodiments, $R^1$ is selected from H, D, halo, CN, $C_{1-6}$ alkyl, $C_{1-6}$ haloalkyl, 4-7 membered heterocycloalkyl, $OR^{a1}$, and $NR^{c1}R^{d1}$, wherein said $C_{1-6}$ alkyl, $C_{1-6}$ haloalkyl, and 4-7 membered heterocycloalkyl are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{1A}$ substituents;

each $R^{1A}$ is independently selected from D, halo, CN, $C_{1-6}$ alkyl, $C_{2-6}$ alkenyl, $C_{2-6}$ alkynyl, $C_{1-6}$ haloalkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$;

each $R^{a11}$, $R^{c11}$, and $R^{d11}$ is independently selected from H, $C_{1-6}$ alkyl, and $C_{1-6}$ haloalkyl; and each $R^{b11}$ is independently selected from $C_{1-6}$ alkyl and $C_{1-6}$ haloalkyl.

In some embodiments, $R^1$ is selected from H, D, halo, CN, $C_{1-6}$ alkyl, $C_{1-6}$ haloalkyl, 4-7 membered heterocycloalkyl, $OR^{a1}$, and $NR^{c1}R^{d1}$, wherein said $C_{1-6}$ alkyl, $C_{1-6}$ haloalkyl, and 4-7 membered heterocycloalkyl are each optionally substituted with 1 or 2 independently selected $R^{1A}$ substituents;

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{1A}$ substituents;

each $R^{1A}$ is independently selected from D, halo, $C_{1-6}$ alkyl, $C_{2-6}$ alkenyl, $C_{2-6}$ alkynyl, $C_{1-6}$ haloalkyl, $OR^{a11}$, $NR^{c11}R^{d11}$; and each $R^{a11}$, $R^{c11}$, and $R^{d11}$ is independently selected from H, $C_{1-6}$ alkyl, and $C_{1-6}$ haloalkyl.

In some embodiments, $R^1$ is H, Cl, CN, $CH_3$, $CF_3$, $OCH_3$, $NHCH_3$, $N(CH_3)_2$, $NHCH_2C(CH_3)_2OH$, morpholin-4-yl, or pyrrolidinyl substituted with $N(CH_3)_2$.

In some embodiments, $R^1$ is H, CN, $CH_3$, $CF_3$, $OCH_3$, $NHCH_3$, $N(CH_3)_2$, $NHCH_2C(CH_3)_2OH$, morpholin-4-yl, or pyrrolidinyl substituted with $N(CH_3)_2$.

In some embodiments, the "heterocycloalkyl" in the definitions of $R^1$, $R^{a1}$, $R^{b1}$, $R^{c1}$, and $R^{d1}$ refers to a heterocycloalkyl ring system in which each ring in the ring stem is fully saturated or partially unsaturated.

In some embodiments, $R^3$ is H or $CH_3$.

In some embodiments, $R^3$ is H.

In some embodiments, $R^3$ is $CH_3$.

In some embodiments, X is N.

In some embodiments, X is CH.

In some embodiments, n is 0 or 1.

In some embodiments, n is 0.

In some embodiments, n is 1.

In some embodiments, p is 0, 1, or 2.

In some embodiments, p is 0.

In some embodiments, p is 1.

In some embodiments, p is 2.

In some embodiments, each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a7}$, $SR^{a7}$, $NHOR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, and $OS(O)_2R^{b7}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7A}$ substituents;

or, any $R^{c7}$ and $R^{d7}$ attached to the same N atom, together with the N atom to which they are attached, form a 4-7 membered heterocycloalkyl group, which is optionally substituted with 1, 2, 3, or 4 independently selected $R^{7A}$ substituents; and each $R^{b7}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{7A}$ substituents.

In some embodiments, each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $OR^{a7}$, $SR^{a7}$, $NHOR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{d7}$, $NR^{c7}C(O)$ $NR^{c7}R^{d7}$, $NR^{c7}S(O)NR^{c7}R^{d7}$, $NR^{c7}S(O)R^{b7}$, $NR^{c7}S(O)_2$ $R^{b7}$, $NR^{c7}S(O)_2NR^{c7}R^{d7}$, $S(O)R^{b7}$, $S(O)NR^{c7}R^{d7}$, $S(O)_2$ $R^{b7}$, $S(O)_2NR^{c7}R^{d7}$, and $OS(O)_2R^{b7}$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl, are each optionally substituted with 1, 2, 3, or 4 independently selected $R^{7A}$ substituents; and each $R^{b7}$ is independently selected from $C_{1-6}$ alkyl, $C_{1-6}$ haloalkyl, $C_{2-6}$ alkenyl, and $C_{2-6}$ alkynyl, which are each optionally substituted with 1, 2, 3, or 4 independently selected $R^{7A}$ substituents.

In some embodiments, each $R^{7A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a71}$, $SR^{a71}$, $NHOR^{a71}$, $C(O)R^{b71}$, $C(O)NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)R^{b71}$, $NR^{c71}C(O)OR^{a71}$, $NR^{c71}C(O)NR^{c71}R^{d71}$, $NR^{c71}S(O)NR^{c71}R^{d71}$, $NR^{c71}S(O)R^{b71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2$ $R^{b71}$, and $S(O)_2NR^{c71}R^{d71}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{b71}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{7B}$ substituents;

each $R^{7B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a72}$, $SR^{a72}$, $NHOR^{a72}$, $C(O)R^{b72}$, $C(O)$ $NR^{c72}R^{d72}$, $C(O)OR^{a72}$, $OC(O)R^{b72}$, $OC(O)$ $NR^{c72}R^{d72}$, $NR^{c72}R^{d72}$, $NR^{c72}C(O)R^{b72}$, $NR^{c72}C(O)$ $OR^{a72}$, $NR^{c72}C(O)NR^{c72}R^{d72}$, $NR^{c72}S(O)NR^{c72}R^{d72}$, $NR^{c72}S(O)R^{b72}$, $NR^{c72}S(O)_2R^{b72}$, $NR^{c72}S(O)_2$ $NR^{c72}R^{d72}$, $S(O)R^{b72}$, $S(O)NR^{c72}R^{d72}$, $S(O)_2R^{b72}$, and $S(O)_2NR^{c72}R^{d72}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b72}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

In some embodiments, each $R^{7A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a71}$, $SR^{a71}$, $NHOR^{a71}$, $C(O)R^{b71}$, $C(O)NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)R^{b71}$, $NR^{c71}C(O)OR^{a71}$, $NR^{c71}C(O)NR^{c71}R^{d71}$, $NR^{c71}S(O)NR^{c71}R^{d71}$, $NR^{c71}S(O)R^{b71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2$ $R^{b71}$, and $S(O)_2NR^{c71}R^{d71}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{b71}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{b71}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{7B}$ substituents;

each $R^{7B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a72}$, $SR^{a72}$, $NHOR^{a72}$, $C(O)R^{b72}$, $C(O)$ $NR^{c72}R^{d72}$, $C(O)OR^{a72}$, $OC(O)R^{b72}$, $OC(O)$ $NR^{c72}R^{d72}$, $NR^{c72}R^{d72}$, $NR^{c72}C(O)R^{b72}$, $NR^{c72}C(O)$ $OR^{a72}$, $NR^{c72}C(O)NR^{c72}R^{d72}$, $NR^{c72}S(O)NR^{c72}R^{d72}$, $NR^{c72}S(O)R^{b72}$, $NR^{c72}S(O)_2R^{b72}$, $NR^{c72}S(O)_2$ $NR^{c72}R^{d72}$, $S(O)R^{b72}$, $S(O)NR^{c72}R^{d72}$, $S(O)_2R^{b72}$, and $S(O)_2NR^{c72}R^{d72}$;

each $R^{a72}$, $R^{c72}$, and $R^{d72}$ is independently selected from H, $C_{1-6}$ alkyl, $C_{1-6}$ haloalkyl, $C_{2-6}$ alkenyl, and $C_{2-6}$ alkynyl; and each $R^{b72}$ is independently selected from $C_{1-6}$ alkyl, $C_{1-6}$ haloalkyl, $C_{2-6}$ alkenyl, and $C_{2-6}$ alkynyl.

In some embodiments, each $R^{7A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a71}$, $SR^{a71}$, $NHOR^{a71}$, $C(O)R^{b71}$, $C(O)NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)R^{b71}$, $NR^{c71}C(O)OR^{a71}$, $NR^{c71}C(O)NR^{c71}R^{d71}$, $NR^{c71}S(O)NR^{c71}R^{d71}$, $NR^{c71}S(O)R^{b71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2$ $R^{b71}$, and $S(O)_2NR^{c71}R^{d71}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{b71}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{7B}$ substituents;

each $R^{7B}$ is independently selected from D, halo, CN, $C_{1-6}$ alkyl, $C_{2-6}$ alkenyl, $C_{2-6}$ alkynyl, $C_{1-6}$ haloalkyl, $OR^{a72}$, $SR^{a72}$, $NHOR^{a72}$, $C(O)R^{b72}$, $C(O)NR^{c72}R^{d72}$, $C(O)$ $OR^{a72}$, $OC(O)R^{b72}$, $OC(O)NR^{c72}R^{d72}$, $NR^{c72}R^{d72}$, $NR^{c72}C(O)R^{b72}$, $NR^{c72}C(O)OR^{a72}$, $NR^{c72}C(O)$ $NR^{c72}R^{d72}$, $NR^{c72}S(O)NR^{c72}R^{d72}$, $NR^{c72}S(O)R^{b72}$, $NR^{c72}S(O)_2R^{b72}$, $NR^{c72}S(O)_2NR^{c72}R^{d72}$, $S(O)R^{b72}$, $S(O)NR^{c72}R^{d72}$, $S(O)_2R^{b72}$, and $S(O)_2NR^{c72}R^{d72}$;

each $R^{a72}$, $R^{b72}$, and $R^{d72}$ is independently selected from H, $C_{1-6}$ alkyl, $C_{1-6}$ haloalkyl, $C_{2-6}$ alkenyl, and $C_{2-6}$ alkynyl; and each $R^{b72}$ is independently selected from $C_{1-6}$ alkyl, $C_{1-6}$ haloalkyl, $C_{2-6}$ alkenyl, and $C_{2-6}$ alkynyl.

In some embodiments, each $R^{7A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a71}$, $SR^{a71}$, $NHOR^{a71}$, $C(O)R^{b71}$, $C(O)NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)$ $R^{b71}$, $NR^{c71}C(O)OR^{a71}$, $NR^{c71}C(O)NR^{c71}R^{d71}$, $NR^{c71}S(O)$ $NR^{c71}R^{d71}$, $NR^{c71}S(O)R^{b71}$, $NR^{c71}S(O)_2R^{b71}$, $NR^{c71}S(O)_2$ $NR^{c71}R^{d71}$, $S(O)R^{b71}$, $S(O)NR^{c71}R^{d71}$, $S(O)_2R^{b71}$, and $S(O)_2$ $NR^{c71}R^{d71}$;

each $R^{a71}$, $R^{c71}$, and $R^{d71}$ is independently selected from H, $C_{1-6}$ alkyl, and $C_{1-6}$ haloalkyl; and each $R^{b71}$ is independently selected from $C_{1-6}$ alkyl and $C_{1-6}$ haloalkyl.

In some embodiments, each $R^{7A}$ is independently selected from D, halo, CN, $C_{1-6}$ alkyl, $C_{2-6}$ alkenyl, $C_{2-6}$ alkynyl, $C_{1-6}$ haloalkyl, $OR^{a71}$, $SR^{a71}$, $NHOR^{a71}$, $C(O)R^{b71}$, $C(O)$ $NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)R^{b71}$, $NR^{c71}C(O)OR^{a71}$, $NR^{c71}C(O)$ $NR^{c71}R^{d71}$, $NR^{c71}S(O)NR^{c71}R^{d71}$, $NR^{c71}S(O)R^{b71}$, $NR^{c71}S$ $(O)_2R^{b71}$, $NR^{c71}S(O)_2NR^{c71}R^{d71}$, $S(O)R^{b71}$, $S(O)$ $NR^{c71}R^{d71}$, $S(O)_2R^{b71}$, and $S(O)_2NR^{c71}R^{d71}$;

each $R^{a71}$, $R^{b71}$, and $R^{c71}$ is independently selected from H, $C_{1-6}$ alkyl, and $C_{1-6}$ haloalkyl; and each $R^{b71}$ is independently selected from $C_{1-6}$ alkyl and $C_{1-6}$ haloalkyl.

In some embodiments, each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $OR^{a7}$, $SR^{a7}$, $NHOR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)$ $NR^{c7}R^{d7}$, $NR^{c7}S(O)NR^{c7}R^{d7}$, $NR^{c7}S(O)R^{b7}$, $NR^{c7}S(O)_2$ $R^{b7}$, $NR^{c7}S(O)_2NR^{c7}R^{d7}$, $S(O)R^{b7}$, $S(O)NR^{c7}R^{d7}$, $S(O)_2$ $R^{b7}$, $S(O)_2NR^{c7}R^{d7}$, and $OS(O)_2R^{b7}$;

each $R^{a7}$, $R^{c7}$, and $R^{d7}$ is independently selected from H, $C_{1-6}$ alkyl, and $C_{1-6}$ haloalkyl, $C_{2-6}$ alkenyl, and $C_{2-6}$ alkynyl; and each $R^{b7}$ is independently selected from $C_{1-6}$ alkyl, $C_{1-6}$ haloalkyl, $C_{2-6}$ alkenyl, and $C_{2-6}$ alkynyl.

In some embodiments, each $R^7$ is independently selected from D, OH, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^7$ is independently selected from OH and halo.

In some embodiments, each $R^7$ is independently selected from OH and fluoro.

In some embodiments, each $R^7$ is OH.

In some embodiments, each $R^7$ is halo.

In some embodiments, each $R^7$ is fluoro.

In some embodiments, Ring B is phenyl, pyridine, pyrazine, pyridazine, pyrimidine, piperidine, piperazine, tetrahydropyrimidine, morpholine, thiomorpholine, tetrahydro-2H-pyran, 1,3-oxazinane, 1,3-dioxane, or 1,4-dioxane, each of which is optionally substituted 1, 2, or 3 independently selected $R^5$ substituents.

In some embodiments, Ring B is phenyl, pyridine, pyrazine, pyridazine, or pyrimidine, each of which is optionally substituted 1, 2, or 3 independently selected $R^5$ substituents.

In some embodiments, Ring B is phenyl, pyridine, or pyrazine, each of which is optionally substituted 1, 2, or 3 independently selected $R^5$ substituents.

In some embodiments, Ring C is pyrazole, pyrrole, imidazole, thiophene, isoxazole, oxazole, thiazole, isothiazole, triazolyl, or diazaoxaole, each of which is optionally substituted 1, 2, or 3 independently selected $R^6$ substituents.

In some embodiments, Ring C is pyrazole, triazole, or imidazole, each of which is optionally substituted 1 or 2 independently selected $R^6$ substituents.

In some embodiments, Ring B is phenyl, pyridine, pyrazine, pyridazine, pyrimidine, piperidine, piperazine, tetrahydropyrimidine, morpholine, thiomorpholine, tetrahydro-2H-pyran, 1,3-oxazinane, 1,3-dioxane, or 1,4-dioxane, each of which is optionally substituted 1, 2, or 3 independently selected $R^5$ substituents; and Ring C is pyrazole, pyrrole, imidazole, thiophene, isoxazole, oxazole, thiazole, isothiazole, triazolyl, or diazaoxaole, each of which is optionally substituted 1, 2, or 3 independently selected $R^6$ substituents.

In some embodiments, Ring B is phenyl, pyridine, pyrazine, pyridazine, pyrimidine, piperidine, piperazine, tetrahydropyrimidine, morpholine, thiomorpholine, tetrahydro-2H-pyran, 1,3-oxazinane, 1,3-dioxane, or 1,4-dioxane, each of which is optionally substituted 1, 2, or 3 independently selected $R^5$ substituents; and Ring C is pyrazole, triazole, or imidazole, each of which is optionally substituted 1 or 2 independently selected $R^6$ substituents.

In some embodiments, Ring B is phenyl, pyridine, pyrazine, pyridazine, or pyrimidine, each of which is optionally substituted 1, 2, or 3 independently selected $R^5$ substituents; and Ring C is pyrazole, pyrrole, imidazole, thiophene, isoxazole, oxazole, thiazole, isothiazole, triazolyl, or diazaoxaole, each of which is optionally substituted 1, 2, or 3 independently selected R substituents.

In some embodiments, Ring B is phenyl, pyridine, pyrazine, pyridazine, or pyrimidine, each of which is optionally substituted 1, 2, or 3 independently selected $R^5$ substituents; and Ring C is pyrazole, triazole, or imidazole, each of which is optionally substituted 1 or 2 independently selected $R^6$ substituents.

In some embodiments, Ring B is phenyl, pyridine, or pyrazine, each of which is optionally substituted 1, 2, or 3 independently selected $R^5$ substituents; and Ring C is pyrazole, pyrrole, imidazole, thiophene, isoxazole, oxazole, thiazole, isothiazole, triazolyl, or diazaoxaole, each of which is optionally substituted 1, 2, or 3 independently selected $R^6$ substituents.

In some embodiments, Ring B is phenyl, pyridine, or pyrazine, each of which is optionally substituted 1, 2, or 3 independently selected $R^5$ substituents; and Ring C is pyrazole, triazole, or imidazole, each of which is optionally substituted 1 or 2 independently selected $R^6$ substituents.

In some embodiments, Ring B is pyrrolidine, tetrahydrofuran, oxazolidine, isoxazolidine, imidazolidine, pyrazole, pyrrole, imidazole, thiophene, isoxazole, oxazole, thiazole, isothiazole, triazolyl, or diazaoxaole, each of which is optionally substituted 1, 2, or 3 independently selected $R^5$ substituents.

In some embodiments, Ring B is pyrrolidine, pyrazole, pyrrole, imidazole, thiophene, isoxazole, oxazole, thiazole, or triazolyl, each of which is optionally substituted 1, 2, or 3 independently selected $R^5$ substituents.

In some embodiments, Ring C is phenyl, pyridine, pyrazine, or pyridazine, pyrimidine, each of which is optionally substituted 1, 2, or 3 independently selected $R^6$ substituents.

In some embodiments, Ring C is phenyl, pyridine, or pyrazine, each of which is optionally substituted 1 or 2 independently selected $R^6$ substituents.

In some embodiments, Ring C is phenyl or pyridine, each of which is optionally substituted 1 or 2 independently selected $R^6$ substituents.

In some embodiments, Ring B is pyrrolidine, tetrahydrofuran, oxazolidine, isoxazolidine, imidazolidine, pyrazole, pyrrole, imidazole, thiophene, isoxazole, oxazole, thiazole, isothiazole, triazolyl, or diazaoxaole, each of which is optionally substituted 1, 2, or 3 independently selected $R^5$ substituents; and Ring C is phenyl, pyridine, or pyrazine, each of which is optionally substituted 1 or 2 independently selected $R^6$ substituents.

In some embodiments, Ring B is pyrrolidine, tetrahydrofuran, oxazolidine, isoxazolidine, imidazolidine, pyrazole, pyrrole, imidazole, thiophene, isoxazole, oxazole, thiazole, isothiazolyl, triazolyl, or diazaoxaole, each of which is optionally substituted 1, 2, or 3 independently selected $R^5$ substituents; and Ring C is phenyl or pyridine, each of which is optionally substituted 1 or 2 independently selected $R^6$ substituents.

In some embodiments, Ring B is pyrrolidine, tetrahydrofuran, oxazolidine, isoxazolidine, imidazolidine, pyrazole, pyrrole, imidazole, thiophene, isoxazole, oxazole, thiazole, isothiazole, triazolyl, or diazaoxaole, each of which is optionally substituted 1, 2, or 3 independently selected $R^5$ substituents; and Ring C is phenyl, pyridine, pyrazine, or pyridazine, pyrimidine, each of which is optionally substituted 1, 2, or 3 independently selected $R^6$ substituents.

In some embodiments, Ring B is pyrrolidine, pyrazole, pyrrole, imidazole, thiophene, isoxazole, oxazole, thiazole, or triazolyl, each of which is optionally substituted 1, 2, or 3 independently selected $R^5$ substituents; and Ring C is phenyl, pyridine, or pyrazine, each of which is optionally substituted 1 or 2 independently selected $R^6$ substituents.

In some embodiments, Ring B is pyrrolidine, pyrazole, pyrrole, imidazole, thiophene, isoxazole, oxazole, thiazole, or triazolyl, each of which is optionally substituted 1, 2, or 3 independently selected $R^5$ substituents; and Ring C is phenyl or pyridine, each of which is optionally substituted 1 or 2 independently selected $R^6$ substituents.

In some embodiments, Ring B is pyrrolidine, pyrazole, pyrrole, imidazole, thiophene, isoxazole, oxazole, thiazole, or triazolyl, each of which is optionally substituted 1, 2, or 3 independently selected $R^5$ substituents; and Ring C is phenyl, pyridine, pyrazine, or pyridazine, pyrimidine, each of which is optionally substituted 1, 2, or 3 independently selected $R^6$ substituents.

In some embodiments, Ring B is imidazole, which is optionally substituted 1, 2, 3, or 4 independently selected $R^5$ substituents.

In some embodiments, Ring B is cyclopentyl, which is optionally substituted 1, 2, 3, or 4 independently selected $R^5$ substituents.

In some embodiments, Ring C is pyridine, pyrazine, pyridazine, or pyrimidine, each of which is optionally substituted 1, 2, or 3 independently selected $R^6$ substituents.

In some embodiments, Ring C is pyrazine, each of which is optionally substituted 1, 2, or 3 independently selected $R^6$ substituents.

In some embodiments, Ring C is pyridine, each of which is optionally substituted 1, 2, or 3 independently selected $R^6$ substituents.

In some embodiments, Ring B is cyclopentyl, which is optionally substituted 1, 2, 3, or 4 independently selected $R^5$ substituents; and Ring C is pyridine, pyrazine, pyridazine, or pyrimidine, each of which is optionally substituted 1, 2, or 3 independently selected $R^6$ substituents.

In some embodiments, Ring B is cyclopentyl, which is optionally substituted 1, 2, 3, or 4 independently selected $R^5$ substituents; and Ring C is pyridine, each of which is optionally substituted 1, 2, or 3 independently selected $R^6$ substituents.

In some embodiments, the moiety is selected from:

73

-continued

74

-continued wherein Ring B is optionally substituted with 1 or 2 independently selected $R^5$ substituents; and wherein Ring C is optionally substituted with 1 or 2 independently selected $R^6$ substituents.

In some embodiments, the moiety is selected from:

wherein Ring B is optionally substituted with 1 or 2 independently selected $R^5$ substituents; and wherein Ring C is optionally substituted with 1 or 2 independently selected $R^6$ substituents.

In some embodiments, each $R^5$ is independently selected from oxo, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $OS(O)_2R^{b5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents; and each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents.

In some embodiments, each $R^5$ is independently selected from oxo, D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $OS(O)_2R^{b5}$; wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents; or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents; and each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5A}$ substituents.

In some embodiments, each $R^5$ is independently selected from oxo, D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $OS(O)_2R^{b5}$; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{5A}$ substituents; and each $R^{b5}$ is independently selected from $C_{1-6}$ alkyl, $C_{1-6}$ haloalkyl, $C_{2-6}$ alkenyl, $C_{2-6}$ alkynyl, and $C_{3-4}$ cycloalkyl, which are each optionally substituted with 1, 2, 3, or 4 independently selected $R^{5A}$ substituents.

In some embodiments, each $R^5$ is independently selected from oxo, D, halo, CN, $C_{1-6}$ alkyl, $C_{2-6}$ alkenyl, $C_{2-6}$ alkynyl, $C_{1-6}$ haloalkyl, $OR^{a5}$, and $NR^{c5}R^{d5}$; wherein said $C_{1-6}$ alkyl, $C_{2-6}$ alkenyl, $C_{2-6}$ alkynyl, and $C_{1-6}$ haloalkyl are each optionally substituted by 1 or 2 independently selected $R^{5A}$ substituents; and each $R^{a5}$, $R^{c5}$, and $R^{d5}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^A$ substituents.

In some embodiments, each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ substituents;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)NR^{c52}R^{d52}$, $NR^{c52}S(O)R^{b52}$, $NR^{c52}S(O)_2R^{b52}$, $NR^{c52}S(O)_2$ $NR^{c52}R^{d52}$, $S(O)R^{b52}$, $S(O)NR^{c52}R^{d52}$, $S(O)_2R^{b52}$, and $S(O)_2NR^{c52}R^{d52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

In some embodiments, each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2$ $R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ substituents;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)NR^{c52}R^{d52}$, $NR^{c52}S(O)R^{b52}$, $NR^{c52}S(O)_2R^{b52}$, $NR^{c52}S(O)_2$ $NR^{c52}R^{d52}$, $S(O)R^{b52}$, $S(O)NR^{c52}R^{d52}$, $S(O)_2R^{b52}$, and $S(O)_2NR^{c52}R^{d52}$;

each $R^{a52}$, $R^{c52}$, and $R^{d52}$ is independently selected from H, $C_{1-6}$ alkyl, $C_{1-6}$ haloalkyl, $C_{2-6}$ alkenyl, and $C_{2-6}$ alkynyl; and each $R^{b52}$ is independently selected from $C_{1-6}$ alkyl, $C_{1-6}$ haloalkyl, $C_{2-6}$ alkenyl, and $C_{2-6}$ alkynyl.

In some embodiments, each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2$ $R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ substituents;

each $R^{5B}$ is independently selected from D, halo, CN, $C_{1-6}$ alkyl, $C_{2-6}$ alkenyl, $C_{2-6}$ alkynyl, $C_{1-6}$ haloalkyl, $OR^{a52}$, $SR^{a52}$, $NHOR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)$ $NR^{c52}R^{d52}$, $NR^{c52}S(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, and $S(O)_2NR^{c52}R^{d52}$;

each $R^{a52}$, $R^{c52}$, and $R^{d52}$ is independently selected from H, $C_{1-6}$ alkyl, $C_{1-6}$ haloalkyl, $C_{2-6}$ alkenyl, and $C_{2-6}$ alkynyl; and each $R^{b52}$ is independently selected from $C_{1-6}$ alkyl, $C_{1-6}$ haloalkyl, $C_{2-6}$ alkenyl, and $C_{2-6}$ alkynyl.

In some embodiments, each $R^{5A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$ $SR^{a51}$ $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl; and each $R^{b51}$ is independently selected from $C_{1-6}$ alkyl and $C_{1-6}$ haloalkyl.

In some embodiments, each $R^{5A}$ is independently selected from D, halo, CN, $C_{1-6}$ alkyl, $C_{2-6}$ alkenyl, $C_{2-6}$ alkynyl, $C_{1-6}$ haloalkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl; and each $R^{b51}$ is independently selected from $C_{1-6}$ alkyl and $C_{1-6}$ haloalkyl.

In some embodiments, each $R^5$ is independently selected from oxo, D, halo, CN, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl, and $C_{1-6}$ haloalkyl are each optionally substituted by 1 or 2 independently selected $R^{5A}$ substituents;

each $R^{5A}$ is independently selected from D, halo, CN, $C_{1-6}$ alkyl, $C_{2-6}$ alkenyl, $C_{2-6}$ alkynyl, $C_{1-6}$ haloalkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl; and each $R^{b51}$ is independently selected from $C_{1-6}$ alkyl and $C_{1-6}$ haloalkyl.

In some embodiments, each $R^5$ is independently selected from oxo, D, halo, CN, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl, and $C_{1-6}$ haloalkyl are each optionally substituted by 1 or 2 independently selected $R^{5A}$ substituents;

each $R^{5A}$ is independently selected from D, halo, CN, $C_{1-3}$ alkyl, $C_{1-3}$ haloalkyl, and $OR^{a51}$; and each $R^{a51}$ is independently selected from H and $C_{1-3}$ alkyl.

In some embodiments, each $R^5$ is independently selected from oxo, D, halo, CN, $C_{1-6}$ alkyl, $C_{2-6}$ alkenyl, $C_{2-6}$ alkynyl, and $C_{1-6}$ haloalkyl, wherein each $C_{1-6}$ alkyl is optionally substituted by OH.

In some embodiments, each $R^5$ is independently selected from oxo, $C_{1-6}$ alkyl, and $C_{1-6}$ haloalkyl, wherein each $C_{1-6}$ alkyl is optionally substituted by OH.

In some embodiments, each $R^5$ is independently selected from oxo, $C_{1-3}$ alkyl, and $C_{1-3}$ haloalkyl, wherein each $C_{1-3}$ alkyl is optionally substituted by OH.

In some embodiments, each $R^5$ is independently selected from oxo, $CH_3$, $CH_2CH_2OH$, and $CHF_2$.

In some embodiments, each $R^6$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a6}$, $SR^{a6}$, $NHOR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6A}$ substituents;

or, any $R^{c6}$ and $R^{d6}$ attached to the same N atom, together with the N atom to which they are attached, form a 4-10 membered heterocycloalkyl group, which is optionally substituted with 1, 2, 3, or 4 independently selected $R^{6A}$ substituents; and each $R^{b6}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{6A}$ substituents.

In some embodiments, each $R^6$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a6}$, $SR^{a6}$, $NHOR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)$ R$^{b6}$, S(O)NR$^{c6}$R$^{d6}$, S(O)$_2$R$^{b6}$, S(O)$_2$NR$^{c6}$R$^{d6}$, and OS(O)$_2$
R$^{b6}$; wherein said C$_{1-6}$ alkyl, C$_{2-6}$ alkenyl, C$_{2-6}$ alkynyl, C$_{1-6}$
haloalkyl, C$_{3-7}$ cycloalkyl, phenyl, 4-7 membered heterocy-
cloalkyl, 5-6 membered heteroaryl, C$_{3-7}$ cycloalkyl-C$_{1-4}$
alkyl, phenyl-C$_{1-4}$ alkyl, 4-7 membered heterocycloalkyl-
C$_{1-4}$ alkyl, and 5-6 membered heteroaryl-C$_{1-4}$ alkyl are each
optionally substituted by 1, 2, 3, or 4 independently selected
R$^{6A}$ substituents;

each R$^{a6}$, R$^{c6}$, and R$^{d6}$ is independently selected from H,
C$_{1-6}$ alkyl, C$_{1-6}$ haloalkyl, C$_{2-6}$ alkenyl, C$_{2-6}$ alkynyl,
C$_{3-7}$ cycloalkyl, phenyl, 4-7 membered heterocycloal-
kyl, 5-6 membered heteroaryl, C$_{3-7}$ cycloalkyl-C$_{1-4}$
alkyl, phenyl-C$_{1-4}$ alkyl, 4-7 membered heterocycloal-
kyl-C$_{1-4}$ alkyl, and 5-6 membered heteroaryl-C$_{1-4}$
alkyl, wherein said C$_{1-6}$ alkyl, C$_{2-6}$ alkenyl, C$_{2-6}$ alky-
nyl, C$_{1-6}$ haloalkyl, C$_{3-7}$ cycloalkyl, phenyl, 4-7 mem-
bered heterocycloalkyl, 5-6 membered heteroaryl, C$_{3-7}$
cycloalkyl-C$_{1-4}$ alkyl, phenyl-C$_{1-4}$ alkyl, 4-7 membered
heterocycloalkyl-C$_{1-4}$ alkyl, and 5-6 membered het-
eroaryl-C$_{1-4}$ alkyl are each optionally substituted with
1, 2, 3, or 4 independently selected R$^{6A}$ substituents;

or, any R$^{c6}$ and R$^{d6}$ attached to the same N atom, together
with the N atom to which they are attached, form a 4-7
membered heterocycloalkyl group, which is optionally
substituted with 1, 2, 3, or 4 independently selected R$^{6A}$
substituents; and each R$^{b6}$ is independently selected from C$_{1-6}$ alkyl, C$_{1-6}$
haloalkyl, C$_{2-6}$ alkenyl, C$_{2-6}$ alkynyl, C$_{3-7}$ cycloalkyl,
phenyl, 4-7 membered heterocycloalkyl, 5-6 membered
heteroaryl, C$_{3-7}$ cycloalkyl-C$_{1-4}$ alkyl, phenyl-C$_{1-4}$
alkyl, 4-7 membered heterocycloalkyl-C$_{1-4}$ alkyl, and
5-6 membered heteroaryl-C$_{1-4}$ alkyl, which are each
optionally substituted with 1, 2, 3, or 4 independently
selected R$^{6A}$ substituents.

In some embodiments, each R$^6$ is independently selected
from D, halo, CN, C$_{1-6}$ alkyl, C$_{2-6}$ alkenyl, C$_{2-6}$ alkynyl, C$_{1-6}$
haloalkyl, C$_{3-4}$ cycloalkyl, 4-7 membered heterocycloalkyl,
OR$^{a6}$, SR$^{a6}$, C(O)NR$^{c6}$R$^{d6}$, C(O)OR$^{a6}$, OC(O)R$^{b6}$, OC(O)
NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C
(O)NR$^{c6}$R$^{d6}$, NR$^{c6}$S(O)NR$^{c6}$R$^{d6}$, NR$^{c6}$S(O)R$^{b6}$, NR$^{c6}$S(O)$_2$
R$^{b6}$, NR$^{c6}$S(O)$_2$NR$^{c6}$R$^{d6}$, S(O)R$^{b6}$, S(O)NR$^{c6}$R$^{d6}$, S(O)$_2$
R$^{b6}$, S(O)$_2$NR$^{c6}$R$^{d6}$, and OS(O)$_2$R$^{b6}$; wherein said C$_{1-6}$
alkyl, C$_{2-6}$ alkenyl, C$_{2-6}$ alkynyl, C$_{1-6}$ haloalkyl, C$_{3-4}$
cycloalkyl, and 4-7 membered heterocycloalkyl, are each
optionally substituted by 1, 2, 3, or 4 independently selected
R$^{6A}$ substituents;

each R$^{a6}$, R$^{c6}$, and R$^{d6}$ is independently selected from H,
C$_{1-6}$ alkyl, C$_{1-6}$ haloalkyl, C$_{2-6}$ alkenyl, C$_{2-6}$ alkynyl,
and C$_{3-4}$ cycloalkyl, wherein said C$_{1-6}$ alkyl, C$_{1-6}$
haloalkyl, C$_{2-6}$ alkenyl, C$_{2-6}$ alkynyl, and C$_{3-4}$ cycloal-
kyl are each optionally substituted with 1, 2, 3, or 4
independently selected R$^{6A}$ substituents; and each R$^{b6}$ is independently selected from C$_{1-6}$ alkyl, C$_{1-6}$
haloalkyl, C$_{2-6}$ alkenyl, C$_{2-6}$ alkynyl, C$_{3-4}$ cycloalkyl,
and 4-7 membered heterocycloalkyl, which are each
optionally substituted with 1, 2, 3, or 4 independently
selected R$^{6A}$ substituents.

alkenyl, C$_{2-6}$ alkynyl, C$_{1-6}$ haloalkyl, and C$_{3-4}$ cycloalkyl are
each optionally substituted by 1, 2, 3, or 4 independently
selected R$^{6A}$ substituents;

each R$^{a6}$, R$^{c6}$, and R$^{d6}$ is independently selected from H,
C$_{1-6}$ alkyl, C$_{1-6}$ haloalkyl, C$_{2-6}$ alkenyl, C$_{2-6}$ alkynyl,
and C$_{3-4}$ cycloalkyl, wherein said C$_{1-6}$ alkyl, C$_{1-6}$
haloalkyl, C$_{2-6}$ alkenyl, C$_{2-6}$ alkynyl, and C$_{3-4}$ cycloal-
kyl are each optionally substituted with 1, 2, 3, or 4
independently selected R$^{6A}$ substituents; and each R$^{b6}$ is independently selected from C$_{1-6}$ alkyl, C$_{1-6}$
haloalkyl, C$_{2-6}$ alkenyl, C$_{2-6}$ alkynyl, and C$_{3-4}$ cycloal-
kyl, which are each optionally substituted with 1, 2, 3,
or 4 independently selected R$^{6A}$ substituents.

In some embodiments, each R$^6$ is independently selected
from oxo, D, halo, CN, C$_{1-6}$ alkyl, C$_{2-6}$ alkenyl, C$_{2-6}$ alkynyl,
C$_{1-6}$ haloalkyl, 4-7 membered heterocycloalkyl, OR$^{a6}$, C(O)
R$^{b6}$, and NR$^{c6}$R$^{d6}$; wherein said C$_{1-6}$ alkyl, C$_{2-6}$ alkenyl,
C$_{2-6}$ alkynyl, C$_{1-6}$ haloalkyl, and 4-7 membered heterocy-
cloalkyl, are each optionally substituted by 1, 2, or 3
independently selected R$^{6A}$ substituents; and each R$^{a6}$, R$^{c6}$, and R$^{d6}$ is independently selected from H,
C$_{1-6}$ alkyl, and C$_{1-6}$ haloalkyl, wherein said C$_{1-6}$ alkyl
and C$_{1-6}$ haloalkyl are each optionally substituted with
1 or 2 independently selected R$^{6A}$ substituents; and each R$^{b6}$ is independently selected from C$_{1-6}$ alkyl, C$_{1-6}$
haloalkyl, C$_{2-6}$ alkenyl, C$_{2-6}$ alkynyl, C$_{3-4}$ cycloalkyl,
and 4-7 membered heterocycloalkyl, which are each
optionally substituted with 1 or 2 independently
selected R$^{6A}$ substituents.

In some embodiments, each R$^6$ is independently selected
from oxo, D, halo, CN, C$_{1-6}$ alkyl, C$_{2-6}$ alkenyl, C$_{2-6}$ alkynyl,
C$_{1-6}$ haloalkyl, OR$^{a6}$, and NR$^{c6}$R$^{d6}$; wherein said C$_{1-6}$ alkyl,
C$_{2-6}$ alkenyl, C$_{2-6}$ alkynyl, and C$_{1-6}$ haloalkyl are each
optionally substituted by 1 or 2 independently selected R$^{6A}$
substituents; and each R$^{a6}$, R$^{c6}$, and R$^{d6}$ is independently selected from H,
C$_{1-6}$ alkyl, and C$_{1-6}$ haloalkyl, wherein said C$_{1-6}$ alkyl
and C$_{1-6}$ haloalkyl are each optionally substituted with
1 or 2 independently selected R$^{6A}$ substituents.

In some embodiments, each R$^{6A}$ is independently selected
from D, halo, CN, NO$_2$, C$_{1-6}$ alkyl, C$_{2-6}$ alkenyl, C$_{2-6}$
alkynyl, C$_{1-6}$ haloalkyl, C$_{3-7}$ cycloalkyl, phenyl, 4-7 mem-
bered heterocycloalkyl, 5-6 membered heteroaryl, C$_{3-7}$
cycloalkyl-C$_{1-4}$ alkyl, phenyl-C$_{1-4}$ alkyl, 4-7 membered het-
erocycloalkyl-C$_{1-4}$ alkyl, 5-6 membered heteroaryl-C$_{1-4}$
alkyl, OR$^{a61}$, SR$^{a61}$, NHOR$^{a61}$, C(O)R$^{b61}$, C(O)NR$^{c61}$R$^{d61}$,
C(O)OR$^{a61}$, OC(O)R$^{b61}$, OC(O)NR$^{c61}$R$^{d61}$, NR$^{c61}$R$^{d61}$,
NR$^{c61}$C(O)R$^{b61}$, NR$^{c61}$C(O)OR$^{a61}$, NR$^{c61}$C(O)NR$^{c61}$R$^{d61}$,
NR$^{c61}$S(O)NR$^{c61}$R$^{d61}$, NR$^{c61}$S(O)R$^{b61}$, NR$^{c61}$S(O)$_2$R$^{b61}$,
NR$^{c61}$S(O)$_2$NR$^{c61}$R$^{d61}$, S(O)R$^{b61}$, S(O)NR$^{c61}$R$^{d61}$, S(O)$_2$
R$^{b61}$, and S(O)$_2$NR$^{c61}$R$^{d61}$, wherein said C$_{1-6}$ alkyl, C$_{2-6}$
alkenyl, C$_{2-6}$ alkynyl, C$_{1-6}$ haloalkyl, C$_{3-7}$ cycloalkyl, phe-
nyl, 4-7 membered heterocycloalkyl, 5-6 membered het-
eroaryl, C$_{3-7}$ cycloalkyl-C$_{1-4}$ alkyl, phenyl-C$_{1-4}$ alkyl, 4-7
membered heterocycloalkyl-C$_{1-4}$ alkyl, and 5-6 membered
heteroaryl-C$_{1-4}$ alkyl are each optionally substituted with 1,
2, 3, or 4 independently selected R$^{6B}$ substituents;

each R$^{a61}$, R$^{c61}$, and R$^{d61}$ is independently selected from
H, C$_{1-6}$ alkyl, C$_{1-6}$ haloalkyl, C$_{2-6}$ alkenyl, C$_{2-6}$ alky-
nylC$_{3-7}$ cycloalkyl, phenyl, 4-7 membered heterocy-
cloalkyl, 5-6 membered heteroaryl, C$_{3-7}$ cycloalkyl-
C$_{1-4}$ alkyl, phenyl-C$_{1-4}$ alkyl, 4-7 membered
heterocycloalkyl-C$_{1-4}$ alkyl, and 5-6 membered het-
eroaryl-C$_{1-4}$ alkyl, wherein said C$_{1-6}$ alkyl, C$_{2-6}$ alk-
enyl, C$_{2-6}$ alkynyl, C$_{1-6}$ haloalkyl, C$_{3-7}$ cycloalkyl, phe-
nyl, 4-7 membered heterocycloalkyl, 5-6 membered
heteroaryl, C$_{3-7}$ cycloalkyl-C$_{1-4}$ alkyl, phenyl-C$_{1-4}$
alkyl, 4-7 membered heterocycloalkyl-C$_{1-4}$ alkyl, and 5-6 membered heteroaryl-$C_{1-4}$ alkyl are each optionally substituted with 1, 2, 3, or 4 independently selected $R^{6B}$ substituents;

each $R^{b61}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{6B}$ substituents;

each $R^{6B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a62}$, $SR^{a62}$, $NHOR^{a62}$, $C(O)R^{b62}$, $C(O)NR^{c62}R^{d62}$, $C(O)OR^{a62}$, $OC(O)R^{b62}$, $OC(O)NR^{c62}R^{d62}$, $NR^{c62}R^{d62}$, $NR^{c62}C(O)R^{b62}$, $NR^{c62}C(O)OR^{a62}$, $NR^{c62}C(O)NR^{c62}R^{d62}$, $NR^{c62}S(O)NR^{c62}R^{d62}$, $NR^{c62}S(O)R^{b62}$, $NR^{c62}S(O)_2R^{b62}$, $NR^{c62}S(O)_2NR^{c62}R^{d62}$, $S(O)R^{b62}$, $S(O)NR^{c62}R^{d62}$, $S(O)_2R^{b62}$, and $S(O)_2NR^{c62}R^{d62}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents;

each $R^{a62}$, $R^{c62}$, and $R^{d62}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents; and each $R^{b62}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{G}$ substituents.

In some embodiments, each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl, 5-6 membered hetmembered heterocycloalkyl-$C_{1-4}$ alkyl, and 5-6 membered heteroaryl-$C_{1-4}$ alkyl are each optionally substituted with 1, 2, 3, or 4 independently selected $R^{6B}$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6B}$ substituents;

each $R^{b61}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{6B}$ substituents;

each $R^{6B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a62}$, $SR^{a62}$, $NHOR^{a62}$, $C(O)R^{b62}$, $C(O)NR^{c62}R^{d62}$, $C(O)OR^{a62}$, $OC(O)R^{b62}$, $OC(O)NR^{c62}R^{d62}$, $NR^{c62}R^{d62}$, $NR^{c62}C(O)R^{b62}$, $NR^{c62}C(O)OR^{a62}$, $NR^{c62}C(O)NR^{c62}R^{d62}$, $NR^{c62}S(O)NR^{c62}R^{d62}$, $NR^{c62}S(O)R^{b62}$, $NR^{c62}S(O)_2R^{b62}$, $NR^{c62}S(O)_2NR^{c62}R^{d62}$, $S(O)R^{b62}$, $S(O)NR^{c62}R^{d62}$, $S(O)_2R^{b62}$, and $S(O)_2NR^{c62}R^{d62}$;

each $R^{a62}$, $R^{c62}$, and $R^{d62}$ is independently selected from H, $C_{1-6}$ alkyl, $C_{1-6}$ haloalkyl, $C_{2-6}$ alkenyl, and $C_{2-6}$ alkynyl; and each $R^{b62}$ is independently selected from $C_{1-6}$ alkyl, $C_{1-6}$ haloalkyl, $C_{2-6}$ alkenyl, and $C_{2-6}$ alkynyl.

In some embodiments, each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6B}$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6B}$ substituents;

each $R^{b61}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{6B}$ substituents;

each $R^{6B}$ is independently selected from D, halo, CN, $C_{1-6}$ alkyl, $C_{2-6}$ alkenyl, $C_{2-6}$ alkynyl, $C_{1-6}$ haloalkyl, $OR^{a62}$, $SR^{a62}$, $NHOR^{a62}$, $C(O)R^{b62}$, $C(O)NR^{c62}R^{d62}$, $C(O)OR^{a62}$, $OC(O)R^{b62}$, $OC(O)NR^{c62}R^{d62}$, $NR^{c62}R^{d62}$, $NR^{c62}C(O)R^{b62}$, $NR^{c62}C(O)OR^{a62}$, $NR^{c62}C(O)NR^{c62}R^{d62}$, $NR^{c62}S(O)NR^{c62}R^{d62}$, $NR^{c62}S(O)R^{b62}$, $NR^{c62}S(O)_2R^{b62}$, $NR^{c62}S(O)_2NR^{c62}R^{d62}$, $S(O)R^{b62}$, $S(O)NR^{c62}R^{d62}$, $S(O)_2R^{b62}$, and $S(O)_2NR^{c62}R^{d62}$;

each $R^{a62}$, $R^{c62}$, and $R^{d62}$ is independently selected from H, $C_{1-6}$ alkyl, $C_{1-6}$ haloalkyl, $C_{2-6}$ alkenyl, and $C_{2-6}$ alkynyl; and each $R^{b62}$ is independently selected from $C_{1-6}$ alkyl, $C_{1-6}$ haloalkyl, $C_{2-6}$ alkenyl, and $C_{2-6}$ alkynyl.

In some embodiments, each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl; and each $R^{b61}$ is independently selected from $C_{1-6}$ alkyl and $C_{1-6}$ haloalkyl.

In some embodiments, each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl; and each $R^{b61}$ is independently selected from $C_{1-6}$ alkyl and $C_{1-6}$ haloalkyl.

In some embodiments, each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-6}$ cycloalkyl, 4-7 membered heterocycloalkyl, $OR^{a6}$, $C(O)R^{b6}$, and $NR^{c6}R^{d6}$; wherein said $C_{1-6}$ alkyl, $C_{2-6}$ alkenyl, $C_{2-6}$ alkynyl, and $C_{1-6}$ haloalkyl are each optionally substituted by 1, 2, or 3 independently selected $R^{6A}$ substituents;

each $R^{a6}$, $R^{c6}$, and $R^{d6}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-4}$ cycloalkyl, and 4-7 membered heterocycloalkyl, which are each optionally substituted with 1 or 2 independently selected $R^{6A}$ substituents;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl; and each $R^{b61}$ is independently selected from $C_{1-6}$ alkyl and $C_{1-6}$ haloalkyl In some embodiments, each $R^6$ is independently selected from D, halo, CN, $C_{1-6}$ alkyl, $C_{2-6}$ alkenyl, $C_{2-6}$ alkynyl, $C_{1-6}$ haloalkyl, $OR^{a6}$, and $NR^{c6}R^{d6}$; wherein said $C_{1-6}$ alkyl, $C_{2-6}$ alkenyl, $C_{2-6}$ alkynyl, and $C_{1-6}$ haloalkyl are each optionally substituted by 1 or 2 independently selected $R^{6A}$ substituents;

each $R^{a6}$, $R^{c6}$, and $R^{d6}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{6A}$ substituents;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl; and each $R^{b61}$ is independently selected from $C_{1-6}$ alkyl and $C_{1-6}$ haloalkyl.

In some embodiments, each $R^6$ is independently selected from D, halo, CN, $C_{1-6}$ alkyl, $C_{1-6}$ haloalkyl, $C_{3-4}$ cycloalkyl, 4-7 membered heterocycloalkyl, $OR^{a6}$, and $C(O)R^{b6}$; wherein said $C_{1-6}$ alkyl, $C_{1-6}$ haloalkyl, $C_{3-4}$ cycloalkyl, and 4-7 membered heterocycloalkyl, are each optionally substituted by 1, 2, or 3 independently selected $R^{6A}$ substituents;

each $R^{a6}$ is independently selected from H and $C_{1-6}$ alkyl, wherein said $C_{1-6}$ alkyl is optionally substituted with 1 or 2 independently selected $R^{6A}$ substituents;

each $R^{b6}$ is independently selected from $C_{1-6}$ alkyl, $C_{1-6}$ haloalkyl, and 4-7 membered heterocycloalkyl;

each $R^{6A}$ is independently selected from D, $OR^{a61}$, and $NR^{c61}R^{d61}$; and each $R^{a61}$, $R^{c61}$, and $R^{d61}$ is independently selected from H, and $C_{1-6}$ alkyl.

In some embodiments, each $R^6$ is independently selected from D, halo, CN, $C_{1-6}$ alkyl, $C_{2-6}$ alkenyl, $C_{2-6}$ alkynyl, and $C_{1-6}$ haloalkyl.

In some embodiments, each $R^6$ is independently selected from halo, $C_{1-6}$ alkyl, $C_{1-6}$ haloalkyl, and $C_{3-6}$ cycloalkyl.

In some embodiments, each $R^6$ is independently selected from halo, $C_{1-6}$ alkyl, and $C_{3-6}$ cycloalkyl.

In some embodiments, each $R^6$ is independently selected from halo, $C_{1-3}$ alkyl, and $C_{3-6}$ cycloalkyl.

In some embodiments, each $R^6$ is independently selected from halo and $C_{1-3}$ alkyl.

In some embodiments, each $R^6$ is independently selected from $C_{1-6}$ alkyl, and $C_{1-6}$ haloalkyl.

In some embodiments, each $R^6$ is independently selected from $C_{1-6}$ alkyl.

In some embodiments, each $R^6$ is independently selected from $C_{1-3}$ alkyl.

In some embodiments, each $R^6$ is independently selected from fluoro, chloro, bromo, methyl, ethyl, isopropyl, trideuteromethyl, cyano, methoxymethyl, cyclopropyl, pyrrolidinyl, morpholinyl, pyrrolidinylcarbonyl, and morpholinylcarbonyl.

In some embodiments, each $R^6$ is independently selected from bromo, methyl, isopropyl, and cyclopropyl.

In some embodiments, each $R^6$ is fluoro.

In some embodiments, each $R^6$ is chloro.

In some embodiments, each $R^6$ is bromo.

In some embodiments, each $R^6$ is $CH_3$.

In some embodiments, each $R^6$ is $CD_3$.

In some embodiments, each $R^6$ is methyl.

In some embodiments, each $R^6$ is independently methyl or bromo.

In some embodiments, each $R^6$ is isopropyl.

In some embodiments, each $R^6$ is independently methyl or isopropyl.

In some embodiments, each $R^6$ is cyano.

In some embodiments, each $R^6$ is cyclopropyl.

In some embodiments, each $R^6$ is pyrrolidinyl.

In some embodiments, each $R^6$ is morpholinyl.

In some embodiments, each $R^6$ is N-morpholinyl.

In some embodiments, each $R^6$ is morpholinylcarbonyl.

In some embodiments, each $R^6$ is pyrrolidinylcarbonyl.

In some embodiments, k is 1.

In some embodiments, k is 2.

In some embodiments, each $R^W$, attached to the C ring, is independently:

-continued

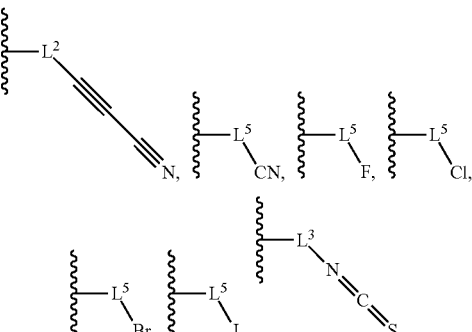

89

-continued $$R^{83}(O)C \begin{array}{c} L^2 \\ R^{81} \end{array} \begin{array}{c} R^{82} \quad R^{82} \\ R^{81} \end{array} \begin{array}{c} L^2 \\ S(O)_i R^{83}, \end{array}$$

and structures including $L^4 - C(=O)$ with $R^9$, bicyclic $L^4 - S(O_2)$ structures, $$L^2 \begin{array}{c} X^1 \\ R^{81} \end{array} C(O)R^{82},$$

$$L^2 \begin{array}{c} R^{82} \\ R^{81} \end{array}, \text{ or } L^1 - Ar.$$

In some embodiments, each $R^W$, attached to the B ring or C ring, is independently:

$$\begin{array}{c} L^1 \\ R^{81} \quad R^{82} \end{array} Cl, \begin{array}{c} L^1 \\ R^{81} \quad R^{82} \end{array} Br, \begin{array}{c} L^1 \\ R^{81} \quad R^{82} \end{array} F, \begin{array}{c} L^1 \\ R^{81} \end{array} CN,$$

$$\begin{array}{c} L^1 \\ O \end{array} (\phantom{)})_q R^{81}, \begin{array}{c} L^1 \\ S \end{array} (\phantom{)})_q R^{81}, \begin{array}{c} L^2 \\ R^{83} \end{array} \begin{array}{c} R^{82} \\ R^{81} \end{array},$$

$$\begin{array}{c} L^2 \\ R^{81} \end{array} \begin{array}{c} R^{82} \\ C(O)R^{83} \end{array}, \begin{array}{c} L^2 \\ R^{81} \end{array} \begin{array}{c} R^{82} \\ S(O)_i R^{83} \end{array}, \begin{array}{c} L^2 \\ R^{81} \end{array},$$

$$\begin{array}{c} L^2 \\ X^1 \\ R^{81} \end{array}, \begin{array}{c} L^2 \quad R^{81} \quad R^{82} \\ O \\ R^{82} \end{array},$$

$$\begin{array}{c} L^2 \\ R^{81} \\ O \end{array} \begin{array}{c} O \\ R^{82} \\ R^{82} \end{array}, \begin{array}{c} L^2 \\ N \end{array} R^{85},$$

90

-continued $$\begin{array}{c} L^2 \quad R^{81} \\ R^{81} \\ N \\ CN \end{array} \begin{array}{c} R^{82} \\ (\phantom{)})_u R^{81} \\ R^{82} \end{array}, \begin{array}{c} L^2 \\ O \end{array} \begin{array}{c} R^{82}, \\ O \end{array}$$

$$\begin{array}{c} L^2 \quad R^{81} \\ R^{81} \\ N \\ O \\ R^{81} \quad R^{83} \end{array} \begin{array}{c} R^{82} \\ (\phantom{)})_u R^{81} \\ R^{82} \end{array}, \begin{array}{c} L^2 \quad R^{81} \quad R^{82} \\ N \quad (\phantom{)})_u R^{82}, \\ O \\ R^{81} \end{array}$$

$$\begin{array}{c} L^3 \\ N \\ O \\ R^{81} \end{array} \begin{array}{c} O \\ R^{82}, \end{array} \begin{array}{c} L^3 \quad R^{81} \\ N \\ O \\ R^{82} \\ R^{81} \quad R^{82} \end{array},$$

$$\begin{array}{c} L^3 \quad R^{81} \quad R^{82} \\ N \\ O \\ R^{81} \quad R^{82} \end{array} \begin{array}{c} R^{81} \\ R^{82} \\ R^{81} \end{array}, \begin{array}{c} L^4 \\ O \end{array} (\phantom{)})_q R^{84},$$

$$\begin{array}{c} L^4 \\ S \\ O \end{array} (\phantom{)})_q R^{84}, \begin{array}{c} L^2 \\ R^{83} \end{array} \begin{array}{c} R^{81} \\ C \\ R^{82} \end{array},$$

$$\begin{array}{c} L^2 \\ N \end{array}, \begin{array}{c} L^5 \\ CN, \end{array} \begin{array}{c} L^5 \\ F, \end{array} \begin{array}{c} L^5 \\ Cl, \end{array}$$

$$\begin{array}{c} L^5 \\ Br, \end{array} \begin{array}{c} L^5 \\ I, \end{array} \begin{array}{c} L^3 \\ N \\ C \\ S, \end{array}$$

$$\begin{array}{c} L^4 \\ O \end{array} \begin{array}{c} L^2 \quad R^{82} \\ R^{81} \end{array}, R^{83}(O)C \begin{array}{c} L^2 \quad R^{82} \\ R^{81} \end{array}, \begin{array}{c} R^{82} \quad L^2 \\ R^{81} \end{array} S(O)_i R^{83},$$

91

-continued

92

-continued

In some embodiments, each $R^W$, attached to the C ring, is independently:

In some embodiments, each $R^W$, attached to the C ring, is independently:

-continued

-continued

In some embodiments, each $R^W$, attached to the C ring, is independently:

In some embodiments, each $R^W$, attached to the C ring, is independently:

In some embodiments, each $R^W$, attached to the C ring, is independently:

-continued

-continued

In some embodiments, each $R^W$, attached to the C ring, is independently:

In some embodiments, each $R^W$, attached to the C ring, is independently:

-continued

In some embodiments, each $R^W$, attached to the C ring, is independently:

In some embodiments, each $R^W$, attached to the C ring, is independently:

In some embodiments, each $R^W$, attached to the C ring, is independently:

In some embodiments, each $R^W$, attached to the C ring, is independently:

In some embodiments, each $R^W$, attached to the C ring, is independently:

In some embodiments, each $R^W$, attached to the B ring or C ring, is independently:

In some embodiments, each $R^W$, attached to the B ring or C ring, is independently:

In some embodiments, $L^1$ is NHC(O) or N(CH$_3$)C(O).

In some embodiments, $L^1$ is NHC(O).

In some embodiments, $L^2$ is a bond, NHC(O), N(tetrahydrofuran)C(O), or N(CH$_3$)C(O).

In some embodiments, $L^2$ is NHC(O) or N(CH$_3$)C(O).

In some embodiments, $L^2$ is a bond.

In some embodiments, $L^2$ is N(tetrahydrofuran)C(O).

In some embodiments, $L^2$ is NHC(O).

In some embodiments, $L^2$ is N(CH$_3$)C(O).

In some embodiments, $L^3$ is NHC(O) or N(CH$_3$)C(O).

In some embodiments, $L^3$ is NHC(O).

In some embodiments, $L^3$ is N(CH$_3$)C(O).

In some embodiments, $L^4$ is NHC(O) or N(CH$_3$)C(O).

In some embodiments, $L^4$ is NHC(O).

In some embodiments, $L^5$ is NHC(O) or N(CH$_3$)C(O).

In some embodiments, $L^5$ is NHC(O).

In some embodiments, $L^6$ is NHC(O), N(CH$_3$)C(O), or C(O).

In some embodiments, $L^6$ is NHC(O) or C(O).

In some embodiments, $L^6$ is NHC(O).

In some embodiments, $L^6$ is C(O).

In some embodiments, $X^1$ is O.

In some embodiments, each Ring D is independently a 4-10 membered heterocycloalkyl, C$_{3-7}$ cycloalkyl, C$_{6-10}$ aryl, or a 5-6 membered heteroaryl, each of which is optionally substituted with 1, 2, 3, or 4 independently selected C$_{1-6}$ alkyl groups.

In some embodiments, each Ring D is independently a 4-8 membered heterocycloalkyl, C$_{3-7}$ cycloalkyl, phenyl, or a 5-6 membered heteroaryl, each of which is optionally substituted with 1, 2, 3, or 4 independently selected C$_{1-6}$ alkyl groups.

In some embodiments, each Ring D is independently a 4-8 membered heterocycloalkyl, each of which is optionally substituted with 1, 2, 3, or 4 independently selected C$_{1-6}$ alkyl groups.

In some embodiments, each Ring D is independently a 4-8 membered heterocycloalkyl, each of which is optionally substituted with 1 or 2 independently selected C$_{1-6}$ alkyl groups.

In some embodiments, each Ring D is independently a monocyclic 4-7 membered heterocycloalkyl, bicyclic 7-10 membered heterocycloalkyl, or a spirocyclic 7-10 membered heterocycloalkyl, each of which is optionally substituted by 1 or 2 independently selected C$_{1-6}$ alkyl groups.

In some embodiments, each Ring D is independently a monocyclic 4-7 membered heterocycloalkyl, bicyclic 7-10 membered heterocycloalkyl, or a spirocyclic 7-10 membered heterocycloalkyl, each of which is optionally substituted by 1 or 2 methyl groups.

In some embodiments, each Ring D is independently pyrrolidinyl, piperidinyl, piperazinyl, 2,5-diazabicyclo[2.2.1]heptanyl, 3,8-diazabicyclo[3.2.1]octane, or 1,6-diazaspiro[3.3]heptanyl, each of which is optionally substituted by 1 or 2 methyl groups.

In some embodiments, each Ring D is independently pyrrolidinyl, piperidinyl, piperazinyl, 2,5-diazabicyclo[2.2.1]heptanyl, 3,8-diazabicyclo[3.2.1]octane, or 1,6-diazaspiro[3.3]heptanyl, wherein the piperazinyl is optionally substituted by 1 or 2 methyl groups.

In some embodiments, each Ring D is independently pyrrolidinyl, piperidinyl, piperazinyl, dimethylpiperazinyl, 2,5-diazabicyclo[2.2.1]heptanyl, 3,8-diazabicyclo[3.2.1]octane, or 1,6-diazaspiro[3.3]heptanyl.

In some embodiments, each Ring D is independently pyrrolidinyl, piperidinyl, dimethylpiperazinyl, 2,5-diazabicyclo[2.2.1]heptanyl, 3,8-diazabicyclo[3.2.1]octane, or 1,6-diazaspiro[3.3]heptanyl.

In some embodiments, each $R^{81}$, $R^{82}$, and $R^{83}$ are independently selected from H, D, halo, CN, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)OR$^{a8}$, NR$^{c8}$C(O)NR$^{c8}$R$^{d8}$, NR$^{c8}$S(O)NR$^{c8}$R$^{d8}$, NR$^{c8}$S(O)R$^{b8}$, NR$^{c8}$S(O)$_2$R$^{b8}$, NR$^{c8}$S(O)$_2$NR$^{c8}$R$^{d8}$, S(O)R$^{b8}$, S(O)NR$^{c8}$R$^{d8}$, S(O)$_2$R$^{b8}$, and S(O)$_2$NR$^{c8}$R$^{d8}$; wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted by 1, 2, 3, or 4 independently selected R$^G$ substituents;

each R$^{a8}$, R$^{c8}$, and R$^{d8}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b8}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

In some embodiments, each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, $C_{1-6}$ haloalkyl, and 4-7 membered heterocycloalkyl-$C_{1-4}$ alkyl; wherein said $C_{1-6}$ alkyl, $C_{2-6}$ alkenyl, $C_{2-6}$ alkynyl, $C_{1-6}$ haloalkyl, and 4-7 membered heterocycloalkyl-$C_{1-4}$ alkyl are each optionally substituted by 1, 2, 3, or 4 independently selected $R^G$ substituents; and each $R^{a8}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^G$ substituents.

In some embodiments, each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, $C_{1-6}$ haloalkyl, and $C_{3-4}$ cycloalkyl; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^G$ substituents;

each $R^{a8}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^G$ substituents.

In some embodiments, each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ substituents; and each $R^{a8}$ is independently selected from H, $C_{1-6}$ alkyl, $C_{1-6}$ haloalkyl, $C_{2-6}$ alkenyl, and $C_{2-6}$ alkynyl.

In some embodiments, each $R^G$ is independently selected from OH, $C_{1-3}$ alkyl, $C_{2-3}$ alkenyl, $C_{2-3}$ alkynyl, $C_{1-3}$ haloalkyl, $C_{1-3}$ alkoxy, amino, $C_{1-3}$ alkylamino, and di($C_{1-3}$ alkyl)amino.

In some embodiments, each $R^G$ is independently selected from OH, $C_{1-3}$ alkoxy, amino, $C_{1-3}$ alkylamino, and di($C_{1-3}$ alkyl)amino.

In some embodiments, each $R^G$ is independently selected from OH, $C_{1-3}$ alkoxy, and di($C_{1-3}$ alkyl)amino.

In some embodiments, each $R^G$ is selected from OH, methoxy, and dimethylamino.

In some embodiments, $R^{81}$, $R^{82}$, $R^{83}$, and $R^{84}$ are each independently selected from H, D, halo, C(O)OH, OH, $C_{1-3}$ alkoxy, $C_{1-3}$ haloalkoxy, amino, $C_{1-3}$ alkyl, $C_{1-3}$ haloalkyl, and 4-7 membered heterocycloalkyl-$C_{1-4}$ alkyl, wherein each $C_{1-3}$ alkyl is optionally substituted with 1 or 2 $R^G$ substituents independently selected from OH, $C_{1-3}$ alkoxy, amino, $C_{1-3}$ alkylamino, and di($C_{1-3}$ alkyl)amino.

In some embodiments, $R^{81}$, $R^{82}$, $R^{83}$, and $R^{84}$ are each independently selected from H, D, halo, C(O)OH, OH, $C_{1-3}$ alkoxy, $C_{1-3}$ haloalkoxy, amino, $C_{1-3}$ alkyl, and $C_{1-3}$ haloalkyl, wherein each $C_{1-3}$ alkyl is optionally substituted with 1 or 2 $R^G$ substituents independently selected from amino, $C_{1-3}$ alkylamino, and di($C_{1-3}$ alkyl)amino.

In some embodiments, $R^{81}$, $R^{82}$, and $R^{83}$ are each independently selected from H, D, halo, C(O)OH, OH, $C_{1-3}$ alkoxy, $C_{1-3}$ haloalkoxy, amino, $C_{1-3}$ alkyl, and $C_{1-3}$ haloalkyl, wherein each $C_{1-3}$ alkyl is optionally substituted with 1 or 2 $R^G$ substituents independently selected from amino, $C_{1-3}$ alkylamino, and di($C_{1-3}$ alkyl)amino.

In some embodiments, $R^{81}$, $R^{82}$, and $R^{83}$ are each independently selected from H, halo, C(O)OH, $C_{1-3}$ alkoxy, $C_{1-3}$ alkyl, and $C_{1-3}$ haloalkyl, wherein each $C_{1-3}$ alkyl is optionally substituted with 1 or 2 $R^G$ substituents independently selected from amino, $C_{1-3}$ alkylamino, and di($C_{1-3}$ alkyl)amino.

In some embodiments, $R^{81}$, $R^{82}$, and $R^{83}$ are each independently selected from H, halo, C(O)OH, $C_{1-3}$ alkoxy, $C_{1-3}$ alkyl, and $C_{1-3}$ haloalkyl, wherein each $C_{1-3}$ alkyl is optionally substituted with di($C_{1-3}$ alkyl)amino.

In some embodiments, $R^{81}$, $R^{82}$, and $R^{83}$ are each independently selected from H, chloro, fluoro, C(O)OH, $OCH_2CH_3$, $CH_3$, $CH_2CH_3$, $CH_2F$, $CH_2N(CH_3)_2$, $CH_2OH$, $C(CH_3)_2OH$, $CH_2OCH_3$, and $CH_2$-piperidine.

In some embodiments, $R^{81}$, $R^{82}$, and $R^{83}$ are each independently selected from H, chloro, fluoro, C(O)OH, $OCH_2CH_3$, $CH_3$, $CH_2CH_3$, $CH_2F$, and $CH_2N(CH_3)_2$.

In some embodiments:

each $R^{81}$ is independently selected from H, D, halo, C(O)OH, OH, $C_{1-3}$ alkoxy, $C_{1-3}$ haloalkoxy, amino, $C_{1-3}$ alkyl, $C_{1-3}$ haloalkyl, and 4-7 membered heterocycloalkyl-$C_{1-4}$ alkyl, wherein each $C_{1-3}$ alkyl is optionally substituted with 1 or 2 $R^G$ substituents independently selected from OH, $C_{1-3}$ alkoxy, amino, $C_{1-3}$ alkylamino, and di($C_{1-3}$ alkyl)amino;

each $R^{82}$ is H; and each $R^{83}$ is independently selected from H, halo, and $C_{1-3}$ alkoxy.

In some embodiments:

each $R^{81}$ is independently selected from H, chloro, fluoro, C(O)OH, $OCH_2CH_3$, $CH_3$, $CH_2CH_3$, $CH_2F$, $CH_2N(CH_3)_2$, $CH_2OH$, $C(CH_3)_2OH$, $CH_2OCH_3$, and $CH_2$-piperidine;

each $R^{82}$ is H; and each $R^{83}$ is independently selected from H, halo, and $C_{1-3}$ alkoxy.

In some embodiments:

each $R^{81}$ is independently selected from H, C(O)OH, $C_{1-3}$ alkyl, and $C_{1-3}$ haloalkyl, wherein each $C_{1-3}$ alkyl is optionally substituted with di($C_{1-3}$ alkyl)amino;

each $R^{82}$ is H; and each $R^{83}$ is independently selected from H, halo, and $C_{1-3}$ alkoxy.

In some embodiments:

each $R^{81}$ is independently selected from H, C(O)OH, $CH_3$, $CH_2CH_3$, $CH_2F$, $CH_2N(CH_3)_2$, $CH_2OH$, $C(CH_3)_2$ OH, $CH_2OCH_3$, and $CH_2$-piperidine;

each $R^{82}$ is H; and each $R^{83}$ is independently selected from H, chloro, fluoro, and $OCH_2CH_3$.

In some embodiments:

each $R^{81}$ is independently selected from H, C(O)OH, $CH_3$, $CH_2CH_3$, $CH_2F$, and $CH_2N(CH_3)_2$;

each $R^{82}$ is H; and each $R^{83}$ is independently selected from H, chloro, fluoro, and $OCH_2CH_3$.

In some embodiments, each $R^{84}$ is independently H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-6 membered heterocycloalkyl, 5-6 membered heteroaryl, $C_{3-7}$ cycloalkyl-$C_{1-4}$ alkyl, phenyl-$C_{1-4}$ alkyl, 4-6 membered heterocycloalkyl-$C_{1-4}$ alkyl, or 5-6 membered heteroaryl-$C_{1-4}$ alkyl, wherein said $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-6 membered heterocycloalkyl, 5-6 membered heteroaryl, $C_{3-7}$ cycloalkyl-$C_{1-4}$ alkyl, phenyl-$C_{1-4}$ alkyl, 4-6 membered heterocycloalkyl-$C_{1-4}$ alkyl, or 5-6 membered heteroaryl-$C_{1-4}$ alkyl are each optionally substituted by 1, 2, 3, or 4 independently selected $R^G$ substituents.

In some embodiments, each $R^{84}$ is independently H, D, halo, CN, $C_{1-3}$ alkoxy, $C_{1-3}$ haloalkoxy, $C_{1-6}$ alkyl, $C_{2-6}$ alkenyl, $C_{2-6}$ alkynyl, or $C_{1-6}$ haloalkyl, wherein said $C_{1-3}$ alkoxy, $C_{1-3}$ haloalkoxy, $C_{1-6}$ alkyl, $C_{2-6}$ alkenyl, $C_{2-6}$ alkynyl, or $C_{1-6}$ haloalkyl are each optionally substituted by 1, 2, 3, or 4 independently selected $R^G$ substituents.

In some embodiments, each $R^{84}$ is independently H, D, halo, CN, $C_{1-3}$ alkoxy, $C_{1-3}$ haloalkoxy, $C_{1-6}$ alkyl, $C_{2-6}$ alkenyl, $C_{2-6}$ alkynyl, or $C_{1-6}$ haloalkyl.

In some embodiments, each $R^{85}$ is independently H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-7}$ cycloalkyl, 4-6 membered heterocycloalkyl, or $C_{3-7}$ cycloalkyl-$C_{1-4}$ alkyl, wherein said $C_{1-6}$ alkyl, $C_{1-6}$ haloalkyl, $C_{3-10}$ cycloalkyl, 4-6 membered heterocycloalkyl, and $C_{3-7}$ cycloalkyl-$C_{1-4}$ alkyl are each optionally substituted by 1, 2, 3, or 4 independently selected $R^G$ substituents.

In some embodiments, each $R^{85}$ is independently H, D, halo, CN, C(O)H, OH, $C_{1-3}$ alkoxy, $C_{1-3}$ haloalkoxy, amino, $C_{1-6}$ alkyl, and $C_{1-6}$ haloalkyl, wherein said $C_{1-6}$ alkyl, $C_{1-6}$ haloalkyl, $C_{3-10}$ cycloalkyl, 4-6 membered heterocycloalkyl, and $C_{3-7}$ cycloalkyl-$C_{1-4}$ alkyl are each optionally substituted by 1, 2, 3, or 4 independently selected $R^G$ substituents.

In some embodiments, each $R^{85}$ is independently H, D, halo, CN, C(O)H, OH, $C_{1-3}$ alkoxy, $C_{1-3}$ haloalkoxy, amino, $C_{1-6}$ alkyl, and $C_{1-6}$ haloalkyl.

In some embodiments, each $R^{85}$ is independently selected from H, halo, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents; and each $R^{b9}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{9A}$ substituents.

In some embodiments, each $R^9$ is independently selected from H, halo, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents; and each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9A}$ substituents.

In some embodiments, each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{b91}$, and $S(O)_2NR^{c91}R^{d91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{b91}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a92}$, $SR^{a92}$, $NHOR^{a92}$, $C(O)R^{b92}$, $C(O)NR^{c92}R^{d92}$, $C(O)OR^{a92}$, $OC(O)R^{b92}$, $OC(O)NR^{c92}R^{d92}$, $NR^{c92}R^{d92}$, $NR^{c92}C(O)R^{b92}$, $NR^{c92}C(O)OR^{a92}$, $NR^{c92}C(O)NR^{c92}R^{d92}$, $NR^{c92}S(O)NR^{c92}R^{d92}$, $NR^{c92}S(O)R^{b92}$, $NR^{c92}S(O)_2R^{b92}$, $NR^{c92}S(O)_2NR^{c92}R^{d92}$, $S(O)R^{b92}$, $S(O)NR^{c92}R^{d92}$, $S(O)_2R^{b92}$, and $S(O)_2NR^{c92}R^{d92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

In some embodiments, each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{b91}$, and $S(O)_2NR^{c91}R^{d91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{b91}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a92}$, $SR^{a92}$, $NHOR^{a92}$, $C(O)R^{b92}$, $C(O)NR^{c92}R^{d92}$, $C(O)OR^{a92}$, $OC(O)R^{b92}$, $OC(O)NR^{c92}R^{d92}$, $NR^{c92}R^{d92}$, $NR^{c92}C(O)R^{b92}$, $NR^{c92}C(O)OR^{a92}$, $NR^{c92}C(O)NR^{c92}R^{d92}$, $NR^{c92}S(O)NR^{c92}R^{d92}$, $NR^{c92}S(O)R^{b92}$, $NR^{c92}S(O)_2R^{b92}$, $NR^{c92}S(O)_2NR^{c92}R^{d92}$, $S(O)R^{b92}$, $S(O)NR^{c92}R^{d92}$, $S(O)_2R^{b92}$, and $S(O)_2NR^{c92}R^{d92}$;

each $R^{a92}$, $R^{c92}$, and $R^{d92}$ is independently selected from H, $C_{1-6}$ alkyl, $C_{1-6}$ haloalkyl, $C_{2-6}$ alkenyl, and $C_{2-6}$ alkynyl; and each $R^{b92}$ is independently selected from $C_{1-6}$ alkyl, $C_{1-6}$ haloalkyl, $C_{2-6}$ alkenyl, and $C_{2-6}$ alkynyl.

In some embodiments, each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{b91}$, and $S(O)_2NR^{c91}R^{d91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{b91}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{9B}$ is independently selected from D, halo, CN, $C_{1-6}$ alkyl, $C_{2-6}$ alkenyl, $C_{2-6}$ alkynyl, $C_{1-6}$ haloalkyl, $OR^{a92}$, $SR^{a92}$, $NHOR^{a92}$, $C(O)R^{b92}$, $C(O)NR^{c92}R^{d92}$, $C(O)$ $OR^{a92}$, $OC(O)R^{b92}$, $OC(O)NR^{c92}R^{d92}$, $NR^{c92}R^{d92}$, $NR^{c92}C(O)R^{b92}$, $NR^{c92}C(O)OR^{a92}$, $NR^{c92}C(O)$ $NR^{c92}R^{d92}$, $NR^{c92}S(O)NR^{c92}R^{d92}$, $NR^{c92}S(O)R^{b92}$, $NR^{c92}S(O)_2R^{b92}$, $NR^{c92}S(O)_2NR^{c92}R^{d92}$, $S(O)R^{b92}$, $S(O)NR^{c92}R^{d92}$, $S(O)_2R^{b92}$, and $S(O)_2NR^{c92}R^{d92}$;

each $R^{a92}$, $R^{c92}$, and $R^{d92}$ is independently selected from H, $C_{1-6}$ alkyl, $C_{1-6}$ haloalkyl, $C_{2-6}$ alkenyl, and $C_{2-6}$ alkynyl; and each $R^{b92}$ is independently selected from $C_{1-6}$ alkyl, $C_{1-6}$ haloalkyl, $C_{2-6}$ alkenyl, and $C_{2-6}$ alkynyl.

In some embodiments, each $R^{9A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)$ $R^{b91}$, $NR^{c91}C(O)OR^{a91}$, $NR^{c91}C(O)NR^{c91}R^{d91}$, $NR^{c91}S(O)$ $NR^{c91}R^{d91}$, $NR^{c91}S(O)R^{b91}$, $NR^{c91}S(O)_2R^{b91}$, $NR^{c91}S(O)_2$ $NR^{c91}R^{d91}$, $S(O)R^{b91}$, $S(O)NR^{c91}R^{d91}$, $S(O)_2R^{b91}$, and $S(O)_2$ $NR^{c91}R^{d91}$;

each $R^{a91}$, $R^{c91}$, and $R^{d91}$ is independently selected from H, $C_{1-6}$ alkyl, and $C_{1-6}$ haloalkyl; and each $R^{b91}$ is independently selected from $C_{1-6}$ alkyl and $C_{1-6}$ haloalkyl.

In some embodiments, each $R^{9A}$ is independently selected from D, halo, CN, $C_{1-6}$ alkyl, $C_{2-6}$ alkenyl, $C_{2-6}$ alkynyl, $C_{1-6}$ haloalkyl, $OR^{a91}$, $SR^{a91}$, $NHOR^{a91}$, $C(O)R^{b91}$, $C(O)$ $NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)$ $NR^{c91}R^{d91}$, $NR^{c91}S(O)NR^{c91}R^{d91}$, $NR^{c91}S(O)R^{b91}$, $NR^{c91}S$ $(O)_2R^{b91}$, $NR^{c91}S(O)_2NR^{c91}R^{d91}$, $S(O)R^{b91}$, $S(O)$ $NR^{c91}R^{d91}$, $S(O)_2R^{b91}$, and $S(O)_2NR^{c91}R^{d91}$;

each $R^{a91}$, $R^{c91}$, and $R^{d91}$ is independently selected from H, $C_{1-6}$ alkyl, and $C_{1-6}$ haloalkyl; and each $R^{b91}$ is independently selected from $C_{1-6}$ alkyl and $C_{1-6}$ haloalkyl.

In some embodiments, each Ar is independently phenyl or 5-6 membered heteroaryl, which are each optionally substituted with 1, 2, 3, or 4 independently selected $R^{9A}$ substituents.

In some embodiments, each Ar is independently 5-6 membered heteroaryl, which are each optionally substituted with 1, 2, 3, or 4 independently selected $R^{9A}$ substituents.

In some embodiments, each Ar is independently $C_{6-10}$ aryl or 5-10 membered heteroaryl, wherein said $C_{6-10}$ aryl or 5-10 membered heteroaryl are each substituted with 1, 2, 3, or 4 substituents independently selected from CN and halo; and wherein said $C_{6-10}$ aryl or 5-10 membered heteroaryl are each optionally substituted with 1, 2, 3, or 4 independently selected $R^{9A}$ substituents.

In some embodiments, each Ar is independently phenyl or 5-6 membered heteroaryl, wherein said phenyl or 5-6 membered heteroaryl are each substituted with 1, 2, 3, or 4 substituents independently selected from CN and halo; and wherein said phenyl or 5-6 membered heteroaryl are each optionally substituted with 1, 2, 3, or 4 independently selected $R^{9A}$ substituents.

In some embodiments:

each $\equiv$ is independently a single or a double bond;

k is 1 or 2;

n is 0 or 1;

p is 0, 1, or 2;

X is CH or N;

Y is $CR^4$ or N; and W is $CR^2$; or

Y is $NR^{4y}$, O or S; and W is absent;

Ring A is a monocyclic 5-6 membered heteroaryl ring;

Ring B and Ring C together form a fused bicycle;

Ring B is phenyl, 6-membered heteroaryl, or 6-membered heterocycloalkyl, each of which is optionally substituted with 1, 2, or 3 independently selected $R^5$ substituents; and Ring C is 5-membered heteroaryl, each of which is optionally substituted with 1 or 2 independently selected $R^6$ substituents; or Ring B is 5-membered heteroaryl or 5-membered heterocycloalkyl, each of which is optionally substituted with 1, 2, 3, or 4 independently selected $R^5$ substituents; and Ring C is phenyl or a 6-membered heteroaryl, each of which is optionally substituted with 1, 2, or 3 independently selected $R^6$ substituents; or Ring B is cyclopentyl, which is optionally substituted with 1, 2, 3, or 4 independently selected $R^5$ substituents; and Ring C is 6-membered heteroaryl, each of which is optionally substituted with 1, 2, or 3 independently selected $R^6$ substituents;

each $R^W$, attached to the C ring, is independently:

-continued each $L^1$ is NHC(O);

each $L^2$ is a bond, NHC(O), N(tetrahydrofuran)C(O), or N(CH$_3$)C(O);

each $L^4$ is NHC(O);

each $L^6$ is NHC(O) or C(O);

each $X^1$ independently is O or NR$^9$;

each q is independently 0 or 1;

each Ring D is independently a 4-8 membered heterocycloalkyl, C$_{3-7}$ cycloalkyl, phenyl, or a 5-6 membered heteroaryl, each of which is optionally substituted with 1, 2, 3, or 4 independently selected C$_{1-6}$ alkyl groups;

each R$^{81}$, R$^{82}$, and R$^{83}$ are independently selected from H, D, halo, CN, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)OR$^{a8}$, NR$^{c8}$C(O)NR$^{c8}$R$^{d8}$, NR$^{c8}$S(O)NR$^{c8}$R$^{d8}$, NR$^{c8}$S(O)R$^{b8}$, NR$^{c8}$S(O)$_2$R$^{b8}$, NR$^{c8}$S(O)$_2$ NR$^{c8}$R$^{d8}$, S(O)R$^{b8}$, S(O)NR$^{c8}$R$^{d8}$, S(O)$_2$R$^{b8}$, and S(O)$_2$NR$^{c8}$R$^{d8}$; wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted by 1, 2, 3, or 4 independently selected R$^G$ substituents;

each R$^{a8}$, R$^{c8}$, and R$^{d8}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{b8}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^G$ substituents;

each R$^{84}$ is independently H, D, halo, CN, OH, C$_{1-3}$ alkoxy, C$_{1-3}$ haloalkoxy, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, or 5-10 membered heteroaryl-C$_{1-4}$ alkyl, each of which is optionally substituted by 1, 2, 3, or 4 independently selected R$^G$ substituents;

each R$^9$ is independently selected from H, halo, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, 5-10 membered heteroaryl-C$_{1-4}$ alkyl, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O)NR$^{c9}$R$^{d9}$, NR$^{c9}$S(O)NR$^{c9}$R$^{d9}$, NR$^{c9}$S(O)R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, and S(O)$_2$NR$^{c9}$R$^{d9}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^{9A}$ substituents;

each R$^{a9}$, R$^{c9}$, and R$^{d9}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

each $R^{b9}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{9A}$ substituents;

each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{b91}$, and $S(O)_2NR^{c91}R^{d91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{b91}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl- $C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a92}$, $SR^{a92}$, $NHOR^{a92}$, $C(O)R^{b92}$, $C(O)NR^{c92}R^{d92}$, $C(O)OR^{a92}$, $OC(O)R^{b92}$, $OC(O)NR^{c92}R^{d92}$, $NR^{c92}R^{d92}$, $NR^{c92}C(O)R^{b92}$, $NR^{c92}C(O)OR^{a92}$, $NR^{c92}C(O)NR^{c92}R^{d92}$, $NR^{c92}S(O)NR^{c92}R^{d92}$, $NR^{c92}S(O)R^{b92}$, $NR^{c92}S(O)_2R^{b92}$, $NR^{c92}S(O)_2NR^{c92}R^{d92}$, $S(O)R^{b92}$, $S(O)NR^{c92}R^{d92}$, $S(O)_2R^{b92}$, and $S(O)_2NR^{c92}R^{d92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, 4-10 membered heterocycloalkyl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR)^{a1}$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, and $OS(O)_2R^{b1}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, are each optionally substituted with 1, 2, 3, or 4 independently selected $R^{1A}$ substituents;

or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, which are each optionally substituted with 1, 2, 3, or 4 independently selected $R^{1A}$ substituents;

each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1C}$ substituents;

each $R^{1C}$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^2$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, and $OS(O)_2R^{b2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents;

each $R^{2A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{b21}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^3$ is H or $C_{1-6}$ alkyl;

$R^4$ is H, D, halo, CN, or $C_{1-6}$ alkyl;

$R^{4y}$ is H, $C_{1-4}$ alkyl, or $C_{1-4}$ haloalkyl;

each $R^5$ is independently selected from oxo, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $OS(O)_2R^{b5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents;

each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b5}$s is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ substituents;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, and $S(O)_2NR^{c52}R^{d52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^6$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a6}$, $SR^{a6}$, $NHOR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$, and $OS(O)_2R^{b6}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6A}$ substituents;

or, any $R^{c6}$ and $R^{d6}$ attached to the same N atom, together with the N atom to which they are attached, form a 4-10 membered heterocycloalkyl group, which is optionally substituted with 1, 2, 3, or 4 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{6A}$ substituents;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-C$_{1-4}$ alkyl are each optionally substituted with 1, 2, 3, or 4 independently selected R$^{6B}$ substituents;

each R$^{a61}$, R$^{c61}$, and R$^{d61}$ is independently selected from H, C$_{1-6}$ alkyl, C$_{1-6}$ haloalkyl, C$_{2-6}$ alkenyl, C$_{2-6}$ alkynylC$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{6B}$ substituents;

each R$^{b61}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^{6B}$ substituents;

each R$^{6B}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a62}$, SR$^{a62}$, NHOR$^{a62}$, C(O)R$^{b62}$, C(O)NR$^{c62}$R$^{d62}$, C(O)OR$^{a62}$, OC(O)R$^{b62}$, OC(O)NR$^{c62}$R$^{d62}$, NR$^{c62}$R$^{d62}$, NR$^{c62}$C(O)R$^{b62}$, NR$^{c62}$C(O)OR$^{a62}$, NR$^{c62}$C(O)NR$^{c62}$R$^{d62}$, NR$^{c62}$S(O)NR$^{c62}$R$^{d62}$, NR$^{c62}$S(O)R$^{b62}$, NR$^{c62}$S(O)$_2$R$^{b62}$, NR$^{c62}$S(O)$_2$NR$^{c62}$R$^{d62}$, S(O)R$^{b62}$, S(O)NR$^{c62}$R$^{d62}$, S(O)$_2$R$^{b62}$, and S(O)$_2$NR$^{c62}$R$^{d62}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{a62}$, R$^{c62}$, and R$^{d62}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{b62}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^G$ substituents;

each R$^7$ is independently selected from D, halo, NO$_2$, CN, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a7}$, SR$^{a7}$, NHOR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, NR$^{c7}$S(O)NR$^{c7}$R$^{d7}$, NR$^{c7}$S(O)R$^{b7}$, NR$^{c7}$S(O)$_2$R$^{b7}$, NR$^{c7}$S(O)$_2$ NR$^{c7}$R$^{d7}$, S(O)R$^{b7}$, S(O)NR$^{c7}$R$^{d7}$, S(O)$_2$R$^{b7}$, S(O)$_2$ NR$^{c7}$R$^{d7}$, and OS(O)$_2$R$^{b7}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted by 1, 2, 3, or 4 independently selected R$^{74}$ substituents;

each R$^{a7}$, R$^{c7}$, and R$^{d7}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{74}$ substituents;

or, any R$^{c7}$ and R$^{d7}$ attached to the same N atom, together with the N atom to which they are attached, form a 4-7 membered heterocycloalkyl group, which is optionally substituted with 1, 2, 3, or 4 independently selected R$^{74}$ substituents;

each R$^{b7}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^{74}$ substituents;

each R$^{74}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a71}$, SR$^{a71}$, NHOR$^{a71}$, C(O)R$^{b71}$, C(O)NR$^{c71}$R$^{d71}$, C(O)OR$^{a71}$, OC(O)R$^{b71}$, OC(O)NR$^{c71}$R$^{d71}$, NR$^{c71}$R$^{d71}$, NR$^{c71}$C(O)R$^{b71}$, NR$^{c71}$C(O)OR$^{a71}$, NR$^{c71}$C(O)NR$^{c71}$R$^{d71}$, NR$^{c71}$S(O)NR$^{c71}$R$^{d71}$, NR$^{c71}$S(O)R$^{b71}$, NR$^{c71}$S(O)$_2$R$^{b71}$, NR$^{c71}$S(O)$_2$ NR$^{c71}$R$^{d71}$, S(O)R$^{b71}$, S(O)NR$^{c71}$R$^{d71}$, S(O)$_2$R$^{b71}$, and S(O)$_2$NR$^{c71}$R$^{d71}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{7B}$ substituents;

each R$^{a71}$, R$^{c71}$, and R$^{d7}$ is independently selected from H, C$_{1-6}$ alkyl, C$_{1-6}$ haloalkyl, C$_{2-6}$ alkenyl, C$_{2-6}$ alkynylC$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{7B}$ substituents;

each R$^{b7}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^{7B}$ substituents;

each R$^{7B}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a72}$, SR$^{a72}$, NHOR$^{a72}$, C(O)R$^{b72}$, C(O)NR$^{c72}$R$^{d72}$, C(O)OR$^{a72}$, OC(O)R$^{b72}$, OC(O)NR$^{c72}$R$^{d72}$, NR$^{c72}$R$^{d72}$, NR$^{c72}$C(O)R$^{b72}$, NR$^{c72}$C(O)OR$^{a72}$, NR$^{c72}$C(O)NR$^{c72}$R$^{d72}$, NR$^{c72}$S(O)NR$^{c72}$R$^{d72}$, NR$^{c72}$S(O)R$^{b72}$, NR$^{c72}$S(O)$_2$R$^{b72}$, NR$^{c72}$S(O)$_2$NR$^{c72}$R$^{d72}$, S(O)R$^{b72}$, S(O)NR$^{c72}$R$^{d72}$, S(O)$_2$R$^{b72}$, and S(O)$_2$NR$^{c72}$R$^{d72}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{a72}$, R$^{c72}$, and R$^{d72}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{b72}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^G$ substituents;

each R$^G$ is independently selected from D, OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl) amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-3}$ alkoxycarbonyl, C$_{1-3}$ alkylcarbonyloxy, C$_{1-3}$ alkylcarbonylamino, C$_{1-3}$ alkoxycarbonylamino, C$_{1-3}$ alkylaminocarbonyloxy, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino.

In some embodiments, L$^2$ of the previous embodiment is NHC(O) or N(CH$_3$)C(O).

In some embodiments:

each ═══ is independently a single or a double bond;

k is 1 or 2;

n is 0 or 1;

p is 0, 1, or 2;

X is CH or N;

Y is CR$^4$ or N; and W is CR$^2$; or

Y is NR$^{4y}$, O or S; and W is absent;

Ring A is a monocyclic 5-6 membered heteroaryl ring;

Ring B and Ring C together form a fused bicycle;

Ring B is phenyl, 6-membered heteroaryl, or 6-membered heterocycloalkyl, each of which is optionally substituted with 1, 2, or 3 independently selected R$^5$ substituents; and Ring C is 5-membered heteroaryl, each of which is optionally substituted with 1 or 2 independently selected R$^6$ substituents; or Ring B is 5-membered heteroaryl or 5-membered heterocycloalkyl, each of which is optionally substituted with 1, 2, 3, or 4 independently selected R$^5$ substituents; and Ring C is phenyl or a 6-membered heteroaryl, each of which is optionally substituted with 1, 2, or 3 independently selected R$^6$ substituents; or Ring B is cyclopentyl, which is optionally substituted with 1, 2, 3, or 4 independently selected R$^5$ substituents; and Ring C is 6-membered heteroaryl, each of which is optionally substituted with 1, 2, or 3 independently selected R$^6$ substituents;

each R$^W$, attached to the C ring, is independently:

each $L^1$ is NHC(O);

each $L^2$ is a bond, NHC(O), N(tetrahydrofuran)C(O), or N(CH$_3$)C(O);

each $L^4$ is NHC(O);

each $X^1$ independently is O or NR$^9$;

each q is independently 0 or 1;

each R$^{81}$, R$^{82}$, and R$^{83}$ are independently selected from H, D, halo, CN, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a8}$, SR$^{a8}$, C(O)R$^{b8}$, C(O)NR$^{c8}$R$^{d8}$, C(O)OR$^{a8}$, OC(O)R$^{b8}$, OC(O)NR$^{c8}$R$^{d8}$, NR$^{c8}$R$^{d8}$, NR$^{c8}$C(O)R$^{b8}$, NR$^{c8}$C(O)OR$^{a8}$, NR$^{c8}$C(O)NR$^{c8}$R$^{d8}$, NR$^{c8}$S(O)NR$^{c8}$R$^{d8}$, NR$^{c8}$S(O)R$^{b8}$, NR$^{c8}$S(O)$_2$R$^{b8}$, NR$^{c8}$S(O)$_2$ NR$^{c8}$R$^{d8}$, S(O)R$^{b8}$, S(O)NR$^{c8}$R$^{d8}$, S(O)$_2$R$^{b8}$, and S(O)$_2$NR$^{c8}$R$^{d8}$; wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted by 1, 2, 3, or 4 independently selected R$^G$ substituents;

each R$^{a8}$, R$^{c8}$, and R$^{d8}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{b8}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^G$ substituents;

each R$^{84}$ is independently H, D, halo, CN, OH, C$_{1-3}$ alkoxy, C$_{1-3}$ haloalkoxy, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, or 5-10 membered heteroaryl-C$_{1-4}$ alkyl, each of which is optionally substituted by 1, 2, 3, or 4 independently selected R$^G$ substituents;

each R$^9$ is independently selected from H, halo, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, 5-10 membered heteroaryl-C$_{1-4}$ alkyl, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O)NR$^{c9}$R$^{d9}$, NR$^{c9}$S(O)NR$^{c9}$R$^{d9}$, NR$^{c9}$S(O) R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, and S(O)$_2$NR$^{c9}$R$^{d9}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^{9A}$ substituents;

each R$^{a9}$, R$^{c9}$, and R$^{d9}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{9A}$ substituents;

each R$^{b9}$ is independently selected from C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, which are each optionally substituted with 1, 2, 3, or 4 independently selected R$^{9A}$ substituents;

each R$^{9A}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a91}$, SR$^{a91}$, NHOR$^{a91}$, C(O)R$^{b91}$, C(O)NR$^{c91}$R$^{d91}$, C(O)OR$^{a91}$, OC(O)R$^{b91}$, OC(O)NR$^{c91}$R$^{d91}$, NR$^{c91}$R$^{d91}$, NR$^{c91}$C(O)R$^{b91}$, NR$^{c91}$C(O)OR$^{a91}$, NR$^{c91}$C(O)NR$^{c91}$R$^{d91}$, NR$^{c91}$S(O)NR$^{c91}$R$^{d91}$, NR$^{c91}$S(O)R$^{b91}$, NR$^{c91}$S(O)$_2$R$^{b91}$, NR$^{c91}$S(O)$_2$NR$^{c91}$R$^{d91}$, S(O)R$^{b91}$, S(O)NR$^{c91}$R$^{d91}$, S(O)$_2$R$^{b91}$, and S(O)$_2$NR$^{c91}$R$^{d91}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{9B}$ substituents;

each R$^{a91}$, R$^{c91}$, and R$^{d91}$ is independently selected from H, C$_{1-6}$ alkyl, C$_{1-6}$ haloalkyl, C$_{2-6}$ alkenyl, C$_{2-6}$ alkynylC$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{9B}$ substituents;

each R$^{b91}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a92}$, $SR^{a92}$, $NHOR^{a92}$, $C(O)R^{b92}$, $C(O)NR^{c92}R^{d92}$, $C(O)OR^{a92}$, $OC(O)R^{b92}$, $OC(O)NR^{c92}R^{d92}$, $NR^{c92}R^{d92}$, $NR^{c92}C(O)R^{b92}$, $NR^{c92}C(O)OR^{a92}$, $NR^{c92}C(O)NR^{c92}R^{d92}$, $NR^{c92}S(O)NR^{c92}R^{d92}$, $NR^{c92}S(O)R^{b92}$, $NR^{c92}S(O)_2R^{b92}$, $NR^{c92}S(O)_2NR^{c92}R^{d92}$, $S(O)R^{b92}$, $S(O)NR^{c92}R^{d92}$, $S(O)_2R^{b92}$, and $S(O)_2NR^{c92}R^{d92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, 4-10 membered heterocycloalkyl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, and $OS(O)_2R^{b1}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{14}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, are each optionally substituted with 1, 2, 3, or 4 independently selected $R^{14}$ substituents;

or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{14}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, which are each optionally substituted with 1, 2, 3, or 4 independently selected $R^{14}$ substituents;

each $R^{14}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)$ $OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1C}$ substituents;

each $R^{1C}$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^2$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, and $OS(O)_2R^{b2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents;

each $R^{2A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents;

each $R^{b21}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^3$ is H or $C_{1-6}$ alkyl;

$R^4$ is H, D, halo, CN, or $C_{1-6}$ alkyl;

$R^{4y}$ is H, $C_{1-4}$ alkyl, or $C_{1-4}$ haloalkyl;

each $R^5$ is independently selected from oxo, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $OS(O)_2R^{b5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents;

each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)$ $NR^{c51}R^{d51}$, $C(O)OR^{a51}$, $OC(O)R^{b51}$, $OC(O)$ $NR^{c51}R^{d51}$, $NR^{c51}R^{d51}$, $NR^{c51}C(O)R^{b51}$, $NR^{c51}C(O)$ $OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2$ $NR^{c51}R^{d51}$, $S(O)R^{b51}$, $S(O)NR^{c51}R^{d51}$, $S(O)_2R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ substituents;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)$ $NR^{c52}R^{d52}$, $C(O)OR^{a52}$, $OC(O)R^{b52}$, $OC(O)$ $NR^{c52}R^{d52}$, $NR^{c52}R^{d52}$, $NR^{c52}C(O)R^{b52}$, $NR^{c52}C(O)$ $OR^{a52}$, $NR^{c52}C(O)NR^{c52}R^{d52}$, $NR^{c52}S(O)NR^{c52}R^{d52}$, $NR^{c52}S(O)R^{b52}$, $NR^{c52}S(O)_2R^{b52}$, $NR^{c52}S(O)_2$ $NR^{c52}R^{d52}$, $S(O)R^{b52}$, $S(O)NR^{c52}R^{d52}$, $S(O)_2R^{b52}$, and $S(O)_2NR^{c52}R^{d52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^6$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a6}$, $SR^{a6}$, $NHOR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{6A}$ substituents;

or, any $R^{c6}$ and $R^{d6}$ attached to the same N atom, together with the N atom to which they are attached, form a 4-10 membered heterocycloalkyl group, which is optionally substituted with 1, 2, 3, or 4 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{6A}$ substituents;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)$ $NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6B}$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6B}$ substituents;

each $R^{b61}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{6B}$ substituents;

each $R^{6B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a62}$, $SR^{a62}$, $NHOR^{a62}$, $C(O)R^{b62}$, $C(O)NR^{c62}R^{d62}$, $C(O)OR^{a62}$, $OC(O)R^{b62}$, $OC(O)NR^{c62}R^{d62}$, $NR^{c62}R^{d62}$, $NR^{c62}C(O)R^{b62}$, $NR^{c62}C(O)OR^{a62}$, $NR^{c62}C(O)NR^{c62}R^{d62}$, $NR^{c62}S(O)NR^{c62}R^{d62}$, $NR^{c62}S(O)R^{b62}$, $NR^{c62}S(O)_2R^{b62}$, $NR^{c62}S(O)_2NR^{c62}R^{d62}$, $S(O)R^{b62}$, $S(O)NR^{c62}R^{d62}$, $S(O)_2R^{b62}$, and $S(O)_2NR^{c62}R^{d62}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a62}$, $R^{c62}$, and $R^{d62}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{b62}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a7}$, $SR^{a7}$, $NHOR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)NR^{c7}R^{d7}$, $NR^{c7}S(O)R^{b7}$, $NR^{c7}S(O)_2R^{b7}$, $NR^{c7}S(O)_2 NR^{c7}R^{d7}$, $S(O)R^{b7}$, $S(O)NR^{c7}R^{d7}$, $S(O)_2R^{b7}$, $S(O)_2 NR^{c7}R^{d7}$, and $OS(O)_2R^{b7}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7A}$ substituents;

or, any $R^{c7}$ and $R^{d7}$ attached to the same N atom, together with the N atom to which they are attached, form a 4-7 membered heterocycloalkyl group, which is optionally substituted with 1, 2, 3, or 4 independently selected $R^{7A}$ substituents;

each $R^{b7}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{7A}$ substituents;

each $R^{7A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a71}$, $SR^{a71}$, $NHOR^{a71}$, $C(O)R^{b71}$, $C(O)NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)R^{b71}$, $NR^{c71}C(O)OR^{a71}$, $NR^{c71}C(O)NR^{c71}R^{d71}$, $NR^{c71}S(O)R^{b71}$, $NR^{c71}S(O)_2R^{b71}$, $NR^{c71}S(O)_2 NR^{c71}R^{d71}$, $S(O)R^{b71}$, $S(O)NR^{c71}R^{d71}$, $S(O)_2R^{b71}$, and $S(O)_2NR^{c71}R^{d71}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{7B}$ substituents;

each $R^{b7}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{7B}$ substituents;

each $R^{7B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a72}$, $SR^{a72}$, $NHOR^{a72}$, $C(O)R^{b72}$, $C(O)NR^{c72}R^{d72}$, $C(O)OR^{a72}$, $OC(O)R^{b72}$, $OC(O)NR^{c72}R^{d72}$, $NR^{c72}R^{d72}$, $NR^{c72}C(O)R^{b72}$, $NR^{c72}C(O)OR^{a72}$, $NR^{c72}C(O)NR^{c72}R^{d72}$, $NR^{c72}S(O)NR^{c72}R^{d72}$, $NR^{c72}S(O)R^{b72}$, $NR^{c72}S(O)_2R^{b72}$, $NR^{c72}S(O)_2 NR^{c72}R^{d72}$, $S(O)R^{b72}$, $S(O)NR^{c72}R^{d72}$, $S(O)_2R^{b72}$, and $S(O)_2NR^{c72}R^{d72}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{b72}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^G$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments of the previous embodiment, $L^2$ is NHC(O) or N($CH_3$)C(O).

In some embodiments:

each ═ is independently a single or a double bond;

k is 1 or 2;

n is 0 or 1;

p is 0, 1, or 2;

X is CH or N;

Y is $CR^4$ or N; and W is $CR^2$; or

Y is $NR^{4y}$, O or S; and W is absent;

Ring A is a monocyclic 5-6 membered heteroaryl ring;

Ring B and Ring C together form a fused bicycle;

Ring B is phenyl, 6-membered heteroaryl, or 6-membered heterocycloalkyl, each of which is optionally substituted with 1, 2, or 3 independently selected $R^5$ substituents; and Ring C is 5-membered heteroaryl, each of which is optionally substituted with 1 or 2 independently selected $R^6$ substituents; or Ring B is 5-membered heteroaryl or 5-membered heterocycloalkyl, each of which is optionally substituted with 1, 2, 3, or 4 independently selected $R^5$ substituents; and Ring C is phenyl or a 6-membered heteroaryl, each of which is optionally substituted with 1, 2, or 3 independently selected $R^6$ substituents; or Ring B is cyclopentyl, which is optionally substituted with 1, 2, 3, or 4 independently selected $R^5$ substituents; and Ring C is 6-membered heteroaryl, each of which is optionally substituted with 1, 2, or 3 independently selected $R^6$ substituents;

each $R^W$, attached to the C ring, is independently:

-continued each $L^1$ is NHC(O);

each $L^2$ is a bond, NHC(O), N(tetrahydrofuran)C(O), or N($CH_3$)C(O);

each $L^4$ is NHC(O);

each $L^6$ is NHC(O) or C(O)

each $X^1$ independently is O or $NR^9$ each q is independently 0 or 1;

each Ring D is independently a 4-8 membered heterocycloalkyl, each of which is optionally substituted with 1, 2, 3, or 4 independently selected $C_{1-6}$ alkyl groups;

each $R^{81}$, $R^{82}$, and $R^{83}$ are independently selected from H, D, halo, CN, $OR^{a8}$, C(O)$OR^{a8}$, $C_{1-6}$ alkyl, $C_{2-6}$ alkenyl, $C_{2-6}$ alkynyl, $C_{1-6}$ haloalkyl, and $C_{3-4}$cycloalkyl; wherein said $C_{1-6}$ alkyl, $C_{2-6}$ alkenyl, $C_{2-6}$ alkynyl, $C_{1-6}$ haloalkyl, and $C_{3-4}$cycloalkyl are each optionally substituted by 1, 2, 3, or 4 independently selected $R^G$ substituents;

each $R^{a8}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^G$ substituents;

each $R^{84}$ is independently H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, or 5-10 membered heteroaryl-$C_{1-4}$ alkyl, each of which is optionally substituted by 1, 2, 3, or 4 independently selected $R^G$ substituents;

each $R^9$ is independently selected from H, halo, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(O)$$R^{b9}$, $C(O)NR^{c9}R^{d9}$, $C(O)OR^{a9}$, $OC(O)R^{b9}$, $OC(O)$$NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)NR^{c9}R^{d9}$, $NR^{c9}S(O)$$R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9A}$ substituents;

each $R^{9A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)$$OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)$$NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{b91}$, and $S(O)_2NR^{c91}R^{d91}$;

each $R^{a91}$, $R^{c91}$, and $R^{d91}$ is independently selected from H, $C_{1-6}$ alkyl, and $C_{1-6}$ haloalkyl;

each $R^{b91}$ is independently selected from $C_{1-6}$ alkyl and $C_{1-6}$ haloalkyl;

$R^1$ is selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $OR^{a1}$, and $NR^{c1}R^{d1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, and 4-7 membered heterocycloalkyl are each optionally substituted with 1, 2, 3, or 4 independently selected $R^A$ substituents;

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{1A}$ substituents;

each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)$$NR^{c11}R^{d11}$, $C(O)OR^{a11}$, $OC(O)R^{b11}$, $OC(O)$$NR^{c11}R^{d11}$, $NR^{c11}R^{d11}$, $NR^{c11}C(O)R^{b11}$, $NR^{c11}C(O)$$OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2$$NR^{c11}R^{d11}$, $S(O)R^{b11}$, $S(O)NR^{c11}R^{d11}$, $S(O)_2R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $C_{1-6}$ alkyl, $C_{2-6}$ alkenyl, $C_{2-6}$ alkynyl, $C_{1-6}$ haloalkyl, $OR^{a12}$, $SR^{a12}$, $NHOR^{a12}$, $C(O)R^{b12}$, $C(O)NR^{c12}R^{d12}$, $C(O)$$OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)$$NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$;

each $R^{a12}$, $R^{c12}$, and $R^{d12}$ is independently selected from H, $C_{1-6}$ alkyl, $C_{1-6}$ haloalkyl, $C_{2-6}$ alkenyl, and $C_{2-6}$ alkynyl;

each $R^{b12}$ is independently selected from $C_{1-6}$ alkyl, $C_{1-6}$ haloalkyl, $C_{2-6}$ alkenyl, and $C_{2-6}$ alkynyl;

$R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl, 4-6 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, and 5-6 membered heteroaryl are each optionally substituted with 1, 2, 3, or 4 independently selected $R^{2A}$ substituents;

each $R^{24}$ is independently selected from D, halo, CN, $C_{1-6}$ alkyl, $C_{2-6}$ alkenyl, $C_{2-6}$ alkynyl, $C_{1-6}$ haloalkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$;

each $R^{a21}$, $R^{c21}$, and $R^{b21}$ is independently selected from H, $C_{1-6}$ alkyl, and $C_{1-6}$ haloalkyl; each $R^{b21}$ is independently selected from $C_{1-6}$ alkyl and $C_{1-6}$ haloalkyl;

$R^3$ is H or $CH_3$;

$R^4$ is H, D, halo, CN, or $C_{1-6}$ alkyl;

$R^{4y}$ is H, $C_{1-4}$ alkyl, or $C_{1-4}$ haloalkyl;

each $R^5$ is independently selected from oxo, D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, and $OS(O)_2R^{b5}$; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, and $C_{3-4}$ cycloalkyl, which are each optionally substituted with 1, 2, 3, or 4 independently selected $R^{5A}$ substituents;

each $R^{5A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl;

each $R^{b51}$ is independently selected from $C_{1-6}$ alkyl and $C_{1-6}$ haloalkyl;

each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, 4-7 membered heterocycloalkyl, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$; wherein said $C_{1-6}$ alkyl, $C_{2-6}$ alkenyl, $C_{2-6}$ alkynyl, $C_{1-6}$ haloalkyl, $C_{3-4}$ cycloalkyl, and 4-7 membered heterocycloalkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-4}$ cycloalkyl, and 4-7 membered heterocycloalkyl which are each optionally substituted with 1, 2, 3, or 4 independently selected $R^{6A}$ substituents;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl;

each $R^{b61}$ is independently selected from $C_{1-6}$ alkyl and $C_{1-6}$ haloalkyl;

each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $OR^{a7}$, $SR^{a7}$, $NHOR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)NR^{c7}R^{d7}$, $NR^{c7}S(O)R^{b7}$, $NR^{c7}S(O)_2R^{b7}$, $NR^{c7}S(O)_2 NR^{c7}R^{d7}$, $S(O)R^{b7}$, $S(O)NR^{c7}R^{d7}$, $S(O)_2R^{b7}$, $S(O)_2 NR^{c7}R^{d7}$, and $OS(O)_2R^{b7}$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl, are each optionally substituted with 1, 2, 3, or 4 independently selected $R^{7A}$ substituents;

each $R^{b7}$ is independently selected from $C_{1-6}$ alkyl, $C_{1-6}$ haloalkyl, $C_{2-6}$ alkenyl, and $C_{2-6}$ alkynyl, which are each optionally substituted with 1, 2, 3, or 4 independently selected $R^{7A}$ substituents;

each $R^{7A}$ is independently selected from D, halo, CN, $C_{1-6}$ alkyl, $C_{2-6}$ alkenyl, $C_{2-6}$ alkynyl, $C_{1-6}$ haloalkyl, $OR^{a71}$, $SR^{a71}$, $NHOR^{a71}$, $C(O)R^{b71}$, $C(O)NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)R^{b71}$, $NR^{c71}C(O)OR^{a71}$, $NR^{c71}C(O)NR^{c71}R^{d71}$, $NR^{c71}S(O)NR^{c71}R^{d71}$, $NR^{c71}S(O)R^{b71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2R^{b71}$, and $S(O)_2NR^{c71}R^{d71}$;

each $R^{a71}$, $R^{c71}$, and $R^{d71}$ is independently selected from H, $C_{1-6}$ alkyl, and $C_{1-6}$ haloalkyl;

each $R^{b71}$ is independently selected from $C_{1-6}$ alkyl and $C_{1-6}$ haloalkyl; and each $R^G$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, $HO$—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)

amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments of the previous embodiment, $L^2$ is NHC(O) or N(CH$_3$)C(O)

In some embodiments of the previous two embodiments, each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{6A}$ substituents; and each $R^{b6}$ is independently selected from $C_{1-6}$ alkyl, $C_{1-6}$ haloalkyl, $C_{2-6}$ alkenyl, $C_{2-6}$ alkynyl, and $C_{3-4}$ cycloalkyl, which are each optionally substituted with 1, 2, 3, or 4 independently selected $R^{6A}$ substituents.

In some embodiments:

each $\equiv$ is independently a single or a double bond;

k is 1 or 2;

n is 0 or 1;

p is 0, 1, or 2;

X is CH or N;

Y is $CR^4$ or N; and W is $CR^2$; or

Y is $NR^{4y}$, O or S; and W is absent;

Ring A is a monocyclic 5-6 membered heteroaryl ring;

Ring B and Ring C together form a fused bicycle;

Ring B is phenyl, 6-membered heteroaryl, or 6-membered heterocycloalkyl, each of which is optionally substituted with 1, 2, or 3 independently selected $R^5$ substituents; and Ring C is 5-membered heteroaryl, each of which is optionally substituted with 1 or 2 independently selected $R^6$ substituents; or Ring B is 5-membered heteroaryl or 5-membered heterocycloalkyl, each of which is optionally substituted with 1, 2, 3, or 4 independently selected $R^5$ substituents; and Ring C is phenyl or a 6-membered heteroaryl, each of which is optionally substituted with 1, 2, or 3 independently selected $R^6$ substituents; or Ring B is cyclopentyl, which is optionally substituted with 1, 2, 3, or 4 independently selected $R^5$ substituents; and Ring C is 6-membered heteroaryl, each of which is optionally substituted with 1, 2, or 3 independently selected $R^6$ substituents;

each $R^W$, attached to the C ring, is independently:

each $L^1$ is NHC(O);

each $L^2$ is a bond, NHC(O), N(tetrahydrofuran)C(O), or N(CH$_3$)C(O);

each $L^4$ is NHC(O);

each $X^1$ independently is O or $NR^9$;

each q is independently 0 or 1;

each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, $C_{1-6}$ haloalkyl, $C_{3-4}$ cycloalkyl, and 4-7 membered heterocycloalkyl-$C_{1-4}$ alkyl; wherein said $C_{1-6}$ alkyl, $C_{2-6}$ alkenyl, $C_{2-6}$ alkynyl, $C_{1-6}$ haloalkyl, $C_{3-4}$ cycloalkyl, and 4-7 membered heterocycloalkyl-$C_{1-4}$ alkyl are each optionally substituted by 1, 2, 3, or 4 independently selected $R^G$ substituents;

each $R^{a8}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^G$ substituents;

each $R^{84}$ is independently H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, or 5-10 membered heteroaryl-$C_{1-4}$ alkyl, each of which is optionally substituted by 1, 2, 3, or 4 independently selected $R^G$ substituents;

each $R^9$ is independently selected from H, halo, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9A}$ substituents;

each $R^{9A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{b91}$, and $S(O)_2NR^{c91}R^{d91}$;

each $R^{a91}$, $R^{c91}$, and $R^{d91}$ is independently selected from H, $C_{1-6}$ alkyl, and $C_{1-6}$ haloalkyl;

each $R^{b91}$ is independently selected from $C_{1-6}$ alkyl and $C_{1-6}$ haloalkyl;

$R^1$ is selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $OR^{a1}$, and $NR^{c1}R^{d1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, and 4-7 membered heterocycloalkyl are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{1A}$ substituents;

each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $C_{1-6}$ alkyl, $C_{2-6}$ alkenyl, $C_{2-6}$ alkynyl, $C_{1-6}$ haloalkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$;

each $R^{a12}$, $R^{c12}$, and $R^{d12}$ is independently selected from H, $C_{1-6}$ alkyl, $C_{1-6}$ haloalkyl, $C_{2-6}$ alkenyl, and $C_{2-6}$ alkynyl;

each $R^{b12}$ is independently selected from $C_{1-6}$ alkyl, $C_{1-6}$ haloalkyl, $C_{2-6}$ alkenyl, and $C_{2-6}$ alkynyl;

$R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl, 4-6 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, and 5-6 membered heteroaryl are each optionally substituted with 1, 2, 3, or 4 independently selected $R^{2A}$ substituents;

each $R^{2A}$ is independently selected from D, halo, CN, $C_{1-6}$ alkyl, $C_{2-6}$ alkenyl, $C_{2-6}$ alkynyl, $C_{1-6}$ haloalkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$;

each $R^{a21}$, $R^{c21}$, and $R^{d21}$ is independently selected from H, $C_{1-6}$ alkyl, and $C_{1-6}$ haloalkyl;

each $R^{b21}$ is independently selected from $C_{1-6}$ alkyl and $C_{1-6}$ haloalkyl;

$R^3$ is H or $CH_3$;

$R^4$ is H, D, halo, CN, or $C_{1-6}$ alkyl;

$R^{4y}$ is H, $C_{1-4}$ alkyl, or $C_{1-4}$ haloalkyl;

each $R^5$ is independently selected from oxo, D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2$ $R^{b5}$, $S(O)_2NR^{c5}R^{d5}$, and $OS(O)_2R^{b5}$; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, and $C_{3-4}$ cycloalkyl, which are each optionally substituted with 1, 2, 3, or 4 independently selected $R^{A}$ substituents;

each $R^{5A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl;

each $R^{b51}$ is independently selected from $C_{1-6}$ alkyl and $C_{1-6}$ haloalkyl;

each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, 4-7 membered heterocycloalkyl, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$; wherein said $C_{1-6}$ alkyl, $C_{2-6}$ alkenyl, $C_{2-6}$ alkynyl, $C_{1-6}$ haloalkyl, $C_{3-4}$ cycloalkyl, and 4-7 membered heterocycloalkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-4}$ cycloalkyl, and 4-7 membered heterocycloalkyl which are each optionally substituted with 1, 2, 3, or 4 independently selected $R^{6A}$ substituents;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)$ $OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl;

each $R^{b61}$ is independently selected from $C_{1-6}$ alkyl and $C_{1-6}$ haloalkyl;

each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $OR^{a7}$, $SR^{a7}$, $NHOR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)NR^{c7}R^{d7}$, $NR^{c7}S(O)R^{b7}$, $NR^{c7}S(O)_2R^{b7}$, $NR^{c7}S(O)_2$ $NR^{c7}R^{d7}$, $S(O)R^{b7}$, $S(O)NR^{c7}R^{d7}$, $S(O)_2R^{b7}$, $S(O)_2$ $NR^{c7}R^{d7}$, and $OS(O)_2R^{b7}$, wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^{7A}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl, are each optionally substituted with 1, 2, 3, or 4 independently selected $R^{7A}$ substituents;

each $R^{b7}$ is independently selected from $C_{1-6}$ alkyl, $C_{1-6}$ haloalkyl, $C_{2-6}$ alkenyl, and $C_{2-6}$ alkynyl, which are each optionally substituted with 1, 2, 3, or 4 independently selected $R^{7A}$ substituents;

each $R^{7A}$ is independently selected from D, halo, CN, $C_{1-6}$ alkyl, $C_{2-6}$ alkenyl, $C_{2-6}$ alkynyl, $C_{1-6}$ haloalkyl, $OR^{a71}$, $SR^{a71}$, $NHOR^{a71}$, $C(O)R^{b71}$, $C(O)NR^{c71}R^{d71}$, $C(O)OR^{a71}$, $OC(O)R^{b71}$, $OC(O)NR^{c71}R^{d71}$, $NR^{c71}R^{d71}$, $NR^{c71}C(O)R^{b71}$, $NR^{c71}C(O)OR^{a71}$, $NR^{c71}C(O)NR^{c71}R^{d71}$, $NR^{c71}S(O)NR^{c71}R^{d71}$, $NR^{c71}S(O)R^{b71}$, $NR^{c71}S(O)_2R^{b71}$, $NR^{c71}S(O)_2NR^{c71}R^{d71}$, $S(O)R^{b71}$, $S(O)NR^{c71}R^{d71}$, $S(O)_2R^{b71}$, and $S(O)_2NR^{c71}R^{d71}$;

each $R^{a71}$, $R^{c71}$, and $R^{d71}$ is independently selected from H, $C_{1-6}$ alkyl, and $C_{1-6}$ haloalkyl;

each $R^{b71}$ is independently selected from $C_{1-6}$ alkyl and $C_{1-6}$ haloalkyl; and each $R^G$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments of the previous embodiment, $L^2$ is NHC(O) or N(CH$_3$)C(O).

In some embodiments of the previous two embodiments, each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, $C_{1-6}$ haloalkyl, and $C_{3-4}$ cycloalkyl; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^G$ substituents.

In some embodiments of the previous three embodiments, each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2R^{b6}$; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{6A}$ substituents; and each $R^{b6}$ is independently selected from $C_{1-6}$ alkyl, $C_{1-6}$ haloalkyl, $C_{2-6}$ alkenyl, $C_{2-6}$ alkynyl, and $C_{3-4}$ cycloalkyl, which are each optionally substituted with 1, 2, 3, or 4 independently selected $R^{6A}$ substituents.

In some embodiments:

each $\equiv\equiv$ is independently a single or a double bond;

k is 1 or 2;

n is 0 or 1;

p is 0, 1, or 2;

X is CH or N;

Y is $CR^4$ or N; and W is $CR^2$; or

Y is $NR^{4y}$, O or S; and W is absent;

Ring A is a monocyclic 5-6 membered heteroaryl ring;

Ring B and Ring C together form a fused bicycle;

Ring B is phenyl, 6-membered heteroaryl, or 6-membered heterocycloalkyl, each of which is optionally substituted with 1, 2, or 3 independently selected $R^5$ substituents; and Ring C is 5-membered heteroaryl, each of which is optionally substituted with 1 or 2 independently selected $R^6$ substituents; or Ring B ring is 5-membered heteroaryl or 5-membered heterocycloalkyl, each of which is optionally substituted with 1, 2, 3, or 4 independently selected $R^5$ substituents; and Ring C is phenyl or a 6-membered heteroaryl, each of which is optionally substituted with 1, 2, or 3 independently selected $R^6$ substituents; or Ring B ring is cyclopentyl, which is optionally substituted with 1, 2, 3, or 4 independently selected $R^5$ substituents; and Ring C ring is 6-membered heteroaryl, each of which is optionally substituted with 1, 2, or 3 independently selected $R^6$ substituents;

each $R^W$, attached to the C ring, is independently:

-continued each $L^1$ is NHC(O);

each $L^2$ is independently a bond, NHC(O), N(tetrahydrofuran)C(O), or $N(CH_3)C(O)$;

each $L^6$ is independently NHC(O) or C(O);

each $X^1$ is O;

each Ring D is independently a monocyclic 4-7 membered heterocycloalkyl, bicyclic 7-10 membered heterocycloalkyl, or a spirocyclic 7-10 membered heterocycloalkyl, each of which is optionally substituted by 1 or 2 independently selected $C_{1-6}$ alkyl groups;

each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, $C_{1-6}$ haloalkyl, and 4-7 membered heterocycloalkyl-$C_{1-4}$ alkyl; wherein said $C_{1-6}$ alkyl, $C_{2-6}$ alkenyl, $C_{2-6}$ alkynyl, $C_{1-6}$ haloalkyl, and 4-7 membered heterocycloalkyl-$C_{1-4}$ alkyl are each optionally substituted by 1, 2, 3, or 4 independently selected $R^G$ substituents;

each $R^{a8}$ is independently selected from H, $C_{1-6}$ alkyl, $C_{1-6}$ haloalkyl, $C_{2-6}$ alkenyl, and $C_{2-6}$ alkynyl;

each $R^{84}$ is independently selected from H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, and $C_{1-6}$ haloalkyl, each of which is optionally substituted by 1, 2, 3, or 4 independently selected $R^G$ substituents;

$R^1$ is selected from H, D, halo, CN, $C_{1-6}$ alkyl, $C_{1-6}$ haloalkyl, 4-7 membered heterocycloalkyl, $OR^{a1}$, and $NR^{c1}R^{d1}$, wherein said $C_{1-6}$ alkyl, $C_{1-6}$ haloalkyl, and 4-7 membered heterocycloalkyl are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{1A}$ substituents;

each $R^{1A}$ is independently selected from D, halo, CN, $C_{1-6}$ alkyl, $C_{2-6}$ alkenyl, $C_{2-6}$ alkynyl, $C_{1-6}$ haloalkyl, $OR^{a11}$, $SR^{a11}$, $NHOR^{a11}$, $C(O)R^{b11}$, $C(O)NR^{c11}R^{d11}$, $C(O)$ $OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)$ $NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$;

each $R^{a11}$, $R^{c11}$, and $R^{d11}$ is independently selected from H, $C_{1-6}$ alkyl, and $C_{1-6}$ haloalkyl;

each $R^{b11}$ is independently selected from $C_{1-6}$ alkyl and $C_{1-6}$ haloalkyl;

$R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl, 4-6 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, and 5-6 membered heteroaryl are each optionally substituted with 1 or 2 independently selected $R^{2A}$ substituents;

each $R^{2A}$ is independently selected from D, halo, CN, $C_{1-6}$ alkyl, $C_{2-6}$ alkenyl, $C_{2-6}$ alkynyl, $C_{1-6}$ haloalkyl, $OR^{a21}$, $SR^{a21}$, $NHOR^{a21}$, $C(O)R^{b21}$, $C(O)NR^{c21}R^{d21}$, $C(O)$ $OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)$ $NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$;

each $R^{a21}$, $R^{c21}$, and $R^{d21}$ is independently selected from H, $C_{1-6}$ alkyl, and $C_{1-6}$ haloalkyl;

each $R^{b21}$ is independently selected from $C_{1-6}$ alkyl and $C_{1-6}$ haloalkyl;

$R^3$ is H or $CH_3$;

$R^4$ is H, D, halo, CN, or $C_{1-6}$ alkyl;

$R^{4y}$ is H, $C_{1-4}$ alkyl, or $C_{1-4}$ haloalkyl;

each $R^5$ is independently selected from oxo, D, halo, CN, $C_{1-6}$ alkyl, $C_{2-6}$ alkenyl, $C_{2-6}$ alkynyl, $C_{1-6}$ haloalkyl, $OR^{a5}$, and $NR^{c5}R^{d5}$; wherein said $C_{1-6}$ alkyl, $C_{2-6}$ alkenyl, $C_{2-6}$ alkynyl, and $C_{1-6}$ haloalkyl are each optionally substituted by 1 or 2 independently selected $R^{5A}$ substituents;

each $R^{a5}$, $R^{c5}$, and $R^{d5}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{5A}$ substituents;

each $R^{5A}$ is independently selected from D, halo, CN, $C_{1-6}$ alkyl, $C_{2-6}$ alkenyl, $C_{2-6}$ alkynyl, $C_{1-6}$ haloalkyl, $OR^{a51}$, $SR^{a51}$, $NHOR^{a51}$, $C(O)R^{b51}$, $C(O)NR^{c51}R^{d51}$, $C(O)$ $OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)$ $NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl;

each $R^{b51}$ is independently selected from $C_{1-6}$ alkyl and $C_{1-6}$ haloalkyl;

each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, 4-7 membered heterocycloalkyl, $OR^{a6}$, $C(O)R^{b6}$, and $NR^{c6}R^{d6}$; wherein said $C_{1-6}$ alkyl, $C_{2-6}$ alkenyl, $C_{2-6}$ alkynyl, $C_{1-6}$ haloalkyl, $C_{3-4}$ cycloalkyl, and 4-7 membered heterocycloalkyl, are each optionally substituted by 1, 2, or 3 independently selected $R^{6A}$ substituents;

each $R^{a6}$, $R^{c6}$, and $R^{d6}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-4}$ cycloalkyl, and 4-7 membered heterocycloalkyl, which are each optionally substituted with 1 or 2 independently selected $R^{6A}$ substituents;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $OR^{a61}$, $SR^{a61}$, $NHOR^{a61}$, $C(O)R^{b61}$, $C(O)$ $NR^{c61}R^{d61}$, $C(O)OR^{a61}$, $OC(O)R^{b61}$, $OC(O)$ $NR^{c61}R^{d61}$, $NR^{c61}R^{d61}$, $NR^{c61}C(O)R^{b61}$, $NR^{c61}C(O)$ $OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2$ $NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl;

each $R^{b61}$ is independently selected from $C_{1-6}$ alkyl and $C_{1-6}$ haloalkyl;

each $R^7$ is independently selected from D, OH, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino; and each $R^G$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments of the previous embodiment, $L^2$ is NHC(O) or N($CH_3$)C(O).

In some embodiments of the previous two embodiments, each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ substituents.

In some embodiments of the previous three embodiments, each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a6}$, and $NR^{c6}R^{d6}$; wherein said $C_{1-6}$ alkyl, $C_{2-6}$ alkenyl, $C_{2-6}$ alkynyl, $C_{1-6}$ haloalkyl, and $C_{3-4}$ cycloalkyl, are each optionally substituted by 1 or 2 independently selected $R^{6A}$ substituents; and each $R^{a6}$, $R^{c6}$, and $R^{d6}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{6A}$ substituents; each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$.

In some embodiments:

each $\stackrel{---}{}$ is independently a single or a double bond;

k is 1 or 2;

n is 0 or 1;

p is 0, 1, or 2;

X is CH or N;

Y is $CR^4$ or N; and W is $CR^2$; or

Y is $NR^{4y}$, O or S; and W is absent;

Ring A is a monocyclic 5-6 membered heteroaryl ring;

Ring B and Ring C together form a fused bicycle;

Ring B is phenyl, 6-membered heteroaryl, or 6-membered heterocycloalkyl, each of which is optionally substituted with 1, 2, or 3 independently selected $R^5$ substituents; and Ring C is 5-membered heteroaryl, each of which is optionally substituted with 1 or 2 independently selected $R^6$ substituents; or Ring B ring is 5-membered heteroaryl or 5-membered heterocycloalkyl, each of which is optionally substituted with 1, 2, 3, or 4 independently selected $R^5$ substituents; and Ring C is phenyl or a 6-membered heteroaryl, each of which is optionally substituted with 1, 2, or 3 independently selected $R^6$ substituents; or Ring B ring is cyclopentyl, which is optionally substituted with 1, 2, 3, or 4 independently selected $R^5$ substituents; and Ring C ring is 6-membered heteroaryl, each of which is optionally substituted with 1, 2, or 3 independently selected $R^6$ substituents;

each $R^W$, attached to the C ring, is independently:

-continued each $L^1$ is NHC(O);

each $L^2$ is independently a bond, NHC(O), N(tetrahydrofuran)C(O), or $N(CH_3)C(O)$;

each $X^1$ is O;

each $R^1$, $R^2$, and $R^3$ are independently selected from H, D, halo, CN, $OR^{a8}$, $C(O)OR^{a8}$, $C_{1-6}$ alkyl, $C_{2-6}$ alkenyl, $C_{2-6}$ alkynyl, $C_{1-6}$ haloalkyl, and 4-7 membered heterocycloalkyl-$C_{1-4}$ alkyl; wherein said $C_{1-6}$ alkyl, $C_{2-6}$ alkenyl, $C_{2-6}$ alkynyl, $C_{1-6}$ haloalkyl, and 4-7 membered heterocycloalkyl-$C_{1-4}$ alkyl are each optionally substituted by 1, 2, 3, or 4 independently selected $R^G$ substituents;

each $R^{a8}$ is independently selected from H, $C_{1-6}$ alkyl, $C_{1-6}$ haloalkyl, $C_{2-6}$ alkenyl, and $C_{2-6}$ alkynyl;

$R^1$ is selected from H, D, halo, CN, $C_{1-6}$ alkyl, $C_{1-6}$ haloalkyl, 4-7 membered heterocycloalkyl, $OR^{a1}$, and $NR^{c1}R^{d1}$, wherein said $C_{1-6}$ alkyl, $C_{1-6}$ haloalkyl, and 4-7 membered heterocycloalkyl are each optionally substituted with 1, 2, 3, or 4 independently selected $R^{14}$ substituents;

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{14}$ substituents;

each $R^{14}$ is independently selected from D, halo, CN, $C_{1-6}$ alkyl, $C_{2-6}$ alkenyl, $C_{2-6}$ alkynyl, $C_{1-6}$ haloalkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$;

each $R^{a11}$, $R^{c11}$, and $R^{d11}$ is independently selected from H, $C_{1-6}$ alkyl, and $C_{1-6}$ haloalkyl;

each $R^{b11}$ is independently selected from $C_{1-6}$ alkyl and $C_{1-6}$ haloalkyl;

$R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl, 4-6 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, and 5-6 membered heteroaryl are each optionally substituted with 1 or 2 independently selected $R^{24}$ substituents;

each $R^{24}$ is independently selected from D, halo, CN, $C_{1-6}$ alkyl, $C_{2-6}$ alkenyl, $C_{2-6}$ alkynyl, $C_{1-6}$ haloalkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$;

each $R^{a21}$, $R^{c21}$, and $R^{d21}$ is independently selected from H, $C_{1-6}$ alkyl, and $C_{1-6}$ haloalkyl;

each $R^{b21}$ is independently selected from $C_{1-6}$ alkyl and $C_{1-6}$ haloalkyl;

$R^3$ is H or $CH_3$;

$R^4$ is H, D, halo, CN, or $C_{1-6}$ alkyl;

$R^{4y}$ is H, $C_{1-4}$ alkyl, or $C_{1-4}$ haloalkyl;

each $R^5$ is independently selected from oxo, D, halo, CN, $C_{1-6}$ alkyl, $C_{2-6}$ alkenyl, $C_{2-6}$ alkynyl, $C_{1-6}$ haloalkyl, $OR^{a5}$, and $NR^{c5}R^{d5}$; wherein said $C_{1-6}$ alkyl, $C_{2-6}$ alkenyl, $C_{2-6}$ alkynyl, and $C_{1-6}$ haloalkyl are each optionally substituted by 1 or 2 independently selected $R^{5A}$ substituents;

each $R^{a5}$, $R^{c5}$, and $R^{d5}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{5A}$ substituents;

each $R^{5A}$ is independently selected from D, halo, CN, $C_{1-6}$ alkyl, $C_{2-6}$ alkenyl, $C_{2-6}$ alkynyl, $C_{1-6}$ haloalkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl;

each $R^{b51}$ is independently selected from $C_{1-6}$ alkyl and $C_{1-6}$ haloalkyl;

each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-6}$ cycloalkyl, 4-7 membered heterocycloalkyl, $OR^{a6}$, $C(O)R^{b6}$, and $NR^{c6}R^{d6}$; wherein said $C_{1-6}$ alkyl, $C_{2-6}$ alkenyl, $C_{2-6}$ alkynyl, $C_{1-6}$ haloalkyl, $C_{3-6}$ cycloalkyl, 4-7 membered heterocycloalkyl, are each optionally substituted by 1, 2, or 3 independently selected $R^{6A}$ substituents;

each $R^{a6}$, $R^{c6}$, and $R^{d6}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-4}$ cycloalkyl, and 4-7 membered heterocycloalkyl, which are each optionally substituted with 1 or 2 independently selected $R^{6A}$ substituents;

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl;

each $R^{b61}$ is independently selected from $C_{1-6}$ alkyl and $C_{1-6}$ haloalkyl;

each $R^7$ is independently selected from D, OH, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino; and each $R^G$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments of the previous embodiment, $L^2$ is NHC(O) or $N(CH_3)C(O)$.

In some embodiments of the previous two embodiments, each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ substituents.

In some embodiments of the previous three embodiments, each $R^6$ is independently selected from D, halo, CN, $C_{1-6}$ alkyl, $C_{2-6}$ alkenyl, $C_{2-6}$ alkynyl, $C_{1-6}$ haloalkyl, $OR^{a6}$, and $NR^{c6}R^{d6}$; wherein said $C_{1-6}$ alkyl, $C_{2-6}$ alkenyl, $C_{2-6}$ alkynyl, and $C_{1-6}$ haloalkyl are each optionally substituted by 1 or 2 independently selected $R^{6A}$ substituents; and each $R^{a6}$, $R^{c6}$, and $R^{d6}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{6A}$ substituents.

In some embodiments:

each ==== is independently a single or a double bond;

k is 1;

n is 0 or 1;

p is 0, 1, or 2;

X is CH or N;

Y is CH or N; and W is $CR^2$; or

Y is S; and W is absent;

Ring A is a monocyclic 5-6 membered heteroaryl ring;

Ring B and Ring C together form a fused bicycle;

Ring B is phenyl or 6-membered heteroaryl, each of which is optionally substituted with 1 or 2 independently selected $R^5$ substituents; and Ring C is 5-membered heteroaryl, each of which is optionally substituted with 1 or 2 independently selected $R^6$ substituents; or Ring B ring is 5-membered heteroaryl or 5-membered heterocycloalkyl, each of which is optionally substituted with 1 or 2 independently selected $R^5$ substituents; and Ring C is phenyl or a 6-membered heteroaryl, each of which is optionally substituted with 1 or 2 independently selected $R^6$ substituents;

$R^W$, attached to the C ring, is:

-continued $L^2$
$R^{81}$, $L^1$ $Br$
$R^{81}$ $R^{82}$, $L^1$ $Cl$
$R^{81}$ $R^{82}$, $L^2$ $X^1$
$R^{81}$, $L^2$
D $L^6$
$R^{82}$
$R^{83}$ $R^{81}$, or $L^2$
D $L^6$
$R^{81}$.

each $L^1$ is NHC(O);

each $L^2$ is independently a bond, NHC(O), N(tetrahydrofuran)C(O), or N(CH$_3$)C(O);

each $L^6$ is independently NHC(O) or C(O);

each $X^1$ is O;

each Ring D is independently a monocyclic 4-7 membered heterocycloalkyl, bicyclic 7-10 membered heterocycloalkyl, or a spirocyclic 7-10 membered heterocycloalkyl, each of which is optionally substituted by 1 or 2 independently selected $C_{1-6}$ alkyl groups;

each $R^{81}$, $R^{82}$, and $R^{83}$ are independently selected from H, halo, $OR^{a8}$, $C(O)OR^{a8}$, $C_{1-6}$ alkyl, $C_{1-6}$ haloalkyl, and 4-7 membered heterocycloalkyl-$C_{1-4}$ alkyl; wherein said $C_{1-6}$ alkyl, is optionally substituted by 1, 2, or 3 independently selected $R^G$ substituents;

each $R^{a8}$ is independently selected from H and $C_{1-6}$ alkyl;

$R^1$ is selected from H, CN, $C_{1-6}$ alkyl, $C_{1-6}$ haloalkyl, 4-7 membered heterocycloalkyl, $OR^{a1}$, and $NR^{c1}R^{d1}$, wherein said $C_{1-6}$ alkyl, $C_{1-6}$ haloalkyl, and 4-7 membered heterocycloalkyl are each optionally substituted with 1, 2, 3, or 4 independently selected $R^{1A}$ substituents;

each $R^{a1}$, $R^{c1}$, and $R^{d1}$ is independently selected from H and $C_{1-6}$ alkyl, wherein said $C_{1-6}$ alkyl is optionally substituted with 1, 2, or 3 independently selected $R^{1A}$ substituents;

each $R^{1A}$ is independently selected from $C_{1-6}$ alkyl, $OR^{a11}$, and $NR^{c11}R^{d11}$;

each $R^{a11}$, $R^{c11}$, and $R^{d11}$ is independently selected from H and $C_{1-6}$ alkyl;

$R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, and 5-6 membered heteroaryl are each optionally substituted with 1 or 2 independently selected $R^{2A}$ substituents;

each $R^{2A}$ is independently selected from $OR^{a21}$ and $NR^{c21}R^{d21}$;

each $R^{a21}$, $R^{c21}$, and $R^{d21}$ is independently selected from H and $C_{1-6}$ alkyl;

$R^3$ is H or CH$_3$;

$R^4$ is H;

each $R^5$ is independently selected from oxo, halo, CN, $C_{1-6}$ alkyl, and $C_{1-6}$ haloalkyl; wherein said $C_{1-6}$ alkyl is optionally substituted by 1 or 2 independently selected $R^{5A}$ substituents;

each $R^{5A}$ is independently selected from $OR^{a51}$ and $NR^{b51}R^{d51}$;

each $R^{a51}$, $R^{c51}$, and $R^{d51}$ is independently selected from H and $C_{1-6}$ alkyl;

each $R^6$ is independently selected from D, halo, CN, $C_{1-6}$ alkyl, $C_{1-6}$ haloalkyl, $C_{3-4}$ cycloalkyl, 4-7 membered heterocycloalkyl, $OR^{a6}$, and $C(O)R^{b6}$; wherein said $C_{1-6}$ alkyl, $C_{1-6}$ haloalkyl, $C_{3-4}$ cycloalkyl, and 4-7 membered heterocycloalkyl, are each optionally substituted by 1, 2, or 3 independently selected $R^{6A}$ substituents;

each $R^{a6}$ is independently selected from H and $C_{1-6}$ alkyl, wherein said $C_{1-6}$ alkyl is optionally substituted with 1 or 2 independently selected $R^{6A}$ substituents;

each $R^{b6}$ is independently selected from $C_{1-6}$ alkyl, $C_{1-6}$ haloalkyl, and 4-7 membered heterocycloalkyl;

each $R^{6A}$ is independently selected from D, $OR^{a61}$, and $NR^{c61}R^{d61}$;

each $R^{a61}$, $R^{c61}$, and $R^{d61}$ is independently selected from H, and $C_{1-6}$ alkyl;

each $R^7$ is independently selected from OH, CN, halo, $C_{1-3}$ alkoxy, and $C_{1-3}$ haloalkoxy; and each $R^G$ is independently selected from D, OH, CN, halo, $C_{1-3}$ alkyl, $C_{1-3}$ haloalkyl, $C_{1-3}$ alkoxy, $C_{1-3}$ haloalkoxy, amino, and $C_{1-3}$ alkylamino, di($C_{1-3}$ alkyl)amino.

In some embodiments:

(a) each $L^5$ is independently -L-O-$L^x$-, -L-NR$^9$-$L^x$-, -L-S-$L^x$-, -L-C(O)-$L^x$-, —NR$^9$C(O)-$L^x$-, -L-OC(O)-$L^x$-, -L-S(O)-$L^x$-, -L-S(O)$_2$-$L^x$-, —NR$^9$S(O)-$L^x$-, -L-OS(O)-$L^x$-, -L-NR$^9$S(O)NR$^9$-$L^x$-, -L-NR$^9$S(O)O-$L^x$-, -L-OS(O)NR$^9$-$L^x$-, —NR$^9$S(O)$_2$-$L^x$-, -L-OS(O)$_2$-$L^x$-, -L-NR$^9$S(O)$_2$NR$^9$-$L^x$-, -L-NR$^9$S(O)$_2$O-$L^x$-, -L-S(O)(NR$^9$)-$L^x$-, -L-S(O)$_2$(NR$^9$)-$L^x$-, or -L-OS(O)$_2$NR$^9$-$L^x$-, wherein $L^5$ is attached to Ring C through the L linking group; or (b) $R^1$ is selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, 8-10 membered heterocycloalkyl, $C_{3-10}$ cycloalkyl-$C_{1-4}$ alkyl, 4-10 membered heterocycloalkyl-$C_{1-4}$ alkyl, $OR^{m1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2 NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl are each optionally substituted with 1, 2, 3, or 4 independently selected $R^{1A}$ substituents; and each $R^{m1}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1A}$ substituents; or (c) $R^2$ is selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 6-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $S(O)(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 6-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents; and each $R^{c2}$ and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents.

In some embodiments:

each $L^5$ is independently -L-O-$L^x$-, -L-$NR^9$-$L^x$-, -L-S-$L^x$-, -L-C(O)-$L^x$-, —$NR^9C(O)$-$L^x$-, -L-OC(O)-$L^x$-, -L-S(O)-$L^x$-, -L-S(O)$_2$-$L^x$-, —$NR^9S(O)$-$L^x$-, -L-OS(O)-$L^x$-, -L-$NR^9S(O)NR^9$-$L^x$-, -L-$NR^9S(O)O$-$L^x$-, -L-OS(O)$NR^9$-$L^x$-, —$NR^9S(O)_2$-$L^x$-, -L-OS(O)$_2$-$L^x$-, -L-$NR^9S(O)_2NR^9$-$L^x$-, -L-$NR^9S(O)_2O$-$L^x$-, -L-S(O)($NR^9$)-$L^x$-, -L-S(O)$_2$($NR^9$)-$L^x$-, or -L-OS(O)$_2NR^9$-$L^x$-, wherein $L^5$ is attached to Ring C through the L linking group;

$R^1$ is selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, 8-10 membered heterocycloalkyl, $C_{3-10}$ cycloalkyl-$C_{1-4}$ alkyl, 4-10 membered heterocycloalkyl-$C_{1-4}$ alkyl, $OR^{m1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl are each optionally substituted with 1, 2, 3, or 4 independently selected $R^{1A}$ substituents;

each $R^{m1}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1A}$ substituents;

$R^2$ is selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 6-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $S(O)(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 6-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents; and each $R^{c2}$ and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents.

In some embodiments, the compound of Formula (I) is a compound of Formula (II):

(II)

or a pharmaceutically acceptable salt thereof.

In some embodiments, the compound of Formula (I) is a compound of Formula (IIa):

(IIa)

or a pharmaceutically acceptable salt thereof.

In some embodiments, the compound of Formula (I) is a compound of Formula (IIb):

(IIb)

or a pharmaceutically acceptable salt thereof.

In some embodiments, the compound of Formula (I) is a compound of Formula (IIc):

(IIc)

or a pharmaceutically acceptable salt thereof.

In some embodiments, the compound of Formula (I) is a compound of Formula (IId):

(IId)

or a pharmaceutically acceptable salt thereof.

In some embodiments, the compound of Formula (I) is a compound of Formula (IIe):

(IIe)

or a pharmaceutically acceptable salt thereof.

In some embodiments, the compound of Formula (I) is a compound of Formula (IIf):

(IIf)

or a pharmaceutically acceptable salt thereof.

In some embodiments, the compound of Formula (I) is a compound of Formula (IIg):

(IIg)

or a pharmaceutically acceptable salt thereof.

In some embodiments, the compound of Formula (I) is a compound of Formula (IIh):

(IIh)

or a pharmaceutically acceptable salt thereof.

In some embodiments, the compound of Formula (I) is a compound of Formula (III):

(III)

or a pharmaceutically acceptable salt thereof.

In some embodiments, the compound of Formula (I) is a compound of Formula (IIIa):

(IIIa)

or a pharmaceutically acceptable salt thereof.

In some embodiments, the compound of Formula (I) is a compound of Formula (IIIb):

(IIIb)

or a pharmaceutically acceptable salt thereof.

In some embodiments, the compound of Formula (I) is a compound of Formula (IV):

(IV)

or a pharmaceutically acceptable salt thereof.

In some embodiments, the compound of Formula (I) is a compound of Formula (IVa):

(IVa)

or a pharmaceutically acceptable salt thereof.

In some embodiments, the compound of Formula (I) is a compound of Formula (IVb):

(IVb)

or a pharmaceutically acceptable salt thereof.

In some embodiments, the compound of Formula (I) is a compound of Formula (V):

(V)

or a pharmaceutically acceptable salt thereof.

In some embodiments, the compound of Formula (I) is a compound of Formula (Va):

(Va)

or a pharmaceutically acceptable salt thereof.

In some embodiments, the compound of Formula (I) is a compound of Formula (Vb):

(Vb)

or a pharmaceutically acceptable salt thereof.

In some embodiments, the compound of Formula (I) is a compound of Formula (Vc):

(Vc)

or a pharmaceutically acceptable salt thereof.

In some embodiments, the compound of Formula (I) is a compound of Formula (Vd):

(Vd)

or a pharmaceutically acceptable salt thereof.

In some embodiments, the compound of Formula (I) is a compound of Formula (Ve):

(Ve)

or a pharmaceutically acceptable salt thereof.

In some embodiments, the compound of Formula (I) is a compound of Formula (Vf):

(Vf)

or a pharmaceutically acceptable salt thereof.

In some embodiments, the compound of Formula (I) is a compound of Formula (Vg):

(Vg)

or a pharmaceutically acceptable salt thereof.

In some embodiments, the compound of Formula (I) is a compound of Formula (VI):

(VI)

or a pharmaceutically acceptable salt thereof.

In some embodiments, the compound of Formula (I) is a compound of Formula (VIa):

(VIa)

or a pharmaceutically acceptable salt thereof.

In some embodiments, the compound of Formula (I) is a compound of Formula (VIb):

(VIb)

or a pharmaceutically acceptable salt thereof.

In some embodiments, the compound of Formula (I) is a compound of Formula (VIc):

(VIc)

or a pharmaceutically acceptable salt thereof.

In some embodiments, the compound of Formula (I) is a compound of Formula (VId):

(VId)

In some embodiments, the compound of Formula (I) is a compound of Formula (VII):

(VII)

or a pharmaceutically acceptable salt thereof.

In some embodiments, the compound of Formula (I) is a compound of Formula (VIIa):

(VIIa)

or a pharmaceutically acceptable salt thereof.

In some embodiments, the compound of Formula (I) is a compound of Formula (VIIb):

(VIIb)

or a pharmaceutically acceptable salt thereof.

In some embodiments, the compound of Formula (I) is a compound of Formula (VIIc):

(VIIc)

or a pharmaceutically acceptable salt thereof.

In some embodiments, in any of Formulas (V), (Va), (Vb), (Vc), (Vd), (Ve), (Vf), (Vg), (VI), (VIa), (VIb), (VIc), (VId), (VII), (VIIa), (VIIb), or (VIIc) p is 0.

In some embodiments, in any of Formulas (VII), (VIIa), (VIIb), or (VIIc), p is 1.

In some embodiments, in any of Formulas (VII), (VIIa), (VIIb), or (VIIc), p is 2.

In some embodiments, in any of Formulas (V), (Va), (Vb), (Vc), (Vd), (Ve), (Vf), (Vg), (VI), (VIa), (VIb), (VIc), or (VId), p is 0.

In some embodiments, in any of Formulas (VI), (VIa), (VIb), (VIc), (VId), (VII), (VIIa), (VIIb), or (VIIc), Y is S. In some embodiments, in any of Formulas (VI), (VIa), (VIb), (VIc), (VId), (VII), (VIIa), (VIIb), or (VIIc), Y is O. In some embodiments, in any of Formulas (VI), (VIa), (VIb), (VIc), (VId), (VII), (VIIa), (VIIb), or (VIIc), Y is $NR^{4y}$.

In some embodiments, in any of Formulas (VI), (VIa), (VIb), (VIc), or (VId), Y is S. In some embodiments, in any of Formulas (VI), (VIa), (VIb), (VIc), or (VId), Y is O. In some embodiments, in any of Formulas (VI), (VIa), (VIb), (VIc), or (VId), Y is $NR^{4y}$.

In some embodiments, 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-4}$ alkyl-" and "alkylene" linking groups, as described herein, are optionally replaced by deuterium atoms.

It is further appreciated that certain features of the invention, which are, for clarity, described in the context of separate embodiments, can also be provided in combination in a single embodiment (as if the embodiments were written in multiply dependent form). Conversely, various features of the invention which are, for brevity, described in the context of a single embodiment, can also be provided separately or in any suitable subcombination.

At various places in the present specification, divalent linking substituents are described. Unless otherwise specified, it is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency, that the designated atom's normal valency is not exceeded, and that the substitution results in a stable compound.

As used herein, the term "independently selected from" means that each occurrence of a variable or substituent are independently selected at each occurrence from the applicable list.

As used herein, the phrase "each 'variable' is independently selected from" means substantially the same as wherein "at each occurrence 'variable' is selected from."

When any variable (e.g., $R^G$) occurs more than one time in any constituent or formula for a compound, its definition at each occurrence is independent of its definition at every other occurrence. Thus, for example, if a group is shown to be substituted with 1, 2, 3, or 4 independently selected $R^G$ substituents, then said group may optionally be substituted with up to four $R^G$ groups and $R^G$ at each occurrence is selected independently from the definition of $R^G$.

In some embodiments, when an optionally multiple substituent is designated in the form:

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms.

Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (i-Pr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms. As used herein, the term "$C_{n-m}$ alkoxy", employed alone or in combination with other terms, refers to a group of formula-O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —$NH_2$.

As used herein, the term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. In some embodiments, the aryl group has 6 to 10 carbon atoms. In some embodiments, the aryl group is phenyl or naphthyl. In some embodiments, the aryl is phenyl.

As used herein, "halo" refers to F, Cl, Br, or I. In some embodiments, halo is F, Cl, or Br.

In some embodiments, halo is F or Cl. In some embodiments, halo is F. In some embodiments, halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group of the haloalkyl has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, the term "$C_{n-m}$ fluoroalkyl" refers to an alkyl group having from one fluoro atom to 2s+1 fluoro atoms, where "s" is the number of carbon atoms in the alkyl group, wherein the alkyl group has n to m carbon atoms. In some embodiments, the alkyl group of the fluoroalkyl has 1 to 6, 1 to 4, or 1 to 3 carbon atoms. Example fluoroalkyl groups include $CF_3$, $C_2F_5$, $CHF_2$, $CH_2F$, and the like.

As used herein, the term "thio" refers to a group of formula —SH.

As used herein, the term "$C_{n-m}$ alkylamino" refers to a group of formula —NH(alkyl), wherein the alkyl group has n to m carbon atoms. In some embodiments, the alkyl group of the alkylamino has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group of the alkoxycarbonyl has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group of the alkylcarbonyl has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group of the alkylcarbonylamino has 1 to 6, 1 to 4, or 1 to 3 carbon atoms.

As used herein, the term "$C_{n-m}$ alkoxycarbonylamino" refers to a group of formula —NHC(O)O($C_{n-m}$ alkyl), wherein the alkyl group has n to m carbon atoms. In some embodiments, the alkyl group of the alkoxycarbonylamino has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group of the alkylsulfonylamino has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group of the alkylaminosulfonyl has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group of the dialkylaminosulfonyl has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group of the alkylaminosulfonylamino has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group of the dialkylaminosulfonylamino has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group of the alkylaminocarbonylamino has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group of the dialkylaminocarbonylamino has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group of the alkylcarbamyl has 1 to 6, 1 to 4, or 1 to 3 carbon atoms.

As used herein, the term "$C_{n-m}$ alkylthio" refers to a group of formula —S-alkyl, wherein the alkyl group has n to m carbon atoms. In some embodiments, the alkyl group of the alkylthio has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group of the alkylsulfinyl has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group of the alkylsulfonyl has 1 to 6, 1 to 4, or 1 to 3 carbon atoms.

As used herein, the term "cyano-$C_{n-m}$ alkyl" refers to a group of formula —($C_{n-m}$ alkylene)-CN, wherein the alkylene group has n to m carbon atoms. As used herein, the term "cyano-$C_{1-6}$ alkyl" refers to a group of formula —($C_{1-6}$ alkylene)-CN. As used herein, the term "cyano-$C_{1-3}$ alkyl" refers to a group of formula —($C_{1-3}$ alkylene)-CN.

As used herein, the term "HOC$_{n-m}$ alkyl" refers to a group of formula —($C_{n-m}$ alkylene)-OH, wherein the alkylene group has n to m carbon atoms. As used herein, the term "HO—$C_{1-3}$ alkyl" refers to a group of formula —($C_{1-3}$ alkylene)-OH.

As used herein, the term "$C_{n-m}$ alkoxy-$C_{o-p}$ alkyl" refers to a group of formula —($C_{n-m}$ alkylene)-O($C_{o-p}$ alkyl), wherein the alkylene group has n to m carbon atoms and the alkyl group has o to p carbon atoms. As used herein, the term "$C_{1-6}$ alkoxy-$C_{1-6}$ alkyl" refers to a group of formula —($C_{1-6}$ alkylene)-O($C_{1-6}$ alkyl). As used herein, the term "$C_{1-3}$ alkoxy-$C_{1-3}$ alkyl" refers to a group of formula —($C_{1-3}$ alkylene)-O($C_{1-3}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group of the dialkylamino independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group of the dialkylcarbamyl independently has 1 to 6, 1 to 4, or 1 to 3 carbon atoms.

As used herein, the term "$C_{n-m}$ alkylcarbonyloxy" is a group of formula —OC(O)-alkyl, wherein the alkyl group has n to m carbon atoms. In some embodiments, the alkyl group of the alkylcarbonyloxy has 1 to 6, 1 to 4, or 1 to 3 carbon atoms.

As used herein, "aminocarbonyloxy" is a group of formula —OC(O)—NH$_2$.

As used herein, "$C_{n-m}$ alkylaminocarbonyloxy" is a group of formula —OC(O)—NH-alkyl, wherein the alkyl group has n to m carbon atoms. In some embodiments, the alkyl group of the alkylaminocarbonyloxy has 1 to 6, 1 to 4, or 1 to 3 carbon atoms.

As used herein, "di($C_{n-m}$ alkyl)aminocarbonyloxy" is a group of formula —OC(O)—N(alkyl)$_2$, wherein each alkyl group has, independently, n to m carbon atoms. In some embodiments, each alkyl group of the dialkylaminocarbonyloxy independently has 1 to 6, 1 to 4, or 1 to 3 carbon atoms.

As used herein "$C_{n-m}$ alkoxycarbonylamino" refers to a group of formula —NHC(O)—O— alkyl, wherein the alkyl group has n to m carbon atoms.

As used herein, the term "carbamyl" to a group of formula —C(O)NH$_2$.

As used herein, the term "carbonyl", employed alone or in combination with other terms, refers to a —C(O)— group.

As used herein, "cycloalkyl" refers to non-aromatic cyclic hydrocarbons including cyclized alkyl and alkenyl groups. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2, 3, or 4 fused rings) aromatic heterocycle having at least one heteroatom ring member selected from N, O, or S. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, and S. In some embodiments, the heteroaryl group contains 5 to 10 or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridyl, pyrimidinyl, pyrazinyl, pyridazinyl, pyrrolyl, pyrazolyl, azolyl, oxazolyl, isoxazolyl, thiazolyl, isothiazolyl, imidazolyl, furyl, thienyl, triazolyl (e.g., 1,2,3-triazolyl, 1,2,4-triazolyl, 1,3,4-triazolyl), tetrazolyl, thiadiazolyl (e.g., 1,2,3-thiadiazolyl, 1,2,4-thiadiazolyl, 1,3,4-thiadiazolyl), quinolinyl, isoquinolinyl, indolyl, benzothienyl, benzofuranyl, benzisoxazolyl, benzoimidazolyl, benzothiazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, oxadiazolyl (e.g., 1,2,3-oxadiazolyl, 1,2,4-oxadiazolyl, 1,3,4-oxadiazolyl), 1,2-dihydro-1,2-azoborinyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, or S, and wherein the ring-forming carbon atoms and heteroatoms of the heterocycloalkyl group can be optionally substituted by one or more oxo or sulfido (e.g., C(O), S(O), C(S), or S(O)$_2$, etc.). As used herein, the term "partially unsaturated ring" refers to a ring having at least one point of saturation and wherein said ring is non-aromatic. Heterocycloalkyl groups include monocyclic and polycyclic (e.g., having 2 fused rings) systems. Included in heterocycloalkyl are monocyclic and polycyclic 4-10-, 4-7-, and 5-6-membered heterocycloalkyl groups. Heterocycloalkyl groups can also include spirocycles and bridged rings. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. A heterocycloalkyl group containing a partially unsaturated ring can also include a fused aromatic ring attached through any ring-forming atom including a ring-forming atom of the fused aromatic ring, wherein said partially unsaturated ring moiety has at least one point of saturation and wherein said partially unsaturated ring is non-aromatic. In some embodiments, the heterocycloalkyl group contains 4 to 10 ring-forming atoms, 4 to 7 ring-forming atoms, 4 to 6 ring-forming atoms or 5 to 6 ring-forming atoms. In some embodiments, the heterocycloalkyl group has 1 to 4 heteroatoms, 1 to 3 heteroatoms, 1 to 2 heteroatoms or 1 heteroatom.

In some embodiments, the heterocycloalkyl is a 4-10 membered monocyclic, bicyclic, or tricyclic heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido. In some embodiments, the heterocycloalkyl is a 4-10 membered bicyclic heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido. In some embodiments, the heterocycloalkyl is a 4-7 membered monocyclic heterocycloalkyl having 1 or 2 ring-forming heteroatoms independently selected from N, O, and S, and wherein 1, 2 or 3 ring-forming carbon or heteroatoms can be optionally substituted by one or more oxo or sulfido. In some embodiments, the heterocycloalkyl is a monocyclic 4-6 membered heterocycloalkyl having 1 or 2 heteroatoms independently selected from N, O, S, and B and having one or more oxidized ring members.

Examples of heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, isoindolinonyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, azabicyclo[2.2.1]heptan-7-yl, azabicyclo[2.2.1]heptan-2-yl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl, and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon ring members and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, the term "alkylene" refers a divalent straight chain or branched alkyl linking group. Examples of "alkylene groups" include methylene, ethan-1,1-diyl, ethan-1,2-diyl, propan-1,3-dilyl, propan-1,2-diyl, propan-1,1-diyl and the like.

As used herein, the term "alkenylene" refers a divalent straight chain or branched alkenyl linking group. Examples of "alkenylene groups" include ethen-1,1-diyl, ethen-1,2-diyl, propen-1,3-diyl, 2-buten-1,4-diyl, 3-penten-1,5-diyl, 3-hexen-1,6-diyl, 3-hexen-1,5-diyl, and the like.

As used herein, the term "alkynylene" refers a divalent straight chain or branched alkynyl linking group. Examples of "alkynylene groups" include propyn-1,3-diyl, 2-butyn-1,4-diyl, 3-pentyn-1,5-diyl, 3-hexyn-1,6-diyl, 3-hexyn-1,5-diyl, and the like.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-dilyl, propan-1,2-diyl, propan-1,1-diyl and the like.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent are independently selected at each occurrence from the applicable list.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g., hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes, such as those provided in the Schemes below.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "r.t." as used herein, are understood in the art, and refer generally to a temperature, e.g., a reaction temperature, that is about the temperature of the room in which the reaction is carried out, for example, a temperature from about 20° C. to about 30° C.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups,* (Thieme, 2007); Robertson, *Protecting Group Chemistry,* (Oxford University Press, 2000); Smith et al., *March's Advanced Organic Chemistry: Reactions, Mechanisms, and Structure,* 6th Ed. (Wiley, 2007); Peturssion et al., "Protecting Groups in Carbohydrate Chemistry," *J Chem. Educ.,* 1997, 74(11), 1297; and Wuts et al., *Protective Groups in Organic Synthesis,* 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, for example, using a process as illustrated in Scheme 1. In the process depicted in Scheme 1, compounds of formula 1-1 can react with compounds 1-2 via nucleophilic aromatic substitution reactions (e.g., in the presence of a base, such as N,N-diisopropylethylamine) or Buchwald-Hartwig cross-coupling reactions (e.g., in the presence of a palladium catalyst, such as Xantphos Pd G3, and a base, such as cesium carbonate), followed by deprotection of the protecting group, e.g. under acidic conditions, such as treatment with HCl or TFA, resulting in the formation of the compounds of formula 1-3. The compounds 1-3 are further reacted with compounds 1-5 through nucleophilic aromatic substitution (e.g., in the presence of a base, such as N,N-diisopropylethylamine) to form compounds of formula 1-4. Reaction of compounds of formula 1-4 with carboxylic acids via amide formation (e.g., in the presence of EDC or T3P) or through the reaction with acid halides (e.g., in the presence of a base, such as N,N-diisopropylethylamine) results in the formation of the desired compounds of Formula (I). Additionally, $R^1$ may be further modified via nucleophilic aromatic substitution reactions or cross-coupling reactions. Alternatively, the cross-coupling reaction of compound 1-4, including Sonogashira (e.g., in the presence of a palladium catalyst, such as $PdCl_2(PPh_3)_2$, a copper catalyst, such as CuI, and a base, such as triethylamine), Buchwald-Hartwig (e.g., in the presence of a palladium catalyst, such as Xantphos Pd G3, and a base, such as cesium carbonate), and others, results in the formation of the desired compounds of Formula (I).

Scheme 1

When X is CH and BC bicyclic ring is benzo[d]imidazol-2-yl in Formula (I), compounds of Formula (II) can be prepared, for example, using a process as illustrated in Scheme 2. In the process depicted in Scheme 2, the compounds of formula 2-1 can couple with the compounds of formula 2-2, using standard amide coupling agents (e.g., HBTU, HATU, or EDC), to afford compounds of formula 2-3. The intramolecular cyclization of 2-3 under acidic conditions, followed by NH deprotection of the protecting group (e.g., treatment with HCl or TFA) results in compounds of formula 2-4. The compounds of formula 2-4 can react with the compounds of formula 2-5 under $S_NAr$ conditions (e.g., heating under basic conditions) to give compounds of formula 2-6. An $R^1$ group (e.g., halogen) in the compounds of formula 2-6 can be further replaced through $S_NAr$ (e.g., heating with amines under basic conditions) or cross-coupling reactions, including Suzuki (e.g., in the presence of a palladium catalyst, such as Xphos Pd G2, and a base, such as potassium phosphate), Negishi or Stille (e.g., in the presence of a palladium(0) catalyst, such as tetrakis(triphenylphosphine)palladium(0)) and others, to further derivatize the $R^1$ group in the compounds of formula 2-6. The aniline moiety in the compounds of formula 2-7 can be prepared via Buchwald coupling (e.g., Z=halogen, in the presence of tris(dibenzylideneacetone)dipalladium(0), BrettPhos and cesium carbonate) followed by NH deprotection of the protecting group (e.g., treatment with HCl or TFA) or nitro group reduction (e.g., Z=NO$_2$, in the presence of zinc(0), ammonium chloride and water). Finally, the compounds of formula 2-7 can be coupled with carboxylic acids using standard amide coupling agents (e.g., HBTU, HATU or EDC) or an acid chloride to provide the desired compounds of Formula (II).

Scheme 2

-continued

Z = halogen or NO$_2$
2-3

1) Cyclization
2) NH deprotection

Z = halogen or NO$_2$
2-4

2-5
S$_N$Ar substitution 2-7

Z = halogen
1) Buchwald coupling
2) NH deprotection

Z = NO$_2$
Reduction

Z = halogen or NO$_2$
2-5

Amide formation (II)

When X is CH and BC bicyclic ring is 1-oxoisoindolin-2-yl in Formula (I), compounds of Formula (III) can be prepared, for example, using a process as illustrated in Scheme 3. In the process depicted in Scheme 3, the compounds of formula 3-1 can cyclize with the compounds of formula 3-2, under basic conditions (e.g., DIPEA) with heat, to afford compounds of formula 3-3. The NH deprotection of the compounds of formula 3-3, followed by the reaction with the compounds of formula 3-4 under S$_N$Ar conditions (e.g., heating under basic conditions) results in the compounds of formula 3-5. An R$^1$ group (e.g., halogens) in the compounds of formula 3-5 can be further replaced through S$_N$Ar (e.g., heating with amines under basic conditions) or cross-coupling reactions, including Suzuki (e.g., in the presence of a palladium catalyst, such as Xphos Pd G2, and a base, such as potassium phosphate), Negishi or Stille (e.g., in the presence of a palladium(0) catalyst, such as tetrakis(triphenylphosphine)palladium(0)) and others, to further derivatized the R$^1$ group in the compounds of formula 3-6. A Z group (Z=halogen or NO$_2$) in the compounds of formula 3-5 can be converted into an amino group via Buchwald coupling (e.g., Z=halogen, in the presence of tris(dibenzylideneacetone)dipalladium(0), BrettPhos and cesium carbonate) followed by NH deprotection of the protecting group (e.g., treatment with HCl or TFA) or nitro group reduction (e.g., Z=NO$_2$, in the presence of zinc(0), ammonium chloride and water). Finally, the resulted aniline from compounds of formula 3-5 can be coupled to a carboxylic acid using standard amide coupling agents (e.g., HBTU, HATU or EDC) or an acid chloride to provide the desired compounds of Formula (III).

Alternatively, a Z group (Z=halogen or NO$_2$) in the compounds of formula 3-3 can be converted into an amino group via Buchwald coupling (e.g., Z=halogen, in the presence of tris(dibenzylideneacetone)dipalladium(0), BrettPhos and cesium carbonate) followed by NH deprotection of the protecting group (e.g., treatment with HCl or TFA) or nitro group reduction (e.g., Z=NO$_2$, in the presence of zinc(0), ammonium chloride and water). The resulted aniline from compounds of formula 3-3 can be coupled to a carboxylic acid using standard amide coupling agents (e.g., HBTU, HATU or EDC) or an acid chloride to provide enylphosphine)palladium(0)) and others, to further derivatized the $R^1$ group in the compounds of Formula (III).

Scheme 3

Z = halogen or NO₂

3-1      3-2

3-3
Z = halogen or NO2

1) NH deprotection
2) S$_N$Ar substitution 3-4

3-5
Z = halogen or NO2

Z = halogen
1) Buchwald coupling
2) NH deprotection
3) Amide formation

Z = NO₂
1) Reduction
2) Amide formation

Z = halogen
1) Buchwald coupling
2) NH deprotection
3) Amide formation

Z = NO₂
1) Reduction
2) Amide formation 3-6

1) NH deprotection
2) S$_N$Ar substitution 3-4

(III)

compounds of formula 3-6. The NH deprotection of the compounds of formula 3-6, followed by the reaction with the compounds of formula 3-4 under S$_N$Ar conditions (e.g., heating under basic conditions) to give compounds of Formula (III).

An $R^1$ group (e.g., halogens) in the compounds of Formula (III) can be further replaced through S$_N$Ar (e.g., heating with amines under basic conditions) or cross-coupling reactions, including Suzuki (e.g., in the presence of a palladium catalyst, such as Xphos Pd G2, and a base, such as potassium phosphate), Negishi or Stille (e.g., in the presence of a palladium(0) catalyst, such as tetrakis(triph- When X is CH and BC bicyclic ring is benzo[d]imidazol-1-yl in Formula (I), compounds of Formula (IV) can be prepared using a process as illustrated in Scheme 4. In the process depicted in Scheme 4, the compounds of formula 4-1 can react with the compounds of formula 4-2 under S$_N$Ar conditions (e.g., heating under basic conditions), followed by nitro group reduction (e.g., Z=NO₂, in the presence of zinc(0), ammonium chloride and water) to afford compounds of formula 4-3. The imidazole formation of 4-3 under acidic conditions (e.g., triethyl orthoformate and p-TsOH), followed by NH deprotection of the protecting group (e.g., treatment with HCl or TFA) results in compounds of formula 4-4. The compounds of formula 4-4 can react with the compounds of formula 4-5 under $S_NAr$ conditions (e.g., heating under basic conditions) to give compounds of formula 4-6. An $R^1$ group (e.g., halogens) in the compounds of formula 4-6 can be further replaced through $S_NAr$ (e.g., heating with amines under basic conditions) or cross-coupling reactions, including Suzuki (e.g., in the presence of a palladium catalyst, such as Xphos Pd G2, 4-7 can be prepared via Buchwald coupling (e.g., Z=halogen, in the presence of tris(dibenzylideneacetone) dipalladium(0), BrettPhos and cesium carbonate) followed by NH deprotection of the protecting group (e.g., treatment with HCl or TFA). Finally, the compounds of formula 4-7 can be coupled to a carboxylic acid using standard amide coupling agents (e.g., HBTU, HATU or EDC) or an acid chloride to provide the desired compounds of Formula (IV).

Scheme 4 and a base, such as potassium phosphate), Negishi or Stille (e.g., in the presence of a palladium(0) catalyst, such as tetrakis(triphenylphosphine)palladium(0)) and others, to further derivatized the $R^1$ group in the compounds of formula 4-6. The aniline moiety in the compounds of formula For the synthesis of particular compounds, the general schemes described above can be modified. For example, the products or intermediates can be modified to introduce particular functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis, Vols.* 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

Methods of Use

Compounds of the present disclosure can inhibit CDK12 and therefore are useful for treating diseases wherein the underlying pathology is wholly or partially mediated by CDK12. Such diseases include cancer and other diseases with proliferation disorder. In some embodiments, the present disclosure provides treatment of an individual or a patient in vivo using a compound of Formula (I) or a salt thereof such that growth of cancerous tumors is inhibited. A compound of Formula (I) or of any of the formulas as described herein, or a compound as recited in any of the claims and described herein, or a salt thereof, can be used to inhibit the growth of cancerous tumors with aberrations that activate the CDK12 kinase activity.

Alternatively, a compound of Formula (I) or of any of the formulas as described herein, or a compound as recited in any of the claims and described herein, or a salt thereof, can be used in conjunction with other agents or standard cancer treatments, as described below.

In some embodiments, the present disclosure provides a method for inhibiting growth of tumor cells in vitro. The method includes contacting the tumor cells in vitro with a compound of Formula (I), or any of the formulas as described herein, or a compound as recited in any of the claims and described herein, or a salt thereof.

In some embodiments, provided herein is a method of inhibiting CDK12, comprising contacting the CDK12 with a compound of Formula (I), or any of the formulas as described herein, a compound as recited in any of the claims and described herein, or a salt thereof. In some embodiments, provided herein is a method of inhibiting CDK12 in a patient, comprising administering to the patient a compound of Formula (I), or any of the formulas as described herein, a compound as recited in any of the claims and described herein, or a salt thereof.

In some embodiments, the compounds of the present disclosure are selective inhibitors of CDK12 over one or more other CDKs. For example, some of the compounds described herein, or a pharmaceutically acceptable salts thereof, preferentially inhibit CDK12 over one or more of CDK1, CDK2, CDK4, CDK5, CDK6, CDK7, CDK9, and CDK13 as determined by one or more assays disclosed herein.

In some embodiments, the compounds of the present disclosure are selective inhibitors of CDK12 over one or more of CDK1, CDK2, CDK7, and CDK9.

In some embodiments, the compounds of the present disclosure are selective inhibitors of CDK12 over one or more of CDK1, CDK2, and CDK7.

In some embodiments, provided herein is a method for treating cancer. The method includes administering to a patient (in need thereof), a therapeutically effective amount of a compound of Formula (I), or any of the formulas as described herein, a compound as recited in any of the claims and described herein, or a salt thereof.

In some embodiments, provided herein is a method of treating a disease or disorder associated with CDK12 in a patient, comprising administering to the patient a therapeutically effective amount of a compound of Formula (I), or any of the formulas as described herein, a compound as recited in any of the claims and described herein, or a salt thereof.

In some embodiments, the disease or disorder associated with CDK12 is a cancer.

In some embodiments, the disease or disorder associated with CDK12 is a cancer which has been previously identified as homologous recombination deficiency (HRD) high. In some embodiments, the patient has been identified as a patient having homologous recombination deficiency (HRD). In some embodiments, the patient has been identified as having a positive test result for deleterious or suspected deleterious mutations in BRCA1 or BRCA2 genes. In some embodiments, the patient has been identified as having a positive Genomic Instability Score (see e.g., myChoice® CDx, Myriad Genetics, 2019, https://myriad-.com/products-services/precision-medicine/mychoice-cdx/).

In some embodiments, the cancer is ovarian cancer, breast cancer, Ewing's sarcoma, osteosarcoma, liver cancer, hepatocellular carcinoma, or colorectal cancer.

In some embodiments, the cancer is ovarian cancer.

In some embodiments, the cancer is serous ovarian carcinoma.

In some embodiments, the cancer is HRD high grade serous ovarian carcinoma (see Bajrami, I., et al., *Cancer Res,* 2014. 74(1): 287-297).

In some embodiments, the cancer is breast cancer.

In some embodiments, the cancer is homologous recombination deficient breast cancer (see Johnson, S. F., et al., *Cell Rep,* 2016. 17(9): 2367-2381).

In some embodiments, the cancer is Ewing's sarcoma (see Iniguez, A. B., et al., *Cancer Cell,* 2018. 33(2): 202-216).

In some embodiments, the cancer is osteosarcoma (see Bayles, I., et al., *JCI,* 2019. 129(10): 4377-4392).

In some embodiments, the cancer is liver cancer.

In some embodiments, the cancer is hepatocellular carcinoma (see Wang, C., et al., *Gut,* 2020. 69(4): 727-736).

In some embodiments, the cancer is colorectal cancer (see Jiang, B., et al., *Nat. Chem. Biol.,* 2021. 17: 675-683; and Dieter, S. M., et al., *Cell Rep.,* 2021, 36, 109394).

In some embodiments, the cancer is uterine carcinosarcoma.

In some embodiments, the cancer is melanoma.

In some embodiments, the cancer is lung squamous cell carcinoma, lung adenocarcinoma, pancreatic adenocarcinoma, breast invasive carcinoma, uterine carcinosarcoma, ovarian serous cystadenocarcinoma, stomach adenocarcinoma, esophageal carcinoma, bladder urothelial carcinoma, mesothelioma, or sarcoma.

In some embodiments, the cancer is lung adenocarcinoma, breast invasive carcinoma, uterine carcinosarcoma, ovarian serous cystadenocarcinoma, or stomach adenocarcinoma.

In some embodiments, the cancer is an adenocarcinoma, carcinoma, or cystadenocarcinoma.

In some embodiments, the cancer is uterine cancer, ovarian cancer, stomach cancer, esophageal cancer, lung cancer, bladder cancer, pancreatic cancer, or breast cancer.

In some embodiments, the breast cancer is chemotherapy or radiotherapy resistant breast cancer, endocrine resistant breast cancer, trastuzumab resistant breast cancer, or breast cancer demonstrating primary or acquired resistance to CDK4/6 inhibition. In some embodiments, the breast cancer is advanced or metastatic breast cancer.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include melanoma (e.g., metastatic malignant melanoma, BRAF and HSP90 inhibition-resistant melanoma), renal cancer (e.g., clear cell carcinoma), prostate cancer (e.g., hormone refractory prostate adenocarcinoma), breast cancer, colon cancer, lung cancer (e.g., non-small cell lung cancer and small cell lung cancer), squamous cell head and neck cancer, urothelial cancer (e.g., bladder) and cancers with high microsatellite instability ($MSI^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including follicular lymphoma, including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer (SCLC), bronchogenic carcinoma, squamous cell, undifferentiated small cell, undifferentiated large cell, adenocarcinoma, alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, Merkel cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual", "patient," and "subject" used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The present disclosure further provides a compound described herein (i.e., a compound of Formula (I), or any of the formulas as described herein, a compound as recited in any of the claims and described herein, or a salt thereof), for use in any of the methods described herein.

The present disclosure further provides uses of a compound described herein (i.e., a compound of Formula (I), or any of the formulas as described herein, a compound as recited in any of the claims and described herein, or a salt thereof), for the preparation of a medicament for use in any of the methods described herein.

Combination Therapies

I. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, and CDK4/6 kinase inhibitors such as, for example, those described in WO 2006/056399 can be used in combination with the compounds of the present disclosure for treatment of CDK12-associated diseases, disorders or conditions. Other agents such as therapeutic antibodies can be used in combination with the compounds of the present disclosure for treatment of CDK12-associated diseases, disorders or conditions. The one or more additional pharmaceutical agents can be administered to a patient simultaneously or sequentially.

In some embodiments, the CDK12 inhibitor is administered or used in combination with a BCL2 inhibitor or a CDK4/6 inhibitor.

The compounds as disclosed herein can be used in combination with one or more other enzyme/protein/receptor inhibitors therapies for the treatment of diseases, such as cancer and other diseases or disorders described herein. Examples of diseases and indications treatable with combination therapies include those as described herein. Examples of cancers include solid tumors and non-solid tumors, such as liquid tumors, and blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK4/6, TGF-βR, PKA, PKG, PKC, CaM-kinase, phosphorylase kinase, MEKK, ERK, MAPK, mTOR, EGFR, HER2, HER3, HER4, INS—R, IDH2, IGF-1R, IR—R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCB54828), INCB62079), an EGFR inhibitor (also known as ErB-1 or HER-1; e.g., erlotinib, gefitinib, vandetanib, osimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2, e.g., ruxolitinib or baricitinib; JAK1, e.g., itacitinib (INCB39110), INCB052793, or INCB054707), an IDO inhibitor (e.g., epacadostat, NLG919, or BMS-986205, MK7162), an LSD1 inhibitor (e.g., GSK2979552, INCB59872 and INCB60003), a TDO inhibitor, a PI3K-delta inhibitor (e.g., parsaclisib (INCB50465) or INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer; e.g., INCB081776), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptosar, topotecan, paclitaxel, docetaxel, epothilones, tamoxifen, 5-fluorouracil, methotrexate, temozolomide, cyclophosphamide, SCH 66336, R115777, L778,123, BMS 214662, IRESSA™(gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovorin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bis-pecific or multi-specific antibody, antibody drug conjugate, adoptive T cell transfer, Toll receptor agonists, RIG-I ago-nists, oncolytic virotherapy and immunomodulating small molecules, including thalidomide or JAK1/2 inhibitor, PI3Kδ inhibitor and the like. The compounds can be admin-istered in combination with one or more anti-cancer drugs, such as a chemotherapeutic agent. Examples of chemothera-peutics include any of: abarelix, aldesleukin, alemtuzumab, alitretinoin, allopurinol, altretamine, anastrozole, arsenic trioxide, asparaginase, azacitidine, bevacizumab, bexaro-tene, baricitinib, bleomycin, bortezomib, busulfan intrave-nous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculi-zumab, epirubicin, erlotinib, estramustine, etoposide phos-phate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosf-amide, imatinib mesylate, interferon alfa 2a, irinotecan, lapatinib ditosylate, lenalidomide, letrozole, leucovorin, leu-prolide acetate, levamisole, lomustine, mechlorethamine, megestrol acetate, melphalan, mercaptopurine, methotrex-ate, methoxsalen, mitomycin C, mitotane, mitoxantrone, nandrolone phenpropionate, nelarabine, nofetumomab, oxa-liplatin, paclitaxel, pamidronate, panitumumab, pegaspar-gase, pegfilgrastim, pemetrexed disodium, pentostatin, pipo-broman, plicamycin, procarbazine, quinacrine, rasburicase, rituximab, ruxolitinib, sorafenib, streptozocin, sunitinib, sunitinib maleate, tamoxifen, temozolomide, teniposide, tes-tolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include pro-teasome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexam-ethasone or prednisone.

Example Bcr-Abl inhibitors include imatinib mesylate (GLEEVAC™), nilotinib, dasatinib, bosutinib, and pona-tinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically accept-able salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their phar-maceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharma-ceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemothera-peutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immu-nomodulatory agent. Examples of an alkylating agent include cyclophosphamide (CY), melphalan (MEL), and bendamustine. In some embodiments, the proteasome inhibitor is carfilzomib. In some embodiments, the corticos-teroid is dexamethasone (DEX). In some embodiments, the immunomodulatory agent is lenalidomide (LEN) or pomalidomide (POM). Additive or synergistic effects are desirable outcomes of combining a CDK12 inhibitor of the present disclosure with an additional agent.

The agents can be combined with the present compound in a single or continuous dosage form, or the agents can be administered simultaneously or sequentially as separate dos-age forms.

The compounds of the present disclosure can be used in combination with one or more other inhibitors or one or more therapies for the treatment of infections. Examples of infections include viral infections, bacterial infections, fun-gus infections or parasite infections.

In some embodiments, a corticosteroid such as dexam-ethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, puri-fied tumor antigens (including recombinant proteins, pep-tides, and carbohydrate molecules), cells, and cells trans-fected with genes encoding immune stimulating cytokines.

Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful include pathogens for which there is currently no effective vaccine, or pathogens for which conventional vaccines are less than completely effective. These include, but are not limited to, HIV, Hepatitis (A, B, & C), Influenza, *Herpes, Giardia,* Malaria, *Leishmania, Staphylococcus aureus, Pseudomonas Aeruginosa.*

Viruses causing infections treatable by methods of the present disclosure include, but are not limited to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackie virus, cornavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumococci, meningococci and conococci, *Klebsiella, Proteus, Serratia, Pseudomonas, Legionella,* diphtheria, *Salmonella,* bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis,* etc.), *Cryptococcus neoformans, Aspergillus* (*fumigatus, niger,* etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis.*

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

II. Immune-Checkpoint Therapies

Compounds of the present disclosure can be used in combination with one or more immune checkpoint inhibitors for the treatment of diseases, such as cancer or infections.

Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (IBI308), AB122 (GLS-010), AMP-224, AMP-514/MEDI-0680, BMS936559, JTX-4014, BGB-108, SHR-1210, MED14736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217, 149, WO 03042402, WO 2008156712, WO 2010089411, WO 2010036959, WO 2011066342, WO 2011159877, WO 2011082400, or WO 2011161699, which are each incorporated herein by reference in its entirety.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MED14736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MEDI1873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), or more, such as about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration.

Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.
Labeled Compounds and Assay Methods Another aspect of the present disclosure relates to labeled compounds of the disclosure (radio-labeled, fluorescent-labeled, etc.) that would be useful not only in imaging techniques but also in assays, both in vitro and in vivo, for localizing and quantitating CDK12 in tissue samples, including human, and for identifying CDK12 activators by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes CDK12 assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups of the disclosed Formulas (e.g., Formula (I)) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene and alkynylene linking groups, as described herein, are optionally replaced by deuterium atoms.

Synthetic methods for including isotopes into organic compounds are known in the art (Deuterium Labeling in Organic Chemistry by Alan F. Thomas, New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et al. *J. Med. Chem.* 2011, 54, 201-210; R. Xu et al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro CDK12 labeling and competition assays, compounds that incorporate $^3$H, $^{14}$C, $^{82}$Br, $^{125}$I, $^{131}$I, or $^{35}$S can be useful. For radio-imaging applications $^{11}$C, $^{18}$F, $^{125}$I, $^{123}$I, $^{124}$I, $^{131}$I, $^{75}$Br, $^{76}$Br, or $^{77}$Br can be useful.

It is understood that a "radio-labeled" or "labeled compound" is a compound that has incorporated at least one radionuclide. In some embodiments, the radionuclide is selected from the group consisting of 3H, $^{14}$C, $^{125}$I, $^{35}$S, and $^{82}$Br.

The present disclosure can further include synthetic methods for incorporating radio-isotopes into compounds of the disclosure. Synthetic methods for incorporating radio-isotopes into organic compounds are well known in the art, and one of ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind and activate CDK12 by monitoring its concentration variation when contacting with CDK12, through tracking of the labeling. For example, a test compound (labeled) can be evaluated for its ability to reduce binding of another compound which is known to inhibit CDK12 (i.e., standard compound). Accordingly, the ability of a test compound to compete with the standard compound for binding to CDK12 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of CDK12-associated diseases or disorders (such as, e.g., cancer) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g., "Two-Pump at-Column Dilution Configuration for Preparative LC-MS," K. Blom, *J. Combi. Chem.*, 4, 295 (2002); "Optimizing Preparative LC-MS Configurations and Methods for Parallel Synthesis Purification," K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization," K. Blom, B. Glass, R. Sparks, A. Combs, *J. Combi. Chem.*, 6, 874-883 (2004). The separated compounds were typically subjected to analytical liquid chromatography mass spectrometry (LCMS) for purity check under the following conditions: Instrument: Agilent 1100 series, LC/MSD; Column: Waters Sunfire™ $C_{18}$ 5 μm particle size, 2.1×5.0 mm; Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see "Preparative LCMS Purification: Improved Compound Specific Method Optimization," K. Blom, B. Glass, R. Sparks, A. Combs, J. Comb. Chem., 6, 874-883 (2004)). Typically, the flow rate used with the 30×100 mm column was 60 mL/minute. pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature (See "Preparative LCMS Purification: Improved Compound Specific Method Optimization," K. Blom, B. Glass, R. Sparks, A. Combs, *J. Comb. Chem.*, 6, 874-883 (2004)). Typically, the flow rate used with 30×100 mm column was 60 mL/minute.

Intermediate A. 2-(((1R,3S)-3-(5-Amino-1-methyl-1H-benzo[d]imidazol-2-yl)cyclohexyl)amino)-4-methoxypyrimidine-5-carbonitrile Step 1. tert-Butyl ((1S,3R)-3-((2-(methylamino)-5-nitrophenyl)carbamoyl)cyclohexyl)carbamate This compound was prepared according to the procedures described in Example 47, with $N^1$-methyl-4-nitrobenzene-1,2-diamine replacing $N^1$-(2-((tert-butyldimethylsilyl)oxy)ethyl)-4-nitrobenzene-1,2-diamine in Step 2. LCMS calculated for $C_{19}H_{29}N_4O_5$ $(M+H)^+$: m/z=393.2; found: 393.1.

Step 2. (1R,3S)-3-(1-Methyl-5-nitro-1H-benzo[d]imidazol-2-yl)cyclohexan-1-amine

This compound was prepared according to the procedures described in Example 47, with tert-butyl ((1S,3R)-3-((2-(methylamino)-5-nitrophenyl)carbamoyl)cyclohexyl)carbamate replacing tert-butyl ((1R,3S)-3-((2-((2-((tert-butyldimethylsilyl)oxy)ethyl)amino)-5-nitrophenyl)carbamoyl)cyclohexyl)carbamate in Step 3. LCMS calculated for $C_{14}H_{19}N_4O_2$ (M+H)$^+$: m/z=275.1; found: 275.1.

Step 3. 4-Methoxy-2-(((1R,3S)-3-(1-methyl-5-nitro-1H-benzo[d]imidazol-2-yl)cyclohexyl)amino)py-rimidine-5-carbonitrile This compound was prepared according to the procedures described in Example 47, with (1R,3S)-3-(1-methyl-5-nitro-1H-benzo[d]imidazol-2-yl)cyclohexan-1-amine replacing 2-(2-((1S,3R)-3-aminocyclohexyl)-5-nitro-1H-benzo[d]imidazol-1-yl)ethyl acetate in Step 4. LCMS calculated for $C_{20}H_{22}N_7O_3$ (M+H)$^+$: m/z=408.2; found: 408.2.

Step 4. 2-(((1R,3S)-3-(5-Amino-1-methyl-1H-benzo[d]imidazol-2-yl)cyclohexyl)amino)-4-methoxypy-rimidine-5-carbonitrile This compound was prepared according to the procedures described in Example 47, with 4-methoxy-2-(((1R,3S)-3-(1-methyl-5-nitro-1H-benzo[d]imidazol-2-yl)cyclohexyl)amino)pyrimidine-5-carbonitrile replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{20}H_{24}N_7O$ (M+H)$^+$: m/z=378.2; found: 378.2.

Intermediate B. 2-((1S,3R)-3-Aminocyclohexyl)-6-nitroisoindolin-1-one

To a vial containing methyl 2-(bromomethyl)-5-nitrobenzoate (500 mg, 1.824 mmol) and tert-butyl ((1R,3S)-3-aminocyclohexyl)carbamate (391 mg, 1.824 mmol) in DMF (9.12 mL) was added DIPEA (0.64 mL, 3.65 mmol). After stirring at 80° C. for 16 h, the reaction mixture was quenched with water and the mixture was extracted with diethyl ether. The organic phase was washed with brine, dried over MgSO$_4$ and concentrated in vacuo. The crude material was redissolved in CH$_2$Cl$_2$ (2.0 mL) and TFA (2.0 mL). After stirring at 40° C. for 1 h, the reaction mixture was concentrated in vacuo. The crude material was redissolved in CH$_2$Cl$_2$ (10 mL) and the pH of the mixture was adjusted to ~10 with ammonia aqueous solution and then extracted into CH$_2$Cl$_2$. The organic phase was washed with brine, dried over MgSO$_4$ and concentrated in vacuo. The obtained crude product was used in the next step without further purification. LCMS calculated for $C_{14}H_{18}N_3O_3$ (M+H)$^+$: m/z=276.1; found: 276.1.

Intermediate C. 2-(((1R,3S)-3-(6-Amino-1-oxoisoin-dolin-2-yl)cyclohexyl)amino)-4-methoxypyrimidine-5-carbonitrile Step 1. 4-Methoxy-2-(((1R,3S)-3-(6-nitro-1-oxoi-soindolin-2-yl)cyclohexyl)amino)pyrimidine-5-car-bonitrile To a vial containing 2-((1S,3R)-3-aminocyclohexyl)-6-nitroisoindolin-1-one (200 mg, 0.726 mmol), DIPEA (381 µL, 2.179 mmol) in EtOH (4.8 mL) was added 2-chloro-4-methoxypyrimidine-5-carbonitrile (123 mg, 0.726 mmol). After stirring at 45° C. for 1 h, the solvent was evaporated in vacuo. The obtained crude product was purified by Biotage Isolera to give the desired product as yellow foam. LCMS calculated for $C_{20}H_{21}N_6O_4$ (M+H)$^+$: m/z=409.2; found: 409.1.

Step 2. 2-(((1R,3S)-3-(6-Amino-1-oxoisoindolin-2-yl)cyclohexyl)amino)-4-methoxypyrimidine-5-car-bonitrile This compound was prepared according to the procedures described in Example 47, with 4-methoxy-2-(((1R,3S)-3-(6- nitro-1-oxoisoindolin-2-yl)cyclohexyl)amino)pyrimidine-5-carbonitrile replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{20}H_{23}N_6O_2$ (M+H)$^+$: m/z=379.2; found: 379.2.

Intermediate D. N-(2-((1S,3R)-3-((4-Chloro-5-(trifluoromethyl)pyrimidin-2-yl)amino)cyclohexyl)-3-oxoisoindolin-5-yl)acrylamide Step 1. tert-Butyl ((1R,3S)-3-(6-nitro-1-oxoisoindolin-2-yl)cyclohexyl)carbamate To a vial containing methyl 2-(bromomethyl)-5-nitrobenzoate (500 mg, 1.824 mmol) and tert-butyl ((1R,3S)-3-aminocyclohexyl)carbamate (391 mg, 1.824 mmol) in DMF (9.12 mL) was added DIPEA (0.64 mL, 3.65 mmol). After stirring at 80° C. for 16 h, the reaction mixture was quenched with water and the mixture was extracted with diethyl ether. The organic phase was washed with brine, dried over $MgSO_4$ and concentrated in vacuo. The crude material was used in the next step without further purification. LCMS calculated for $C_{19}H_{26}N_3O_5$ (M+H)$^+$: m/z=376.2; found: 376.1.

Step 2. tert-Butyl ((1R,3S)-3-(6-amino-1-oxoisoindolin-2-yl)cyclohexyl)carbamate This compound was prepared according to the procedures described in Example 47, with tert-butyl ((1R,3S)-3-(6-nitro-1-oxoisoindolin-2-yl)cyclohexyl)carbamate replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{19}H_{28}N_3O_3$ (M+H)$^+$: m/z=346.2; found: 346.2.

Step 3. N-(2-((1S,3R)-3-Aminocyclohexyl)-3-oxoisoindolin-5-yl)acrylamide

To a vial containing tert-butyl ((1R,3S)-3-(6-amino-1-oxoisoindolin-2-yl)cyclohexyl)carbamate (200 mg, 0.579 mmol) and DIPEA (253 µL, 1.447 mmol) in $CH_2Cl_2$ (7.3 mL) was added acryloyl chloride (79 mg, 0.868 mmol) at 0° C. After stirring at 0° C. for 10 min, the reaction mixture was quenched with MeOH and concentrated in vacuo. The crude material was redissolved in $CH_2Cl_2$ (1.0 mL) and TFA (1.0 mL). After stirring at 40° C. for 1 h, the reaction mixture was concentrated in vacuo. The crude material was redissolved in $CH_2Cl_2$ (8 mL) and the pH of the mixture was adjusted to ~10 with ammonia aqueous solution and then extracted into $CH_2Cl_2$. The organic phase was washed with brine, dried over $MgSO_4$ and concentrated in vacuo. The obtained crude product was used in the next step without further purification. LCMS calculated for $C_{17}H_{22}N_3O_2$ (M+H)$^+$: m/z=300.2; found: 300.2.

Step 4. N-(2-((1S,3R)-3-((4-Chloro-5-(trifluoromethyl)pyrimidin-2-yl)amino)cyclohexyl)-3-oxoisoindolin-5-yl)acrylamide To a vial containing N-(2-((1S,3R)-3-aminocyclohexyl)-3-oxoisoindolin-5-yl)acrylamide (250 mg, 0.835 mmol), DIPEA (365 µL, 2.09 mmol) in EtOH (2.3 mL) at −20° C. was added 2,4-dichloro-5-(trifluoromethyl)pyrimidine (181 mg, 0.835 mmol). After stirring at −20° C. for 1 h, the solvent was evaporated in vacuo. The obtained crude product was used in the next step without further purification. LCMS calculated for $C_{22}H_{22}ClF_3N_5O_2$ (M+H)$^+$: m/z=480.1; found: 480.1.

Intermediate E. N-((3R,5R)-1-(8-Chloroimidazo[1,5-a]pyrazin-3-yl)-5-fluoropiperidin-3-yl)-5-(trifluoromethyl)pyrimidin-2-amine

Step 1. tert-Butyl ((3R,5R)-1-(((3-chloropyrazin-2-yl)methyl)carbamoyl)-5-fluoropiperidin-3-yl)carbamate To a vial containing bis(2,5-dioxopyrrolidin-1-yl) carbonate (775 mg, 3 mmol) in acetonitrile (6.3 mL) was added a solution of (3-chloropyrazin-2-yl)methanamine hydrochloride (544 mg, 3 mmol) and DIPEA (528 µL, 3 mmol) in acetonitrile (6.3 mL) dropwise. After stirring at r.t. for 20 min, tert-butyl ((3R,5R)-5-fluoropiperidin-3-yl)carbamate (PharmaBlock; 550 mg, 2.52 mmol) was added to the reaction mixture. After stirring at 60° C. for 30 min, the solvent was evaporated in vacuo, and the residue was redissolved in $CH_2Cl_2$ (20 mL). The organic phase was washed with aqueous saturated sodium bicarbonate solution and extracted with $CH_2Cl_2$. The organic phase was washed with brine, dried over $MgSO_4$ and concentrated in vacuo. The obtained crude product was purified by Biotage Isolera to give the desired product as pale yellow oil. LCMS calculated for $C_{16}H_{24}ClFN_5O_3(M+H)^+$: m/z=388.2; found: 388.2.

Step 2. (3R,5R)-3-Amino-N-((3-chloropyrazin-2-yl)methyl)-5-fluoropiperidine-1-carboxamide To a vial containing tert-butyl ((3R,5R)-1-(((3-chloropyrazin-2-yl)methyl)carbamoyl)-5-fluoropiperidin-3-yl)carbamate (910 mg, 2.4 mmol) in $CH_2Cl_2$ (2.0 mL) was added TFA (2.0 mL). After stirring at 40° C. for 1 h, the reaction mixture was concentrated in vacuo. The crude material was redissolved in $CH_2Cl_2$ (15 mL), and pH of the mixture was adjusted to ~10 with minimal amount of ammonia aqueous solution. The desired product was then extracted into $CH_2Cl_2$. The organic phase was washed with brine, dried over $MgSO_4$ and concentrated in vacuo. The obtained crude product was used in the next step without further purification. LCMS calculated for $C_{11}H_{16}ClFN_5O$ $(M+H)^+$: m/z=288.1; found: 288.1.

Step 3. (3R,5R)—N-((3-Chloropyrazin-2-yl)methyl)-3-fluoro-5-((5-(trifluoromethyl)pyrimidin-2-yl)amino)piperidine-1-carboxamide This compound was prepared according to the procedures described in Example 47, with (3R,5R)-3-amino-N-((3-chloropyrazin-2-yl)methyl)-5-fluoropiperidine-1-carboxamide replacing 2-(2-((1S,3R)-3-aminocyclohexyl)-5-nitro-1H-benzo[d]imidazol-1-yl)ethyl acetate in Step 4. LCMS calculated for $C_{16}H_{17}ClF_4N_7O$ $(M+H)^+$: m/z=434.1; found: 434.1.

Step 4. N-((3R,5R)-1-(8-Chloroimidazo[1,5-a]pyrazin-3-yl)-5-fluoropiperidin-3-yl)-5-(trifluoromethyl)pyrimidin-2-amine To a vial containing (3R,5R)—N-((3-chloropyrazin-2-yl)methyl)-3-fluoro-5-((5-(trifluoromethyl)pyrimidin-2-yl)amino)piperidine-1-carboxamide (400 mg, 0.92 mmol) and pyridine (149 µL, 1.84 mmol) in acetonitrile (3.7 mL) was added phosphoryl chloride (258 µL, 2.8 mmol) at 0° C. After stirring r.t. for 20 min, the reaction mixture was diluted with acetonitrile (5 mL) and cooled down to −20° C. The cold reaction mixture was slowly added to the mixture of ammonia aqueous solution and ice (1:1). The solvent was evaporated in vacuo, and the remaining aqueous phase was extracted with $CH_2Cl_2$. The organic phase was washed with brine, dried over $MgSO_4$ and concentrated in vacuo. The obtained crude product was purified by Biotage Isolera to give the desired product as pale yellow foam. LCMS calculated for $C_{16}H_{15}ClF_4N_7(M+H)^+$: m/z=416.1; found: 416.1.

Intermediate F. (R)—N-(1-(8-Chloroimidazo[1,5-a]pyrazin-3-yl)piperidin-3-yl)-5-(trifluoromethyl)pyrimidin-2-amine

Step 1. (R)—N-(Piperidin-3-yl)-5-(trifluoromethyl)pyrimidin-2-amine

To a vial containing tert-butyl (R)-3-aminopiperidine-1-carboxylate (800 mg, 4 mmol), DIPEA (873 μl, 5 mmol) in ethanol (8 mL) was added 2-chloro-5-(trifluoromethyl)pyrimidine (729 mg, 4 mmol). After stirring r.t. for 16 h, the solvent was evaporated in vacuo and the residue was redissolved in $CH_2Cl_2$ (5 mL), and then added TFA (5 mL). After stirring at 40° C. for 1 h, the reaction mixture was concentrated in vacuo. The crude material was redissolved in $CH_2Cl_2$ (20 mL) and the pH of the mixture was adjusted to ~10 with ammonia aqueous solution and then extracted into $CH_2Cl_2$. The organic phase was washed with brine, dried over $MgSO_4$ and concentrated in vacuo. The obtained crude product was used in the next step without further purification. LCMS calculated for $C_{10}H_{14}F_3N_4$ $(M+H)^+$: m/z=247.1; found: 247.1.

Step 2. (R)—N-((3-Chloropyrazin-2-yl)methyl)-3-((5-(trifluoromethyl)pyrimidin-2-yl)amino)piperidine-1-carboxamide This compound was prepared according to the procedures described in Intermediate E, with (R)—N-(piperidin-3-yl)-5-(trifluoromethyl)pyrimidin-2-amine replacing tert-butyl ((3R,5R)-5-fluoropiperidin-3-yl)carbamate in Step 1. LCMS calculated for $C_{16}H_{18}ClF_3N_7O$ $(M+H)^+$: m/z=416.1; found: 416.1.

Step 3. (R)—N-(1-(8-Chloroimidazo[1,5-a]pyrazin-3-yl)piperidin-3-yl)-5-(trifluoromethyl)pyrimidin-2-amine This compound was prepared according to the procedures described in Intermediate E, with (R)—N-((3-chloropyrazin-2-yl)methyl)-3-((5-(trifluoromethyl)pyrimidin-2-yl)amino)piperidine-1-carboxamide replacing (3R,5R)—N-((3-chloropyrazin-2-yl)methyl)-3-fluoro-5-((5-(trifluoromethyl)pyrimidin-2-yl)amino)piperidine-1-carboxamide in Step 4. LCMS calculated for $C_{16}H_{16}ClF_3N_7$ $(M+H)^+$: m/z=398.1; found: 398.2.

Example 1. (R)—N-(6-(3-((5-Cyano-4-methoxypyrimidin-2-yl)amino)piperidin-1-yl)-1-methyl-1H-pyrazolo[4,3-c]pyridin-3-yl)acrylamide Step 1. tert-Butyl (R)-(1-(4-chloro-5-cyanopyridin-2-yl)piperidin-3-yl)carbamate To a round-bottom flask containing a solution of 4,6-dichloronicotinonitrile (0.80 g, 4.62 mmol) in THF (20 mL) was added tert-butyl (R)-piperidin-3-ylcarbamate (1.11 g, 5.55 mmol), followed by DIEA (1.66 mL, 9.48 mmol). The reaction mixture was stirred at room temperature for 2 h, then concentrated in vacuo. The crude material was purified by Biotage Isolera (DCM/MeOH, up to 10% MeOH) to give a mixture, containing desired and undesired products, as white solid (1.20 g, 77%). LCMS calculated for $C_{16}H_{22}ClN_4O_2$ $(M+H)^+$: m/z=337.2; found: 337.1.

Step 2. tert-Butyl (R)-(1-(3-amino-1-methyl-1H-pyrazolo[4,3-c]pyridin-6-yl)piperidin-3-yl)carbamate A solution of tert-butyl (R)-(1-(4-chloro-5-cyanopyridin-2-yl)piperidin-3-yl)carbamate (0.51 g, 1.51 mmol) and methylhydrazine (0.70 g, 15 mmol) in ethanol (4 mL) was heated to 80° C. for 2 h. The reaction mixture was cooled to room temperature and then condensed in vacuo. The crude material was purified by Biotage Isolera (DCM/MeOH, up to 10% MeOH) to give the desired product as colorless oil (0.30 g, 57%). LCMS calculated for $C_{17}H_{27}N_6O_2$ $(M+H)^+$: m/z=347.2; found: 347.2.

Step 3. (R)-6-(3-Aminopiperidin-1-yl)-1-methyl-1H-pyrazolo[4,3-c]pyridin-3-amine To a solution of tert-butyl (R)-(1-(3-amino-1-methyl-1H-pyrazolo[4,3-c]pyridin-6-yl)piperidin-3-yl)carbamate (0.30 g, 0.88 mmol) in MeOH was added 4N HCl in 1,4-dioxane (2.5 mL). The reaction was stirred at room temperature for 1 h. Then the solvents were evaporated in vacuo, and obtained product was used in the next step without further purification. LCMS calculated for $C_{12}H_{19}N_6$ $(M+H)^+$: m/z=247.2; found: 247.2.

Step 4. (R)-2-((1-(3-Amino-1-methyl-1H-pyrazolo[4,3-c]pyridin-6-yl)piperidin-3-yl)amino)-4-methoxypyrimidine-5-carbonitrile To a mixture of (R)-6-(3-aminopiperidin-1-yl)-1-methyl-1H-pyrazolo[4,3-c]pyridin-3-amine (0.035 g, 0.142 mmol) in ethanol (1 mL) was added 2-chloro-4-methoxypyrimidine-5-carbonitrile (0.024 g, 0.142 mmol), and N-ethyl-N-isopropylpropan-2-amine (0.074 mL, 0.426 mmol). The reaction mixture was stirred at r.t for 2 h. The reaction mixture was condensed in vacuo, and the crude product was used in the next step without further purification. LCMS calculated for $C_{18}H_{22}N_9O$ $(M+H)^+$: m/z=380.2; found: 380.2.

Step 5. (R)—N-(6-(3-((5-Cyano-4-methoxypyrimidin-2-yl)amino)piperidin-1-yl)-1-methyl-1H-pyrazolo[4,3-c]pyridin-3-yl)acrylamide To a solution of (R)-2-((1-(3-amino-1-methyl-1H-pyrazolo[4,3-c]pyridin-6-yl)piperidin-3-yl)amino)-4-methoxypyrimidine-5-carbonitrile (50 mg, 0.132 mmol) in acetonitrile (1.0 mL) and water (0.110 mL) was added DIEA (69.0 μL, 0.395 mmol), followed by a solution of acryloyl chloride (12 mg, 0.132 mmol) in acetonitrile (1.0 mL) and the reaction mixture was stirred at r.t for 30 min. The mixture was diluted with $CH_3CN$ and water and purified by prep-LCMS (XBridge C18 column, eluting with a gradient of acetonitrile/water containing 0.1% TFA, at flow rate of 60 mL/min) to give product as white powder (11 mg, 20%). LCMS calculated for $C_{21}H_{24}N_9O_2$ $(M+H)^+$: m/z=434.4; found: 434.3.

Example 2. (R)—N-(6-(3-((5-Cyano-4-methoxypyrimidin-2-yl)amino)pyrrolidin-1-yl)-1-methyl-1H-pyrazolo[4,3-c]pyridin-3-yl)acrylamide This compound was prepared according to the procedures described in Example 1, with tert-butyl (R)-pyrrolidin-3-ylcarbamate replacing tert-butyl (R)-piperidin-3-ylcarbamate in Step 1. LCMS calculated for $C_{20}H_{22}N_9O_2$ $(M+H)^+$: m/z=420.2; found: 420.3.

Example 3. (R)—N-(8-(3-((5-Cyano-4-methoxypyrimidin-2-yl)amino)pyrrolidin-1-yl)-[1,2,4]triazolo[1,5-a]pyrazin-2-yl)acrylamide

Step 1. (R)-8-(3-Aminopyrrolidin-1-yl)-[1,2,4]triazolo[1,5-a]pyrazin-2-amine hydrochloride A microwave vessel containing a mixture of 8-chloro-[1,2,4]triazolo[1,5-a]pyrazin-2-amine (66 mg, 0.39 mmol), tert-butyl (R)-pyrrolidin-3-ylcarbamate (73 mg, 0.39 mmol), DIPEA (102 μL, 0.59 mmol) and DMSO (1 mL) was irradiated at 150° C. for 1 h using a Biotage Initator+ Microwave Synthesizer. After cooling to room temperature, the reaction mixture was extracted into $CH_2Cl_2$. The organic phase was then washed with water (2×), brine, then dried over $MgSO_4$, filtered, and concentrated in vacuo. The resulting crude residue was dissolved with MeOH (3 mL) and 4M HCl/dioxane (3 mL) and stirred overnight. The resulting solid was filtered and dried under vacuum to give the desired product which was taken on to the next step without further purification. LCMS calculated for $C_9H_{14}N_7$ $(M+H)^+$: m/z=220.1; found 220.1.

Step 2. (R)-2-((1-(2-Amino-[1,2,4]triazolo[1,5-a]pyrazin-8-yl)pyrrolidin-3-yl)amino)-4-methoxypyrimidine-5-carbonitrile A vial containing (R)-8-(3-aminopyrrolidin-1-yl)-[1,2,4] triazolo[1,5-a]pyrazin-2-amine hydrochloride (38 mg, 0.15 mmol), 2-chloro-4-methoxypyrimidine-5-carbonitrile (25 mg, 0.15 mmol) and DIPEA (77 µL, 0.44 mmol) as a solution in EtOH (1 mL) was stirred at r.t. for 2 h. The reaction mixture was concentrated in vacuo and used in the next step without further purification. LCMS calculated for $C_{15}H_{17}N_{10}O$ (M+H)$^+$: m/z=353.2; found 353.1.

Step 3. (R)—N-(8-(3-((5-Cyano-4-methoxypyrimi-din-2-yl)amino)pyrrolidin-1-yl)-[1,2,4]triazolo[1,5-a]pyrazin-2-yl)acrylamide To a vial containing (R)-2-((1-(2-amino-[1,2,4]triazolo[1,5-a]pyrazin-8-yl)pyrrolidin-3-yl)amino)-4-methoxypyrimidine-5-carbonitrile (20 mg, 0.06 mmol) as a solution in THF (1 mL) was added sodium hydride (60% dispersion in mineral oil, 23 mg, 0.57 mmol) and the resulting mixture was stirred at r.t. for 15 min. Acryloyl chloride (23 µL, 0.29 mmol) was then added in a dropwise fashion, and the reaction was stirred for 1 h. The reaction mixture was then diluted with TFA, water, and purified with prep-LCMS (XBridge C18 column, eluting with a gradient of acetonitrile/water containing 0.1% TFA, at flow rate of 60 mL/min). LCMS calculated for $C_{18}H_{19}N_{10}O_2$ (M+H)$^+$: m/z=407.2; found 407.3.

Example 4. N-(2-((1S,3R)-3-((5-(4-Methoxyphenyl) pyrimidin-2-yl)amino)cyclohexyl)-3-oxoisoindolin-5-yl)acrylamide

Step 1. tert-Butyl ((1R,3S)-3-(6-nitro-1-oxoisoindo-lin-2-yl)cyclohexyl)carbamate A solution of tert-butyl ((1R,3S)-3-aminocyclohexyl)carbamate (0.86 g, 4.01 mmol), methyl 2-(bromomethyl)-5-nitrobenzoate (1.1 g, 4.01 mmol) and DIPEA (1.037 g, 8.03 mmol) in 10 mL of DMF was heated at 80° C. for 3 h. The reaction mixture was cooled to r.t. before water and DCM were added. The organic phase was separated and concentrated in vacuo. The obtained crude product was purified by Biotage Isolera, eluted with 0-70% EtOAc in hexanes. The fractions contained product were combined and concentrated in vacuo. 1.45 g of the desired product was obtained as pale-yellow solid (96% yield). LCMS calculated for $C_{14}H_{17}N_3O_3$ (M-Boc+H)$^+$: m/z=276.1; found: 276.1.

Step 2. 2-((1S,3R)-3-Aminocyclohexyl)-6-nitroi-soindolin-1-one

TFA (2 mL) was added to a solution of tert-butyl ((1R,3S)-3-(6-nitro-1-oxoisoindolin-2-yl)cyclohexyl)carbamate (0.60 g, 1.598 mmol) in DCM (2 mL) and the reaction mixture was stirred at r.t. for 3 h. Then the solvents were removed in vacuo. The resulting material was used directly in the next step without further purification. LCMS calculated for $C_{14}H_{18}N_3O_3$ (M+H)$^+$: m/z=276.1; found: 276.2.

Step 3. 2-((1S,3R)-3-((5-Bromopyrimidin-2-yl) amino)cyclohexyl)-6-nitroisoindolin-1-one A mixture of 2-((1S,3R)-3-aminocyclohexyl)-6-nitroi-soindolin-1-one (0.16 g, 0.581 mmol), 5-bromo-2-fluoropyrimidine (0.103 g, 0.581 mmol) and DIPEA (0.20 g) in ethanol (2 mL) was heated at 85° C. for 20 h. The resulting solution was then concentrated in vacuo and purified by Biotage Isolera. The fractions containing the product were combined and concentrated in vacuo to yield a white solid. LCMS calculated for $C_{18}H_{19}BrN_5O_3$ (M+H)$^+$: m/z=432.1, 434.1; found: 432.1, 434.1.

Step 4. 2-((1S,3R)-3-((5-(4-Methoxyphenyl)pyrimi-din-2-yl)amino)cyclohexyl)-6-nitroisoindolin-1-one A mixture of 2-((1S,3R)-3-((5-bromopyrimidin-2-yl) amino)cyclohexyl)-6-nitroisoindolin-1-one (0.060 g, 0.139 mmol), (4-methoxyphenyl)boronic acid (0.11 g, 0.724 mmol), X-Phos Pd G2 (15 mg), and $Cs_2CO_3$ (100 mg) in dioxanes (2 mL) and water (0.2 mL) was heated at 80° C. for 2 h. The reaction mixture was then concentrated in vacuo and the product was purified by Biotage Isolera, eluted with 0-100% EtOAc in hexanes. LCMS calculated for $C_{25}H_{26}N_5O_4$ (M+H)$^+$: m/z=460.2; found: 460.3.

Step 5. 6-Amino-2-((1S,3R)-3-((5-(4-methoxyphenyl)pyrimidin-2-yl)amino)cyclohexyl)isoindolin-1-one A mixture of 2-((1S,3R)-3-((5-(4-Methoxyphenyl)pyrimidin-2-yl)amino)cyclohexyl)-6-nitroisoindolin-1-one (0.010 g, 0.022 mmol), iron powder (30 mg), saturated $NH_4Cl$ solution (1 mL) in ethanol (2 mL) was heated at 60° C. for 1 h. The resulted mixture was then diluted with EtOAc (20 mL), filtered through celite, and concentrated in vacuo. Crude material was used directly in the next step without further purification. LCMS calculated for $C_{25}H_{28}N_5O_2$ (M+H)$^+$: m/z=430.2; found: 430.3.

Step 6. N-(2-((1S,3R)-3-((5-(4-Methoxyphenyl)pyrimidin-2-yl)amino)cyclohexyl)-3-oxoisoindolin-5-yl)acrylamide Acryloyl chloride was slowly added at 0° C. to a solution of 6-amino-2-((1S,3R)-3-((5-(4-methoxyphenyl)pyrimidin-2-yl)amino)cyclohexyl)isoindolin-1-one (0.010 g, 0.023 mmol) and DIPEA (0.5 mL) in DCM (1 mL). The reaction mixture was stirred at 0° C. for 30 min, before being concentrated in vacuo. The crude was dissolved in DMF (5 mL), filtered and purified by prep-LCMS (XBridge C18 column, eluting with a gradient of acetonitrile/water containing 0.1% TFA, at flow rate of 60 mL/min). LCMS calculated for $C_{28}H_{30}N_5O_3$ (M+H)$^+$: m/z=484.2; found: 484.3.

Example 5. N-(2-((1S,3R)-3-((5-Methyl-4-(trifluoromethyl)pyrimidin-2-yl)amino)cyclohexyl)-3-oxoisoindolin-5-yl)acrylamide

Step 1. 2-((1S,3R)-3-((5-Bromo-4-(trifluoromethyl)pyrimidin-2-yl)amino)cyclohexyl)-6-nitroisoindolin-1-one 5-Bromo-2-chloro-4-(trifluoromethyl)pyrimidine (0.380 g, 1.453 mmol) was added to a solution of 2-((1S,3R)-3-aminocyclohexyl)-6-nitroisoindolin-1-one (0.40 g, 1.453 mmol) and TEA (0.2 g) in EtOH (3 mL). After stirring at room temperature for 30 min, the reaction mixture was kept in the refrigerator overnight. The mixture was then concentrated in vacuo. The obtained crude product was purified by Biotage Isolera, eluted with 0-100% EtOAc in hexanes. The fractions contained product were combined and concentrated in vacuo. LCMS calculated for $C_{19}H_{18}BrF_3N_5O_3$ (M+H)$^+$: m/z=500.1, 502.1; found: 500.1, 502.1.

Step 2. 2-((1S,3R)-3-((5-Methyl-4-(trifluoromethyl)pyrimidin-2-yl)amino)cyclohexyl)-6-nitroisoindolin-1-one A mixture of 2-((1S,3R)-3-((5-bromo-4-(trifluoromethyl)pyrimidin-2-yl)amino)cyclohexyl)-6-nitroisoindolin-1-one (0.120 g, 0.240 mmol), $Cs_2CO_3$ (0.10 g), Pd(dppf)$_2$Cl$_2$ (0.060 g) and 2,4,6-trimethyl-1,3,5,2,4,6-trioxatriborinane (0.151 g, 1.199 mmol) in dioxane (3 mL) and water (0.6 mL) was flushed with nitrogen, sealed with a cap and heated at 80° C. for 2 h. The reaction mixture was then concentrated in vacuo. The obtained crude product was purified by Biotage Isolera, eluted with 0-100% EtOAc in hexanes. The fractions contained product were combined and concentrated in vacuo. LCMS calculated for $C_{20}H_{21}F_3N_5O_3$ (M+H)$^+$: m/z=436.4; found: 436.2.

Step 3. 6-Amino-2-((1S,3R)-3-((5-methyl-4-(trifluo-romethyl)pyrimidin-2-yl)amino)cyclohexyl)isoindo-lin-1-one This compound was prepared according to the procedures described in Example 4, with 2-((1S,3R)-3-((5-methyl-4-(trifluoromethyl)pyrimidin-2-yl)amino)cyclohexyl)-6-ni-troisoindolin-1-one replacing 6-amino-2-((1S,3R)-3-((5-(4-methoxyphenyl)pyrimidin-2-yl)amino)cyclohexyl) isoindolin-1-one in Step 5. LCMS calculated for $C_{20}H_{23}F_3N_5O$ (M+H)$^+$: m/z=406.2; found: 406.2.

Step 4. N-(2-((1S,3R)-3-((5-Methyl-4-(trifluorom-ethyl)pyrimidin-2-yl)amino)cyclohexyl)-3-oxoisoin-dolin-5-yl)acrylamide This compound was prepared according to the procedures described in Example 4, with 6-amino-2-((1S,3R)-3-((5-methyl-4-(trifluoromethyl)pyrimidin-2-yl)amino)cyclo-hexyl)isoindolin-1-one replacing 6-amino-2-((1S,3R)-3-((5-(4-methoxyphenyl)pyrimidin-2-yl)amino)cyclohexyl) isoindolin-1-one in Step 6. LCMS calculated for $C_{23}H_{25}F_3N_5O_2$ (M+H)$^+$: m/z=460.2; found: 460.2.

Example 6. N-(2-((1S,3R)-3-((5-(Difluoromethoxy) pyrimidin-2-yl)amino)cyclohexyl)-3-oxoisoindolin-5-yl)acrylamide Step 1. tert-Butyl ((1R,3S)-3-(6-amino-1-oxoisoin-dolin-2-yl)cyclohexyl)carbamate This compound was prepared according to the procedures described in Example 4, with tert-butyl ((1R,3S)-3-(6-nitro-1-oxoisoindolin-2-yl)cyclohexyl)carbamate replacing 2-((1S,3R)-3-((5-(4-methoxyphenyl)pyrimidin-2-yl)amino) cyclohexyl)-6-nitroisoindolin-1-one in Step 5. LCMS cal-culated for $C_{14}H_{19}N_3O$ (M-Boc+H)$^+$: m/z=245.2; found: 245.2.

Step 2. tert-Butyl ((1R,3S)-3-(6-acrylamido-1-oxoi-soindolin-2-yl)cyclohexyl)carbamate This compound was prepared according to the procedures described in Example 4, with tert-butyl ((1R,3S)-3-(6-amino-1-oxoisoindolin-2-yl)cyclohexyl)carbamate replac-ing 6-amino-2-((1S,3R)-3-((5-(4-methoxyphenyl)pyrimi-din-2-yl)amino)cyclohexyl)isoindolin-1-one in Step 6. LCMS calculated for $C_{17}H_{21}N_3O_2$ (M-Boc+H)$^+$: m/z=299.2; found: 299.2.

Step 3. N-(2-((1S,3R)-3-Aminocyclohexyl)-3-oxoi-soindolin-5-yl)acrylamide

This compound was prepared according to the procedures described in Example 4, with tert-butyl ((1R,3S)-3-(6-acry-lamido-1-oxoisoindolin-2-yl)cyclohexyl)carbamate replac-ing tert-butyl ((1R,3S)-3-(6-nitro-1-oxoisoindolin-2-yl)cy-clohexyl)carbamate in Step 2. LCMS calculated for $C_{17}H_{22}N_3O_2$ (M+H)$^+$: m/z=300.2; found: 300.2.

Step 4. N-(2-((1S,3R)-3-((5-(Difluoromethoxy)py-rimidin-2-yl)amino)cyclohexyl)-3-oxoisoindolin-5-yl)acrylamide A mixture of N-(2-((1S,3R)-3-aminocyclohexyl)-3-oxoi-soindolin-5-yl)acrylamide (0.020 g, 0.067 mmol), 2-chloro-5-(difluoromethoxy)pyrimidine (20 mg, 0.111 mmol) and TEA (0.10 g) in n-BuOH (1 mL) was stirred at 120° C. overnight. The mixture was then diluted with 4 mL of methanol, filtered, and purified by prep-LCMS (XBridge C18 column, eluting with a gradient of acetonitrile/water containing 0.1% TFA, at flow rate of 60 mL/min). LCMS calculated for $C_{22}H_{24}F_2N_5O_3$ (M+H)$^+$: m/z=444.2; found: 444.2.

223

Example 7. N-(3-Oxo-2-((1S,3R)-3-((5-vinylpyrimi-
din-2-yl)amino)cyclohexyl)isoindolin-5-yl)acrylam-
ide This compound was prepared according to the procedures described in Example 6, with 2-chloro-5-vinylpyrimidine replacing 2-chloro-5-(difluoromethoxy)pyrimidine in Step 4. LCMS calculated for $C_{23}H_{26}N_5O_2$ (M+H)$^+$: m/z=404.2; found: 404.2.

Example 8. N-(2-((1S,3R)-3-((5-(1-Methyl-1H-
pyrazol-4-yl)pyrimidin-2-yl)amino)cyclohexyl)-3-
oxoisoindolin-5-yl)acrylamide This compound was prepared according to the procedures described in Example 6, with 2-chloro-5-(1-methyl-1H-pyrazol-4-yl)pyrimidine replacing 2-chloro-5-(difluo-romethoxy)pyrimidine in Step 4. LCMS calculated for $C_{25}H_{28}N_7O_2$ (M+H)$^+$: m/z=458.2; found: 458.2.

Example 9. N-(2-((1S,3R)-3-((5-Cyano-4-methylpy-
rimidin-2-yl)amino)cyclohexyl)-3-oxoisoindolin-5-
yl)acrylamide

224

Step 1. N-(2-((1S,3R)-3-((4-Chloro-5-cyanopyrimi-
din-2-yl)amino)cyclohexyl)-3-oxoisoindolin-5-yl)
acrylamide 2,4-Dichloropyrimidine-5-carbonitrile (0.349 g, 2.0 mmol) was added to a solution of N-(2-((1S,3R)-3-amino-cyclohexyl)-3-oxoisoindolin-5-yl)acrylamide (0.60 g, 2.004 mmol) and DIPEA (0.5 g) in ethanol (10 mL). After stirring at r.t. for 30 min, the reaction flask was kept in the refrig-erator overnight. The mixture was then concentrated in vacuo and purified by Biotage Isolera, eluted with 0-100% EtOAc in hexanes. LCMS calculated for $C_{22}H_{22}ClN_6O_2$ (M+H)$^+$: m/z=437.2; found: 437.3.

Step 2. N-(2-((1S,3R)-3-((5-Cyano-4-methylpyrimi-
din-2-yl)amino)cyclohexyl)-3-oxoisoindolin-5-yl)
acrylamide This compound was prepared according to the procedures described in Example 5, with N-(2-((1S,3R)-3-((4-chloro-5-cyanopyrimidin-2-yl)amino)cyclohexyl)-3-oxoisoindolin-5-yl)acrylamide replacing 2-((1S,3R)-3-((5-bromo-4-(trif-luoromethyl)pyrimidin-2-yl)amino)cyclohexyl)-6-nitroisoindolin-1-one. LCMS calculated for $C_{23}H_{25}N_6O_2$ (M+H)$^+$: m/z=417.2; found: 417.2.

Example 10. N-(2-((1S,3R)-3-((5-Ethylpyrimidin-2-
yl)amino)cyclohexyl)-3-oxoisoindolin-5-yl)acrylam-
ide This compound was prepared according to the procedures described in Example 6, with 2-chloro-5-ethylpyrimidine replacing 2-chloro-5-(difluoromethoxy)pyrimidine in Step 4. LCMS calculated for $C_{23}H_{28}N_5O_2$ (M+H)$^+$: m/z=406.2; found: 406.3.

Example 11. N-(2-((1S,3R)-3-((5-Cyclopropylpy-rimidin-2-yl)amino)cyclohexyl)-3-oxoisoindolin-5-yl)acrylamide Example 14. (R)—N-(8-(3-((5-Cyano-4-methoxypy-rimidin-2-yl)amino)piperidin-1-yl)-2-methylimidazo[1,2-a]pyrazin-3-yl)acrylamide This compound was prepared according to the procedures described in Example 6, with 2-chloro-5-cyclopropylpy-rimidine replacing 2-chloro-5-(difluoromethoxy)pyrimidine in Step 4. LCMS calculated for $C_{24}H_{28}N_5O_2$ (M+H)$^+$: m/z=418.2; found: 418.3.

Example 12. N-(2-((1S,3R)-3-((5-Isopropylpyrimi-din-2-yl)amino)cyclohexyl)-3-oxoisoindolin-5-yl)acrylamide This compound was prepared according to the procedures described in Example 6, with 2-chloro-5-isopropylpyrimi-dine replacing 2-chloro-5-(difluoromethoxy)pyrimidine in Step 4. LCMS calculated for $C_{24}H_{30}N_5O_2$ (M+H)$^+$: m/z=420.2; found: 420.2.

Example 13. N-(2-((1S,3R)-3-((4-Methoxy-5-meth-ylpyrimidin-2-yl)amino)cyclohexyl)-3-oxoisoindo-lin-5-yl)acrylamide This compound was prepared according to the procedures described in Example 6, with 2-chloro-4-methoxy-5-meth-ylpyrimidine replacing 2-chloro-5-(difluoromethoxy)py-rimidine in Step 4. LCMS calculated for $C_{23}H_{28}N_5O_3$ (M+H)$^+$: m/z=422.2; found: 422.2.

Step 1. tert-Butyl (R)-(1-(3-aminopyrazin-2-yl)pip-eridin-3-yl)carbamate

A mixture of 3-chloropyrazin-2-amine (1.0 g, 7.72 mmol), tert-butyl (R)-piperidin-3-ylcarbamate (2.3 g, 11.48 mmol) and DIPEA (1 mL) in DMF (6 mL) was heated at 120° C. overnight. After cooling to r.t., water and ethyl acetate were added. The organic layer was separated, dried over sodium sulfate, and concentrated in vacuo. The obtained crude product was purified by Biotage Isolera, eluted with 0-100% EtOAc in hexanes. The fractions contained product were combined and concentrated in vacuo. LCMS calculated for $C_{14}H_{24}N_5O_2$ (M+H)$^+$: m/z=294.2; found: 294.2.

Step 2. tert-Butyl (R)-(1-(2-methyl-3-((2,4,4-trim-ethylpentan-2-yl)amino)imidazo[1,2-a]pyrazin-8-yl)piperidin-3-yl)carbamate Acetaldehyde (0.34 g, 7.82 mmol), 2-isocyano-2,4,4-trimethylpentane (0.435 g, 3.13 mmol) and ytterbium(III) triflate (0.194 g, 0.313 mmol) were added to a solution of tert-butyl (R)-(1-(3-aminopyrazin-2-yl)piperidin-3-yl)car-bamate (0.49 g, 1.56 mmol) in MeOH (5 mL). The suspen-sion was heated at 65° C. overnight. Then the reaction mixture was concentrated in vacuo. The obtained crude product was purified by Biotage Isolera, eluted with 0-70% EtOAc in hexanes. The fractions contained product were combined and concentrated in vacuo. LCMS calculated for $C_{25}H_{43}N_6O_2$ (M+H)$^+$: m/z=459.3; found: 459.2.

Step 3. tert-Butyl (R)-(1-(3-amino-2-methylimidazo [1,2-a]pyrazin-8-yl)piperidin-3-yl)carbamate 2 mL of TFA was slowly added to a solution of tert-butyl (R)-(1-(2-methyl-3-((2,4,4-trimethylpentan-2-yl)amino) imidazo[1,2-a]pyrazin-8-yl)piperidin-3-yl)carbamate (0.5 g, 1.09 mmol) in 2 mL of DCM. The reaction mixture was stirred at r.t. for 1 h and then concentrated in vacuo. The resulting residue was directly used in the next step. LCMS calculated for $C_{17}H_{27}N_6O_2$ (M+H)$^+$: m/z=347.3; found: 347.2.

Step 4. tert-Butyl (R)-(1-(3-acrylamido-2-methyl-imidazo[1,2-a]pyrazin-8-yl)piperidin-3-yl)carbamate One drop of acryloyl chloride was added to a solution of tert-butyl (R)-(1-(3-amino-2-methylimidazo[1,2-a]pyrazin-8-yl)piperidin-3-yl)carbamate (0.080 g, 0.231 mmol) and DIPEA (0.1 mL) in DCM (1 mL). The reaction mixture was stirred at room temperature for 30 min and then quenched with water. The organic layer was separated, dried over sodium sulfate, and concentrated in vacuo. The obtained crude product was purified by Biotage Isolera, eluted with 0-100% EtOAc in hexanes. The fractions contained product were combined and concentrated in vacuo. LC-MS calculated for $C_{20}H_{29}N_6O_3$ (M+H)$^+$: m/z=401.3; found: 401.3.

Step 5. (R)—N-(8-(3-Aminopiperidin-1-yl)-2-meth-ylimidazo[1,2-a]pyrazin-3-yl)acrylamide TFA (1.5 mL) was added to a solution of tert-butyl (R)-(1-(3-acrylamido-2-methylimidazo[1,2-a]pyrazin-8-yl) piperidin-3-yl)carbamate (0.080 g, 0.200 mmol) in 1 mL of DCM. The reaction mixture was stirred at room temperature for 1 h. The mixture was then concentrated in vacuo. The obtained crude product was directly used in the next step. LCMS calculated for $C_{15}H_{21}N_6O$ (M+H)$^+$: m/z=301.1; found: 301.0.

Step 6. (R)—N-(8-(3-((5-Cyano-4-methoxypyrimi-din-2-yl)amino)piperidin-1-yl)-2-methylimidazo[1, 2-a]pyrazin-3-yl)acrylamide DIPEA (0.1 mL) was added to a solution of (R)—N-(8-(3-aminopiperidin-1-yl)-2-methylimidazo[1,2-a]pyrazin-3-yl)acrylamide (0.050 g, 0.166 mmol) and 2-chloro-4-methoxypyrimidine-5-carbonitrile (0.050 g, 0.327 mmol) in methanol (1 mL), and the reaction mixture was stirred at room temperature overnight. The reaction mixture was then diluted with 4 mL of methanol and filtered. The product was purified by prep-LCMS (XBridge C18 column, eluting with a gradient of acetonitrile/water containing 0.10% TFA, at flow rate of 60 mL/min). LCMS calculated for $C_{21}H_{24}N_9O_2$ (M+H)$^+$: m/z=434.2; found: 434.3.

Example 15. N-(2-((1S,3R)-3-((5-Cyano-6-meth-ylpyridin-2-yl)amino)cyclohexyl)-3-oxoisoindolin-5-yl)acrylamide DIPEA (0.10 mL) was added to a solution of N-(2-((1S, 3R)-3-aminocyclohexyl)-3-oxoisoindolin-5-yl)acrylamide (0.020 g, 0.067 mmol) and 6-fluoro-2-methylnicotinonitrile (20 mg, 0.147 mmol) in ethanol (1 mL), and the reaction mixture was stirred at 90° C. overnight. The reaction mixture was then diluted with 4 mL methanol and filtered. The product was purified by prep-LCMS (XBridge C18 column, eluting with a gradient of acetonitrile/water containing 0.1%

TFA, at flow rate of 60 mL/min). LCMS calculated for $C_{24}H_{26}N_5O_2$ $(M+H)^+$: m/z=416.2; found: 416.3.

Example 16. N-(2-((1S,3R)-3-((5-Cyano-4-methylpyridin-2-yl)amino)cyclohexyl)-3-oxoisoindolin-5-yl)acrylamide This compound was prepared according to the procedures described in Example 15, with 6-chloro-4-methylnicotinonitrile replacing 6-fluoro-2-methylnicotinonitrile LCMS calculated for $C_{24}H_{26}N_5O_2$ $(M+H)^+$: m/z=416.2; found: 416.3.

Example 17. N-(2-((1S,3R)-3-((5-Ethynylpyrimidin-2-yl)amino)cyclohexyl)-3-oxoisoindolin-5-yl)acrylamide This compound was prepared according to the procedures described in Example 15, with 5-ethynyl-2-chloropyrimidine replacing 6-fluoro-2-methylnicotinonitrile. LCMS calculated for $C_{23}H_{24}N_5O_2$ $(M+H)^+$: m/z=402.2; found: 402.3.

Example 18. N-(2-((1S,3R)-3-((5-Cyano-4-(trifluoromethyl)pyridin-2-yl)amino)cyclohexyl)-3-oxoisoindolin-5-yl)acrylamide DIPEA (0.05 g) was added to a solution of N-(2-((1S,3R)-3-aminocyclohexyl)-3-oxoisoindolin-5-yl)acrylamide (0.020 g, 0.067 mmol) and 6-chloro-4-(trifluoromethyl)nicotinonitrile (30 mg, 0.145 mmol) in methanol (1 mL), and the reaction mixture was stirred at room temperature overnight. The reaction mixture was then diluted with 4 mL of methanol and filtered. The product was then purified by prep-LCMS (XBridge C18 column, eluting with a gradient of acetonitrile/water containing 0.10% TFA, at flow rate of 60 mL/min). LCMS calculated for $C_{24}H_{23}F_3N_5O_2$ $(M+H)^+$: m/z=470.2; found: 470.3.

Example 19. N-(2-((1S,3R)-3-((4-Cyano-5-(trifluoromethyl)pyridin-2-yl)amino)cyclohexyl)-3-oxoisoindolin-5-yl)acrylamide This compound was prepared according to the procedures described in Example 18, with 2-chloro-5-(trifluoromethyl)isonicotinonitrile replacing 6-chloro-4-(trifluoromethyl)nicotinonitrile. LCMS calculated for $C_{24}H_{23}F_3N_5O_2$ $(M+H)^+$: m/z=470.2; found: 470.3.

Example 20. (R)—N-(7-(3-((5-Cyanopyrimidin-2-yl)amino)pyrrolidin-1-yl)-1-methyl-1H-indazol-3-yl)acrylamide Step 1. tert-butyl (R)-(1-(4-cyano-3-fluorophenyl)pyrrolidin-3-yl)carbamate 4-Bromo-2-fluorobenzonitrile (0.50 g, 2.500 mmol) and tert-butyl (R)-pyrrolidin-3-ylcarbamate (0.466 g, 2.500 mmol) and XantPhos Pd G2 (0.40 g), $Cs_2CO_3$ (1.8 g) and dioxane (15 mL) were mixed together and vacuumed. The mixture was then heated at 85° C. for 20 h. The mixture was worked up in water and EtOAc. Organic phase was concentrated in vacuo. The obtained crude product was purified by Biotage Isolera, eluted with 0-80% EtOAc in hexanes. The fractions contained product were combined and concentrated in vacuo. 0.52 g of pure product was obtained (68% yield). LCMS calculated for $C_{16}H_{20}FN_3O_2$ (M-Boc+H)$^+$: m/z=306.2; found: 306.3.

Step 2. tert-Butyl (R)-(1-(3-amino-1-methyl-1H-indazol-7-yl)pyrrolidin-3-yl)carbamate tert-Butyl (R)-(1-(3-cyano-2-fluorophenyl)pyrrolidin-3-yl)carbamate (0.20 g, 0.655 mmol) and methylhydrazine (0.302 g, 6.55 mmol) and ethanol (3 mL) were mixed together, sealed in a microwave tube, and heated at 120° C. for 8 h. The resulting solution was concentrated in vacuo. The obtained crude product was purified by Biotage Isolera, eluted with 0-100% EtOAc. 0.066 g of pure product was obtained (30% yield). LCMS calculated for $C_{17}H_{25}N_5O_2$ (M+H)$^+$: m/z=332.2; found: 332.3.

Step 3. (R)—N-acryloyl-N-(7-(3-aminopyrrolidin-1-yl)-1-methyl-1H-indazol-3-yl)acrylamide tert-Butyl (R)-(1-(3-amino-1-methyl-1H-indazol-7-yl) pyrrolidin-3-yl)carbamate (0.066 g, 0.199 mmol) was dissolved in DCM (3 mL), followed with addition of DIPEA (0.50 mL). Acryloyl chloride (0.054 g, 0.597 mmol) was slowly added. After stirring at room temperature for 1 h, water (5 mL) was added. The organic phase was concentrated in vacuo. The obtained crude product was purified by Biotage Isolera, eluted with 0-70% EtOAc in hexanes. Fractions contained product was concentrated in vacuo. The residue was mixed with 1 mL of DCM and 1 mL of TFA, stirred at room temperature for 1 h, and concentrated in vacuo. LCMS calculated for $C_{11}H_{21}N_5O_2$ (M+H)$^+$: m/z=340.2; found: 340.3.

Step 4. (R)—N-(7-(3-((5-cyanopyrimidin-2-yl) amino)pyrrolidin-1-yl)-1-methyl-1H-indazol-3-yl) acrylamide To a mixture of 2-chloropyrimidine-5-carbonitrile (14 mg, 0.100 mmol) and (R)—N-acryloyl-N-(7-(3-aminopyrrolidin-1-yl)-1-methyl-1H-indazol-3-yl)acrylamide (34 mg, 0.100 mmol) in DMF (1 mL) was added $Cs_2CO_3$ (20 mg). The reaction mixture was sealed in a tube and heated at 140° C. in microwave reactor for 20 min. After cooling to room temperature, the reaction mixture was diluted with MeOH (4 mL), filtered through a plug, and purified by prep-LCMS (XBridge C18 column, eluting with a gradient of acetonitrile/water containing 0.10% TFA, at flow rate of 60 mL/min). LCMS calculated for $C_{20}H_{20}N_8O$ (M+H)$^+$: m/z=389.2; found: 389.3.

Example 21. (R)—N-(6-(3-((5-Cyano-4-methoxypyrimidin-2-yl)amino)pyrrolidin-1-yl)-1-methyl-1H-indazol-3-yl)acrylamide Step 1. tert-Butyl (R)-(1-(3-cyano-2-fluorophenyl) pyrrolidin-3-yl)carbamate This compound was prepared according to the procedures described in Example 20, with 3-bromo-2-fluorobenzonitrile replacing 4-bromo-2-fluorobenzonitrile in Step 1. LCMS calculated for $C_{16}H_{20}FN_3O_2$ (M-Boc+H)$^+$: m/z=306.2; found: 306.3.

Step 2. tert-Butyl (R)-(1-(3-amino-1-methyl-1H-indazol-6-yl)pyrrolidin-3-yl)carbamate This compound was prepared according to the procedures described in Example 20, with tert-butyl (R)-(1-(3-cyano-2-fluorophenyl)pyrrolidin-3-yl)carbamate replacing tert-butyl (R)-(1-(4-cyano-3-fluorophenyl)pyrrolidin-3-yl)carbamate in Step 2. LCMS calculated for $C_{17}H_{25}N_5O_2$ (M+H)$^+$: m/z=332.2; found: 332.3.

Step 3. (R)—N-Acryloyl-N-(6-(3-aminopyrrolidin-1-yl)-1-methyl-1H-indazol-3-yl)acrylamide This compound was prepared according to the procedures described in Example 20, with tert-butyl (R)-(1-(3-amino-1-methyl-1H-indazol-6-yl)pyrrolidin-3-yl)carbamate replacing tert-butyl (R)-(1-(3-amino-1-methyl-1H-indazol-7-yl)pyrrolidin-3-yl)carbamate in Step 3. LCMS calculated for $C_{11}H_{21}N_5O_2$ (M+H)$^+$: m/z=340.2; found: 340.3.

Step 4. (R)—N-(6-(3-((5-cyano-4-methoxypyrimi-din-2-yl)amino)pyrrolidin-1-yl)-1-methyl-1H-inda-zol-3-yl)acrylamide This compound was prepared according to the procedures described in Example 20, with (R)—N-acryloyl-N-(6-(3-aminopyrrolidin-1-yl)-1-methyl-1H-indazol-3-yl)acrylam-ide replacing and (R)—N-acryloyl-N-(7-(3-aminopyrroli-din-1-yl)-1-methyl-1H-indazol-3-yl)acrylamide and 2-chloro-4-methoxypyrimidine-5-carbonitrile replacing 2-chloropyrimidine-5-carbonitrile in Step 4. LCMS calcu-lated for $C_{21}H_{22}N_8O_2$ (M+H)$^+$: m/z=419.2; found: 419.3.

Example 22. (R)—N-(5-(3-((5-Cyano-4-methoxypy-rimidin-2-yl)amino)piperidin-1-yl)-[1,2,4]triazolo[1,5-a]pyridin-2-yl)acrylamide Step 1. tert-Butyl (R)-(1-(2-amino-[1,2,4]triazolo[1,5-a]pyridin-5-yl)piperidin-3-yl)carbamate tert-Butyl (R)-piperidin-3-ylcarbamate (0.496 g, 2.478 mmol) and 5-bromo-[1,2,4]triazolo[1,5-a]pyridin-2-amine (0.132 g, 0.620 mmol) and $Cs_2CO_3$ (0.404 g, 1.239 mmol), X-Phos (29 mg), $Pd_2(DBA)_3$ (20 mg), DMF (5 mL) were mixed in a tube, which was then sealed and heated in microwave reactor at 180° C. for 20 min. The mixture was worked up in DCM and water, and the organic phase was concentrated in vacuo. The obtained crude product was purified by Biotage Isolera, eluted with 0-100% EtOAc in hexanes. 0.080 g of pure product was obtained (39% yield). LCMS calculated for $C_{16}H_{24}N_6O_2$ (M+H)$^+$: m/z=333.1; found: 333.1.

Step 2. tert-Butyl (R)-(1-(2-amino-[1,2,4]triazolo[1,5-a]pyridin-5-yl)piperidin-3-yl)carbamate This compound was prepared according to the procedures described in Example 20, with tert-butyl (R)-(1-(2-amino-

[1,2,4]triazolo[1,5-a]pyridin-5-yl)piperidin-3-yl)carbamate replacing tert-butyl (R)-(1-(3-amino-1-methyl-1H-indazol-7-yl)pyrrolidin-3-yl)carbamate in Step 3. LCMS calculated for $C_{17}H_{20}N_6O_2$ (M+H)$^+$: m/z=341.2; found: 341.3.

Step 3. (R)—N-(5-(3-((5-cyano-4-methoxypyrimidin-2-yl)amino)piperidin-1-yl)-[1,2,4]triazolo[1,5-a]pyridin-2-yl)acrylamide

[C]

This compound was prepared according to the procedures described in Example 20, with tert-butyl (R)-(1-(2-amino-[1,2,4]triazolo[1,5-a]pyridin-5-yl)piperidin-3-yl)carbamate replacing tert-butyl (R)-(1-(3-amino-1-methyl-1H-indazol-7-yl)pyrrolidin-3-yl)carbamate and 2-chloro-4-methoxypyrimidine-5-carbonitrile replacing 2-chloropyrimidine-5-carbonitrile in Step 4. LCMS calculated for $C_{20}H_{21}N_9O_2$ (M+H)$^+$: m/z=420.2; found: 420.3.

Example 23. (R)—N-(5-(3-((5-Cyano-4-methoxypyrimidin-2-yl)amino)pyrrolidin-1-yl)-[1,2,4]triazolo[1,5-a]pyridin-2-yl)acrylamide Step 1. tert-Butyl (R)-(1-(2-amino-[1,2,4]triazolo[1,5-a]pyridin-5-yl)pyrrolidin-3-yl)carbamate This compound was prepared according to the procedures described in Example 22, with tert-butyl (R)-pyrrolidin-3-ylcarbamate replacing tert-butyl (R)-piperidin-3-ylcarbamate in Step 1. LCMS calculated for $C_{15}H_{22}N_6O_2$ (M+H)$^+$: m/z=319.2; found: 319.1.

Step 2. tert-Butyl (R)-(1-(2-amino-[1,2,4]triazolo[1,5-a]pyridin-5-yl)piperidin-3-yl)carbamate This compound was prepared according to the procedures described in Example 20, with tert-butyl (R)-(1-(2-amino-[1,2,4]triazolo[1,5-a]pyridin-5-yl)pyrrolidin-3-yl)carbamate replacing tert-butyl (R)-(1-(3-amino-1-methyl-1H-indazol-7-yl)pyrrolidin-3-yl)carbamate in Step 3. LCMS calculated for $C_{16}H_{18}N_6O_2$ (M+H)$^+$: m/z=327.2; found: 327.3.

Step 3. (R)—N-(5-(3-((5-Cyano-4-methoxypyrimidin-2-yl)amino)pyrrolidin-1-yl)-[1,2,4]triazolo[1,5-a]pyridin-2-yl)acrylamide This compound was prepared according to the procedures described in Example 20, with tert-butyl (R)-(1-(2-amino-[1,2,4]triazolo[1,5-a]pyridin-5-yl)piperidin-3-yl)carbamate replacing (R)—N-acryloyl-N-(7-(3-aminopyrrolidin-1-yl)-1-methyl-1H-indazol-3-yl)acrylamide and 2-chloro-4-methoxypyrimidine-5-carbonitrile replacing 2-chloropyrimidine-5-carbonitrile in Step 4. LCMS calculated for $C_{19}H_{19}N_9O_2$ (M+H)$^+$: m/z=406.2; found: 406.3.

Example 24. N-(1-((1S,3R)-3-((5-Cyano-4-methoxypyrimidin-2-yl)amino)cyclohexyl)-1H-indazol-4-yl)acrylamide Step 1. tert-Butyl ((1R,3S)-3-(4-nitro-1H-indazol-1-yl)cyclohexyl)carbamate To a solution of 4-nitro-1H-indazole (76 mg, 0.464 mmol) and tert-butyl ((1R,3R)-3-hydroxycyclohexyl)carbamate (50 mg, 0.232 mmol) in THF (1 mL) was added triphenylphosphine (152 mg, 0.581 mmol) at 0° C. After stirring for 15 min, diisopropyl (E)-diazene-1,2-dicarboxylate (114 μL, 0.581 mmol) was slowly added to the solution at 0° C. After stirring at 50° C. for 24 h, the solvent was removed in vacuo and EtOAc and hexane were added. The mixture was stirred at r.t. for 2 h, filtered, and concentrated in vacuo. Crude material was purified by Biotage isolera to give the desired product as yellow powder. LCMS calculated for $C_{18}H_{25}N_4O_4$ (M+H)$^+$: m/z=361.2; found 361.2.

Step 2. (1R,3S)-3-(4-Nitro-1H-indazol-1-yl)cyclohexan-1-amine tert-Butyl ((1R,3S)-3-(4-nitro-1H-indazol-1-yl)cyclohexyl)carbamate (0.084 g, 0.232 mmol) was added to 2 mL solution of 50% TFA in DCM. After stirring for 30 min, the solvent was removed in vacuo. The obtained crude product was used in the next step without further purification. LCMS calculated for $C_{13}H_{17}N_4O_2$ (M+H)$^+$: m/z=261.1; found 261.2.

Step 3. 4-Methoxy-2-(((1R,3S)-3-(4-nitro-1H-indazol-1-yl)cyclohexyl)amino)pyrimidine-5-carbonitrile To a solution of (1R,3S)-3-(4-nitro-1H-indazol-1-yl)cyclohexan-1-amine (0.060 g, 0.232 mmol) in EtOH (1 mL) was added N-ethyl-N-isopropylpropan-2-amine (0.090 g, 0.696 mmol) and 2-chloro-4-methoxypyrimidine-5-carbonitrile (0.047 g, 0.278 mmol) at r.t. After stirring overnight at 50° C., the solvent was removed in vacuo. The obtained crude product was used in the next step without further purification. LCMS calculated for $C_{19}H_{20}N_7O_3$ (M+H)$^+$: m/z=394.2; found 394.2.

Step 4. 2-(((1R,3S)-3-(4-Amino-1H-indazol-1-yl)cyclohexyl)amino)-4-methoxypyrimidine-5-carbonitrile To a solution of 4-methoxy-2-(((1R,3S)-3-(4-nitro-1H-indazol-1-yl)cyclohexyl)amino)pyrimidine-5-carbonitrile (0.091 g, 0.232 mmol) in THF (1 mL) and water (0.5 mL) was added zinc dust (0.152 g, 2.32 mmol) and ammonium chloride (0.124 g, 2.320 mmol) at r.t. After stirring at 50° C. for 1 h, the reaction mixture was diluted with EtOAc and filtered through Celite pad. The organic layer was further washed with brine, dried over sodium sulfate, filtered and concentrated in vacuo. The obtained crude product was used in the next step without further purification. LCMS calculated for $C_{19}H_{22}N_7O$ (M+H)$^+$: m/z=364.2; found 364.2.

Step 5. N-(1-((1S,3R)-3-((5-Cyano-4-methoxypyrimidin-2-yl)amino)cyclohexyl)-1H-indazol-4-yl)acrylamide To a solution of 2-(((1R,3S)-3-(4-amino-1H-indazol-1-yl)cyclohexyl)amino)-4-methoxypyrimidine-5-carbonitrile (13 mg, 0.036 mmol) in DCM (1 mL) was added N-ethyl-N-isopropylpropan-2-amine (19 μL, 0.108 mmol) and acryloyl chloride (4 μL, 0.054 mmol) at 0° C. After stirring at 0° C. for 20 min, the solvent was removed in vacuo. The reaction mixture was diluted with $CH_3CN$ and water and purified by prep-LCMS (XBridge C18 column, eluting with a gradient of acetonitrile/water containing 0.10% TFA, at flow rate of 60 mL/min). LCMS calculated for $C_{22}H_{24}N_7O_2$ (M+H)$^+$: m/z=418.2; found 418.2.

Example 25. N-(1-((1S,3R)-3-((5-Cyano-4-methoxypyrimidin-2-yl)amino)cyclohexyl)-1H-indazol-5-yl)acrylamide This compound was prepared according to the procedures described in Example 24, with 5-nitro-1H-indazole replacing 4-nitro-1H-indazole. LCMS calculated for $C_{22}H_{24}N_7O_2$ $(M+H)^+$: m/z=418.2; found: 418.2.

Example 26. N-(1-((1S,3R)-3-((5-Cyano-4-methoxypyrimidin-2-yl)amino)cyclohexyl)-1H-indol-5-yl)acrylamide This compound was prepared according to the procedures described in Example 24, with 5-nitro-1H-indole replacing 4-nitro-1H-indazole. LCMS calculated for $C_{23}H_{25}N_6O_2$ $(M+H)^+$: m/z=417.2; found: 417.2.

Example 27. N-(1-((1S,3R)-3-((5-Cyano-4-methoxypyrimidin-2-yl)amino)cyclohexyl)-1H-benzo[d]imidazol-4-yl)acrylamide Step 1. tert-Butyl ((1R,3S)-3-((3-bromo-2-nitrophenyl)amino)cyclohexyl)carbamate To a solution of 1-bromo-3-fluoro-2-nitrobenzene (500 mg, 2.27 mmol) and tert-butyl ((1R,3S)-3-aminocyclohexyl) carbamate (487 mg, 2.27 mmol) in acetonitrile (15 mL) was added potassium carbonate (785 mg, 5.68 mmol). After stirring at 85° C. for 6 h, the solids were filtered off. The solvent was removed in vacuo. The obtained crude product was used in the next step without further purification. LCMS calculated for $C_{17}H_{25}BrN_3O_4$ $(M+H)^+$: m/z=414.1; found 414.1.

Step 2. tert-Butyl ((1R,3S)-3-((2-amino-3-bromophenyl)amino)cyclohexyl)carbamate To a solution of tert-butyl ((1R,3S)-3-((3-bromo-2-nitrophenyl)amino)cyclohexyl)carbamate (0.942 g, 2.273 mmol) in THF (5 mL) and water (2.5 mL) was added zinc dust (1.49 g, 22.73 mmol) and ammonium chloride (1.22 g, 22.73 mmol). After stirring at 50° C. for 1 h, the reaction mixture was filtered and the product was extracted with EtOAc. The organic layer was further washed with brine, dried over sodium sulfate, filtered, and concentrated in vacuo. The obtained crude was purified by Biotage Isolera to give the desired product as white solid. LCMS calculated for $C_{17}H_{27}BrN_3O_2$ $(M+H)^+$: m/z=384.1; found 384.1.

Step 3. tert-Butyl ((1R,3S)-3-(4-bromo-1H-benzo[d] imidazol-1-yl)cyclohexyl)carbamate To a solution of tert-butyl ((1R,3S)-3-((2-amino-3-bromophenyl)amino)cyclohexyl)carbamate (0.874 g, 2.273 mmol) in toluene (5 mL) was added 4-methylbenzenesulfonic acid hydrate (0.043 g, 0.227 mmol) and triethoxymethane (1.9 mL, 11.37 mmol). After stirring at 110° C. for 2 h, the solvent was removed in vacuo. The obtained crude product was used in the next step without further purification. LCMS calculated for $C_{18}H_{25}BrN_3O_2$ $(M+H)^+$: m/z=394.1; found 394.1.

Step 4. (1R,3S)-3-(4-Bromo-1H-benzo[d]imidazol-1-yl)cyclohexan-1-amine tert-Butyl ((1R,3S)-3-(4-bromo-1H-benzo[d]imidazol-1-yl)cyclohexyl)carbamate (0.032 g, 0.08 mmol) was added to 1 mL solution of 50% TFA in DCM. After stirring for 30 min, the solvent was removed in vacuo. The obtained crude product was used in the next step without further purification. LCMS calculated for $C_{13}H_{17}BrN_3$ (M+H)$^+$: m/z=294.1; found 294.1.

Step 5. 2-(((1R,3S)-3-(4-Bromo-1H-benzo[d]imidazol-1-yl)cyclohexyl)amino)-4-methoxypyrimidine-5-carbonitrile To a solution of (1R,3S)-3-(4-bromo-1H-benzo[d]imidazol-1-yl)cyclohexan-1-amine (0.024 g, 0.08 mmol) in EtOH (1 mL) was added 2-chloro-4-methoxypyrimidine-5-carbonitrile (0.016 g, 0.096 mmol) and N-ethyl-N-isopropylpropan-2-amine (10 mg, 0.080 mmol). After stirring overnight at 50° C., the solvent was removed in vacuo. The obtained crude was purified by Biotage Isolera to give the desired product as white solid. LCMS calculated for $C_{19}H_{20}BrN_6O$ (M+H)$^+$: m/z=427.1; found 427.1.

Step 6. tert-Butyl (1-((1S,3R)-3-((5-cyano-4-methoxypyrimidin-2-yl)amino)cyclohexyl)-1H-benzo[d]imidazol-4-yl)carbamate To a solution of 2-(((1R,3S)-3-(4-bromo-1H-benzo[d]imidazol-1-yl)cyclohexyl)amino)-4-methoxypyrimidine-5-carbonitrile (7 mg, 0.014 mmol) in dioxane (1.5 mL) were added tert-butyl carbamate (8 mg, 0.068 mmol), Brett Phos (3 mg, 5.47 μmol), tris(dibenzylideneacetone)dipalladium (2.5 mg, 2.74 μmol) and cesium carbonate (11 mg, 0.034 mmol). The resulting mixture was degassed with $N_2$ three times. After stirring at 80° C. overnight, the reaction was filtered and the solvent was removed in vacuo. The obtained crude was purified by Biotage Isolera to give the desired product as white solid. LCMS calculated for $C_{24}H_{30}N_7O_3$ (M+H)$^+$: m/z=464.2; found 464.2.

Step 7. 2-(((1R,3S)-3-(4-Amino-1H-benzo[d]imidazol-1-yl)cyclohexyl)amino)-4-methoxypyrimidine-5-carbonitrile tert-Butyl (1-((1S,3R)-3-((5-cyano-4-methoxypyrimidin-2-yl)amino)cyclohexyl)-1H-benzo[d]imidazol-4-yl)carbamate (0.015 g, 0.033 mmol) was added to 1 mL solution of 50% TFA in DCM. After stirring for 30 min, the solvent was removed in vacuo. The obtained crude product was used in the next step without further purification. LCMS calculated for $C_{19}H_{22}N_7O$ (M+H)$^+$: m/z=364.2; found 364.2.

Step 8. N-(1-((1S,3R)-3-((5-Cyano-4-methoxypyrimidin-2-yl)amino)cyclohexyl)-1H-benzo[d]imidazol-4-yl)acrylamide To a solution of 2-(((1R,3S)-3-(4-amino-1H-benzo[d]imidazol-1-yl)cyclohexyl)amino)-4-methoxypyrimidine-5-carbonitrile (0.012 g, 0.033 mmol) in DCM (1 mL) was added N-ethyl-N-isopropylpropan-2-amine (0.057 mL, 0.330 mmol) and acryloyl chloride (4 μL, 0.050 mmol) at 0° C. After stirring at 0° C. for 20 min, the solvent was removed in vacuo. The reaction mixture was diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{22}H_{24}N_7O_2$ (M+H)$^+$: m/z=418.2; found 418.2.

Example 28. (R)—N-(3-(3-((5-Cyano-4-methoxypyrimidin-2-yl)amino)piperidin-1-yl)benzo[d]isoxazol-7-yl)acrylamide

Step 1. (R)-1-(7-Nitrobenzo[d]isoxazol-3-yl)piperidin-3-amine

To a microwave pressure vial containing 3-chloro-7-nitrobenzo[d]isoxazole (100 mg, 0.504 mmol) and tert-butyl (R)-piperidin-3-ylcarbamate (202 mg, 1.007 mmol) was added MeCN (5.04 mL). The reaction vial was sealed and heated to 130° C. under microwave irradiation for 1 h. After cooling to r.t., the reaction mixture was diluted with aqueous saturated sodium bicarbonate solution and DCM. The organic phase was separated and dried over sodium sulfate. The solvent was removed in vacuo and the crude material was treated with a solution of 4:1 DCM/TFA (5.0 mL), and stirred at r.t. for 4 h. The solvents were evaporated in vacuo. Crude material was purified by Biotage Isolera to give the desired product as white solid. LCMS calculated for $C_{12}H_{15}N_4O_3$ (M+H)$^+$: m/z=263.1; found 263.1.

Step 2. (R)-4-Methoxy-2-((1-(7-nitrobenzo[d]isoxazol-3-yl)piperidin-3-yl)amino)pyrimidine-5-carbonitrile To a mixture of 2-chloro-4-methoxypyrimidine-5-carbonitrile (20 mg, 0.116 mmol) and (R)-1-(7-nitrobenzo[d]isoxazol-3-yl)piperidin-3-amine (31 mg, 0.116 mmol) was added N,N-diisopropylethylamine (61 μL, 0.349 mmol) and DMF (3 mL). The reaction mixture was heated to 100° C. for 1 h and then cooled to r.t. Solvent was removed in vacuo and crude material was used in the next step without further purification. LCMS calculated for $C_{18}H_{18}N_7O_4$ (M+H)$^+$: m/z=396.1; found: 396.1.

Step 3. (R)-2-((1-(7-Aminobenzo[d]isoxazol-3-yl)piperidin-3-yl)amino)-4-methoxypyrimidine-5-carbonitrile To a reaction vial containing (R)-4-methoxy-2-((1-(7-nitrobenzo[d]isoxazol-3-yl)piperidin-3-yl)amino)pyrimidine-5-carbonitrile (44 mg, 0.111 mmol) and tin(II) chloride (221 mg, 1.163 mmol) was added EtOAc (2 mL) and MeOH (2 mL). The reaction mixture was heated at 80° C. for 3 h and then cooled to r.t. The reaction was quenched with aqueous saturated sodium bicarbonate solution and allowed to stir. The mixture was extracted with 4:1 DCM/iPrOH and the organic layer was subsequently washed with water and brine, dried over sodium sulfate, and solvents were evaporated in vacuo. The crude material was used in the next step without further purification. LCMS calculated for $C_{18}H_{20}N_7O_2$ (M+H)$^+$: m/z=366.1; found: 366.1.

Step 4. (R)—N-(3-(3-((5-Cyano-4-methoxypyrimidin-2-yl)amino)piperidin-1-yl)benzo[d]isoxazol-7-yl)acrylamide To a solution of (R)-2-((1-(7-aminobenzo[d]isoxazol-3-yl)piperidin-3-yl)amino)-4-methoxypyrimidine-5-carbonitrile (41 mg, 0.111 mmol) in DCM (3 mL) at 0° C. were added N,N-diisopropylethylamine (39 μL, 0.222 mmol) and acryloyl chloride (9 μL, 0.111 mmol). The reaction was stirred at 0° C. for 10 min, then quenched with MeOH (1 mL) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min). LCMS calculated for $C_{21}H_{22}N_7O_3$ (M+H)$^+$: m/z=420.2; found: 420.2. $^1$H NMR (600 MHz, DMSO-d6) δ 10.41 (s, 1H), 8.61 (s, 1H), 8.49 (s, 1H), 8.29 (d, J=7.2 Hz, 1H), 8.17 (d, J=7.8 Hz, 1H), 7.67-7.60 (m, 1H), 7.27 (dt, J=17.8, 7.9 Hz, 1H), 6.71 (dd, J=17.0, 10.2 Hz, 1H), 6.31 (m, 1H), 5.83-5.74 (m, 1H), 4.15-4.08 (m, 1H), 3.94 (s, 3H), 3.86 (s, 2H), 3.15-2.94 (m, 2H), 2.03 (s, 1H), 1.90 (dq, J=13.7, 3.4 Hz, 1H), 1.81-1.60 (m, 1H) ppm.

Example 29. N-(3-Oxo-2-((1S,3R)-3-((5-(trifluoromethyl)thiazol-2-yl)amino)cyclohexyl)isoindolin-5-yl)acrylamide

Step 1. tert-butyl ((1S,3R)-3-((5-(Trifluoromethyl)thiazol-2-yl)amino)cyclohexyl)carbamate To a solution of 2-chloro-5-(trifluoromethyl)thiazole (50 mg, 0.267 mmol) in THF (2 mL) was added tert-butyl ((1S,3R)-3-aminocyclohexyl)carbamate (114 mg, 0.533 mmol) and N-ethyl-N-isopropylpropan-2-amine (237 μL, 1.3 mmol). After stirring at 80° C. overnight, the solvent was removed in vacuo. Crude material was purified by Biotage isolera to give the desired product as white powder. LCMS calculated for $C_{15}H_{23}F_3N_3O_2S$ (M+H)$^+$: m/z=366.2; found 366.2.

Step 2. (1R,3S)—N¹-(5-(Trifluoromethyl)thiazol-2-yl)cyclohexane-1,3-diamine tert-Butyl ((1S,3R)-3-((5-(trifluoromethyl)thiazol-2-yl)amino)cyclohexyl)carbamate (45 mg, 0.123 mmol) was added to 1 mL solution of 50% TFA in DCM. After stirring for 30 min, the solvent was removed in vacuo. The obtained crude product was used in the next step without further purification. LCMS calculated for $C_{10}H_{15}F_3N_3S$ $(M+H)^+$: m/z=266.1; found 266.1.

Step 3. 6-Nitro-2-((1S,3R)-3-((5-(trifluoromethyl)thiazol-2-yl)amino)cyclohexyl)isoindolin-1-one To a solution of (1R,3S)—N-(5-(trifluoromethyl)thiazol-2-yl)cyclohexane-1,3-diamine (0.033 g, 0.123 mmol) in DMF (1 mL) was added methyl 2-(bromomethyl)-5-nitrobenzoate (0.040 g, 0.148 mmol) and N-ethyl-N-isopropylpropan-2-amine (0.238 g, 1.845 mmol). After stirring at 80° C. overnight, the solvent was removed in vacuo. Crude material was purified by Biotage isolera to give the desired product as white powder. LCMS calculated for $C_{18}H_{18}F_3N_4O_3S$ $(M+H)^+$: m/z=427.1; found 427.1.

Step 4. 6-Amino-2-((1S,3R)-3-((5-(trifluoromethyl)thiazol-2-yl)amino)cyclohexyl)isoindolin-1-one To a solution of 6-nitro-2-((1S,3R)-3-((5-(trifluoromethyl)thiazol-2-yl)amino)cyclohexyl)isoindolin-1-one (11 mg, 0.026 mmol) in THF (0.2 mL) and water (0.1 mL) was added zinc dust (17 mg, 0.258 mmol) and ammonium chloride (14 mg, 0.258 mmol). After stirring at 50° C. for 1 h, the reaction mixture was filtered and the product was extracted with EtOAc. The organic layer was further washed with brine, dried over sodium sulfate, filtered, and concentrated in vacuo. The obtained crude was purified by Biotage Isolera to give the desired product as white solid. LCMS calculated for $C_{18}H_{20}F_3N_4OS$ $(M+H)^+$: m/z=397.1; found 397.1.

Step 5. N-(3-Oxo-2-((1S,3R)-3-((5-(trifluoromethyl)thiazol-2-yl)amino)cyclohexyl)isoindolin-5-yl)acrylamide To a solution of 6-amino-2-((1S,3R)-3-((5-(trifluoromethyl)thiazol-2-yl)amino)cyclohexyl)isoindolin-1-one (10 mg, 0.026 mmol) in DCM (1 mL) was added N-ethyl-N-isopropylpropan-2-amine (0.014 mL, 0.078 mmol) and acryloyl chloride (3 μL, 0.034 mmol) at 0° C. After stirring at 0° C. for 20 min, the solvent was removed in vacuo. The reaction mixture was diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{21}H_{22}F_3N_4O_2S$ $(M+H)^+$: m/z=451.1; found 451.1. ¹H NMR (500 MHz, DMSO-d6) δ 10.34 (s, 1H), 8.43 (d, 1H), 8.11 (d, 1H), 7.76 (dd, 1H), 7.58 (m, 1H), 7.53 (d, 1H), 6.45 (dd, 1H), 6.29 (dd, 1H), 5.79 (dd, 1H), 4.40 (m, 1H), 4.13 (m, 1H), 3.72 (m, 1H), 2.19 (d, 1H), 2.01 (d, 1H), 1.85 (m, 1H), 1.74 (m, 1H), 1.52 (m, 3H), 1.23 (m, 1H) ppm.

Example 30. (R)—N-(6-(3-((5-Cyano-4-methoxypyrimidin-2-yl)amino)piperidin-1-yl)-1-methyl-1H-pyrazolo[4,3-c]pyridin-3-yl)but-2-ynamide To a solution of (R)-2-((1-(3-amino-1-methyl-1H-pyrazolo[4,3-c]pyridin-6-yl)piperidin-3-yl)amino)-4-methoxypyrimidine-5-carbonitrile (50 mg, 0.132 mmol) (from Example 1 Step 4) in DMF (1.0 mL) were added DIEA (69.0 μL, 0.395 mmol) and the solution of but-2-ynoic acid (0.011 g, 0.132 mmol) and HATU (0.150 g, 0.395 mmol) in DMF (1.0 mL), and the reaction mixture was stirred at r.t for 30 minutes. The reaction mixture was then diluted with $CH_3CN$ and water and purified by prep-LCMS (XBridge C18 column, eluting with a gradient of acetonitrile/water containing 0.10% TFA, at flow rate of 60 mL/min) to give the product as white solid. LCMS calculated for $C_{22}H_{24}N_9O_2$ $(M+H)^+$: m/z=446.4; found: 446.4.

Example 31. 2-Bromo-N-(6-((R)-3-((5-cyano-4-methoxypyrimidin-2-yl)amino)piperidin-1-yl)-1-methyl-1H-pyrazolo[4,3-c]pyridin-3-yl)butanamide To a solution (R)-2-((1-(3-amino-1-methyl-1H-pyrazolo[4,3-c]pyridin-6-yl)piperidin-3-yl)amino)-4-methoxypyrimidine-5-carbonitrile (50 mg, 0.132 mmol) (from Example 1 Step 4) in acetonitrile (1.0 mL) and water (0.1 mL) were added DIEA (69 μL, 0.395 mmol) and a solution of 2-bromobutanoyl chloride (0.024 g, 0.132 mmol) in acetonitrile (1.0 mL), and the reaction mixture was stirred at r.t for 30 min. The reaction mixture was then diluted with $CH_3CN$ and water and was purified by prep-LCMS (XBridge C18 column, eluting with a gradient of acetonitrile/water containing 0.1% TFA, at flow rate of 60 mL/min) to give the product as white powder. LCMS calculated for $C_{22}H_{27}BrN_9O_2$ $(M+H)^+$: m/z=528.2; found: 528.2.

Example 32. 2-Bromo-N-(6-((R)-3-((5-cyano-4-methoxypyrimidin-2-yl)amino)piperidin-1-yl)-1-methyl-1H-pyrazolo[4,3-c]pyridin-3-yl)propanamide This compound was prepared according to the procedures described in Example 31, with 2-bromopropanoyl chloride replacing 2-bromobutanoyl chloride. LCMS calculated for $C_{21}H_{25}BrN_9O_2$ $(M+H)^+$: m/z=514.4; found: 514.4.

Example 33. (R)-2-Chloro-N-(6-(3-((5-cyano-4-methoxypyrimidin-2-yl)amino)piperidin-1-yl)-1-methyl-1H-pyrazolo[4,3-c]pyridin-3-yl)acetamide This compound was prepared according to the procedures described in Example 31, with 2-chloroacetyl chloride replacing 2-bromobutanoyl chloride. LCMS calculated for $C_{20}H_{23}ClN_9O_2$ $(M+H)^+$: m/z=456.2; found: 456.1.

Example 34. (R)—N-(8-(3-((5-Cyano-4-methoxypyrimidin-2-yl)amino)piperidin-1-yl)imidazo[1,2-a]pyrazin-3-yl)acrylamide Step 1. (R)-1-(3-Bromoimidazo[1,2-a]pyrazin-8-yl)piperidin-3-amine A reaction vial containing 3-bromo-8-chloroimidazo[1,2-a]pyrazine (100 mg, 0.430 mmol), tert-butyl (R)-piperidin-3-ylcarbamate (86 mg, 0.430 mmol), cesium carbonate (350 mg, 1.075 mmol), [(4,5-bis(diphenylphosphino)-9,9-dimethylxanthene)-2-(2'-amino-1,1'-biphenyl)]palladium(II) methanesulfonate (Xantphos Pd G3, 82 mg, 0.086 mmol) was evacuated and back filled with nitrogen. 1,4-Dioxane (4.3 mL) was then added to the reaction mixture, which was then stirred at 50° C. for 18 h. The reaction mixture was cooled to r.t., diluted with DCM, and filtered through celite. The solvents were evaporated in vacuo and the crude material was treated with a solution of 4:1 DCM/TFA (5.0 mL), and stirred at r.t. for 4 h. The solvents were evaporated in vacuo. Crude material was purified by Biotage Isolera to give the desired product as white solid. LCMS calculated for $C_{11}H_{15}BrN_5$ $(M+H)^+$: m/z=296.0; found 296.0.

Step 2. (R)-2-((1-(3-Bromoimidazo[1,2-a]pyrazin-8-yl)piperidin-3-yl)amino)-4-methoxypyrimidine-5-carbonitrile To a mixture of 2-chloro-4-methoxypyrimidine-5-carbo-nitrile (51 mg, 0.303 mmol) and (R)-1-(3-bromoimidazo[1,2-a]pyrazin-8-yl)piperidin-3-amine (90 mg, 0.303 mmol) was added N,N-diisopropylethylamine (159 μL, 0.909 mmol) and DMF (3.03 mL). The reaction mixture was heated to 100° C. for 1 h and then cooled to r.t. Solvent was removed in vacuo and crude material was purified by Biotage Isolera to give the desired product as a white solid. LCMS calculated for $C_{17}H_{18}BrN_8O$ $(M+H)^+$: m/z=429.1; found: 429.0.

Step 3. (R)-2-((1-(3-Aminoimidazo[1,2-a]pyrazin-8-yl)piperidin-3-yl)amino)-4-methoxypyrimidine-5-carbonitrile A reaction vial containing (R)-2-((1-(3-bromoimidazo[1,2-a]pyrazin-8-yl)piperidin-3-yl)amino)-4-methoxypyrimi-dine-5-carbonitrile (130 mg, 0.303 mmol), tert-butyl car-bamate (284 mg, 2.423 mmol), cesium carbonate (296 mg, 0.908 mmol), [(2-di-cyclohexylphosphino-3,6-dimethoxy-2',4',6'-triisopropyl-1,1'-biphenyl)-2-(2'-amino-1,1'-biphe-nyl)]palladium(II) methanesulfonate (BrettPhos Pd G3, 110 mg, 0.121 mmol) was evacuated and backfilled with nitro-gen. 1,4-Dioxane (3.03 mL) was added to the reaction mixture, which was then stirred at 100° C. for 18 h. The reaction mixture was cooled to r.t. and the solvents were evaporated in vacuo. The crude mixture was treated with a solution of 4:1 DCM/TFA (5.0 mL), which was stirred at r.t. for 4 h. The solvents were evaporated in vacuo. Crude material was purified by Biotage Isolera to give the desired product as a yellow oil. LCMS calculated for $C_{17}H_{20}N_9O$ $(M+H)^+$: m/z=366.2; found 366.2.

Step 4. (R)—N-(8-(3-((5-Cyano-4-methoxypyrimi-din-2-yl)amino)piperidin-1-yl)imidazo[1,2-a]pyrazin-3-yl)acrylamide To a solution of (R)-2-((1-(3-aminoimidazo[1,2-a]pyrazin-8-yl)piperidin-3-yl)amino)-4-methoxypyrimidine-5-carbonitrile (111 mg, 0.304 mmol) in DCM (9 mL) at 0° C. was added N,N-diisopropylethylamine (106 μL, 0.608 mmol) and acryloyl chloride (25 μL, 0.304 mmol). The reaction was allowed to stir at 0° C. for 10 min, then quenched with MeOH (1 mL) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min). LCMS calculated for $C_{20}H_{22}N_9O_2$ $(M+H)^+$: m/z=420.2; found: 420.2.

Example 35. (R)—N-(3-(3-((5-Cyano-4-methoxypy-rimidin-2-yl)amino)piperidin-1-yl)-1-methyl-1H-indazol-7-yl)acrylamide

Step 1. tert-Butyl (R)-(1-(1-methyl-7-nitro-1H-inda-zol-3-yl)piperidin-3-yl)carbamate A reaction vial containing 3-bromo-1-methyl-7-nitro-1H-indazole (100 mg, 0.391 mmol), tert-butyl (R)-piperidin-3-ylcarbamate (117 mg, 0.586 mmol), cesium carbonate (318 mg, 0.976 mmol), [(4,5-bis(diphenylphosphino)-9,9-dim-ethylxanthene)-2-(2'-amino-1,1'-biphenyl)]palladium(II) methanesulfonate (Xantphos Pd G3, 111.0 mg, 0.117 mmol) was evacuated and back filled with nitrogen. 1,4-Dioxane (4 mL) was then added to the reaction mixture, which was then stirred at 100° C. for 18 h. The reaction mixture was cooled to r.t., diluted with DCM, and filtered through celite. The solvents were evaporated in vacuo and the crude material was purified by Biotage Isolera to give the desired product as an orange solid. LCMS calculated for $C_{18}H_{26}N_5O_4$ $(M+H)^+$: m/z=376.2; found 376.2.

Step 2. (R)-1-(1-Methyl-7-nitro-1H-indazol-3-yl)
piperidin-3-amine

A solution of 4:1 DCM/TFA (5.0 mL) was added to a reaction vial containing (R)-1-(1-methyl-6-nitro-1H-indazol-3-yl)piperidin-3-amine (147 mg, 0.391 mmol) and stirred at r.t. for 4 h. The solvents were evaporated in vacuo and the crude material was used in the next step without further purification. LCMS calculated for $C_{13}H_{18}N_5O_2$ $(M+H)^+$: m/z=276.1; found 276.1.

Step 3. (R)-4-Methoxy-2-((1-(1-methyl-7-nitro-1H-indazol-3-yl)piperidin-3-yl)amino)pyrimidine-5-carbonitrile To a mixture of 2-chloro-4-methoxypyrimidine-5-carbonitrile (26 mg, 0.151 mmol) and (R)-1-(1-methyl-7-nitro-1H-indazol-3-yl)piperidin-3-amine (42 mg, 0.151 mmol) was added N,N-diisopropylethylamine (79 μL, 0.454 mmol) and DMF (1.5 mL). The reaction mixture was heated to 100° C. for 1 h and then cooled to r.t. Solvent was removed in vacuo and crude material was purified by Biotage Isolera to give the desired product as a yellow solid. LCMS calculated for $C_{19}H_{21}N_8O_3$ $(M+H)^+$: m/z=409.2; found 409.2.

Step 4. (R)-2-((1-(7-Amino-1-methyl-1H-indazol-3-yl)piperidin-3-yl)amino)-4-methoxypyrimidine-5-carbonitrile To a reaction vial containing (R)-4-methoxy-2-((1-(1-methyl-7-nitro-1H-indazol-3-yl)piperidin-3-yl)amino)pyrimidine-5-carbonitrile (62 mg, 0.151 mmol) and tin(II) chloride (287 mg, 1.513 mmol) was added EtOAc (3 mL) and MeOH (3 mL). The reaction mixture was heated to 80° C. for 3 h and then cooled to r.t. The reaction was quenched with aqueous saturated sodium bicarbonate solution and allowed to stir. The mixture was extracted with 4:1 DCM/iPrOH and the organic layer was subsequently washed with water and brine, dried over sodium sulfate, and solvents were evaporated in vacuo. The crude material was used in the next step without further purification. LCMS calculated for $C_{19}H_{23}N_8O$ $(M+H)^+$: m/z=379.2; found 379.2.

Step 5. (R)—N-(3-(3-((5-Cyano-4-methoxypyrimidin-2-yl)amino)piperidin-1-yl)-1-methyl-1H-indazol-7-yl)acrylamide To a solution of (R)-2-((1-(7-amino-1-methyl-1H-indazol-3-yl)piperidin-3-yl)amino)-4-methoxypyrimidine-5-carbonitrile (57 mg, 0.151 mmol) in DCM (4.5 mL) at 0° C. was added N,N-diisopropylethylamine (53 μL, 0.301 mmol) and acryloyl chloride (12 μL, 0.151 mmol). The reaction was stirred at 0° C. for 10 min, then quenched with MeOH (1 mL) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min). LCMS calculated for $C_{22}H_{25}N_8O_2$ $(M+H)^+$: m/z=433.2; found: 433.2.

Example 36. (R)—N-(2-(3-((5-Cyano-4-methoxypyrimidin-2-yl)amino)piperidin-1-yl)benzo[d]oxazol-5-yl)acrylamide Step 1. (R)-1-(5-Nitrobenzo[d]oxazol-2-yl)piperidin-3-amine To a mixture of tert-butyl (R)-piperidin-3-ylcarbamate (101 mg, 0.504 mmol) and 2-chloro-5-nitrobenzo[d]oxazole (100 mg, 0.504 mmol) in DMF (2.5 mL) was added N,N- diisopropylethylamine (264 µL, 1.511 mmol). The reaction mixture was heated to 100° C. for 1 h and then cooled to r.t. The solvents were evaporated in vacuo and the crude material was treated with a solution of 4:1 DCM/TFA (5.0 mL), and stirred at r.t. for 4 h. The solvents were evaporated in vacuo and the crude material was purified by Biotage Isolera to give the desired product as an orange solid. LCMS calculated for $C_{12}H_{15}N_4O_3$ (M+H)$^+$: m/z=263.1; found 263.1.

Step 2. (R)-4-Methoxy-2-((1-(5-nitrobenzo[d]oxazol-2-yl)piperidin-3-yl)amino)pyrimidine-5-carbonitrile To a mixture of 2-chloro-4-methoxypyrimidine-5-carbonitrile (41 mg, 0.240 mmol) and (R)-1-(5-nitrobenzo[d]oxazol-2-yl)piperidin-3-amine (63 mg, 0.240 mmol) in DMF (1.6 mL) was added N,N-diisopropylethylamine (126 µL, 0.721 mmol). The reaction mixture was heated to 100° C. for 1 h and then cooled to r.t. Solvent was removed in vacuo and the crude material was used in the next step without further purification LCMS calculated for $C_{11}H_{18}N_7O_4$ (M+H)$^+$: m/z=396.1; found 396.1.

Step 3. (R)-2-((1-(5-Aminobenzo[d]oxazol-2-yl)piperidin-3-yl)amino)-4-methoxypyrimidine-5-carbonitrile To a reaction vial containing (R)-4-methoxy-2-((1-(5-nitrobenzo[d]oxazol-2-yl)piperidin-3-yl)amino)pyrimidine-5-carbonitrile (95 mg, 0.240 mmol) and tin(II) chloride (455 mg, 2.402 mmol) was added EtOAc (4 mL) and MeOH (4 mL). The reaction mixture was heated to 80° C. for 3 h and then cooled to r.t. The reaction was quenched with aqueous saturated sodium bicarbonate solution and stirred. The mixture was extracted with 4:1 DCM/iPrOH and the organic layer was subsequently washed with water and brine, dried over sodium sulfate, and solvents were evaporated in vacuo. The crude material was used in the next step without further purification. LCMS calculated for $C_{18}H_{20}N_7O_2$ (M+H)$^+$: m/z=366.1; found 366.1.

Step 4. (R)—N-(2-(3-((5-Cyano-4-methoxypyrimidin-2-yl)amino)piperidin-1-yl)benzo[d]oxazol-5-yl)acrylamide To a solution of (R)-2-((1-(5-aminobenzo[d]oxazol-2-yl)piperidin-3-yl)amino)-4-methoxypyrimidine-5-carbonitrile (88 mg, 0.241 mmol) in DCM (7.2 mL) at 0° C. was added N,N-diisopropylethylamine (84 µL, 0.482 mmol) and acryloyl chloride (20 µL, 0.241 mmol). The reaction was stirred at 0° C. for 10 min, then quenched with MeOH (1 mL) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min). LCMS calculated for $C_{21}H_{22}N_7O_3$ (M+H)$^+$: m/z=420.2; found 420.2.

Example 37. (R)—N-(2-(3-((5-Cyano-4-methoxypyrimidin-2-yl)amino)piperidin-1-yl)-1-methyl-1H-benzo[d]imidazol-5-yl)acrylamide

Step 1. (R)-1-(1-Methyl-5-nitro-1H-benzo[d]imidazol-2-yl)piperidin-3-amine

To a mixture of tert-butyl (R)-piperidin-3-ylcarbamate (218 mg, 1.087 mmol) and 2-chloro-1-methyl-5-nitro-1H-benzo[d]imidazole (230 mg, 1.087 mmol) in DMF (7 mL) was added N,N-diisopropylethylamine (570 μL, 3.26 mmol). The reaction mixture was heated to 100° C. for 1 h and then cooled to r.t. The reaction mixture was diluted with EtOAc and the organic phase was washed with 10% aqueous lithium chloride and brine, and was then dried over sodium sulfate and filtered. Solvents were evaporated in vacuo and the crude material was treated with a solution of 4:1 DCM/TFA (10.0 mL), and stirred at r.t. for 4 h. The solvents were evaporated in vacuo and the crude material was used in the next step without further purification. LCMS calculated for $C_{13}H_{18}N_5O_2$ (M+H)$^+$: m/z=276.1; found 276.1.

Step 2. (R)-4-Methoxy-2-((1-(1-methyl-5-nitro-1H-benzo[d]imidazol-2-yl)piperidin-3-yl)amino)pyrimidine-5-carbonitrile To a mixture of 2-chloro-4-methoxypyrimidine-5-carbonitrile (100 mg, 0.59 mmol) and (R)-1-(1-methyl-5-nitro-1H-benzo[d]imidazol-2-yl)piperidin-3-amine (162 mg, 0.59 mmol) in DMF (6 mL) was added N,N-diisopropylethylamine (309 μL, 1.77 mmol). The reaction mixture was heated to 100° C. for 1 h and then cooled to r.t. The reaction mixture was diluted with EtOAc and the organic phase was washed with 10% aqueous lithium chloride and brine, and was then dried over sodium sulfate and filtered. Solvents were evaporated in vacuo and the crude material was used in the next step without further purification LCMS calculated for $C_{19}H_{21}N_8O_3$ (M+H)$^+$: m/z=409.1; found 409.1.

Step 3. (R)-2-((1-(5-Amino-1-methyl-1H-benzo[d]imidazol-2-yl)piperidin-3-yl)amino)-4-methoxypyrimidine-5-carbonitrile To a reaction vial containing (R)-4-methoxy-2-((1-(1-methyl-5-nitro-1H-benzo[d]imidazol-2-yl)piperidin-3-yl)amino)pyrimidine-5-carbonitrile (95 mg, 0.24 mmol) and tin(II) chloride (455 mg, 2.40 mmol) was added EtOAc (4 mL) and MeOH (4 mL). The reaction mixture was heated to 80° C. for 3 h and then cooled to r.t. The reaction was quenched with aqueous saturated sodium bicarbonate solution and allowed to stir. The mixture was extracted with 4:1 DCM/iPrOH and the organic layer was subsequently washed with water and brine, dried over sodium sulfate, filtered, and the solvents were evaporated in vacuo. The crude material was purified by Biotage Isolera to give the product as a yellow solid. LCMS calculated for $C_{19}H_{23}N_8O$ (M+H)$^+$: m/z=379.2; found 379.1.

Step 4. (R)—N-(2-(3-((5-Cyano-4-methoxypyrimidin-2-yl)amino)piperidin-1-yl)-1-methyl-1H-benzo[d]imidazol-5-yl)acrylamide To a solution of (R)-2-((1-(5-amino-1-methyl-1H-benzo[d]imidazol-2-yl)piperidin-3-yl)amino)-4-methoxypyrimidine-5-carbonitrile (11 mg, 0.03 mmol) in DCM (1 mL) at 0° C. was added N,N-diisopropylethylamine (10 μL, 0.03 mmol) and acryloyl chloride (3 μL, 0.03 mmol). The reaction mixture was allowed to stir at 0° C. for 10 min, then quenched with MeOH (2 mL) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min. LCMS calculated for $C_{22}H_{25}N_8O_2$ (M+H)$^+$: m/z=433.2; found: 433.2. $^1$H NMR (600 MHz, DMSO-d6) δ 10.41 (s, 1H), 8.59 (s, 1H), 8.56-8.49 (m, 1H), 8.41 (d, J=7.4 Hz, 1H), 8.12 (d, J=2.0 Hz, 1H), 7.58 (dd, J=8.8, 5.9 Hz, 1H), 7.50 (dd, J=8.9, 2.0 Hz, 1H), 6.46 (dd, J=17.0, 10.2 Hz, 1H), 6.29 (dd, J=17.0, 1.8 Hz, 1H), 5.79 (dd, J=10.1, 1.9 Hz, 1H), 4.18 (m, 1H), 3.96 (d, J=9.4 Hz, 3H), 3.73 (m, 3H), 3.72-3.64 (m, 1H), 3.42 (m, 1H), 3.35 (m, 1H), 3.24 (m, 1H), 2.09-1.90 (m, 1H), 1.86-1.67 (m, 2H) ppm.

Example 38. (R)—N-(2-(3-((5-Cyano-4-methoxypy-rimidin-2-yl)amino)pyrrolidin-1-yl)thiazolo[5,4-c]pyridin-7-yl)acrylamide Step 1. (R)-1-(7-Chlorothiazolo[5,4-c]pyridin-2-yl)pyrrolidin-3-amine To a mixture of tert-butyl (R)-pyrrolidin-3-ylcarbamate (75 mg, 0.401 mmol) and 2-bromo-7-chlorothiazolo[5,4-c]pyridine (100 mg, 0.401 mmol) in DMF (2.0 mL) was added N,N-diisopropylethylamine (210 μL, 1.202 mmol). The reaction mixture was heated to 100° C. for 1 h and then cooled to r.t. The solvents were evaporated in vacuo and the crude material was treated with a solution of 4:1 DCM/TFA (5.0 mL), and stirred at r.t. for 4 h. The solvents were evaporated in vacuo and the crude material was used in the next step without further purification. LCMS calculated for $C_{10}H_{12}ClN_4S$ (M+H)$^+$: m/z=255.1; found 255.1.

Step 2. (R)-2-((1-(7-Chlorothiazolo[5,4-c]pyridin-2-yl)pyrrolidin-3-yl)amino)-4-methoxypyrimidine-5-carbonitrile To a mixture of 2-chloro-4-methoxypyrimidine-5-carbo-nitrile (72 mg, 0.424 mmol) and (R)-1-(7-chlorothiazolo[5,4-c]pyridin-2-yl)pyrrolidin-3-amine (108 mg, 0.424 mmol)

in DMF (2.1 mL) was added N,N-diisopropylethylamine (222 μL, 1.272 mmol). The reaction mixture was heated to 100° C. for 1 h and then cooled to r.t. Solvent was removed in vacuo and the crude material was used in the next step without further purification. LCMS calculated for $C_{16}H_{15}ClN_7OS$ (M+H)$^+$: m/z=388.1; found 388.1.

Step 3. (R)-2-((1-(7-Aminothiazolo[5,4-c]pyridin-2-yl)pyrrolidin-3-yl)amino)-4-methoxypyrimidine-5-carbonitrile A reaction vial containing (R)-2-((1-(7-chlorothiazolo[5,4-c]pyridin-2-yl)pyrrolidin-3-yl)amino)-4-methoxypyrimi-dine-5-carbonitrile (164 mg, 0.423 mmol), tert-butyl car-bamate (396 mg, 3.38 mmol), cesium carbonate (413 mg, 1.269 mmol), [(2-di-cyclohexylphosphino-3,6-dimethoxy-2',4',6'-triisopropyl-1,1'-biphenyl)-2-(2'-amino-1,1'-biphe-nyl)]palladium(II) methanesulfonate (BrettPhos Pd G3, 153.0 mg, 0.169 mmol) was evacuated and backfilled with nitrogen. 1,4-Dioxane (4.2 mL) was added to the reaction mixture, which was then stirred at 100° C. for 18 h. The reaction mixture was cooled to r.t. and the solvents were evaporated in vacuo. The crude mixture was treated with a solution of 4:1 DCM/TFA (5.0 mL), which was stirred at r.t. for 4 h. The solvents were evaporated in vacuo. Crude material was purified by Biotage Isolera to give the desired product as a white solid. LCMS calculated for $C_{16}H_{17}N_8OS$ (M+H)$^+$: m/z=369.1; found 369.1.

Step 4. (R)—N-(2-(3-((5-Cyano-4-methoxypyrimi-din-2-yl)amino)pyrrolidin-1-yl)thiazolo[5,4-c]pyri-din-7-yl)acrylamide To a solution of (R)-2-((1-(7-aminothiazolo[5,4-c]pyri-din-2-yl)pyrrolidin-3-yl)amino)-4-methoxypyrimidine-5-carbonitrile (28 mg, 0.077 mmol) in DCM (2.3 mL) at 0° C. was added N,N-diisopropylethylamine (27 μL, 0.077 mmol) and acryloyl chloride (6 μL, 0.077 mmol). The reaction was stirred at 0° C. for 10 min, then quenched with MeOH (1 mL) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min). LCMS calculated for $C_{19}H_{19}N_8O_2S$ (M+H)$^+$: m/z=423.1; found 423.1.

Example 39. (R)—N-(2-(3-((5-Cyano-4-methoxypy-
rimidin-2-yl)amino)piperidin-1-yl)-1-methyl-1H-
indol-5-yl)acrylamide This compound was prepared according to the procedures described in Example 35, with 2-bromo-1-methyl-5-nitro-1H-indole replacing 3-bromo-1-methyl-7-nitro-1H-indazole in Step 1. LCMS calculated for $C_{23}H_{26}N_7O_2$ $(M+H)^+$: m/z=432.2; found: 432.3.

Example 40. (R)—N-(2-(3-((5-Cyano-4-methoxypy-
rimidin-2-yl)amino)piperidin-1-yl)benzo[d]thiazol-
5-yl)acrylamide This compound was prepared according to the procedures described in Example 36, with 2-chloro-5-nitrobenzo[d]thiazole replacing 2-chloro-5-nitrobenzo[d]oxazole in Step 1. LCMS calculated for $C_{21}H_{22}N_7O_2S$ $(M+H)^+$: m/z=436.1; found: 436.2. 1H NMR (600 MHz, DMSO-d6) δ 10.17 (d, J=6.3 Hz, 1H), 8.60 (s, 1H), 8.52 (s, 1H), 8.45 (d, J=7.2 Hz, 1H), 7.93 (dd, J=7.1, 2.0 Hz, 1H), 7.67 (dd, J=8.5, 4.8 Hz, 1H), 7.31 (ddd, J=10.8, 8.5, 2.1 Hz, 1H), 6.45 (dd, J=17.0, 10.2 Hz, 1H), 6.27 (ddd, J=17.0, 6.9, 2.0 Hz, 1H), 5.76 (dt, J=10.1, 2.1 Hz, 1H), 4.08 (s, 2H), 3.95 (s, 2H), 3.83 (m, 1H), 3.32 (m, 1H), 3.11 (dd, J=12.7, 9.5 Hz, 1H), 2.06-1.97 (m, 1H), 1.90 (dt, J=12.6, 4.0 Hz, 1H), 1.76-1.61 (m, 2H).

Example 41. (R)—N-(2-(3-((5-Cyano-4-methoxypy-
rimidin-2-yl)amino)pyrrolidin-1-yl)benzo[d]thiazol-
5-yl)acrylamide This compound was prepared according to the procedures described in Example 36, with 2-chloro-5-nitrobenzo[d]thiazole replacing 2-chloro-5-nitrobenzo[d]oxazole and with tert-butyl (R)-pyrrolidin-3-ylcarbamate replacing tert-butyl (R)-piperidin-3-ylcarbamate in Step 1. LCMS calculated for $C_{20}H_{20}N_7O_{2S}$ $(M+H)^+$: m/z=422.1; found: 422.2.

Example 42. (R)—N-(3-(3-((5-Cyano-4-methoxypy-
rimidin-2-yl)amino)piperidin-1-yl)benzo[b]thiophen-
6-yl)acrylamide This compound was prepared according to the procedures described in Example 43, with 3-bromo-6-nitrobenzo[b]thiophene replacing 3-bromo-1-methyl-5-nitro-1H-indazole in Step 1. LCMS calculated for $C_{22}H_{23}N_6O_2S$ $(M+H)^+$: m/z=435.1; found: 435.1.

Example 43. (R)—N-(3-(3-((5-Cyano-4-methoxypy-
rimidin-2-yl)amino)piperidin-1-yl)-1-methyl-1H-
indazol-6-yl)acrylamide

Step 1. tert-Butyl (R)-(1-(1-methyl-6-nitro-1H-inda-zol-3-yl)piperidin-3-yl)carbamate

A reaction vial containing 3-bromo-1-methyl-5-nitro-1H-indazole (150 mg, 0.586 mmol), tert-butyl (R)-piperidin-3-ylcarbamate (176 mg, 0.879 mmol), cesium carbonate (477 mg, 1.465 mmol), $Pd_2(dba)_3$ (53.6 mg, 0.059 mmol), and 4,5-bis(diphenylphosphino)-9,9-dimethylxanthene (Xant-phos, 71.2 mg, 0.123 mmol) was evacuated and back filled with nitrogen. 1,4-Dioxane (6 mL) was then added to the reaction mixture, which was then stirred at 80° C. for 18 h. The reaction mixture was cooled to r.t., diluted with DCM, and filtered through celite. The solvents were evaporated in vacuo and the crude material was purified by Biotage Isolera to give the desired product as an orange solid. LCMS calculated for $C_{18}H_{26}N_5O_4$ $(M+H)^+$: m/z=376.2; found 376.2.

Step 2. (R)-1-(1-Methyl-6-nitro-1H-indazol-3-yl) piperidin-3-amine

A solution of 4:1 DCM/TFA (5.0 mL) was added to a reaction vial containing tert-butyl (R)-(1-(1-methyl-6-nitro-1H-indazol-3-yl)piperidin-3-yl)carbamate (77 mg, 0.206 mmol) and stirred at r.t. for 4 h. The solvents were evaporated in vacuo and the crude material was used in the next step without further purification. LCMS calculated for $C_{13}H_{18}N_5O_2$ $(M+H)^+$: m/z=276.1; found 276.1.

Step 3. (R)-4-Methoxy-2-((1-(1-methyl-6-nitro-1H-indazol-3-yl)piperidin-3-yl)amino)pyrimidine-5-carbonitrile

To a mixture of 2-chloro-4-methoxypyrimidine-5-carbo-nitrile (35 mg, 0.206 mmol) and (R)-1-(1-methyl-6-nitro-1H-indazol-3-yl)piperidin-3-amine (57 mg, 0.206 mmol) was added N,N-diisopropylethylamine (108 μL, 0.617 mmol) and DMF (1.0 mL). The reaction mixture was heated to 100° C. for 1 h and then cooled to r.t. Solvent was removed in vacuo and crude material was purified by Biotage Isolera to give the desired product as a yellow solid. LCMS calculated for $C_{19}H_{21}N_8O_3$ $(M+H)^+$: m/z=409.2; found 409.2.

Step 4. (R)-2-((1-(6-Amino-1-methyl-1H-indazol-3-yl)piperidin-3-yl)amino)-4-methoxypyrimidine-5-carbonitrile

To a reaction vial containing (R)-4-methoxy-2-((1-(1-methyl-6-nitro-1H-indazol-3-yl)piperidin-3-yl)amino)py-rimidine-5-carbonitrile (84 mg, 0.206 mmol) and tin(II) chloride (390 mg, 2.056 mmol) was added EtOAc (3 mL) and MeOH (3 mL). The reaction mixture was heated to 80° C. for 3 h and then cooled to r.t. The reaction was quenched with aqueous saturated sodium bicarbonate solution and allowed to stir. The mixture was extracted with 4:1 DCM/iPrOH and the organic layer was subsequently washed with water and brine, dried over sodium sulfate, and solvents were evaporated in vacuo. The crude material was used in the next step without further purification. LCMS calculated for $C_{19}H_{23}N_8O$ $(M+H)^+$: m/z=379.2; found 379.2.

Step 5. (R)—N-(3-(3-((5-Cyano-4-methoxypyrimi-din-2-yl)amino)piperidin-1-yl)-1-methyl-1H-inda-zol-6-yl)acrylamide

To a solution of (R)-2-((1-(6-amino-1-methyl-1H-inda-zol-3-yl)piperidin-3-yl)amino)-4-methoxypyrimidine-5-car-bonitrile (72 mg, 0.189 mmol) in DCM (5.7 mL) at 0° C. was added N,N-diisopropylethylamine (66 μL, 0.378 mmol) and acryloyl chloride (15 μL, 0.189 mmol). The reaction was stirred at 0° C. for 10 min, then quenched with MeOH (1 mL) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min). LCMS calculated for $C_{22}H_{25}N_8O_2$ $(M+H)^+$: m/z=433.2; found: 433.2.

Example 44. (R)—N-(2-(3-((5-Cyano-4-methoxypy-rimidin-2-yl)amino)piperidin-1-yl)-[1,2,4]triazolo[1,5-a]pyridin-6-yl)acrylamide Step 1. tert-Butyl (R)-(1-(6-bromo-[1,2,4]triazolo[1,5-a]pyridin-2-yl)piperidin-3-yl)carbamate To a mixture of tert-butyl (R)-piperidin-3-ylcarbamate (163 mg, 0.813 mmol) and 2,6-dibromo-[1,2,4]triazolo[1,5-a]pyridine (150 mg, 0.542 mmol) in DMF (2.7 mL) was added N,N-diisopropylethylamine (284 μL, 1.625 mmol). The reaction mixture was heated to 85° C. for 1 h and then cooled to r.t. The solvents were evaporated in vacuo and the crude material was purified by Biotage Isolera to give the desired product as a white solid. LCMS calculated for $C_{16}H_{23}BrN_5O_2$ (M+H)$^+$: m/z=396.1; found 396.1.

Step 2. Benzyl (R)-(2-(3-aminopiperidin-1-yl)-[1,2,4]triazolo[1,5-a]pyridin-6-yl)carbamate A reaction vial containing tert-butyl (R)-(1-(6-bromo-[1,2,4]triazolo[1,5-a]pyridin-2-yl)piperidin-3-yl)carbamate (115 mg, 0.289 mmol), benzyl carbamate (131 mg, 0.867 mmol), cesium carbonate (282 mg, 0.867 mmol), and tBuX-Phos Pd G3 (46 mg, 0.058 mmol) was evacuated and back filled with nitrogen. 1,4-Dioxane (3 mL) was then added to the reaction mixture, which was then stirred at 50° C. for 18 h. The reaction mixture was cooled to r.t., diluted with DCM, and filtered through celite. The solvents were evaporated in vacuo and the crude material was treated with a solution of 4:1 DCM/TFA (5.0 mL), which was stirred at r.t. for 4 h. The solvents were evaporated in vacuo and the crude material was purified by Biotage Isolera to give the desired product as a white solid. LCMS calculated for $C_{19}H_{23}N_6O_2$ (M+H)$^+$: m/z=367.2; found 367.1.

Step 3. (R)-2-((1-(6-Amino-[1,2,4]triazolo[1,5-a]pyridin-2-yl)piperidin-3-yl)amino)-4-methoxypy-rimidine-5-carbonitrile To a mixture of 2-chloro-4-methoxypyrimidine-5-carbo-nitrile (27 mg, 0.058 mmol) and benzyl (R)-(2-(3-aminopi-peridin-1-yl)-[1,2,4]triazolo[1,5-a]pyridin-6-yl)carbamate (8 mg, 0.058 mmol) was added N,N-diisopropylethylamine (31 μL, 0.175 mmol) and DMF (0.3 mL). The reaction mixture was heated to 100° C. for 1 h and then cooled to r.t. Solvent was removed in vacuo and to the crude material was added palladium on carbon (12 mg, 5.84 mol) and MeOH (1 mL). The reaction mixture was stirred under an atmosphere of hydrogen for 4 h. The reaction mixture was diluted with Et₂O and filtered through a plug of celite and the solvent was evaporated in vacuo. The crude material was used in the next step without further purification. LCMS calculated for $C_{17}H_{20}N_9O$ (M+H)$^+$: m/z=366.2; found 366.1.

Step 4. (R)—N-(2-(3-((5-Cyano-4-methoxypyrimi-din-2-yl)amino)piperidin-1-yl)-[1,2,4]triazolo[1,5-a]pyridin-6-yl)acrylamide To a solution of (R)-2-((1-(6-amino-[1,2,4]triazolo[1,5-a]pyridin-2-yl)piperidin-3-yl)amino)-4-methoxypyrimidine-5-carbonitrile (21 mg, 0.051 mmol) in DCM (1.5 mL) at 0° C. was added N,N-diisopropylethylamine (18 μL, 0.102 mmol) and acryloyl chloride (4 μL, 0.051 mmol). The reaction was stirred at 0° C. for 10 min, then quenched with MeOH (1 mL) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min). LCMS calculated for $C_{20}H_{22}N_9O_2$ (M+H)$^+$: m/z=420.2; found: 420.4.

Example 45. (R)—N-(2-(3-((5-Cyano-4-methoxypy-rimidin-2-yl)amino)pyrrolidin-1-yl)-[1,2,4]triazolo[1,5-a]pyridin-6-yl)acrylamide This compound was prepared according to the procedures described in Example 44 with tert-butyl (R)-pyrrolidin-3-ylcarbamate replacing tert-butyl (R)-piperidin-3-ylcarbamate in Step 1. LCMS calculated for $C_{19}H_{20}N_9O_2$ (M+H)$^+$: m/z=406.2; found: 406.4.

Example 46. (R)—N-(2-(3-((5-Cyano-4-methoxypy-rimidin-2-yl)amino)piperidin-1-yl)benzo[d]thiazol-6-yl)acrylamide This compound was prepared according to the procedures described in Example 36, with 2-chloro-6-nitrobenzo[d]thiazole replacing 2-chloro-5-nitrobenzo[d]oxazole in Step 1. LCMS calculated for $C_{21}H_{22}N_7O_2S$ (M+H)$^+$: m/z=436.2; found: 436.2.

Example 47. N-(2-((1S,3R)-3-((5-Cyano-4-methoxypyrimidin-2-yl)amino)cyclohexyl)-1-(2-hydroxyethyl)-1H-benzo[d]imidazol-5-yl)acrylamide Step 1. N-(2-((tert-Butyldimethylsilyl)oxy)ethyl)-4-nitrobenzene-1,2-diamine To a vial containing 2-((2-amino-4-nitrophenyl)amino)ethan-1-ol (300 mg, 1.521 mmol) and imidazole (207 mg, 3.04 mmol) in $CH_2Cl_2$ (5.1 mL) was added TBSCl (275 mg, 1.826 mmol). After stirring at r.t. for 4 h, the reaction mixture was quenched with saturated aqueous $NaHCO_3$ and the mixture was extracted with $CH_2Cl_2$. The organic phase was washed with brine, dried over $MgSO_4$, filtered, and the solvent was evaporated in vacuo. The obtained crude product was used in the next step without further purification. LCMS calculated for $C_{14}H_{26}N_3O_3Si$ (M+H)$^+$: m/z=312.2; found 312.2.

Step 2. tert-Butyl ((1S,3R)-3-((2-((2-((tert-butyldimethylsilyl)oxy)ethyl)amino)-5-nitrophenyl)carbamoyl)cyclohexyl)carbamate To a vial containing (1S,3R)-3-((tert-butoxycarbonyl)amino)cyclohexane-1-carboxylic acid (391 mg, 1.605 mmol), DIPEA (839 μL, 4.82 mmol) and HATU (732 mg, 1.926 mmol) in DMF (8 mL) was added $N^1$-(2-((tert-butyldimethylsilyl)oxy)ethyl)-4-nitrobenzene-1,2-diamine (500 mg, 1.605 mmol). After stirring at r.t. for 1 h, the reaction mixture was quenched with water and the mixture was extracted with EtOAc. The organic phase was washed with brine, dried over $MgSO_4$ and concentrated in vacuo. Crude material was purified by Biotage Isolera to give the desired product as brown oil. LCMS calculated for $C_{26}H_{45}N_4O_6Si$ (M+H)$^+$: m/z=537.3; found: 537.2.

267

Step 3. 2-(2-((1S,3R)-3-Aminocyclohexyl)-5-nitro-
1H-benzo[d]imidazol-1-yl)ethyl acetate To a vial containing tert-butyl ((1R,3S)-3-((2-((2-((tert-butyldimethylsilyl)oxy)ethyl)amino)-5-nitrophenyl)car-bamoyl)cyclohexyl)carbamate (805 mg, 1.5 mmol) was added acetic acid (15.0 mL). The reaction mixture was heated to 100° C. for 20 h. After cooling to r.t., the reaction mixture was quenched with 3.0 M NaOH aqueous solution and the mixture was extracted with CH₂Cl₂. The organic phase was washed with brine, dried over MgSO₄, and concentrated in vacuo. The obtained crude product was used in the next step without further purification. LCMS calculated for $C_{17}H_{23}N_4O_4$ (M+H)⁺: m/z=347.2; found: 347.1.

Step 4. 2-(2-((1S,3R)-3-((5-Cyano-4-methoxypy-rimidin-2-yl)amino)cyclohexyl)-5-nitro-1H-benzo[d]imidazol-1-yl)ethyl acetate To a vial containing 2-(2-((1S,3R)-3-aminocyclohexyl)-5-nitro-1H-benzo[d]imidazol-1-yl)ethyl acetate (120 mg, 0.346 mmol), DIPEA (121 µL, 0.693 mmol) in EtOH (2.3 mL) was added 2-chloro-4-methoxypyrimidine-5-carboni-trile (70.5 mg, 0.416 mmol). After stirring at 45° C. for 1 h, the solvent was evaporated in vacuo. The obtained crude product was purified by Biotage Isolera to give the desired product as yellow foam. LCMS calculated for $C_{23}H_{26}N_7O_5$ (M+H)⁺: m/z=480.2; found: 480.2.

Step 5. 2-(5-Amino-2-((1S,3R)-3-((5-cyano-4-methoxypyrimidin-2-yl)amino)cyclohexyl)-1H-benzo[d]imidazol-1-yl)ethyl acetate A vial containing ammonia hydrochloride (67 mg, 1.251 mmol), zinc (82 mg, 1.251 mmol) and 2-(2-((1S,3R)-3-((5-cyano-4-methoxypyrimidin-2-yl)amino)cyclohexyl)-5-ni-tro-1H-benzo[d]imidazol-1-yl)ethyl acetate (60 mg, 0.125 mmol) in THF (0.82 mL) and water (0.41 mL) was heated to 40° C. for 1 h. After cooling to r.t., the reaction mixture was filtered and washed with CH₂Cl₂. The organic phase was separated and washed with brine, dried over MgSO₄, and concentrated in vacuo. The obtained crude product was used in the next step without further purification. LCMS calculated for $C_{23}H_{28}N_7O_5$ (M+H)⁺: m/z=450.2; found: 450.2.

Step 6. 2-(5-Acrylamido-2-((1S,3R)-3-((5-cyano-4-methoxypyrimidin-2-yl)amino)cyclohexyl)-1H-benzo[d]imidazol-1-yl)ethyl acetate To a vial containing 2-(5-amino-2-((1S,3R)-3-((5-cyano-4-methoxypyrimidin-2-yl)amino)cyclohexyl)-1H-benzo[d]imidazol-1-yl)ethyl acetate (30 mg, 0.067 mmol) and DIPEA (35 µL, 0.200 mmol) in CH₂Cl₂ (3.0 mL) was added acryloyl chloride (9 mg, 0.100 mmol) at 0° C. After stirring at 0° C. for 10 min, the reaction mixture was quenched with MeOH and concentrated in vacuo. The obtained crude product was used in the next step without further purifica-tion. LCMS calculated for $C_{26}H_{30}N_7O_4$ (M+H)⁺: m/z=504.2; found: 504.2.

Step 7. N-(2-((1S,3R)-3-((5-Cyano-4-methoxypy-rimidin-2-yl)amino)cyclohexyl)-1-(2-hydroxyethyl)-1H-benzo[d]imidazol-5-yl)acrylamide To a vial containing 2-(5-acrylamido-2-((1S,3R)-3-((5-cyano-4-methoxypyrimidin-2-yl)amino)cyclohexyl)-1H- benzo[d]imidazol-1-yl)ethyl acetate (32 mg, 0.064 mmol) in MeOH (0.5 mL) was added $K_2CO_3$ (18 mg, 0.130 mmol). After stirring at r.t. for 1 h, the reaction mixture was filtered and washed with $CH_3CN$, then diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{24}H_{28}N_7O_3$ (M+H)$^+$: m/z=462.2; found: 462.2.

Example 48. Ethyl (E)-4-((2-((1S,3R)-3-((5-Cyano-4-methoxypyrimidin-2-yl)amino)cyclohexyl)-1-methyl-1H-benzo[d]imidazol-5-yl)amino)-4-oxobut-2-enoate To a vial containing 2-(((1R,3S)-3-(5-amino-1-methyl-1H-benzo[d]imidazol-2-yl)cyclohexyl)amino)-4-methoxy-pyrimidine-5-carbonitrile (Intermediate A, 25 mg, 0.066 mmol), DIPEA (35 μL, 0.199 mmol), (E)-4-ethoxy-4-oxobut-2-enoic acid (19 mg, 0.132 mmol), HOBt (1.0 mg, 6.62 μmol) and DMAP (8 mg, 0.066 mmol) in $CH_2Cl_2$ (0.33 mL) was added EDC (25 mg, 0.132 mmol). After stirring at r.t. for 1 h, the reaction mixture was quenched with MeOH, then diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{26}H_{30}N_7O_4$ (M+H)$^+$: m/z=504.2; found: 504.2.

Example 49. 2-Bromo-N-(2-((1S,3R)-3-((5-cyano-4-methoxypyrimidin-2-yl)amino)cyclohexyl)-1-methyl-1H-benzo[d]imidazol-5-yl)butanamide To a vial containing 2-(((1R,3S)-3-(5-amino-1-methyl-1H-benzo[d]imidazol-2-yl)cyclohexyl)amino)-4-methoxy-pyrimidine-5-carbonitrile (Intermediate A, 25 mg, 0.066 mmol) and DIPEA (35 μL, 0.200 mmol) in $CH_2Cl_2$ (3.0 mL) was added 2-bromobutanoyl chloride (25 mg, 0.132 mmol) at 0° C. After stirring at 0° C. for 10 min, the reaction mixture was quenched with MeOH and concentrated in vacuo. The obtained crude product was diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{24}H_{29}BrN_7O_2$ (M+H)$^+$: m/z=526.1/528.1; found: 526.1/528.1.

Example 50. 2-Chloro-N-(2-((1S,3R)-3-((5-cyano-4-methoxypyrimidin-2-yl)amino)cyclohexyl)-1-methyl-1H-benzo[d]imidazol-5-yl)acetamide This compound was prepared according to the procedures described in Example 49, with 2-chloroacetyl chloride replacing 2-bromobutanoyl chloride. LCMS calculated for $C_{22}H_{25}ClN_7O_2$ (M+H)$^+$: m/z=454.2; found: 454.1.

Example 51. 3-((2-((1S,3R)-3-((5-Cyano-4-methoxypyrimidin-2-yl)amino)cyclohexyl)-1-methyl-1H-benzo[d]imidazol-5-yl)carbamoyl)oxirane-2-carboxylic acid This compound was prepared according to the procedures described in Example 48, with oxirane-2,3-dicarboxylic acid replacing (E)-4-ethoxy-4-oxobut-2-enoic acid. LCMS calculated for $C_{24}H_{26}N_7O_5$ (M+H)$^+$: m/z=492.2; found: 492.2.

Example 52. 2-Bromo-N-(2-((1S,3R)-3-((5-cyano-4-methoxypyrimidin-2-yl)amino)cyclohexyl)-1-methyl-1H-benzo[d]imidazol-5-yl)propanamide This compound was prepared according to the procedures described in Example 48, with 2-bromopropanoic acid replacing (E)-4-ethoxy-4-oxobut-2-enoic acid. LCMS calculated for $C_{23}H_{27}BrN_7O_2$ (M+H)$^+$: m/z=512.1/514.1; found: 512.2/514.1.

Example 53. N-(2-((1S,3R)-3-((5-Cyano-4-methoxypyrimidin-2-yl)amino)cyclohexyl)-1-methyl-1H-benzo[d]imidazol-5-yl)-2-fluoroacrylamide This compound was prepared according to the procedures described in Example 48, with 2-fluoroacrylic acid replacing (E)-4-ethoxy-4-oxobut-2-enoic acid. LCMS calculated for $C_{23}H_{25}FN_7O_2$ (M+H)$^+$: m/z=450.2; found: 450.2.

Example 54. N-(2-((1S,3R)-3-((5-Cyano-4-methoxypyrimidin-2-yl)amino)cyclohexyl)-1-methyl-1H-benzo[d]imidazol-5-yl)but-2-ynamide This compound was prepared according to the procedures described in Example 48, with but-2-ynoic acid replacing (E)-4-ethoxy-4-oxobut-2-enoic acid. LCMS calculated for $C_{24}H_{26}N_7O_2$ (M+H)$^+$: m/z=444.2; found: 444.2.

Example 55. 2-Bromo-N-(2-((1S,3R)-3-((5-cyano-4-methoxypyrimidin-2-yl)amino)cyclohexyl)-3-oxoisoindolin-5-yl)propanamide To a vial containing 2-(((1R,3S)-3-(6-amino-1-oxoisoindolin-2-yl)cyclohexyl)amino)-4-methoxypyrimidine-5-carbonitrile (Intermediate C, 25 mg, 0.066 mmol), DIPEA (35 µL, 0.199 mmol), 2-bromopropanoic acid (20 mg, 0.132 mmol), HOBt (1.0 mg, 6.62 µmol) and DMAP (8.1 mg, 0.066 mmol) in $CH_2Cl_2$ (0.33 mL) was added EDC (25.4 mg, 0.132 mmol). After stirring at r.t. for 1 h, the reaction mixture was quenched with MeOH, then diluted with $CH_3CN$ and water, and purified by prep-LCMS (XBridge C18 column, eluting with a gradient of acetonitrile/water containing 0.1% TFA, at flow rate of 60 mL/min). LCMS calculated for $C_{23}H_{26}BrN_6O_3$ (M+H)$^+$: m/z=513.1/515.1; found: 513.1/515.2.

Example 56. N-(2-((1S,3R)-3-((5-Cyano-4-methoxypyrimidin-2-yl)amino)cyclohexyl)-3-oxoisoindolin-5-yl)-2-fluoroacrylamide This compound was prepared according to the procedures described in Example 55, with 2-fluoroacrylic acid replacing 2-bromopropanoic acid. LCMS calculated for $C_{23}H_{24}FN_6O_3$ (M+H)$^+$: m/z=451.2; found: 451.2.

Example 57. (E)-N-(2-((1S,3R)-3-((5-Cyano-4-methoxypyrimidin-2-yl)amino)cyclohexyl)-3-oxoisoindolin-5-yl)-4-fluorobut-2-enamide This compound was prepared according to the procedures described in Example 55, with (E)-4-fluorobut-2-enoic acid replacing 2-bromopropanoic acid. LCMS calculated for $C_{24}H_{26}FN_6O_3$ (M+H)$^+$: m/z=465.2; found: 465.1.

Example 58. 2-Bromo-N-(2-((1S,3R)-3-((5-cyano-4-methoxypyrimidin-2-yl)amino)cyclohexyl)-3-oxoisoindolin-5-yl)acetamide To a vial containing 2-(((1R,3S)-3-(6-amino-1-oxoisoindolin-2-yl)cyclohexyl)amino)-4-methoxypyrimidine-5-carbonitrile (Intermediate C, 25.0 mg, 0.066 mmol) and DIPEA (35 µL, 0.200 mmol) in $CH_2Cl_2$ (3.0 mL) was added 2-bromoacetyl bromide (26.7 mg, 0.132 mmol) at 0° C. After stirring at 0° C. for 10 min, the reaction mixture was quenched with MeOH and concentrated in vacuo. The obtained crude product was diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{22}H_{24}BrN_6O_3$ (M+H)$^+$: m/z=499.1/501.1; found: 499.2/501.1.

Example 59. 2-Chloro-N-(2-((1S,3R)-3-((5-cyano-4-methoxypyrimidin-2-yl)amino)cyclohexyl)-3-oxoisoindolin-5-yl)acetamide This compound was prepared according to the procedures described in Example 58, with 2-chloroacetyl chloride replacing 2-bromoacetyl bromide. LCMS calculated for $C_{22}H_{24}ClN_6O_3$ (M+H)$^+$: m/z=455.2; found: 455.2.

Example 60. N-(2-((1S,3R)-3-((5-Cyano-4-methoxypyrimidin-2-yl)amino)cyclohexyl)-3-oxoisoindolin-5-yl)but-2-ynamide This compound was prepared according to the procedures described in Example 55, with with but-2-ynoic acid replacing 2-bromopropanoic acid. LCMS calculated for $C_{24}H_{25}N_6O_3$ (M+H)$^+$: m/z=445.2; found: 445.2. $^1$H NMR (500 MHz, DMSO) δ 10.81 (s, 1H), 8.57-8.43 (m, 1H), 8.41-8.21 (m, 1H), 7.99 (s, 1H), 7.71 (dd, J=8.2, 2.0 Hz, 1H), 7.52 (d, J=8.2 Hz, 1H), 4.45-4.32 (m, 2H), 4.16-4.07 (m, 1H), 4.08-3.82 (m, 4H), 2.06 (m, 4H), 1.96-1.81 (m, 2H), 1.73 (m, 1H), 1.63-1.42 (m, 3H), 1.38-1.27 (m, 1H).

Example 61. N-(2-((1S,3R)-3-((4-Methoxy-5-(trif-luoromethyl)pyrimidin-2-yl)amino)cyclohexyl)-3-oxoisoindolin-5-yl)acrylamide A vial containing N-(2-((1S,3R)-3-((4-chloro-5-(trifluoromethyl)pyrimidin-2-yl)amino)cyclohexyl)-3-oxoisoindolin-5-yl)acrylamide (Intermediate D, 25.0 mg, 0.052 mmol) in MeOH (1.0 mL) was cooled to 0° C. and then added sodium tert-butoxide (25.0 mg, 0.260 mmol). After stirring at 45° C. for 1 h, the reaction mixture was quenched with acetic acid and water, then diluted with $CH_3CN$ and water and purified by prep-LCMS (XBridge C18 column, eluting with a gradient of acetonitrile/water containing 0.10% TFA, at flow rate of 60 mL/min). LCMS calculated for $C_{23}H_{25}F_3N_5O_3$ (M+H)$^+$: m/z=476.2; found: 476.2.

Example 62. N-(2-((1S,3R)-3-((4-((R)-3-(Dimethyl-amino)pyrrolidin-1-yl)-5-(trifluoromethyl)pyrimidin-2-yl)amino)cyclohexyl)-3-oxoisoindolin-5-yl)acryl-amide A vial containing N-(2-((1S,3R)-3-((4-chloro-5-(trifluoromethyl)pyrimidin-2-yl)amino)cyclohexyl)-3-oxoisoindolin-5-yl)acrylamide (Intermediate D, 25 mg, 0.052 mmol) and DIPEA (27.3 μL, 0.156 mmol) in EtOH (0.4 mL) and THF (0.2 mL) was cooled to 0° C. and then added (R)—N,N-dimethylpyrrolidin-3-amine (12 mg, 0.104 mmol). After stirring at r.t. for 1 h, the reaction mixture was quenched with TFA, then diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{28}H_{35}F_3N_7O_2$ (M+H)$^+$: m/z=558.3; found: 558.2.

Example 63. (E)-N-(2-((1S,3R)-3-((5-Cyano-4-methoxypyrimidin-2-yl)amino)cyclohexyl)-3-oxoi-soindolin-5-yl)-4-(dimethylamino)but-2-enamide To a vial containing 2-(((1R,3S)-3-(6-amino-1-oxoisoin-dolin-2-yl)cyclohexyl)amino)-4-methoxypyrimidine-5-car-bonitrile (Intermediate C, 33.0 mg, 0.087 mmol), (E)-4-(dimethylamino)but-2-enoic acid hydrochloride (21.7 mg, 0.131 mmol) and DIPEA (46 μL, 0.262 mmol) in $CH_3CN$ (1.0 mL) was added propane phosphonic acid anhydride solution (50% w/w, 208 μL, 0.349 mmol) at 0° C. After stirring at 0° C. for 30 min, the reaction mixture was quenched with MeOH, then diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{26}H_{32}N_7O_3$ (M+H)$^+$: m/z=490.2; found: 490.2. $^1$H NMR (500 MHz, DMSO) δ 10.53 (s, 1H), 9.83 (s, 1H), 8.59-8.43 (m, 1H), 8.42-8.21 (m, 1H), 8.13 (d, J=2.3 Hz, 1H), 7.74 (m, 1H), 7.56 (d, J=8.2 Hz, 1H), 6.78 (dt, J=14.8, 7.1 Hz, 1H), 6.47 (d, J=15.3 Hz, 1H), 4.46-4.35 (m, 2H), 4.17-4.08 (m, 1H), 4.06-3.89 (m, 4H), 2.82 (s, 6H), 2.17-1.99 (m, 1H), 1.97-1.83 (m, 2H), 1.78-1.70 (m, 1H), 1.66-1.43 (m, 3H), 1.39-1.27 (m, 1H).

Example 64. (E)-N-(2-((1S,3R)-3-((5-Cyano-4-methoxypyrimidin-2-yl)amino)cyclohexyl)-3-oxoi-soindolin-5-yl)but-2-enamide This compound was prepared according to the procedures described in Example 55, with (E)-but-2-enoic acid replac-ing 2-bromopropanoic acid. LCMS calculated for $C_{24}H_{27}N_6O_3$ (M+H)$^+$: m/z=447.2; found: 447.2.

Example 65. N-(2-((1S,3R)-3-((5-Cyano-4-methoxypyrimidin-2-yl)amino)cyclohexyl)-3-oxoisoindolin-5-yl)-N-methylacrylamide Step 1. tert-Butyl ((1R,3S)-3-(6-(methylamino)-1-oxoisoindolin-2-yl)cyclohexyl)carbamate To a vial containing tert-butyl ((1R,3S)-3-(6-amino-1-oxoisoindolin-2-yl)cyclohexyl)carbamate (100 mg, 0.289 mmol) in MeOH (1.2 mL) was added sodium methoxide (313 mg, 1.447 mmol) and paraformaldehyde (26.1 mg, 0.868 mmol). The reaction mixture was heated to 60° C. for 2 h. Upon cooling to rt, sodium borohydride (32.9 mg, 0.868 mmol) was added to the reaction mixture. After stirring at 60° C. for 2 h, the reaction was quenched with water and the mixture was extracted with $CH_2Cl_2$. The organic phase was washed with brine, dried over $MgSO_4$ and concentrated in vacuo. The crude material was used in the next step without further purification. LCMS calculated for $C_{20}H_{30}N_3O_3$ $(M+H)^+$: m/z=360.2; found: 360.1.

Step 2. N-(2-((1S,3R)-3-Aminocyclohexyl)-3-oxoisoindolin-5-yl)-N-methylacrylamide This compound was prepared according to the example procedures described in Intermediate D, with tert-butyl ((1R,3S)-3-(6-(methylamino)-1-oxoisoindolin-2-yl)cyclohexyl)carbamate replacing tert-butyl ((1R,3S)-3-(6-amino-1-oxoisoindolin-2-yl)cyclohexyl)carbamate in Step 3. LCMS calculated for $C_{11}H_{24}N_3O_2$ $(M+H)^+$: m/z=314.2; found: 314.2.

Step 5. N-(2-((1S,3R)-3-((5-Cyano-4-methoxypyrimidin-2-yl)amino)cyclohexyl)-3-oxoisoindolin-5-yl)-N-methylacrylamide A vial containing N-(2-((1S,3R)-3-aminocyclohexyl)-3-oxoisoindolin-5-yl)-N-methylacrylamide (30.0 mg, 0.096 mmol), DIPEA (50 μL, 0.287 mmol) in EtOH (0.64 mL) was added 2-chloro-4-methoxypyrimidine-5-carbonitrile (16.2 mg, 0.096 mmol). After stirring at 45° C. for 1 h, the reaction mixture was diluted with $CH_3CN$ and water and purified by prep-LCMS (XBridge C18 column, eluting with a gradient of acetonitrile/water containing 0.1% TFA, at flow rate of 60 mL/min). LCMS calculated for $C_{24}H_{27}N_6O_3$ $(M+H)^+$: m/z=447.2; found: 447.2.

Example 66. N-(2-((1S,3R)-3-((5-Cyano-4-((2-hydroxy-2-methylpropyl)amino)pyrimidin-2-yl)amino)cyclohexyl)-3-oxoisoindolin-5-yl)acrylamide Step 1. N-(2-((1S,3R)-3-((4-Chloro-5-cyanopyrimidin-2-yl)amino)cyclohexyl)-3-oxoisoindolin-5-yl)acrylamide

This compound was prepared according to the procedures described in Intermediate D, with 2,4-dichloropyrimidine-5-carbonitrile replacing 2,4-dichloro-5-(trifluoromethyl)pyrimidine in Step 4. LCMS calculated for $C_{22}H_{22}ClN_6O_2$ (M+H)$^+$: m/z=437.1; found: 437.1.

Step 2. N-(2-((1S,3R)-3-((5-Cyano-4-((2-hydroxy-2-methylpropyl)amino)pyrimidin-2-yl)amino)cyclohexyl)-3-oxoisoindolin-5-yl)acrylamide A vial containing N-(2-((1S,3R)-3-((4-chloro-5-cyanopyrimidin-2-yl)amino)cyclohexyl)-3-oxoisoindolin-5-yl)acrylamide (25 mg, 0.057 mmol), DIPEA (30.0 µL, 0.172 mmol) EtOH (0.4 mL) and THF (0.2 mL) was cooled to 0° C. and then added 1-amino-2-methylpropan-2-ol (5 mg, 0.057 mmol). After stirring at r.t. for 1 h, the reaction mixture was quenched with TFA, then diluted with CH$_3$CN and water and purified by prep-LCMS (XBridge C18 column, eluting with a gradient of acetonitrile/water containing 0.10% TFA, at flow rate of 60 mL/min). LCMS calculated for $C_{26}H_{32}N_7O_3$ (M+H)$^+$: m/z=490.2; found: 490.2.

Example 67. N-(2-((1S,3R)-3-((5-Cyano-4-(methyl-amino)pyrimidin-2-yl)amino)cyclohexyl)-3-oxoisoindolin-5-yl)acrylamide This compound was prepared according to the procedures described in Example 66, with methylamine replacing 1-amino-2-methylpropan-2-ol in Step 2. LCMS calculated for $C_{23}H_{26}N_7O_2$ (M+H)$^+$: m/z=432.2; found: 432.2.

Example 68. N-(2-((1S,3R)-3-((5-Bromopyrimidin-2-yl)amino)cyclohexyl)-3-oxoisoindolin-5-yl)acrylamide

280

Step 1. 2-((1S,3R)-3-((5-Bromopyrimidin-2-yl)amino)cyclohexyl)-6-nitroisoindolin-1-one To a vial containing 2-((1S,3R)-3-aminocyclohexyl)-6-nitroisoindolin-1-one (25.0 mg, 0.091 mmol), DIPEA (48 µL, 0.272 mmol) in EtOH (0.45 mL) was added 5-bromo-2-chloropyrimidine (17.6 mg, 0.091 mmol). After stirring at 80° C. for 5 h, the solvent was evaporated in vacuo. The obtained crude product was purified by Biotage Isolera to give the desired product as yellow foam. LCMS calculated for $C_{18}H_{19}BrN_5O_3$ (M+H)$^+$: m/z=432.1/434.1; found: 432.2/434.1.

Step 2. 6-Amino-2-((1S,3R)-3-((5-bromopyrimidin-2-yl)amino)cyclohexyl)isoindolin-1-one This compound was prepared according to the procedures described in Example 47, with 2-((1S,3R)-3-((5-bromopyrimidin-2-yl)amino)cyclohexyl)-6-nitroisoindolin-1-one replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{18}H_{21}BrN_5O$ (M+H)$^+$: m/z=402.1/404.1; found: 402.1/404.1.

Step 3. N-(2-((1S,3R)-3-((5-Bromopyrimidin-2-yl)amino)cyclohexyl)-3-oxoisoindolin-5-yl)acrylamide To a vial containing 6-amino-2-((1S,3R)-3-((5-bromopyrimidin-2-yl)amino)cyclohexyl)isoindolin-1-one (40 mg, 0.099 mmol), DIPEA (44 µL, 0.249 mmol) in CH$_2$Cl$_2$ (3.0 mL) at 0° C. was added acryloyl chloride (13.5 mg, 0.149 mmol) at 0° C. After stirring at 0° C. for 10 min, the reaction mixture was quenched with MeOH and concentrated in vacuo. The obtained crude product was diluted with CH$_3$CN and water and purified by prep-LCMS (XBridge C18 column, eluting with a gradient of acetonitrile/water containing 0.1% TFA, at flow rate of 60 mL/min). LCMS calculated for $C_{21}H_{23}BrN_5O_2$ (M+H)$^+$: m/z=456.1/458.1; found: 456.1/458.2.

Example 69. N-(1-((1S,3R)-3-((5-Cyanopyrimidin-2-yl)amino)cyclohexyl)-1H-benzo[d]imidazol-4-yl) acrylamide

Step 1. tert-Butyl ((1R,3S)-3-((3-bromo-2-nitrophenyl)amino)cyclohexyl)carbamate To a vial containing 1-bromo-3-fluoro-2-nitrobenzene (154 mg, 0.700 mmol), tert-butyl ((1R,3S)-3-aminocyclohexyl)carbamate (150 mg, 0.700 mmol) and $K_2CO_3$ (242 mg, 1.750 mmol) was added $CH_3CN$ (2.3 mL). The reaction mixture was heated at 85° C. for 8 h. After cooling to r.t., the reaction mixture was filtered through a pad of Celite and washed with $CH_3CN$. The filtrate was evaporated in vacuo. The obtained crude product was purified by Biotage Isolera to give the desired product as orange solid. LCMS calculated for $C_{17}H_{23}BrN_3NaO_4$ $(M+Na)^+$: m/z=436.1/438.1; found: 436.0/438.1.

Step 2. tert-Butyl ((1R,3S)-3-((2-amino-3-bromophenyl)amino)cyclohexyl)carbamate This compound was prepared according to the procedures described in Example 47, with tert-butyl ((1R,3S)-3-((3-bromo-2-nitrophenyl)amino)cyclohexyl)carbamate replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{17}H_{27}BrN_3O_2$ $(M+H)^+$: m/z=384.1/386.1; found: 384.2/386.1.

Step 3. tert-Butyl ((1R,3S)-3-(4-bromo-1H-benzo[d]imidazol-1-yl)cyclohexyl)carbamate To a vial containing tert-butyl ((1R,3S)-3-((2-amino-3-bromophenyl)amino)cyclohexyl)carbamate (35.0 mg, 0.091 mmol) and p-TsOH (1.7 mg, 9.11 μmol) in toluene (0.83 mL) was added triethyl orthoformate (76 μL, 0.455 mmol). After stirring at 110° C. for 2 h, the reaction mixture was cooled to r.t. and concentrated in vacuo. The obtained crude product was purified by Biotage Isolera to give the desired product as off-white solid. LCMS calculated for $C_{18}H_{25}BrN_3O_2$ $(M+H)^+$: m/z=394.1/396.1; found: 394.1/396.1.

Step 4. (1R,3S)-3-(4-Bromo-1H-benzo[d]imidazol-1-yl)cyclohexan-1-amine

To a vial containing tert-butyl ((1R,3S)-3-(4-bromo-1H-benzo[d]imidazol-1-yl)cyclohexyl)carbamate (30 mg, 0.076 mmol) in $CH_2Cl_2$ (1.0 mL) was added TFA (1.0 mL). After stirring at 40° C. for 1 h, the reaction mixture was concentrated in vacuo. The crude material was redissolved in $CH_2Cl_2$ (5 mL) and the pH of the mixture was adjusted to ~10 with ammonia aqueous solution and then extracted into $CH_2Cl_2$. The organic phase was washed with brine, dried over $MgSO_4$ and concentrated in vacuo. The obtained crude product was used in the next step without further purification. LCMS calculated for $C_{13}H_{17}BrN_3$ $(M+H)^+$: m/z=294.1/296.1; found: 294.0/296.1.

Step 5. 2-(((1R,3S)-3-(4-Bromo-1H-benzo[d]imidazol-1-yl)cyclohexyl)amino)pyrimidine-5-carbonitrile To a vial containing (1R,3S)-3-(4-bromo-1H-benzo[d]imidazol-1-yl)cyclohexan-1-amine (25.0 mg, 0.085 mmol), 2-chloropyrimidine-5-carbonitrile (11.9 mg, 0.085 mmol) in DMSO (0.5 mL) was added DIPEA (45 μL, 0.255 mmol). After stirring at 100° C. for 1 h, the reaction mixture was cooled down to r.t. and quenched with water. The reaction mixture was extracted into $CH_2Cl_2$. The organic phase was washed with brine, dried over $MgSO_4$, and concentrated in vacuo. The obtained crude product was purified by Biotage Isolera to give the desired product as off-white solid. LCMS calculated for $C_{18}H_{18}BrN_6$ (M+H)$^+$: m/z=397.1/399.1; found: 397.1/399.1.

Step 6. 2-(((1R,3S)-3-(4-Amino-1H-benzo[d]imidazol-1-yl)cyclohexyl)amino)pyrimidine-5-carbonitrile A vial containing 2-(((1R,3S)-3-(4-bromo-1H-benzo[d] imidazol-1-yl)cyclohexyl)amino)pyrimidine-5-carbonitrile (30.0 mg, 0.076 mmol), tert-butyl carbamate (70.8 mg, 0.604 mmol), $Cs_2CO_3$ (61.5 mg, 0.189 mmol), 2-(dicyclo-hexylphosphino)-3,6-dimethoxy-2'-4'-6'-tri-1-propyl-1,1'-biphenyl (16.2 mg, 0.030 mmol) and $Pd_2(dba)_3$ (13.8 mg, 0.015 mmol) was evacuated and backfilled with nitrogen three times, followed by the addition of dioxane (0.75 mL). The vial was sealed and heated to 100° C. for 4 h. After cooling to r.t., the mixture was filtered through a SiliaPrep SPE thiol cartridge and washed with 10% MeOH in $CH_2Cl_2$. The crude material was concentrated and redissolved in $CH_2Cl_2$ (1.0 mL) and TFA (1.0 mL). After stirring at 40° C. for 1 h, the reaction mixture was concentrated in vacuo. The crude material was redissolved in $CH_2Cl_2$ (5 mL) and the pH of the mixture was adjusted to ~10 with ammonia aqueous solution and then extracted into $CH_2Cl_2$. The organic phase was washed with brine, dried over $MgSO_4$, and concentrated in vacuo. The obtained crude product was used in the next step without further purification. LCMS calculated for $C_{18}H_{20}N_7$ (M+H)$^+$: m/z=334.2; found: 334.2.

Step 7. N-(1-((1S,3R)-3-((5-Cyanopyrimidin-2-yl)amino)cyclohexyl)-1H-benzo[d]imidazol-4-yl)acrylamide This compound was prepared according to the procedures described in Example 68, with 2-(((1R,3S)-3-(4-amino-1H-benzo[d]imidazol-1-yl)cyclohexyl)amino)pyrimidine-5-carbonitrile replacing 6-amino-2-((1S,3R)-3-((5-bromopyrimidin-2-yl)amino)cyclohexyl)isoindolin-1-one in Step 3. LCMS calculated for $C_{21}H_{22}N_7O$ (M+H)$^+$: m/z=388.2; found: 388.2.

Example 70. N-(2-((1S,3R)-3-((5-Cyanopyrimidin-2-yl)amino)cyclopentyl)-1-methyl-1H-benzo[d]imidazol-5-yl)acrylamide

Step 1. tert-Butyl ((1R,3S)-3-((5-bromo-2-(methyl-amino)phenyl)carbamoyl)cyclopentyl)carbamate To a vial containing (1S,3R)-3-((tert-butoxycarbonyl) amino)cyclopentane-1-carboxylic acid (57.0 mg, 0.249 mmol), DIPEA (130 μL, 0.746 mmol) and HATU (113 mg, 0.298 mmol) in DMF (1.3 mL) was added 5-bromo-N-methylbenzene-1,2-diamine (50.0 mg, 0.249 mmol). After stirring at r.t. for 1 h, the reaction mixture was quenched with water and the mixture was extracted with EtOAc. The organic phase was washed with brine, dried over $MgSO_4$, and concentrated in vacuo. Crude material was purified by Biotage Isolera to give the desired product as brown oil. LCMS calculated for $C_{18}H_{27}BrN_3O_3$ (M+H)$^+$: m/z=412.1/414.1; found: 412.1/414.1.

Step 2. (1R,3S)-3-(5-Bromo-1-methyl-1H-benzo[d]imidazol-2-yl)cyclopentan-1-amine This compound was prepared according to the procedures described in Example 47, with tert-butyl ((1R,3S)-3-((5-bromo-2-(methylamino)phenyl)carbamoyl)cyclopentyl)car-bamate replacing tert-butyl ((1R,3S)-3-((2-((2-((tert-butyldimethylsilyl)oxy)ethyl)amino)-5-nitrophenyl) carbamoyl)cyclohexyl)carbamate in Step 3. LCMS calculated for $C_{13}H_{17}BrN_3$ (M+H)$^+$: m/z=296.1/294.1; found: 294.2/296.1.

Step 3. 2-(((1R,3S)-3-(5-Bromo-1-methyl-1H-benzo[d]imidazol-2-yl)cyclopentyl)amino)pyrimidine-5-carbonitrile This compound was prepared according to the procedures described in Example 69, with (1R,3S)-3-(5-bromo-1-methyl-1H-benzo[d]imidazol-2-yl)cyclopentan-1-amine replacing (1R,3S)-3-(4-bromo-1H-benzo[d]imidazol-1-yl)

cyclohexan-1-amine in Step 5. LCMS calculated for $C_{18}H_{18}BrN_6$ (M+H)$^+$: m/z=397.1/399.1; found: 397.1/399.1.

Step 4. 2-(((1R,3S)-3-(5-Amino-1-methyl-1H-benzo[d]imidazol-2-yl)cyclopentyl)amino)pyrimidine-5-carbonitrile This compound was prepared according to the procedures described in Example 69, with 2-(((1R,3S)-3-(5-bromo-1-methyl-1H-benzo[d]imidazol-2-yl)cyclopentyl)amino)pyrimidine-5-carbonitrile replacing 2-(((1R,3S)-3-(4-bromo-1H-benzo[d]imidazol-1-yl)cyclohexyl)amino)pyrimidine-5-carbonitrile in Step 6. LCMS calculated for $C_{18}H_{20}N_7$ (M+H)$^+$: m/z=334.2; found: 334.2.

Step 5. N-(2-((1S,3R)-3-((5-Cyanopyrimidin-2-yl)amino)cyclopentyl)-1-methyl-1H-benzo[d]imidazol-5-yl)acrylamide This compound was prepared according to the procedures described in Example 68, with 2-(((1R,3S)-3-(5-amino-1-methyl-1H-benzo[d]imidazol-2-yl)cyclopentyl)amino)pyrimidine-5-carbonitrile replacing 6-amino-2-((1S,3R)-3-((5-bromopyrimidin-2-yl)amino)cyclohexyl)isoindolin-1-one in Step 3. LCMS calculated for $C_{21}H_{22}N_7O$ (M+H)$^+$: m/z=388.2; found: 388.2.

Example 71. N-(1-((1S,3R)-3-((5-Cyanopyrimidin-2-yl)amino)cyclohexyl)-1H-benzo[d][1,2,3]triazol-5-yl)acrylamide

Step 1. tert-Butyl ((1R,3S)-3-((4-bromo-2-nitrophenyl)amino)cyclohexyl)carbamate This compound was prepared according to the procedures described in Example 69, with 4-bromo-1-fluoro-2-nitrobenzene replacing 1-bromo-3-fluoro-2-nitrobenzene in Step 1. LCMS calculated for $C_{17}H_{24}BrN_3NaO_4$ (M+Na)$^+$: m/z=436.1/438.1; found: 436.0/438.1.

Step 2. tert-Butyl ((1R,3S)-3-((2-amino-4-bromophenyl)amino)cyclohexyl)carbamate This compound was prepared according to the procedures described in Example 47, with tert-butyl ((1R,3S)-3-((4-bromo-2-nitrophenyl)amino)cyclohexyl)carbamate replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{17}H_{27}BrN_3O_2$ (M+H)$^+$: m/z=384.1/386.1; found: 384.2/386.1.

Step 3. tert-Butyl ((1R,3S)-3-(4-bromo-1H-benzo[d][1,2,3]triazol-1-yl)cyclohexyl)carbamate To a vial containing tert-butyl ((1R,3S)-3-((2-amino-4-bromophenyl)amino)cyclohexyl)carbamate (65.0 mg, 0.169 mmol) in acetic acid (1.6 mL) and water (80 μL) at 0° C. was added sodium nitrite (23.3 mg, 0.338 mmol). After stirring at r.t. for 2 h, the reaction mixture was cooled down to r.t. and concentrated in vacuo. The obtained crude product was purified by Biotage Isolera to give the desired product as off-white solid. LCMS calculated for $C_{17}H_{24}BrN_4O_2$ (M+H)$^+$: m/z=395.1/397.1; found: 395.0/397.1.

Step 4. (1R,3S)-3-(4-Bromo-1H-benzo[d][1,2,3]triazol-1-yl)cyclohexan-1-amine This compound was prepared according to the procedures described in Example 69, with tert-butyl ((1R,3S)-3-(4-bromo-1H-benzo[d][1,2,3]triazol-1-yl)cyclohexyl)carbamate replacing tert-butyl ((1R,3S)-3-(4-bromo-1H-benzo[d]imidazol-1-yl)cyclohexyl)carbamate in Step 4. LCMS calculated for $C_{12}H_{16}BrN_4$ (M+H)$^+$: m/z=295.1/297.1; found: 295.1/297.1.

Step 5. 2-(((1R,3S)-3-(4-Bromo-1H-benzo[d][1,2,3]triazol-1-yl)cyclohexyl)amino)pyrimidine-5-carbonitrile This compound was prepared according to the procedures described in Example 69, with (1R,3S)-3-(4-bromo-1H-benzo[d][1,2,3]triazol-1-yl)cyclohexan-1-amine replacing (1R,3S)-3-(4-bromo-1H-benzo[d]imidazol-1-yl)cyclohexan-1-amine in Step 5. LCMS calculated for $C_{17}H_{17}BrN_7$ (M+H)$^+$: m/z=398.1/400.1; found: 398.2/400.1.

Step 6. 2-(((1R,3S)-3-(4-Amino-1H-benzo[d][1,2,3]triazol-1-yl)cyclohexyl)amino)pyrimidine-5-carbonitrile This compound was prepared according to the procedures described in Example 69, with 2-(((1R,3S)-3-(4-bromo-1H-benzo[d][1,2,3]triazol-1-yl)cyclohexyl)amino)pyrimidine-5-carbonitrile replacing 2-(((1R,3S)-3-(4-bromo-1H-benzo[d]imidazol-1-yl)cyclohexyl)amino)pyrimidine-5-carbonitrile in Step 6. $C_{17}H_{19}N_8$ (M+H)$^+$: m/z=335.2; found: 335.2.

Step 7. N-(1-((1S,3R)-3-((5-Cyanopyrimidin-2-yl)amino)cyclohexyl)-1H-benzo[d][1,2,3]triazol-5-yl)acrylamide This compound was prepared according to the procedures described in Example 68, with 2-(((1R,3S)-3-(4-amino-1H-benzo[d][1,2,3]triazol-1-yl)cyclohexyl)amino)pyrimidine-5-carbonitrile replacing 6-amino-2-((1S,3R)-3-((5-bromopyrimidin-2-yl)amino)cyclohexyl)isoindolin-1-one in Step 3. LCMS calculated for $C_{20}H_{21}N_8O$ (M+H)$^+$: m/z=389.2; found: 389.2.

Example 72. N-(1-Methyl-2-((1S,3R)-3-((5-(trifluoromethyl)pyrimidin-2-yl)amino)cyclohexyl)-1H-benzo[d]imidazol-5-yl)acrylamide Step 1. tert-Butyl ((1S,3R)-3-((5-bromo-2-(methylamino)phenyl)carbamoyl)cyclohexyl)carbamate This compound was prepared according to the procedures described in Example 47, with 4-bromo-N$^1$-methylbenzene-1,2-diamine replacing N$^1$-(2-((tert-butyldimethylsilyl)oxy)ethyl)-4-nitrobenzene-1,2-diamine in Step 2. LCMS calculated for $C_{19}H_{29}BrN_3O_3$ (M+H)$^+$: m/z=426.1/428.1; found: 426.1/428.1.

Step 2. (1R,3S)-3-(5-Bromo-1-methyl-1H-benzo[d]imidazol-2-yl)cyclohexan-1-amine

This compound was prepared according to the procedures described in Example 47, with tert-butyl ((1S,3R)-3-((5-bromo-2-(methylamino)phenyl)carbamoyl)cyclohexyl)carbamate replacing tert-butyl ((1R,3S)-3-((2-((2-((tert-butyldimethylsilyl)oxy)ethyl)amino)-5-nitrophenyl)carbamoyl)cyclohexyl)carbamate in Step 3. LCMS calculated for $C_{14}H_{19}BrN_3$ (M+H)$^+$: m/z=308.1/310.1; found: 308.1/310.2.

Step 3. N-((1R,3S)-3-(5-Bromo-1-methyl-1H-benzo[d]imidazol-2-yl)cyclohexyl)-5-(trifluoromethyl)pyrimidin-2-amine To a vial containing (1R,3S)-3-(5-bromo-1-methyl-1H-benzo[d]imidazol-2-yl)cyclohexan-1-amine (30 mg, 0.097 mmol), 2-chloro-5-(trifluoromethyl)pyrimidine (18 mg, 0.097 mmol) in EtOH (1 mL) was added DIPEA (51 μL, 0.292 mmol). After stirring at 80° C. for 1 h, the reaction mixture was concentrated in vacuo. The obtained crude product was purified by Biotage Isolera to give the desired product as off-white solid. LCMS calculated for $C_{19}H_{20}BrF_3N_5$ (M+H)$^+$: m/z=454.1/456.1; found: 454.1/456.1.

Step 4. 1-Methyl-2-((1S,3R)-3-((5-(trifluoromethyl)pyrimidin-2-yl)amino)cyclohexyl)-1H-benzo[d]imidazol-5-amine This compound was prepared according to the procedures described in Example 69, with N-((1R,3S)-3-(5-bromo-1-methyl-1H-benzo[d]imidazol-2-yl)cyclohexyl)-5-(trifluoromethyl)pyrimidin-2-amine replacing 2-(((1R,3S)-3-(4-bromo-1H-benzo[d]imidazol-1-yl)cyclohexyl)amino)pyrimidine-5-carbonitrile in Step 6. LCMS calculated for $C_{19}H_{22}F_3N_6$ (M+H)$^+$: m/z=391.2; found: 391.2.

Step 5. N-(1-Methyl-2-((1S,3R)-3-((5-(trifluoromethyl)pyrimidin-2-yl)amino)cyclohexyl)-1H-benzo[d]imidazol-5-yl)acrylamide This compound was prepared according to the procedures described in Example 68, with 1-methyl-2-((1S,3R)-3-((5-(trifluoromethyl)pyrimidin-2-yl)amino)cyclohexyl)-1H-benzo[d]imidazol-5-amine replacing 6-amino-2-((1S,3R)-3-((5-bromopyrimidin-2-yl)amino)cyclohexyl)isoindolin-1-one in Step 3. LCMS calculated for $C_{22}H_{24}F_3N_6O$ (M+H)$^+$: m/z=445.2; found: 445.2.

Example 73. N-(2-((1S,3R)-3-((5-Cyano-4-methoxypyrimidin-2-yl)amino)cyclohexyl)-1-methyl-1H-benzo[d]imidazol-5-yl)acrylamide This compound was prepared according to the procedures described in Example 68, with 2-(((1R,3S)-3-(5-amino-1-methyl-1H-benzo[d]imidazol-2-yl)cyclohexyl)amino)-4-methoxypyrimidine-5-carbonitrile replacing 6-amino-2-((1S,3R)-3-((5-bromopyrimidin-2-yl)amino)cyclohexyl)isoindolin-1-one in Step 3. LCMS calculated for $C_{23}H_{26}N_7O_2$ (M+H)$^+$: m/z=432.2; found: 432.1.

Example 74. N-(2-((1S,3R)-3-((5-Cyanopyrimidin-2-yl)amino)cyclohexyl)-1-methyl-1H-benzo[d]imidazol-5-yl)acrylamide Step 1. 2-(((1R,3S)-3-(5-Bromo-1-methyl-1H-benzo[d]imidazol-2-yl)cyclohexyl)amino)pyrimidine-5-carbonitrile This compound was prepared according to the procedures described in Example 72, with 2-chloropyrimidine-5-carbonitrile replacing 2-chloro-5-(trifluoromethyl)pyrimidine in Step 3. LCMS calculated for $C_{19}H_{20}BrN_6$ (M+H)$^+$: m/z=411.1/413.1; found: 411.1/413.1.

Step 2. 2-(((1R,3S)-3-(5-Amino-1-methyl-1H-benzo[d]imidazol-2-yl)cyclohexyl)amino)pyrimidine-5-carbonitrile This compound was prepared according to the procedures described in Example 69, with 2-(((1R,3S)-3-(5-bromo-1-methyl-1H-benzo[d]imidazol-2-yl)cyclohexyl)amino)pyrimidine-5-carbonitrile replacing 2-(((1R,3S)-3-(4-bromo-1H-benzo[d]imidazol-1-yl)cyclohexyl)amino)pyrimidine-5-carbonitrile in Step 6. LCMS calculated for $C_{19}H_{22}N_7$ (M+H)$^+$: m/z=348.2; found: 348.2.

Step 3. N-(2-((1S,3R)-3-((5-Cyanopyrimidin-2-yl)amino)cyclohexyl)-1-methyl-1H-benzo[d]imidazol-5-yl)acrylamide This compound was prepared according to the procedures described in Example 68, with 2-(((1R,3S)-3-(5-amino-1-methyl-1H-benzo[d]imidazol-2-yl)cyclohexyl)amino)pyrimidine-5-carbonitrile replacing 6-amino-2-((1S,3R)-3-((5-bromopyrimidin-2-yl)amino)cyclohexyl)isoindolin-1-one in Step 3. LCMS calculated for $C_{22}H_{24}N_7O$ (M+H)$^+$: m/z=402.2; found: 402.1.

Example 75. N-(2-((1S,3R)-3-((5-Bromo-4-(trifluoromethyl)pyrimidin-2-yl)amino)cyclohexyl)-3-oxoisoindolin-5-yl)acrylamide Step 1. 2-((1S,3R)-3-((5-Bromo-4-(trifluoromethyl)pyrimidin-2-yl)amino)cyclohexyl)-6-nitroisoindolin-1-one This compound was prepared according to the procedures described in Intermediate A, with 5-bromo-2-chloro-4-(trifluoromethyl)pyrimidine replacing 2-chloro-4-methoxypyrimidine-5-carbonitrile in Step 1. LCMS calculated for $C_{19}H_{18}BrF_3N_5O_3$ (M+H)$^+$: m/z=500.0/502.0; found: 500.0/502.1.

Step 2. 6-Amino-2-((1S,3R)-3-((5-bromo-4-(trifluoromethyl)pyrimidin-2-yl)amino)cyclohexyl)isoindolin-1-one This compound was prepared according to the procedures described in Example 47, with 2-((1S,3R)-3-((5-bromo-4-(trifluoromethyl)pyrimidin-2-yl)amino)cyclohexyl)-6-nitroisoindolin-1-one replacing 2-(2-((1S,3R)-3-((5-cyano-4-methoxypyrimidin-2-yl)amino)cyclohexyl)-5-nitro-1H-benzo[d]imidazol-1-yl)ethyl acetate Step 5. LCMS calculated for $C_{19}H_{20}BrF_3N_5O$ (M+H)$^+$: m/z=470.1/472.1; found: 470.1/472.1.

Step 3. N-(2-((1S,3R)-3-((5-Bromo-4-(trifluoromethyl)pyrimidin-2-yl)amino)cyclohexyl)-3-oxoisoindolin-5-yl)acrylamide This compound was prepared according to the procedures described in Example 68, with 6-amino-2-((1S,3R)-3-((5-bromo-4-(trifluoromethyl)pyrimidin-2-yl)amino)cyclohexyl)isoindolin-1-one replacing 6-amino-2-((1S,3R)-3-((5-bromopyrimidin-2-yl)amino)cyclohexyl)isoindolin-1-one in Step 3. LCMS calculated for $C_{22}H_{22}BrF_3N_5O_2$ (M+H)$^+$: m/z=524.1/526.1; found: 524.2/526.1.

Example 76. N-(2-((1S,3R)-3-((5-Cyano-4-mor-
pholinopyrimidin-2-yl)amino)cyclohexyl)-3-oxoi-
soindolin-5-yl)acrylamide Step 1. 4-Chloro-2-(((1R,3S)-3-(6-nitro-1-oxoisoin-
dolin-2-yl)cyclohexyl)amino)pyrimidine-5-carboni-
trile To a vial containing 2-((1S,3R)-3-aminocyclohexyl)-6-nitroisoindolin-1-one (100 mg, 0.363 mmol), DIPEA (190 µL, 1.090 mmol) in EtOH (2.3 mL) at −20° C. was added 2,4-dichloropyrimidine-5-carbonitrile (63 mg, 0.363 mmol). After stirring at −20° C. for 1 h, the solvent was evaporated in vacuo. The obtained crude product was used in the next step without further purification. LCMS calculated for $C_{19}H_{18}ClN_6O_3$ (M+H)$^+$: m/z=413.1; found: 413.1.

Step 2. 4-Morpholino-2-(((1R,3S)-3-(6-nitro-1-oxoi-
soindolin-2-yl)cyclohexyl)amino)pyrimidine-5-car-
bonitrile To a vial containing 4-chloro-2-(((1R,3S)-3-(6-nitro-1-oxoisoindolin-2-yl)cyclohexyl)amino)pyrimidine-5-carbonitrile (50 mg, 0.121 mmol), morpholine (106 mg, 1.211 mmol) in THF was added DIPEA (64 µL, 0.363 mmol). After stirring at 60° C. for 1 h, the solvent was evaporated in vacuo. The obtained crude product was used in the next step without further purification. LCMS calculated for $C_{23}H_{26}N_7O_4$ (M+H)$^+$: m/z=464.2; found: 464.2.

Step 3. 2-(((1R,3S)-3-(6-Amino-1-oxoisoindolin-2-
yl)cyclohexyl)amino)-4-morpholinopyrimidine-5-
carbonitrile This compound was prepared according to the procedures described in Example 47, with 4-morpholino-2-(((1R,3S)-3-(6-nitro-1-oxoisoindolin-2-yl)cyclohexyl)amino)pyrimidine-5-carbonitrile replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{23}H_{28}N_7O_2$ (M+H)$^+$: m/z=434.2; found: 434.2.

Step 4. N-(2-((1S,3R)-3-((5-Cyano-4-morpholinopy-
rimidin-2-yl)amino)cyclohexyl)-3-oxoisoindolin-5-
yl)acrylamide This compound was prepared according to the procedures described in Example 68, with 2-(((1R,3S)-3-(6-amino-1-oxoisoindolin-2-yl)cyclohexyl)amino)-4-morpholinopyrimidine-5-carbonitrile replacing 6-amino-2-((1S,3R)-3-((5-bromopyrimidin-2-yl)amino)cyclohexyl)isoindolin-1-one in Step 3. LCMS calculated for $C_{26}H_{30}N_7O_3$ (M+H)$^+$: m/z=488.2; found: 488.1.

Example 77. N-(2-((1S,3R)-3-((5-Cyano-4-(dimethylamino)pyrimidin-2-yl)amino)cyclohexyl)-3-oxoisoindolin-5-yl)acrylamide

Step 1. 4-(Dimethylamino)-2-(((1R,3S)-3-(6-nitro-1-oxoisoindolin-2-yl)cyclohexyl)amino)pyrimidine-5-carbonitrile This compound was prepared according to the procedures described in Example 76, with dimethylamine replacing morpholine in Step 2. LCMS calculated for $C_{21}H_{24}N_7O_3$ (M+H)$^+$: m/z=422.2; found: 422.2.

Step 2. 2-(((1R,3S)-3-(6-Amino-1-oxoisoindolin-2-yl)cyclohexyl)amino)-4-(dimethylamino)pyrimidine-5-carbonitrile This compound was prepared according to the procedures described in Example 47, with 4-(dimethylamino)-2-(((1R,3S)-3-(6-nitro-1-oxoisoindolin-2-yl)cyclohexyl)amino)pyrimidine-5-carbonitrile replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{21}H_{26}N_7O$ (M+H)$^+$: m/z=392.2; found: 392.2.

Step 3. N-(2-((1S,3R)-3-((5-Cyano-4-(dimethylamino)pyrimidin-2-yl)amino)cyclohexyl)-3-oxoisoindolin-5-yl)acrylamide This compound was prepared according to the procedures described in Example 68, with 2-(((1R,3S)-3-(6-amino-1-oxoisoindolin-2-yl)cyclohexyl)amino)-4-(dimethylamino)pyrimidine-5-carbonitrile replacing 6-amino-2-((1S,3R)-3-((5-bromopyrimidin-2-yl)amino)cyclohexyl)isoindolin-1-one in Step 3. LCMS calculated for $C_{24}H_{28}N_7O_2$ (M+H)$^+$: m/z=446.2; found: 446.2.

Example 78. N-(2-((1S,3R)-3-((4-(Methylamino)-5-(trifluoromethyl)pyrimidin-2-yl)amino)cyclohexyl)-3-oxoisoindolin-5-yl)acrylamide This compound was prepared according to the procedures described in Example 62, with methylamine replacing (R)—N,N-dimethylpyrrolidin-3-amine in Step 5. LCMS calculated for $C_{23}H_{26}F_3N_6O_2$ (M+H)$^+$: m/z=475.2; found: 475.2.

Example 79. N-(1-((1S,3R)-3-((5-Cyano-4-methoxypyrimidin-2-yl)amino)cyclohexyl)-1H-benzo[d]imidazol-5-yl)acrylamide

Step 1. tert-Butyl ((1R,3S)-3-(5-bromo-1H-benzo[d]imidazol-1-yl)cyclohexyl)carbamate This compound was prepared according to the procedures described in Example 69, with tert-butyl ((1R,3S)-3-((2-amino-4-bromophenyl)amino)cyclohexyl)carbamate replacing tert-butyl ((1R,3S)-3-((2-amino-3-bromophenyl)amino)cyclohexyl)carbamate in Step 3. LCMS calculated for $C_{18}H_{25}BrN_3O_2$ (M+H)$^+$: m/z=394.1/396.1; found: 394.1/396.1.

Step 2. (1R,3S)-3-(5-Bromo-1H-benzo[d]imidazol-1-yl)cyclohexan-1-amine

This compound was prepared according to the procedures described in Example 69, with tert-butyl ((1R,3S)-3-(5-bromo-1H-benzo[d]imidazol-1-yl)cyclohexyl)carbamate replacing tert-butyl ((1R,3S)-3-(4-bromo-1H-benzo[d]imidazol-1-yl)cyclohexyl)carbamate in Step 4. LCMS calculated for $C_{13}H_{17}BrN_3$ (M+H)$^+$: m/z=294.1/296.1; found: 294.0/296.1.

Step 3. 2-(((1R,3S)-3-(5-Bromo-1H-benzo[d]imidazol-1-yl)cyclohexyl)amino)-4-methoxypyrimidine-5-carbonitrile To a vial containing (1R,3S)-3-(5-bromo-1H-benzo[d]imidazol-1-yl)cyclohexan-1-amine (25 mg, 0.085 mmol), 2-chloropyrimidine-5-carbonitrile (12 mg, 0.085 mmol) in EtOH (0.5 mL) was added DIPEA (45 μL, 0.255 mmol). After stirring at 80° C. for 1 h, the reaction mixture was cooled down to r.t. and concentrated in vacuo. The obtained crude product was purified by Biotage Isolera to give the desired product as off-white solid. LCMS calculated for $C_{19}H_{20}BrN_6O$ (M+H)$^+$: m/z=427.1/429.1; found: 427.2/429.1.

Step 4. 2-(((1R,3S)-3-(5-Amino-1H-benzo[d]imidazol-1-yl)cyclohexyl)amino)-4-methoxypyrimidine-5-carbonitrile This compound was prepared according to the procedures described in Example 69, with 2-(((1R,3S)-3-(5-bromo-1H-benzo[d]imidazol-1-yl)cyclohexyl)amino)-4-methoxypyrimidine-5-carbonitrile replacing 2-(((1R,3S)-3-(4-bromo-1H-benzo[d]imidazol-1-yl)cyclohexyl)amino)pyrimidine-5-carbonitrile in Step 6. LCMS calculated for $C_{19}H_{22}N_7O$ (M+H)$^+$: m/z=364.2; found: 364.2.

Step 5. N-(1-((1S,3R)-3-((5-Cyano-4-methoxypyrimidin-2-yl)amino)cyclohexyl)-1H-benzo[d]imidazol-5-yl)acrylamide This compound was prepared according to the procedures described in Example 68, with 2-(((1R,3S)-3-(5-amino-1H-benzo[d]imidazol-1-yl)cyclohexyl)amino)-4-methoxypyrimidine-5-carbonitrile replacing 6-amino-2-((1S,3R)-3-((5-bromopyrimidin-2-yl)amino)cyclohexyl)isoindolin-1-one in Step 3. LCMS calculated for $C_{22}H_{24}N_7O_2$ (M+H)$^+$: m/z=418.2; found: 418.2.

Example 80. 2-Chloro-N-(2-((1S,3R)-3-((5-cyano-4-methoxypyrimidin-2-yl)amino)cyclohexyl)-1-methyl-1H-benzo[d]imidazol-5-yl)acrylamide This compound was prepared according to the procedures described in Example 63, with 2-chloroacrylic acid replacing (E)-4-(dimethylamino)but-2-enoic acid hydrochloride. LCMS calculated for $C_{23}H_{25}ClN_7O_2$ (M+H)$^+$: m/z=466.2; found: 466.2.

Example 81. N-(2-((1S,3R)-3-((5-Chloro-4-
methoxypyrimidin-2-yl)amino)cyclohexyl)-3-oxoi-
soindolin-5-yl)acrylamide Step 1. 2-((1S,3R)-3-Aminocyclohexyl)-6-bromoi-
soindolin-1-one This compound was prepared according to the procedures described in Intermediate D, with methyl 5-bromo-2-(bromomethyl)benzoate replacing 2-(bromomethyl)-5-nitrobenzoate. LCMS calculated for $C_{14}H_{18}BrN_2O$ (M+H)$^+$: m/z=309.1/311.1; found: 309.1/311.1.

Step 2. 6-Bromo-2-((1S,3R)-3-((5-chloro-4-
methoxypyrimidin-2-yl)amino)cyclohexyl)isoindo-
lin-1-one To a vial containing 2-((1S,3R)-3-aminocyclohexyl)-6-bromoisoindolin-1-one (30 mg, 0.097 mmol), 2,5-dichloro-4-methoxypyrimidine (17 mg, 0.097 mmol) in DMSO (0.5 mL) was added DIPEA (51 μL, 0.291 mmol). After stirring at 100° C. for 3 h, the reaction mixture was cooled down to r.t. and quenched with water. The reaction mixture was extracted into $CH_2Cl_2$.

The organic phase was washed with brine, dried over $MgSO_4$ and concentrated in vacuo. The obtained crude product was purified by Biotage Isolera to give the desired product as off-white solid. LCMS calculated for $C_{19}H_{21}BrClN_4O_2$ (M+H)$^+$: m/z=451.0/453.0; found: 451.1/453.0.

Step 3. 6-Amino-2-((1S,3R)-3-((5-chloro-4-
methoxypyrimidin-2-yl)amino)cyclohexyl)isoindo-
lin-1-one This compound was prepared according to the procedures described in Example 69, with 6-bromo-2-((1S,3R)-3-((5-chloro-4-methoxypyrimidin-2-yl)amino)cyclohexyl)isoindolin-1-one replacing 2-(((1R,3S)-3-(4-bromo-1H-benzo[d]imidazol-1-yl)cyclohexyl)amino)pyrimidine-5-carbonitrile in Step 6. LCMS calculated for $C_{19}H_{23}ClN_5O_2$ (M+H)$^+$: m/z=388.1; found: 388.1.

Step 4. N-(2-((1S,3R)-3-((5-Chloro-4-methoxypy-
rimidin-2-yl)amino)cyclohexyl)-3-oxoisoindolin-5-
yl)acrylamide This compound was prepared according to the procedures described in Example 68, with 6-amino-2-((1S,3R)-3-((5-chloro-4-methoxypyrimidin-2-yl)amino)cyclohexyl)isoindolin-1-one replacing 6-amino-2-((1S,3R)-3-((5-bromopyrimidin-2-yl)amino)cyclohexyl)isoindolin-1-one in Step 3. LCMS calculated for $C_{22}H_{25}ClN_5O_3$ (M+H)$^+$: m/z=442.2; found: 442.1.

Example 82. N-(2-((1S,3R)-3-((5-Chloropyrimidin-
2-yl)amino)cyclohexyl)-3-oxoisoindolin-5-yl)acryl-
amide Step 1. 6-Bromo-2-((1S,3R)-3-((5-chloropyrimidin-2-yl)amino)cyclohexyl)isoindolin-1-one This compound was prepared according to the procedures described in Example 81, with 2,5-dichloropyrimidine replacing 2,5-dichloro-4-methoxypyrimidine in Step 2. LCMS calculated for $C_{18}H_{19}BrClN_4O$ (M+H)$^+$: m/z=421.0/423.0; found: 421.0/423.1.

Step 2. 6-Amino-2-((1S,3R)-3-((5-chloropyrimidin-2-yl)amino)cyclohexyl)isoindolin-1-one This compound was prepared according to the procedures described in Example 69, with 6-bromo-2-((1S,3R)-3-((5-chloropyrimidin-2-yl)amino)cyclohexyl)isoindolin-1-one replacing 2-(((1R,3S)-3-(4-bromo-1H-benzo[d]imidazol-1-yl)cyclohexyl)amino)pyrimidine-5-carbonitrile in Step 6. LCMS calculated for $C_{18}H_{21}ClN_5O$ (M+H)$^+$: m/z=358.1; found: 358.1.

Step 3. N-(2-((1S,3R)-3-((5-Chloropyrimidin-2-yl)amino)cyclohexyl)-3-oxoisoindolin-5-yl)acrylamide This compound was prepared according to the procedures described in Example 68, with 6-amino-2-((1S,3R)-3-((5-chloropyrimidin-2-yl)amino)cyclohexyl)isoindolin-1-one replacing 6-amino-2-((1S,3R)-3-((5-bromopyrimidin-2-yl)amino)cyclohexyl)isoindolin-1-one in Step 3. LCMS calculated for $C_{21}H_{23}ClN_5O_2$ (M+H)$^+$: m/z=412.2; found: 412.1.

Example 83. N-(2-((1S,3R)-3-((5-Cyano-4-methoxypyrimidin-2-yl)amino)cyclohexyl)-3-oxoisoindolin-5-yl)acrylamide This compound was prepared according to the procedures described in Example 58, with acryloyl chloride replacing 2-bromoacetyl bromide. LCMS calculated for $C_{23}H_{25}N_6O_3$ (M+H)$^+$: m/z=433.2; found: 433.2. $^1$H NMR (600 MHz, DMSO) δ 10.35 (s, 1H), 8.63-8.43 (m, 1H), 8.42-8.19 (m, 1H), 8.12 (dd, J=3.8, 2.0 Hz, 1H), 7.75 (ddd, J=8.3, 4.0, 2.0 Hz, 1H), 7.54 (d, J=8.2 Hz, 1H), 6.45 (dd, J=17.0, 10.2 Hz, 1H), 6.29 (dd, J=17.0, 1.9 Hz, 1H), 5.79 (dd, J=10.1, 2.0 Hz, 1H), 4.46-4.33 (m, 2H), 4.18-4.09 (m, 1H), 4.06-3.83 (m, 4H), 2.16-1.99 (m, 1H), 1.97-1.82 (m, 2H), 1.79-1.71 (m, 1H), 1.64-1.43 (m, 3H), 1.37-1.27 (m, 1H).

Example 84. N-(1-((1S,3R)-3-((5-Cyanopyrimidin-2-yl)amino)cyclohexyl)-2-(difluoromethyl)-1H-benzo[d]imidazol-5-yl)acrylamide Step 1. (1R,3S)-3-(5-Bromo-2-(difluoromethyl)-1H-benzo[d]imidazol-1-yl)cyclohexan-1-amine To a vial containing tert-butyl ((1R,3S)-3-((2-amino-4-bromophenyl)amino)cyclohexyl)carbamate (50 mg, 0.130 mmol) in acetic acid (0.87 mL) was added 2,2-difluoroacetic anhydride (25 mg, 0.143 mmol). After stirring at 90° C. for 3 h, the reaction mixture was cooled down to r.t. and concentrated in vacuo. The obtained crude product was redissolved in CH$_2$Cl$_2$ (1.0 mL) and TFA (1.0 mL). After stirring at 40° C. for 1 h, the reaction mixture was concentrated in vacuo. The crude material was redissolved in CH$_2$Cl$_2$ (5 mL) and the pH of the mixture was adjusted to ~10 with ammonia aqueous solution and then extracted into CH$_2$Cl$_2$. The organic phase was washed with brine, dried over MgSO$_4$, and concentrated in vacuo. The obtained crude product was used in the next step without further purification. LCMS calculated for C$_{14}$H$_{17}$BrF$_2$N$_3$ (M+H)$^+$: m/z=344.0/346.0; found: 344.1/346.1.

Step 2. 2-(((1R,3S)-3-(5-Bromo-2-(difluoromethyl)-1H-benzo[d]imidazol-1-yl)cyclohexyl)amino)pyrimidine-5-carbonitrile This compound was prepared according to the procedures described in Example 69, with (1R,3S)-3-(5-bromo-2-(difluoromethyl)-1H-benzo[d]imidazol-1-yl)cyclohexan-1-amine replacing (1R,3S)-3-(4-bromo-1H-benzo[d]imidazol-1-yl)cyclohexan-1-amine in Step 5. LCMS calculated for C$_{19}$H$_{18}$BrF$_2$N$_6$ (M+H)$^+$: m/z=447.1/449.1; found: 447.1/449.1.

Step 3. 2-(((1R,3S)-3-(5-Amino-2-(difluoromethyl)-1H-benzo[d]imidazol-1-yl)cyclohexyl)amino)pyrimidine-5-carbonitrile This compound was prepared according to the procedures described in Example 69, with 2-(((1R,3S)-3-(5-bromo-2-(difluoromethyl)-1H-benzo[d]imidazol-1-yl)cyclohexyl)amino)pyrimidine-5-carbonitrile replacing 2-(((1R,3S)-3-(4-bromo-1H-benzo[d]imidazol-1-yl)cyclohexyl)amino)pyrimidine-5-carbonitrile in Step 6. C$_{19}$H$_{20}$F$_2$N$_7$ (M+H)$^+$: m/z=384.2; found: 384.2.

Step 4. N-(1-((1S,3R)-3-((5-Cyanopyrimidin-2-yl)amino)cyclohexyl)-2-(difluoromethyl)-1H-benzo[d]imidazol-5-yl)acrylamide This compound was prepared according to the procedures described in Example 68, with 2-(((1R,3S)-3-(5-amino-2-(difluoromethyl)-1H-benzo[d]imidazol-1-yl)cyclohexyl)amino)pyrimidine-5-carbonitrile replacing 6-amino-2-((1S,3R)-3-((5-bromopyrimidin-2-yl)amino)cyclohexyl)isoindolin-1-one in Step 3. LCMS calculated for C$_{22}$H$_{22}$F$_2$N$_7$O (M+H)$^+$: m/z=438.2; found: 438.2.

Example 85. N-(3-Oxo-2-((1S,3R)-3-((5-(trifluoromethyl)pyrimidin-2-yl)amino)cyclohexyl)isoindolin-5-yl)acrylamide Step 1. 6-Bromo-2-((1S,3R)-3-((5-(trifluoromethyl)pyrimidin-2-yl)amino)cyclohexyl)isoindolin-1-one This compound was prepared according to the procedures described in Example 72, with 2-((1S,3R)-3-aminocyclohexyl)-6-bromoisoindolin-1-one replacing (1R,3S)-3-(5-bromo-2-methyl-1H-benzo[d]imidazol-2-yl)cyclohexan-1-amine in Step 3. LCMS calculated for C$_{19}$H$_{19}$BrF$_3$N$_4$O (M+H)$^+$: m/z=455.1/457.1; found: 455.1/457.1.

Step 2. 6-Amino-2-((1S,3R)-3-((5-(trifluoromethyl)pyrimidin-2-yl)amino)cyclohexyl)isoindolin-1-one This compound was prepared according to the procedures described in Example 69, with 6-bromo-2-((1S,3R)-3-((5-(trifluoromethyl)pyrimidin-2-yl)amino)cyclohexyl)isoindolin-1-one replacing 2-(((1R,3S)-3-(4-bromo-1H-benzo[d]imidazol-1-yl)cyclohexyl)amino)pyrimidine-5-carbonitrile in Step 6. LCMS calculated for C$_{19}$H$_{21}$F$_3$N$_5$O (M+H)$^+$: m/z=392.2; found: 392.1.

Step 3. N-(3-Oxo-2-((1S,3R)-3-((5-(trifluoromethyl)pyrimidin-2-yl)amino)cyclohexyl)isoindolin-5-yl)acrylamide This compound was prepared according to the procedures described in Example 68, with 6-amino-2-((1S,3R)-3-((5-

(trifluoromethyl)pyrimidin-2-yl)amino)cyclohexyl)isoindo-lin-1-one replacing 6-amino-2-((1S,3R)-3-((5-bromopy-rimidin-2-yl)amino)cyclohexyl)isoindol-1-one in Step 3. LCMS calculated for $C_{22}H_{23}F_3N_5O_2$ (M+H)$^+$: m/z=446.2; found: 446.2. $^1$H NMR (500 MHz, DMSO) δ 10.33 (s, 1H), 8.77-8.51 (m, 2H), 8.15-8.09 (m, 2H), 7.76 (dd, J=8.2, 2.0 Hz, 1H), 7.54 (d, J=8.2 Hz, 1H), 6.45 (dd, J=16.9, 10.1 Hz, 1H), 6.29 (dd, J=17.0, 2.0 Hz, 1H), 5.79 (dd, J=10.0, 2.0 Hz, 1H), 4.47-4.34 (m, 2H), 4.17-4.09 (m, 1H), 4.07-3.91 (m, 1H), 2.07 (d, J=11.7 Hz, 1H), 1.94-1.80 (m, 2H), 1.78-1.72 (m, 1H), 1.64-1.41 (m, 3H), 1.37-1.2 (m, 1H).

Example 86. N—((R)-1-(3-((3R,5R)-3-Fluoro-5-((5-(trifluoromethyl)pyrimidin-2-yl)amino)piperidin-1-yl)imidazo[1,5-a]pyrazin-8-yl)pyrrolidin-3-yl)acryl-amide Step 1. N-((3R,5R)-1-(8-((R)-3-Aminopyrrolidin-1-yl)imidazo[1,5-a]pyrazin-3-yl)-5-fluoropiperidin-3-yl)-5-(trifluoromethyl)pyrimidin-2-amine A vial containing N-((3R,5R)-1-(8-chloroimidazo[1,5-a]pyrazin-3-yl)-5-fluoropiperidin-3-yl)-5-(trifluoromethyl)pyrimidin-2-amine (Intermediate E, 25 mg, 0.06 mmol), tert-butyl (R)-pyrrolidin-3-ylcarbamate (17 mg, 0.090 mmol) and DIPEA (31 μL, 0.018 mmol) in DMSO (50 μL) was heated to 120° C. for 1 h. After cooling to r.t., the reaction mixture was diluted with $CH_2Cl_2$ (0.5 mL) and then TFA was added (0.5 mL). After stirring at 40° C. for 1 h, the reaction mixture was concentrated in vacuo. The crude material was redissolved in $CH_2Cl_2$ (5 mL), and pH of the mixture was adjusted to ~10 with ammonia aqueous solu-tion. The product was then extracted into $CH_2Cl_2$. The organic phase was washed with brine, dried over $MgSO_4$, and concentrated in vacuo. The obtained crude product was used in the next step without further purification. LCMS calculated for $C_{20}H_{24}F_4N_9$ (M+H)$^+$: m/z=466.2; found: 466.2.

Step 2. N—((R)-1-(3-((3R,5R)-3-Fluoro-5-((5-(trif-luoromethyl)pyrimidin-2-yl)amino)piperidin-1-yl) imidazo[1,5-a]pyrazin-8-yl)pyrrolidin-3-yl)acrylam-ide This compound was prepared according to the procedures described in Example 68, with N-((3R,5R)-1-(8-((R)-3-ami-nopyrrolidin-1-yl)imidazo[1,5-a]pyrazin-3-yl)-5-fluoropip-eridin-3-yl)-5-(trifluoromethyl)pyrimidin-2-amine replacing 6-amino-2-((1S,3R)-3-((5-bromopyrimidin-2-yl)amino)cy-clohexyl)isoindol-1-one in Step 3. LCMS calculated for $C_{23}H_{26}F_4N_9O$ (M+H)$^+$: m/z=520.2; found: 520.2.

Example 87. 1-(2-(2-((3R,5R)-3-Hydroxy-5-((5-(trifluoromethyl)pyrimidin-2-yl)amino)piperidin-1-yl)-1-methyl-1H-benzo[d]imidazol-5-yl)piperidin-1-yl)prop-2-en-1-one Step 1. Benzyl ((3R,5R)-1-(5-bromo-1-methyl-1H-benzo[d]imidazol-2-yl)-5-hydroxypiperidin-3-yl) carbamate To a mixture of benzyl ((3R,5R)-5-hydroxypiperidin-3-yl)carbamate (Example 94, Step 2; 0.048 g, 0.19 mmol) and 5-bromo-2-chloro-1-methyl-1H-benzo[d]imidazole (Enam-ine; 0.070 g, 0.285 mmol) in DMF (1 mL) was added DIPEA (0.331 mL, 1.9 mmol). The reaction mixture was heated to 100° C. overnight and then cooled to r.t. The reaction mixture was diluted with EtOAc, and the organic phase was washed with brine, dried over sodium sulfate and filtered. Solvents were evaporated in vacuo and the crude material was purified by Biotage isolera to give the desired product as white solid. LCMS calculated for $C_{21}H_{24}BrN_4O_3$ (M+H)$^+$: m/z=459.1; found 459.1.

Step 2. tert-Butyl 6-(2-((3R,5R)-3-(((benzyloxy)
carbonyl)amino)-5-hydroxypiperidin-1-yl)-1-methyl-
1H-benzo[d]imidazol-5-yl)-3,4-dihydropyridine-1
(2H)-carboxylate To a mixture of benzyl ((3R,5R)-1-(5-bromo-1-methyl-
1H-benzo[d]imidazol-2-yl)-5-hydroxypiperidin-3-yl)car-
bamate (60 mg, 0.131 mmol) and tert-butyl 6-(4,4,5,5-
tetramethyl-1,3,2-dioxaborolan-2-yl)-3,4-dihydropyridine-1
(2H)-carboxylate (61 mg, 0.196 mmol) in dioxane (4 mL)
and water (1 mL) was added sodium carbonate (42 mg,
0.392 mmol) and [1,1'-bis(diphenylphosphino)ferrocene]di-
chloropalladium(II) (21 mg, 0.026 mmol). The reaction
mixture was degassed three times and heated to 80° C. for
1 h, then cooled to r.t. The reaction mixture was diluted with
EtOAc and the organic phase was washed with brine, dried
over sodium sulfate, and filtered. Solvents were evaporated
in vacuo, and the crude material was purified by Biotage
isolera to give the desired product as white solid. LCMS
calculated for $C_{31}H_{40}N_5O_5$ (M+H)$^+$: m/z=562.3; found
562.3.

Step 3. tert-Butyl 2-(2-((3R,5R)-3-amino-5-hy-
droxypiperidin-1-yl)-1-methyl-1H-benzo[d]imida-
zol-5-yl)piperidine-1-carboxylate To a solution of tert-butyl 6-(2-((3R,5R)-3-(((benzyloxy)
carbonyl)amino)-5-hydroxypiperidin-1-yl)-1-methyl-1H-
benzo[d]imidazol-5-yl)-3,4-dihydropyridine-1(2H)-car-
boxylate (0.073 g, 0.13 mmol) in MeOH (2 mL) was added palladium on carbon (0.035 g, 0.325 mmol). After stirring
under hydrogen balloon for 2 h at r.t., the reaction mixture
was filtered through a Celite and rinsed with ethyl acetate.
The solvent was removed in vacuo, and the obtained crude
product was used in the next step without further purifica-
tion. LCMS calculated for $C_{23}H_{36}N_5O_3$ (M+H)$^+$:
m/z=430.3; found 430.3.

Step 4. tert-Butyl 2-(2-((3R,5R)-3-hydroxy-5-((5-
(trifluoromethyl)pyrimidin-2-yl)amino)piperidin-1-
yl)-1-methyl-1H-benzo[d]imidazol-5-yl)piperidine-
1-carboxylate To a mixture of tert-butyl 2-(2-((3R,5R)-3-amino-5-hy-
droxypiperidin-1-yl)-1-methyl-1H-benzo[d]imidazol-5-yl)
piperidine-1-carboxylate (0.029 g, 0.068 mmol) and
2-chloro-5-(trifluoromethyl)pyrimidine (0.015 g, 0.082
mmol) in DMF (1 mL) was added DIPEA (0.035 mL, 0.204
mmol). After stirring at 50° C. for 1 h, the reaction mixture
was diluted with EtOAc and the organic phase was washed
with brine, dried over sodium sulfate and filtered. Solvents
were evaporated in vacuo, and the crude material was
purified by Biotage isolera to give the desired product as
white solid. LCMS calculated for $C_{28}H_{37}F_3N_7O_3$ (M+H)$^+$:
m/z=576.3; found 576.3.

Step 5. 1-(2-(2-((3R,5R)-3-Hydroxy-5-((5-(trifluo-
romethyl)pyrimidin-2-yl)amino)piperidin-1-yl)-1-
methyl-1H-benzo[d]imidazol-5-yl)piperidin-1-yl)
prop-2-en-1-one tert-Butyl 2-(2-((3R,5R)-3-hydroxy-5-((5-(trifluorom-
ethyl)pyrimidin-2-yl)amino)piperidin-1-yl)-1-methyl-1H-
benzo[d]imidazol-5-yl)piperidine-1-carboxylate (0.039 g,
0.068 mmol) was dissolved in 50% TFA in DCM (2 mL).
After stirring at r.t. for 30 min, the solvent was removed in
vacuo and the crude material was dissolved in DCM (1 mL).
To this solution was added DIPEA (0.036 mL, 0.204 mmol)
and acryloyl chloride (8 μl, 0.1 mmol) at 0° C. After stirring
at 0° C. for 15 min, the solvent was removed in vacuo. The
reaction mixture was diluted with $CH_3CN$ and water and
purified by prep-LCMS (XBridge C18 column, eluting with
a gradient of acetonitrile/water containing 0.1% TFA, at flow
rate of 60 mL/min). LCMS calculated for $C_{26}H_{31}F_3N_7O_2$
(M+H)$^+$: m/z=530.3; found 530.3.

Example 88. N-(2-((3R,5R)-3-Hydroxy-5-((5-(trifluoromethyl)pyrimidin-2-yl)amino)piperidin-1-yl)-1-methyl-1H-benzo[d]imidazol-5-yl)acrylamide

Step 1. tert-Butyl ((3R,5R)-5-hydroxy-1-(1-methyl-5-nitro-1H-benzo[d]imidazol-2-yl)piperidin-3-yl)carbamate To a solution of tert-butyl ((3R,5R)-5-hydroxypiperidin-3-yl)carbamate (PharmaBlock; 0.041 g, 0.19 mmol) in DMF (1 mL) was added 2-chloro-1-methyl-5-nitro-1H-benzo[d]imidazole (0.060 g, 0.285 mmol) and DIPEA (0.331 mL, 1.900 mmol). The reaction mixture was heated to 100° C. overnight and then cooled to r.t. The reaction mixture was diluted with EtOAc and the organic phase was washed with brine, dried over sodium sulfate and filtered. Solvents were evaporated in vacuo and the crude material was purified by Biotage isolera to give the desired product as yellow solid. LCMS calculated for $C_{11}H_{26}N_5O_5$ (M+H)$^+$: m/z=392.2; found 392.2.

Step 2. (3R,5R)-1-(1-Methyl-5-nitro-1H-benzo[d]imidazol-2-yl)-5-((5-(trifluoromethyl)pyrimidin-2-yl)amino)piperidin-3-ol tert-Butyl ((3R,5R)-5-hydroxy-1-(1-methyl-5-nitro-1H-benzo[d]imidazol-2-yl)piperidin-3-yl)carbamate (0.022 g, 0.055 mmol) was dissolved in 50% TFA in DCM (2 mL). After stirring at r.t. for 30 min, solvents were evaporated in vacuo and the crude material was dissolved in EtOH (2 mL). To this solution were added DIPEA (0.096 mL, 0.550 mmol) and 2-chloro-5-(trifluoromethyl)pyrimidine (10 mg, 0.055 mmol). After stirring at 50° C. for 1 h, the reaction mixture was diluted with EtOAc and the organic phase was washed with brine, dried over sodium sulfate and filtered. Solvents were evaporated in vacuo and the crude material was purified by Biotage isolera to give the desired product as white solid. LCMS calculated for $C_{18}H_{19}F_3N_7O_3$ (M+H)$^+$: m/z=438.1; found 438.1.

Step 3. (3R,5R)-1-(5-Amino-1-methyl-1H-benzo[d]imidazol-2-yl)-5-((5-(trifluoromethyl)pyrimidin-2-yl)amino)piperidin-3-ol To a solution of (3R,5R)-1-(1-methyl-5-nitro-1H-benzo[d]imidazol-2-yl)-5-((5-(trifluoromethyl)pyrimidin-2-yl)amino)piperidin-3-ol (0.024 g, 0.055 mmol) in THF (2 mL) and water (0.500 mL) was added ammonium chloride (0.029 g, 0.550 mmol) and zinc (0.036 g, 0.550 mmol) at r.t. After stirring at 50° C. for 1 h, the reaction mixture was filtered through a Celite and rinsed with ethyl acetate. The solvent was removed in vacuo, and the obtained crude product was used in the next step without further purification. LCMS calculated for $C_{11}H_{21}F_3N_7O$ (M+H)$^+$: m/z=408.2; found 408.2.

Step 4. N-(2-((3R,5R)-3-Hydroxy-5-((5-(trifluoromethyl)pyrimidin-2-yl)amino)piperidin-1-yl)-1-methyl-1H-benzo[d]imidazol-5-yl)acrylamide To a solution of (3R,5R)-1-(5-amino-1-methyl-1H-benzo[d]imidazol-2-yl)-5-((5-(trifluoromethyl)pyrimidin-2-yl)amino)piperidin-3-ol (0.020 g, 0.05 mmol) in DCM (1 mL) was slowly added DIPEA (0.044 mL, 0.250 mmol) and acryloyl chloride (4 μl, 0.050 mmol) at 0° C. After stirring at 0° C. for 15 min, the solvent was removed in vacuo. The reaction mixture was diluted with CH$_3$CN and water and purified by prep-LCMS (XBridge C18 column, eluting with a gradient of acetonitrile/water containing 0.10% TFA, at flow rate of 60 mL/min). LCMS calculated for $C_{21}H_{23}F_3N_7O_2$ (M+H)$^+$: m/z=462.2; found 462.2.

Example 89. N-(2-((3R,5R)-3-((5-Cyanopyrimidin-2-yl)amino)-5-fluoropiperidin-1-yl)-1-methyl-1H-benzo[d]imidazol-5-yl)acrylamide This compound was prepared according to the procedures described in Example 88, with tert-butyl ((3R,5R)-5-fluoropiperidin-3-yl)carbamate replacing tert-butyl ((3R,5R)-5-hydroxypiperidin-3-yl)carbamate in Step 1, and 2-chloropyrimidine-5-carbonitrile replacing 2-chloro-5-(trifluoromethyl)pyrimidine in Step 2. LCMS calculated for $C_{21}H_{22}FN_8O$ (M+H)$^+$: m/z=421.2; found: 421.2.

Example 90. N-(2-((3S,4R)-4-Fluoro-3-((5-(trifluoromethyl)pyrimidin-2-yl)amino)piperidin-1-yl)-1-methyl-1H-benzo[d]imidazol-5-yl)acrylamide This compound was prepared according to the procedures described in Example 88, with tert-butyl ((3S,4R)-4-fluoropiperidin-3-yl)carbamate (PharmaBlock) replacing tert-butyl ((3R,5R)-5-hydroxypiperidin-3-yl)carbamate in Step 1. LCMS calculated for $C_{21}H_{22}F_4N_7O$ (M+H)$^+$: m/z=464.2; found: 464.2. $^1$H NMR (600 MHz, DMSO) δ 10.36 (s, 1H), 8.73 (s, 2H), 8.44 (d, J=7.9 Hz, 1H), 8.11 (s, 1H), 7.57 (d, J=8.7 Hz, 1H), 7.47 (dd, J=8.8, 1.9 Hz, 1H), 6.45 (dd, J=17.0, 10.2 Hz, 1H), 6.29 (dd, J=16.9, 1.9 Hz, 1H), 5.79 (dd, J=10.1, 1.9 Hz, 1H), 5.23-5.01 (m, 1H), 4.63-4.48 (m, 1H), 3.71-3.63 (m, 1H), 3.62-3.48 (m, 2H), 2.30-2.10 (m, 2H).

Example 91. N-(2-((3S,4S)-4-Fluoro-3-((5-(trifluoromethyl)pyrimidin-2-yl)amino)piperidin-1-yl)-1-methyl-1H-benzo[d]imidazol-5-yl)acrylamide This compound was prepared according to the procedures described in Example 88, with tert-butyl ((3S,4S)-4-fluoropiperidin-3-yl)carbamate (PharmaBlock) replacing tert-butyl ((3R,5R)-5-hydroxypiperidin-3-yl)carbamate in Step 1. LCMS calculated for $C_{21}H_{22}F_4N_7O$ (M+H)$^+$: m/z=464.2; found: 464.2. $^1$H NMR (600 MHz, DMSO) δ 10.36 (s, 1H), 8.72 (s, 2H), 8.54 (d, J=7.8 Hz, 1H), 8.12 (s, 1H), 7.58 (d, J=8.8 Hz, 1H), 7.48 (dd, J=8.7, 2.0 Hz, 1H), 6.45 (dd, J=16.9, 10.2 Hz, 1H), 6.29 (dd, J=17.0, 1.9 Hz, 1H), 5.79 (dd, J=10.1, 1.9 Hz, 1H), 5.01-4.80 (m, 1H), 4.49-4.36 (m, 1H), 3.95 (d, J=12.8 Hz, 1H), 3.46 (s, 1H), 3.32 (t, J=10.9 Hz, 1H), 2.43-2.31 (m, 1H), 2.17-2.00 (m, 1H).

Example 92. (S)—N-(2-(4,4-Difluoro-3-((5-(trifluoromethyl)pyrimidin-2-yl)amino)piperidin-1-yl)-1-methyl-1H-benzo[d]imidazol-5-yl)acrylamide This compound was prepared according to the procedures described in Example 88, with tert-butyl (S)-(4,4-difluoropiperidin-3-yl)carbamate (PharmaBlock) replacing tert-butyl ((3R,5R)-5-hydroxypiperidin-3-yl)carbamate in Step 1. LCMS calculated for $C_{21}H_{21}F_5N_7O$ (M+H)$^+$: m/z=482.2; found: 482.2.

|

Example 93. N-(2-((3R,5R)-3-Fluoro-5-((5-(trifluo-romethyl)pyrimidin-2-yl)amino)piperidin-1-yl)-1-methyl-1H-benzo[d]imidazol-5-yl)acrylamide This compound was prepared according to the procedures described in Example 88, with tert-butyl ((3R,5R)-5-fluoropiperidin-3-yl)carbamate replacing tert-butyl ((3R,5R)-5-hydroxypiperidin-3-yl)carbamate in Step 1. LCMS calculated for $C_{21}H_{22}F_4N_7O$ (M+H)$^+$: m/z=464.2; found: 464.2. $^1$H NMR (600 MHz, DMSO) δ 10.40 (s, 1H), 8.72 (d, J=9.4 Hz, 2H), 8.36 (d, J=7.8 Hz, 1H), 8.13 (d, J=1.9 Hz, 1H), 7.59 (d, J=8.8 Hz, 1H), 7.50 (dd, J=8.8, 1.9 Hz, 1H), 6.46 (dd, J=16.9, 10.2 Hz, 1H), 6.29 (dd, J=17.0, 1.9 Hz, 1H), 5.79 (dd, J=10.1, 1.9 Hz, 1H), 5.48-5.12 (m, 1H), 4.48-4.40 (m, 1H), 4.11-3.94 (m, 2H), 3.69-3.51 (m, 1H), 3.20 (t, J=11.4 Hz, 1H), 2.43-2.31 (m, 1H), 2.13-1.91 (m, 1H).

Example 94. N-(2-((3R,5R)-3-Hydroxy-5-((5-(trif-luoromethyl)pyrimidin-2-yl)amino)piperi-dine-1-yl)-1,6-dimethyl-1H-benzo[d]imidazol-5-yl)acrylamide Step 1. tert-Butyl (3R,5R)-3-(((benzyloxy)carbonyl)amino)-5-hydroxypiperidine-1-carboxylate To a reaction vial containing tert-butyl (3R,5R)-3-amino-5-hydroxypiperidine-1-carboxylate (PharmaBlock; 500 mg, 2.31 mmol) in DCM (10 mL) was added N-(benzyloxycar-bonyloxy)-succinimide (691 mg, 2.77 mmol) and triethyl-amine (946 µL, 6.94 mmol). The reaction mixture was stirred at r.t. for 12 h, then quenched with aqueous saturated sodium bicarbonate solution and allowed to stir. The mixture was extracted with EtOAc and the organic layer was sub-sequently washed with water and brine, dried over sodium sulfate, filtered, and the solvents were evaporated in vacuo. The crude material was purified by Biotage Isolera to give the product as a white solid. LCMS calculated for $C_{11}H_{27}N_2O_5$ (M+H)$^+$: m/z=351.2; found 351.2.

Step 2. Benzyl ((3R,5R)-5-hydroxypiperidin-3-yl)carbamate

To a reaction vial containing tert-butyl (3R,5R)-3-(((ben-zyloxy)carbonyl)amino)-5-hydroxypiperidine-1-carboxy-late (790 mg, 2.25 mmol) was added 4N HCl in dioxane (5 mL). The reaction mixture was stirred at r.t. for 1 h and the solvents were evaporated in vacuo. The crude was used in the next step without further purification. LCMS calculated for $C_{13}H_{19}N_2O_3$ (M+H)$^+$: m/z=251.2; found 251.2.

Step 3. Benzyl ((3R,5R)-1-(1,6-dimethyl-5-nitro-1H-benzo[d]imidazol-2-yl)-5-hydroxypiperidin-3-yl)carbamate This compound was prepared according to the procedures described in Example 100, with benzyl ((3R,5R)-5-hy-droxypiperidin-3-yl)carbamate replacing tert-butyl ((3R, 5R)-5-fluoropiperidin-3-yl)carbamate in Step 4. LCMS cal-culated for $C_{22}H_{26}N_5O_5$ (M+H)$^+$: m/z=440.2; found 440.2.

Step 4. (3R,5R)-5-Amino-1-(1,6-dimethyl-5-nitro-1H-benzo[d]imidazol-2-yl)piperidin-3-ol To a solution of benzyl ((3R,5R)-1-(1,6-dimethyl-5-nitro-1H-benzo[d]imidazol-2-yl)-5-hydroxypiperidin-3-yl)carbamate (373 mg, 0.85 mmol) in AcOH (2 mL) was added 48% aqueous HBr (4 mL). The reaction mixture was allowed to stir at 50° C. for 12 h and then cooled to r.t. The solvents were evaporated in vacuo. The crude was used in the next step without further purification. LCMS calculated for $C_{14}H_{20}N_5O_3$ $(M+H)^+$: m/z=306.2; found 306.2.

Step 5. N-(2-((3R,5R)-3-Hydroxy-5-((5-(trifluoromethyl)pyrimidin-2-yl)amino)piperi-dine-1-yl)-1,6-dimethyl-1H-benzo[d]imidazol-5-yl)acrylamide This compound was prepared according to the procedures described in Example 100 (Step 6-Step 8), with (3R,5R)-5-amino-1-(1,6-dimethyl-5-nitro-1H-benzo[d]imidazol-2-yl)piperidin-3-ol replacing (3R,5R)-1-(1,6-dimethyl-5-nitro-1H-benzo[d]imidazol-2-yl)-5-fluoropiperidin-3-amine in Step 6. LCMS calculated for $C_{22}H_{25}F_3N_7O_2$ $(M+H)^+$: m/z=476.2; found: 476.2. $^1$H NMR (500 MHz, DMSO-d$_6$) δ 9.55 (s, 1H), 8.69 (d, J=9.9 Hz, 2H), 8.29 (d, J=7.7 Hz, 1H), 7.69 (s, 1H), 7.48 (s, 1H), 6.58 (dd, J=17.0, 10.2 Hz, 1H), 6.27 (dd, J=17.0, 2.0 Hz, 1H), 5.78 (dd, J=10.2, 2.0 Hz, 1H), 4.54-4.45 (m, 1H), 4.15 (dd, J=6.1, 3.4 Hz, 1H), 3.91 (d, J=12.1 Hz, 2H), 3.78 (s, 3H), 3.67-3.57 (m, 1H), 3.48 (d, J=13.1 Hz, 1H), 3.23 (dd, J=12.5, 9.2 Hz, 1H), 2.35 (s, 3H), 2.01 (dt, J=12.3, 4.7 Hz, 1H), 1.91 (ddd, J=13.3, 10.2, 3.2 Hz, 1H) ppm.

Example 95. N-(6-Cyclopropyl-2-((3R,5R)-3-fluoro-5-((5-(trifluoromethyl)pyrimidin-2-yl)amino)piperidin-1-yl)-1-methyl-1H-benzo[d]imidazol-5-yl)acrylamide

Step 1. 6-Bromo-2-chloro-1-methyl-5-nitro-1H-benzo[d]imidazole

This compound was prepared according to the procedures described in Example 100, Steps 1-3, with 4-bromo-2-fluoro-5-nitroaniline replacing 2-fluoro-4-methyl-5-nitroaniline in Step 1. LCMS calculated for $C_8H_6BrClN_3O_2$ $(M+H)^+$: m/z=289.9; found: 289.9.

Step 2. 2-Chloro-6-cyclopropyl-1-methyl-5-nitro-1H-benzo[d]imidazole

A reaction vial containing 6-bromo-2-chloro-1-methyl-5-nitro-1H-benzo[d]imidazole (85 mg, 0.29 mmol), cyclopropylboronic acid (50 mg, 0.59 mmol), cesium carbonate (286 mg, 0.88 mmol), [1,1'-bis(diphenylphosphino)ferrocene]dichloropalladium(II) (21.4 mg, 0.029 mmol) was evacuated and backfilled with nitrogen. 1,4-Dioxane (2 mL) and water (0.4 mL) were added to the reaction mixture, which was then stirred at 100° C. for 18 h. The reaction mixture was cooled to r.t and was diluted with EtOAc. The organic layer was subsequently washed with water and brine, dried over sodium sulfate, filtered, and the solvents were evaporated in vacuo. The crude material was purified by Biotage Isolera. LCMS calculated for $C_{11}H_{11}ClN_3O_2$ $(M+H)^+$: m/z=252.1; found 252.1.

Step 3. N-(6-Cyclopropyl-2-((3R,5R)-3-fluoro-5-((5-(trifluoromethyl)pyrimidin-2-yl)amino)piperidin-1-yl)-1-methyl-1H-benzo[d]imidazol-5-yl)acrylamide This compound was prepared according to the procedures described in Example 100, Steps 4-8, with 2-chloro-6-cyclopropyl-1-methyl-5-nitro-1H-benzo[d]imidazole replacing 2-chloro-1,6-dimethyl-5-nitro-1H-benzo[d]imidazole in Step 4. LCMS calculated for $C_{24}H_{26}F_4N_7O$ $(M+H)^+$: m/z=504.2; found: 504.2. $^1$H NMR (600 MHz, DMSO-d$_6$) δ 9.62 (s, 1H), 8.71 (d, J=6.0 Hz, 2H), 8.35 (d, J=7.7 Hz, 1H), 7.72 (s, 1H), 7.21 (s, 1H), 6.62 (dd, J=17.0, 10.2 Hz, 1H), 6.27 (dd, J=17.0, 2.0 Hz, 1H), 5.78 (dd, J=10.1, 2.0 Hz, 1H), 5.20 (d, J=46.2 Hz, 1H), 4.45 (m, 1H), 4.03-3.89 (m, 2H), 3.75 (s, 3H), 3.50 (dd, J=36.5, 14.0 Hz, 1H), 3.13 (s, 1H), 2.40-2.31 (m, 1H), 2.09 (td, J=8.4, 4.1 Hz, 1H), 2.06-1.88 (m, 1H), 0.98 (dt, J=8.4, 3.0 Hz, 2H), 0.69 (td, J=5.1, 2.6 Hz, 2H) ppm.

Example 96. N-(2-((3R,5R)-3-((5-cyanopyrimidin-2-yl)amino)-5-fluoropiperidin-1-yl)-1,6-dimethyl-1H-benzo[d]imidazol-5-yl)acrylamide This compound was prepared according to the procedures described in Example 100, Steps 6-8, with 2-chloropyrimidine-5-carbonitrile replacing 2-chloro-5-(trifluoromethyl)-pyrimidine in Step 6. LCMS calculated for $C_{22}H_{24}FN_8O$ (M+H)$^+$: m/z=435.2; found: 435.2. $^1$H NMR (600 MHz, DMSO-d$_6$) δ 9.58 (s, 1H), 8.85-8.68 (m, 2H), 8.58 (d, J=7.8 Hz, 1H), 7.71 (s, 1H), 7.51 (s, 1H), 6.58 (dd, J=17.0, 10.2 Hz, 1H), 6.27 (dd, J=17.0, 2.0 Hz, 1H), 5.78 (dd, J=10.2, 1.9 Hz, 1H), 5.29-5.10 (m, 1H), 4.46 (m, 1H), 4.04-3.90 (m, 2H), 3.75 (s, 3H), 3.55 (dd, J=36.4, 14.2 Hz, 1H), 3.20 (t, J=11.4 Hz, 1H), 2.35 (s, 3H), 2.00 (m, 1H) ppm.

Example 97. (S)—N-(2-(4,4-Difluoro-3-((5-(trifluoromethyl)pyrimidin-2-yl)amino)piperidin-1-yl)-1,6-dimethyl-1H-benzo[d]imidazol-5-yl)acrylamide This compound was prepared according to the procedures described in Example 100, Steps 4-8, with tert-butyl (S)-(4,4-difluoropiperidin-3-yl)carbamate replacing tert-butyl ((3R,5R)-5-fluoropiperidin-3-yl)carbamate in Step 4. LCMS calculated for $C_{22}H_{23}F_5N_7O$ (M+H)$^+$: m/z=496.2; found: 496.2. H NMR (500 MHz, DMSO-d$_6$) δ 9.56 (s, 1H), 8.74 (s, 2H), 8.61 (d, J=9.2 Hz, 1H), 7.70 (s, 1H), 7.50 (s, 1H), 6.58 (dd, J=17.0, 10.3 Hz, 1H), 6.27 (dd, J=17.0, 2.0 Hz, 1H), 5.77 (dd, J=10.1, 2.0 Hz, 1H), 4.94 (m, 1H), 3.84 (d, J=13.3 Hz, 1H), 3.76 (s, 4H), 3.56 (dd, J=13.3, 8.9 Hz, 2H), 2.51-2.39 (m, 1H), 2.35 (s, 3H) ppm.

Example 98. N-(2-((3S,4R)-4-Fluoro-3-((5-(trifluoromethyl)pyrimidin-2-yl)amino)piperidin-1-yl)-1,6-dimethyl-1H-benzo[d]imidazol-5-yl)acrylamide This compound was prepared according to the procedures described in Example 100, Steps 4-8, with tert-butyl ((3S,4R)-4-fluoropiperidin-3-yl)carbamate replacing tert-butyl ((3R,5R)-5-fluoropiperidin-3-yl)carbamate in Step 4. LCMS calculated for $C_{22}H_{24}F_4N_7O$ (M+H)$^+$: m/z=478.2; found: 478.2. $^1$H NMR (600 MHz, DMSO-d$_6$) δ 9.57 (s, 1H), 8.72 (s, 2H), 8.44 (d, J=8.0 Hz, 1H), 7.71 (s, 1H), 7.51 (s, 1H), 6.58 (dd, J=17.0, 10.2 Hz, 1H), 6.27 (dd, J=17.0, 1.9 Hz, 1H), 5.78 (dd, J=10.2, 2.0 Hz, 1H), 5.19-5.00 (m, 1H), 4.61-4.46 (m, 1H), 3.75 (s, 4H), 3.67 (d, J=13.3 Hz, 1H), 3.59-3.46 (m, 2H), 2.35 (s, 3H), 2.26-2.10 (m, 2H) ppm.

Example 99. N-(2-((3S,4S)-4-Fluoro-3-((5-(trifluoromethyl)pyrimidin-2-yl)amino)piperidin-1-yl)-1,6-dimethyl-1H-benzo[d]imidazol-5-yl)acrylamide This compound was prepared according to the procedures described in Example 100, Steps 4-8, with tert-butyl ((3S,4S)-4-fluoropiperidin-3-yl)carbamate replacing tert-butyl ((3R,5R)-5-fluoropiperidin-3-yl)carbamate in Step 4. LCMS calculated for $C_{22}H_{24}F_4N_7O$ (M+H)$^+$: m/z=478.2; found: 478.2. $^1$H NMR (600 MHz, DMSO-d$_6$) δ 9.58 (s, 1H), 8.72 (s, 2H), 8.54 (d, J=7.9 Hz, 1H), 7.71 (s, 1H), 7.51 (s, 1H), 6.58 (dd, J=17.0, 10.3 Hz, 1H), 6.27 (dd, J=17.0, 2.0 Hz, 1H), 5.78 (dd, J=10.3, 2.1 Hz, 1H), 4.90 (m, 1H), 4.42 (m, 1H), 3.93 (d, J=12.9 Hz, 1H), 3.76 (s, 4H), 3.44 (t, J=11.4 Hz, 1H), 3.31 (dd, J=13.1, 8.7 Hz, 1H), 2.35 (s, 4H), 2.07 (m, 1H) ppm.

Example 100. N-(2-((3R,5R)-3-fluoro-5-((5-(trifluo-romethyl)pyrimidin-2-yl)amino)piperidin-1-yl)-1,6-dimethyl-1H-benzo[d]imidazol-5-yl)acrylamide Step 1. N$^1$,5-Dimethyl-4-nitrobenzene-1,2-diamine To a mixture of 2-fluoro-4-methyl-5-nitroaniline (1.3 g, 7.64 mmol) and methylamine hydrochloride (1.56 g, 22.92 mmol) in DMSO (10 mL) was added N,N-diisopropyleth-ylamine (7.97 mL, 45.8 mmol). The reaction mixture was heated to 110° C. for 48 h and then cooled to r.t. The reaction mixture was diluted with water (100 mL) and filtered. The resulting filter cake was washed with a mixture of 4:1 Hexane/EtOAc (50 mL). The crude was used in the next step without further purification. LCMS calculated for C$_8$H$_{12}$N$_3$O$_2$ (M+H)$^+$: m/z=182.1; found 182.1.

Step 2. 1,6-Dimethyl-5-nitro-1,3-dihydro-2H-benzo[d]imidazol-2-one

To a cooled solution of N$^1$,5-dimethyl-4-nitrobenzene-1,2-diamine (3.88 g, 22.41 mmol) in MeCN (50 mL) was added bis(2,5-dioxopyrrolidin-1-yl) carbonate (7.13 g, 27.8 mmol) portionwise. The reaction mixture was heated to 50° C. for 2 h and then cooled to r.t. The reaction mixture was diluted with water (200 mL) and filtered. The resulting filter cake was washed with cold acetone (10 mL) and diethyl ether (10 mL). The crude was used in the next step without further purification. LCMS calculated for C$_9$H$_{10}$N$_3$O$_3$ (M+H)$^+$: m/z=208.1; found 208.1.

Step 3. 2-Chloro-1,6-dimethyl-5-nitro-1H-benzo[d]imidazole

To a reaction vial containing 1,6-dimethyl-5-nitro-1,3-dihydro-2H-benzo[d]imidazol-2-one (3.78 g, 18.24 mmol) was added phosphoryl chloride (30 mL). The reaction mix-ture was heated to 110° C. for 4 h and then cooled to r.t. The reaction was carefully quenched with 4N aqueous sodium hydroxide solution and allowed to stir. The mixture was filtered and the filter cake was subsequently washed with a mixture of 4:1 Hexane/DCM (50 mL). The crude was used in the next step without further purification. LCMS calcu-lated for C$_9$H$_9$ClN$_3$O$_2$ (M+H)$^+$: m/z=226.0; found 226.0.

Step 4. tert-Butyl ((3R,5R)-1-(1,6-dimethyl-5-nitro-1H-benzo[d]imidazol-2-yl)-5-fluoropiperidin-3-yl)carbamate To a mixture of tert-butyl ((3R,5R)-5-fluoropiperidin-3-yl)carbamate (3.38 g, 15.5 mmol) and 2-chloro-1,6-dim-ethyl-5-nitro-1H-benzo[d]imidazole (3.18 g, 14.09 mmol) in DMSO (20 mL) was added N,N-diisopropylethylamine (6.15 mL, 35.2 mmol). The reaction mixture was heated to 100° C. for 12 h and then cooled to r.t. The reaction mixture was diluted with EtOAc and the organic phase was washed with 10% aqueous lithium chloride and brine, and was then dried over sodium sulfate and filtered. Solvents were evapo-rated in vacuo and the crude material was purified by Biotage Isolera to give the product. LCMS calculated for C$_{19}$H$_{27}$FN$_5$O$_4$ (M+H)$^+$: m/z=408.2; found 408.2.

Step 5. (3R,5R)-1-(1,6-Dimethyl-5-nitro-1H-benzo
[d]imidazol-2-yl)-5-fluoropiperidin-3-amine To a reaction vial containing tert-butyl ((3R,5R)-1-(1,6-dimethyl-5-nitro-1H-benzo[d]imidazol-2-yl)-5-fluoropiperidin-3-yl)carbamate (554 mg, 1.36 mmol) was added 4N HCl in dioxane (6 mL). The reaction mixture was stirred at r.t. for 1 h and the solvents were evaporated in vacuo. The crude was used in the next step without further purification. LCMS calculated for $C_{14}H_{19}FN_5O_2$ $(M+H)^+$: m/z=308.1; found 308.1.

Step 6. N-((3R,5R)-1-(1,6-Dimethyl-5-nitro-1H-benzo[d]imidazol-2-yl)-5-fluoropiperidin-3-yl)-5-(trifluoromethyl)pyrimidin-2-amine To a mixture of 2-chloro-5-(trifluoromethyl)pyrimidine (273 mg, 1.5 mmol) and (3R,5R)-1-(1,6-dimethyl-5-nitro-1H-benzo[d]imidazol-2-yl)-5-fluoropiperidin-3-amine (418 mg, 1.36 mmol) in EtOH (5 mL) was added N,N-diisopropylethylamine (713 μL, 0.74 mmol). The reaction mixture was heated to 60° C. for 1 h and then cooled to r.t. The reaction mixture was diluted with EtOAc and the organic phase was washed with brine. It was then dried over sodium sulfate and filtered. Solvents were evaporated in vacuo and the crude material was purified by Biotage Isolera to give the product. LCMS calculated for $C_{19}H_{20}F_4N_7O_2$ $(M+H)^+$: m/z=454.2; found 454.2.

Step 7. 2-((3R,5R)-3-Fluoro-5-((5-(trifluoromethyl)pyrimidin-2-yl)amino)piperidin-1-yl)-1,6-dimethyl-1H-benzo[d]imidazol-5-amine To a reaction vial containing N-((3R,5R)-1-(1,6-dimethyl-5-nitro-1H-benzo[d]imidazol-2-yl)-5-fluoropiperidin-3-yl)-5-(trifluoromethyl)pyrimidin-2-amine (617 mg, 1.36 mmol), ammonium chloride (728 mg, 13.6 mmol) and zinc powder (890 mg, 13.61 mmol) was added THF (8 mL) and water (4 mL). The reaction mixture was heated to 40° C. for 1 h and then cooled to r.t. The reaction mixture was diluted with EtOAc and filtered through celite pad. The organic layer was subsequently washed with water and brine, dried over sodium sulfate, filtered, and the solvents were evaporated in vacuo. The crude material was purified by Biotage Isolera to give the product. LCMS calculated for $C_{19}H_{22}F_4N_7$ $(M+H)^+$: m/z=424.2; found 424.2.

Step 8. N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)acrylamide To a solution of 2-((3R,5R)-3-fluoro-5-((5-(trifluoromethyl)pyrimidin-2-yl)amino)piperidin-1-yl)-1,6-dimethyl-1H-benzo[d]imidazol-5-amine (5.5 mg, 0.013 mmol) in DCM (0.8 mL) at −20° C. was added N,N-diisopropylethylamine (5 μL, 0.026 mmol) and acryloyl chloride (1.2 μL, 0.014 mmol). The reaction mixture was allowed to stir at −20° C. for 10 min, then quenched with water. The reaction mixture was diluted with DCM and the organic layer was subsequently washed with water and brine, dried over sodium sulfate, filtered, and the solvents were evaporated in vacuo. The crude material was purified by Biotage Isolera. The resulting product was diluted with MeCN and purified by prep-LCMS (XBridge C18 column, eluting with a gradient of acetonitrile/water containing 0.1% TFA, at flow rate of 60 mL/min. LCMS calculated for $C_{22}H_{24}F_4N_7O$ $(M+H)^+$: m/z=478.2; found: 478.2. $^1$H NMR (600 MHz, DMSO-d$_6$) δ 9.61 (s, 1H), 8.71 (d, J=9.0 Hz, 2H), 8.36 (d, J=7.7 Hz, 1H), 7.72 (s, 1H), 7.52 (s, 1H), 6.58 (dd, J=17.1, 10.2 Hz, 1H), 6.27 (dd, J=17.0, 1.9 Hz, 1H), 5.78 (dd, J=10.2, 2.1 Hz, 1H), 5.28-5.12 (m, 1H), 4.45 (m, 1H), 4.02 (m, 2H), 3.77 (s, 3H), 3.57 (dd, J=36.5, 14.2 Hz, 1H), 3.19 (t, J=11.4 Hz, 1H), 2.35 (s, 3H), 2.01 (m, 1H) ppm.

Example 101. N-(2-((3R,5R)-3-Fluoro-5-((5-(trif-luoromethyl)pyrimidin-2-yl)amino)piperidin-1-yl)-6-isopropyl-1-methyl-1H-benzo[d]imidazol-5-yl)acryl-amide

Step 1. tert-Butyl ((3R,5R)-1-(6-bromo-1-methyl-5-nitro-1H-benzo[d]imidazol-2-yl)-5-fluoropiperidin-3-yl)carbamate This compound was prepared according to the procedures described in Example 100, with 6-bromo-2-chloro-1-methyl-5-nitro-1H-benzo[d]imidazole replacing 2-chloro-1, 6-dimethyl-5-nitro-1H-benzo[d]imidazole in Step 4. LCMS calculated for $C_{18}H_{24}BrFN_5O_4$ (M+H)$^+$: m/z=472.1; found: 472.1.

Step 2. tert-Butyl ((3R,5R)-5-fluoro-1-(1-methyl-5-nitro-6-(prop-1-en-2-yl)-1H-benzo[d]imidazol-2-yl)piperidin-3-yl)carbamate A reaction vial containing tert-butyl ((3R,5R)-1-(6-bromo-1-methyl-5-nitro-1H-benzo[d]imidazol-2-yl)-5-fluoropiperidin-3-yl)carbamate (52 mg, 0.11 mmol), 4,4,5,5-tetramethyl-2-(isopropenyl)-1,3,2-dioxaborolane (37 mg, 0.22 mmol), cesium carbonate (108 mg, 0.33 mmol), [1,1'-bis(diphenylphosphino)ferrocene]dichloropalladium(II) (8 mg, 0.011 mol) was evacuated and backfilled with nitrogen. 1,4-Dioxane (1 mL) and water (0.2 mL) were added to the reaction mixture, which was then stirred at 100° C. for 2 h. The reaction mixture was cooled to r.t and was diluted with EtOAc. The organic layer was subsequently washed with water and brine, dried over sodium sulfate, filtered, and the solvents were evaporated in vacuo. The crude material was purified by Biotage Isolera. LCMS calculated for $C_{21}H_{29}FN_5O_4$ (M+H)$^+$: m/z=434.2; found 434.2.

Step 3. tert-Butyl ((3R,5R)-1-(5-amino-6-isopropyl-1-methyl-1H-benzo[d]imidazol-2-yl)-5-fluoropiperi-din-3-yl)carbamate To a solution of tert-butyl ((3R,5R)-5-fluoro-1-(1-methyl-5-nitro-6-(prop-1-en-2-yl)-1H-benzo[d]imidazol-2-yl)pip-eridin-3-yl)carbamate (33 mg, 0.076 mmol) in MeOH (1 mL) and EtOAc (1 mL) was added 10% palladium on carbon (16 mg, 0.015 mmol). The reaction mixture was stirred under an atmosphere of hydrogen for 1 h. The reaction mixture was diluted with Et$_2$O and filtered through a plug of celite and the solvent was evaporated in vacuo. The crude material was used in the next step without further purifica-tion. LCMS calculated for $C_{21}H_{33}FN_5O_2$ (M+H)$^+$: m/z=406.3; found 406.3.

Step 4. 2-((3R,5R)-3-Fluoro-5-((5-(trifluoromethyl) pyrimidin-2-yl)amino)piperidin-1-yl)-6-isopropyl-1-methyl-1H-benzo[d]imidazol-5-amine This compound was prepared according to the procedures described in Example 100, Steps 5-6, with tert-butyl ((3R, 5R)-1-(5-amino-6-isopropyl-1-methyl-1H-benzo[d]imida-zol-2-yl)-5-fluoropiperidin-3-yl)carbamate replacing tert-butyl ((3R,5R)-1-(1,6-dimethyl-5-nitro-1H-benzo[d]

imidazol-2-yl)-5-fluoropiperidin-3-yl)carbamate in Step 5. LCMS calculated for $C_{21}H_{26}F_4N_7$ (M+H)$^+$: m/z=452.2; found: 452.2.

Step 5. N-(2-((3R,5R)-3-Fluoro-5-((5-(trifluoromethyl)pyrimidin-2-yl)amino)piperidin-1-yl)-6-isopropyl-1-methyl-1H-benzo[d]imidazol-5-yl)acrylamide This compound was prepared according to the procedures described in Example 100, with 2-((3R,5R)-3-fluoro-5-((5-(trifluoromethyl)pyrimidin-2-yl)amino)piperidin-1-yl)-6-isopropyl-1-methyl-1H-benzo[d]imidazol-5-amine replacing 2-((3R,5R)-3-fluoro-5-((5-(trifluoromethyl)-pyrimidin-2-yl)amino)piperidin-1-yl)-1,6-dimethyl-1H-benzo[d]imidazol-5-amine in Step 8. LCMS calculated for $C_{24}H_{28}F_4N_7O$ (M+H)$^+$: m/z=506.2; found: 506.2.

Example 102. (R)—N-(1,6-Dimethyl-2-(3-((5-(trifluoromethyl)pyrimidin-2-yl)amino)piperidin-1-yl)-1H-benzo[d]imidazol-5-yl)acrylamide This compound was prepared according to the procedures described in Example 100, Step 4-8, with tert-butyl (R)-piperidin-3-ylcarbamate replacing tert-butyl ((3R,5R)-5-fluoropiperidin-3-yl)carbamate in Step 4. LCMS calculated for $C_{22}H_{25}F_3N_7O$ (M+H)$^+$: m/z=460.2; found: 460.2.

Example 103. (R)—N-(6-Bromo-1,4-dimethyl-2-(3-((5-(trifluoromethyl)pyrimidin-2-yl)amino)piperidin-1-yl)-1H-benzo[d]imidazol-5-yl)acrylamide

Step 1. 1,4-Dimethyl-5-nitro-1H-benzo[d]imidazole

To a cooled solution of 1-methyl-5-nitro-1H-benzo[d]imidazole (460 mg, 2.60 mmol) in THF (10 mL) was added methylmagnesium bromide (1.3 mL, 3.89 mmol, 3M solution in THF) portionwise. The reaction mixture was stirred at 0° C. for 30 min before 2,3-dichloro-5,6-dicyano-1,4-benzoquinone (707 mg, 3.12 mmol) was added. The reaction mixture was allowed to stir at 0° C. for another 30 min before it was diluted with EtOAc and filtered. The organic phase was washed with 10% aqueous lithium chloride and brine, and was then dried over sodium sulfate and filtered. Solvents were evaporated in vacuo and the crude material was purified by Biotage Isolera to give the product. LCMS calculated for $C_9H_{10}N_3O_2$ (M+H)$^+$: m/z=192.1; found 192.1.

Step 2. 2-Chloro-1,4-dimethyl-5-nitro-1H-benzo[d]imidazole

To a solution of 1,4-dimethyl-5-nitro-1H-benzo[d]imidazole (152 mg, 0.795 mmol) in THF (3 mL) at −78° C. was added lithium diisopropylamide (0.6 mL, 1.19 mmol, 2M solution in THF) dropwise. The reaction mixture was stirred at −78° C. for 30 min before N-chlorosuccinimide (212 mg, 1.59 mmol) was added. The reaction mixture was allowed to stir at −78° C. for another 30 min before it was warmed to r.t. The reaction mixture was quenched with water and diluted with DCM. The organic phase was washed with brine, and was then dried over sodium sulfate and filtered. Solvents were evaporated in vacuo and the crude material was purified by Biotage Isolera to give the product. LCMS calculated for $C_9H_9ClN_3O_2$ (M+H)$^+$: m/z=226.0; found 226.0.

Step 3. (R)-1,4-Dimethyl-2-(3-((5-(trifluoromethyl)
pyrimidin-2-yl)amino)piperidin-1-yl)-1H-benzo[d]
imidazol-5-amine This compound was prepared according to the procedures described in Example 100, Steps 4-7, with tert-butyl (R)-piperidin-3-ylcarbamate replacing tert-butyl ((3R,5R)-5-fluoropiperidin-3-yl)carbamate and 2-chloro-1,4-dimethyl-5-nitro-1H-benzo[d]imidazole replacing 2-chloro-1,6-dimethyl-5-nitro-1H-benzo[d]imidazole in Step 4. LCMS calculated for $C_{19}H_{23}F_3N_7$ (M+H)$^+$: m/z=406.2; found: 406.2.

Step 4. (R)-6-Bromo-1,4-dimethyl-2-(3-((5-(trifluoromethyl)pyrimidin-2-yl)amino)piperidin-1-yl)-1H-benzo[d]imidazol-5-amine To a solution of (R)-1,4-dimethyl-2-(3-((5-(trifluoromethyl)pyrimidin-2-yl)amino)piperidin-1-yl)-1H-benzo[d]imidazol-5-amine (80 mg, 0.197 mmol) in AcOH (1 mL) was added bromine (10 μL, 0.197 mmol). The reaction mixture was stirred at r.t. for 10 min, then solvents were evaporated in vacuo and the crude material was purified by Biotage Isolera to give the product. LCMS calculated for $C_{19}H_{22}BrF_3N_7$ (M+H)$^+$: m/z=484.1; found 484.1.

Step 5. (R)—N-(6-Bromo-1,4-dimethyl-2-(3-((5-(trifluoromethyl)pyrimidin-2-yl)amino)piperidin-1-yl)-1H-benzo[d]imidazol-5-yl)acrylamide This compound was prepared according to the procedures described in Example 100, with (R)-6-bromo-1,4-dimethyl-2-(3-((5-(trifluoromethyl)pyrimidin-2-yl)amino)piperidin-1-yl)-1H-benzo[d]imidazol-5-amine replacing 2-((3R,5R)-3-fluoro-5-((5-(trifluoromethyl)-pyrimidin-2-yl)amino)piperidin-1-yl)-1,6-dimethyl-1H-benzo[d]imidazol-5-amine in Step 8. LCMS calculated for $C_{22}H_{24}BrF_3N_7O$ (M+H)$^+$: m/z=538.1; found: 538.1.

Example 104. 1-((2S,6R)-4-(3-((3R,5R)-3-Fluoro-5-((5-(trifluoromethyl)pyrimidin-2-yl)amino)piperidin-1-yl)imidazo[1,5-a]pyrazin-8-yl)-2,6-dimethylpiperazin-1-yl)prop-2-en-1-one Step 1. N-((3R,5R)-1-(8-((3S,5R)-3,5-Dimethylpiperazin-1-yl)imidazo[1,5-a]pyrazin-3-yl)-5-fluoropiperidin-3-yl)-5-(trifluoromethyl)pyrimidin-2-amine This compound was prepared according to the procedures described in Example 86, with tert-butyl (2S,6R)-2,6-dimethylpiperazine-1-carboxylate (AstaTech, Inc.) replacing tert-butyl (R)-pyrrolidin-3-ylcarbamate in Step 1. LCMS calculated for $C_{22}H_{28}F_4N_9$ (M+H)$^+$: m/z=494.2; found: 494.1.

Step 2. 1-((2S,6R)-4-(3-((3R,5R)-3-Fluoro-5-((5-(trifluoromethyl)pyrimidin-2-yl)amino)piperidin-1-yl)imidazo[1,5-a]pyrazin-8-yl)-2,6-dimethylpiperazin-1-yl)prop-2-en-1-one This compound was prepared according to the procedures described in Example 68, with N-((3R,5R)-1-(8-((3S,5R)-3,5-dimethylpiperazin-1-yl)imidazo[1,5-a]pyrazin-3-yl)-5-fluoropiperidin-3-yl)-5-(trifluoromethyl)pyrimidin-2-amine replacing 6-amino-2-(((1S,3R)-3-((5-bromopyrimidin-2-yl)amino)cyclohexyl)isoindolin-1-one in Step 3. LCMS calculated for $C_{25}H_{30}F_4N_9O$ (M+H)$^+$: m/z=548.2; found: 548.2.

Example 105. 1-(6-(3-((3R,5R)-3-Fluoro-5-((5-(trif-luoromethyl)pyrimidin-2-yl)amino)piperidin-1-yl) imidazo[1,5-a]pyrazin-8-yl)-1,6-diazaspiro[3.3]hep-tan-1-yl)prop-2-en-1-one Step 1. N-((3R,5R)-1-(8-(1,6-Diazaspiro[3.3]heptan-6-yl)imidazo[1,5-a]pyrazin-3-yl)-5-fluoropiperidin-3-yl)-5-(trifluoromethyl)pyrimidin-2-amine This compound was prepared according to the procedures described in Example 86, with tert-butyl 1,6-diazaspiro[3.3] heptane-1-carboxylate (AURUM Pharmatech) replacing tert-butyl (R)-pyrrolidin-3-ylcarbamate in Step 1. LCMS calculated for $C_{21}H_{24}F_4N_9$ (M+H)$^+$: m/z=478.2; found: 478.2.

Step 2. 1-(6-(3-((3R,5R)-3-Fluoro-5-((5-(trifluorom-ethyl)pyrimidin-2-yl)amino)piperidin-1-yl)imidazo [1,5-a]pyrazin-8-yl)-1,6-diazaspiro[3.3]heptan-1-yl) prop-2-en-1-one This compound was prepared according to the procedures described in Example 68, with N-((3R,5R)-1-(8-(1,6-diaz-aspiro[3.3]heptan-6-yl)imidazo[1,5-a]pyrazin-3-yl)-5-fluo-ropiperidin-3-yl)-5-(trifluoromethyl)pyrimidin-2-amine replacing 6-amino-2-((1S,3R)-3-((5-bromopyrimidin-2-yl) amino)cyclohexyl)isoindolin-1-one in Step 3. LCMS calcu-lated for $C_{24}H_{26}F_4N_9O$ (M+H)$^+$: m/z=532.2; found: 532.2. $^1$H NMR (500 MHz, DMSO) δ 8.81-8.66 (m, 2H), 8.27 (d, J=7.6 Hz, 1H), 7.90 (s, 1H), 7.30 (d, J=5.8 Hz, 1H), 7.03 (d, J=5.8 Hz, 1H), 6.32 (dd, J=17.0, 10.3 Hz, 1H), 6.17 (dd, J=17.0, 2.2 Hz, 1H), 5.76 (dd, J=10.3, 2.2 Hz, 1H), 5.30-5.05 (m, 2H), 5.03-4.78 (m, 2H), 4.61 (brs, 1H), 4.53-4.44 (m, 1H), 4.14 (t, J=7.3 Hz, 2H), 3.76 (d, J=11.8 Hz, 1H), 3.66 (t, J=12.6 Hz, 1H), 3.35-3.21 (m, 1H), 2.90 (t, J=11.1 Hz, 1H), 2.65-2.55 (m, 2H), 2.38-2.29 (m, 1H), 2.03-1.86 (m, 1H).

Example 106. 1-((1S,4S)-5-(3-((3R,5R)-3-Fluoro-5-((5-(trifluoromethyl)pyrimidin-2-yl)amino)piperidin-1-yl)imidazo[1,5-a]pyrazin-8-yl)-2,5-diazabicyclo [2.2.1]heptan-2-yl)but-2-yn-1-one Step 1. N-((3R,5R)-1-(8-((1S,4S)-2,5-Diazabicyclo [2.2.1]heptan-2-yl)imidazo[1,5-a]pyrazin-3-yl)-5-fluoropiperidin-3-yl)-5-(trifluoromethyl)pyrimidin-2-amine This compound was prepared according to the procedures described in Example 86, with tert-butyl (1S,4S)-2,5-diaz-abicyclo[2.2.1]heptane-2-carboxylate (Combi-blocks) replacing tert-butyl (R)-pyrrolidin-3-ylcarbamate in Step 1. LCMS calculated for $C_{21}H_{24}F_4N_9$ (M+H)$^+$: m/z=478.2; found: 478.2.

Step 2. 1-((1S,4S)-5-(3-((3R,5R)-3-Fluoro-5-((5-(trifluoromethyl)pyrimidin-2-yl)amino)piperidin-1-yl)imidazo[1,5-a]pyrazin-8-yl)-2,5-diazabicyclo [2.2.1]heptan-2-yl)but-2-yn-1-one To a vial containing N-((3R,5R)-1-(8-((1S,4S)-2,5-diaz-abicyclo[2.2.1]heptan-2-yl)imidazo[1,5-a]pyrazin-3-yl)-5-fluoropiperidin-3-yl)-5-(trifluoromethyl)pyrimidin-2-amine (30 mg, 0.063 mmol), but-2-ynoic acid (8 mg, 0.095 mmol) and DIPEA (44 μL, 0.25 mmol) in CH$_3$CN (1.0 mL) was added propane phosphonic acid anhydride solution (50% w/w, 120 μL, 0.19 mmol) at 0° C. After stirring at 0° C. for 30 min, the reaction mixture was quenched with water (0.5 mL), then diluted with CH$_3$CN and water and purified by prep-LCMS (XBridge C18 column, eluting with a gradient of acetonitrile/water containing 0.10% TFA, at flow rate of 60 mL/min). LCMS calculated for $C_{25}H_{26}F_4N_9O$ (M+H)$^+$: m/z=544.2; found: 544.3.

Example 107. 1-((1S,4S)-5-(3-((3R,5R)-3-Fluoro-5-((5-(trifluoromethyl)pyrimidin-2-yl)amino)piperidin-1-yl)imidazo[1,5-a]pyrazin-8-yl)-2,5-diazabicyclo[2.2.1]heptan-2-yl)prop-2-en-1-one Step 1. N-((3R,5R)-1-(8-((1S,4S)-2,5-Diazabicyclo[2.2.1]heptan-2-yl)imidazo[1,5-a]pyrazin-3-yl)-5-fluoropiperidin-3-yl)-5-(trifluoromethyl)pyrimidin-2-amine This compound was prepared according to the procedures described in Example 86, with tert-butyl (1S,4S)-2,5-diazabicyclo[2.2.1]heptane-2-carboxylate replacing tert-butyl (R)-pyrrolidin-3-ylcarbamate in Step 1. LCMS calculated for $C_{21}H_{24}F_4N_9$ (M+H)$^+$: m/z=478.2; found: 478.2.

Step 2. 1-((1S,4S)-5-(3-((3R,5R)-3-Fluoro-5-((5-(trifluoromethyl)pyrimidin-2-yl)amino)piperidin-1-yl)imidazo[1,5-a]pyrazin-8-yl)-2,5-diazabicyclo[2.2.1]heptan-2-yl)prop-2-en-1-one This compound was prepared according to the procedures described in Example 68, with N-((3R,5R)-1-(8-((1S,4S)-2,5-diazabicyclo[2.2.1]heptan-2-yl)imidazo[1,5-a]pyrazin-3-yl)-5-fluoropiperidin-3-yl)-5-(trifluoromethyl)pyrimidin-2-amine replacing 6-amino-2-((1S,3R)-3-((5-bromopyrimidin-2-yl)amino)cyclohexyl)isoindolin-1-one in Step 3. LCMS calculated for $C_{24}H_{26}F_4N_9O$ (M+H)$^+$: m/z=532.2; found: 532.2.

Example 108. 1-(2-(3-((R)-3-((5-(Trifluoromethyl)pyrimidin-2-yl)amino)piperidin-1-yl)imidazo[1,5-a]pyrazin-8-yl)piperidin-1-yl)prop-2-en-1-one Step 1. tert-Butyl (R)-6-(3-(3-((5-(trifluoromethyl)pyrimidin-2-yl)amino)piperidin-1-yl)imidazo[1,5-a]pyrazin-8-yl)-3,4-dihydropyridine-1(2H)-carboxylate A vial containing (R)—N-(1-(8-chloroimidazo[1,5-a]pyrazin-3-yl)piperidin-3-yl)-5-(trifluoromethyl)pyrimidin-2-amine (Intermediate F, 30 mg, 0.075 mmol), tert-butyl 6-(4,4,5,5-tetramethyl-1,3,2-dioxaborolan-2-yl)-3,4-dihydropyridine-1(2H)-carboxylate (35 mg, 0.113 mmol), [1,1'-bis(diphenylphosphino)ferrocene]dichloropalladium(II) $CH_2Cl_2$ adduct (6 mg, 7.5 μmol) and $K_2CO_3$ (21 mg, 0.15 mmol) was evacuated and backfilled with nitrogen three times, followed by the addition of acetonitrile (0.63 mL) and water (0.12 mL). The vial was sealed and heated to 85° C. for 2 h. After cooling to r.t., the mixture was filtered through a SiliaPrep SPE thiol cartridge and washed with 10% MeOH in $CH_2Cl_2$. The crude material was concentrated and redissolved in $CH_2Cl_2$ (0.5 mL). The organic phase was washed with brine, dried over $MgSO_4$, and concentrated in vacuo. The obtained crude product was purified by Biotage Isolera to give the desired product as yellow foam. LCMS calculated for $C_{26}H_{32}F_3N_8O_2$ (M+H)$^+$: m/z=545.3; found: 545.3.

Step 2. N-((3R)-1-(8-(Piperidin-2-yl)imidazo[1,5-a]pyrazin-3-yl)piperidin-3-yl)-5-(trifluoromethyl)pyrimidin-2-amine To a vial containing tert-butyl (R)-6-(3-(3-((5-(trifluoromethyl)pyrimidin-2-yl)amino)piperidin-1-yl)imidazo[1,5-a]pyrazin-8-yl)-3,4-dihydropyridine-1(2H)-carboxylate (32 mg, 0.059 mmol) and Pd/C (10 wt %, 8 mg) was added ethanol (2 mL). The vial was purged with $H_2$ gas for 5 min. It was then stirred at 45° C. for 1.5 h under an atmosphere of $H_2$. After cooling to room temperature, the reaction mixture was filtered and washed with 10% MeOH in $CH_2Cl_2$, followed by concentration of the filtrate in vacuo. The crude material was redissolved in $CH_2Cl_2$ (0.5 mL) and TFA (0.5 mL). After stirring at 40° C. for 1 h, the reaction mixture was concentrated in vacuo. The crude material was redissolved in $CH_2Cl_2$ (5 mL) and the pH of the mixture was adjusted to ~10 with ammonia aqueous solution and then extracted into $CH_2Cl_2$. The organic phase was washed with brine, dried over $MgSO_4$, and concentrated in vacuo. The obtained crude product was purified by Biotage Isolera to give the desired product as yellow foam. LCMS calculated for $C_{21}H_{26}F_3N_8$ $(M+H)^+$: m/z=447.2; found: 447.3.

Step 3. 1-(2-(3-((R)-3-((5-(Trifluoromethyl)pyrimidin-2-yl)amino)piperidin-1-yl)imidazo[1,5-a]pyrazin-8-yl)piperidin-1-yl)prop-2-en-1-one This compound was prepared according to the procedures described in Example 68, with N-((3R)-1-(8-(piperidin-2-yl)imidazo[1,5-a]pyrazin-3-yl)piperidin-3-yl)-5-(trifluoromethyl)pyrimidin-2-amine replacing 6-amino-2-((1S,3R)-3-((5-bromopyrimidin-2-yl)amino)cyclohexyl)isoindolin-1-one in Step 3. LCMS calculated for $C_{24}H_{28}F_3N_8O$ $(M+H)^+$: m/z=501.2; found: 501.2.

Example 109. 1-(3-(3-((R)-3-((5-(Trifluoromethyl)pyrimidin-2-yl)amino)piperidin-1-yl)imidazo[1,5-a]pyrazin-8-yl)-3,8-diazabicyclo[3.2.1]octan-8-yl)prop-2-en-1-one Step 1. N-((3R)-1-(8-(3,8-Diazabicyclo[3.2.1]octan-3-yl)imidazo[1,5-a]pyrazin-3-yl)piperidin-3-yl)-5-(trifluoromethyl)pyrimidin-2-amine This compound was prepared according to the procedures described in Example 86, with tert-butyl 3,8-diazabicyclo[3.2.1]octane-8-carboxylate (Combi-blocks) replacing tert-butyl (R)-pyrrolidin-3-ylcarbamate in Step 1. LCMS calculated for $C_{22}H_{27}F_3N_9$ $(M+H)^+$: m/z=474.2; found: 474.2.

Step 2. 1-(3-(3-((R)-3-((5-(Trifluoromethyl)pyrimidin-2-yl)amino)piperidin-1-yl)imidazo[1,5-a]pyrazin-8-yl)-3,8-diazabicyclo[3.2.1]octan-8-yl)prop-2-en-1-one This compound was prepared according to the procedures described in Example 68, with N-((3R)-1-(8-(3,8-diazabicyclo[3.2.1]octan-3-yl)imidazo[1,5-a]pyrazin-3-yl)piperidin-3-yl)-5-(trifluoromethyl)pyrimidin-2-amine replacing 6-amino-2-((1S,3R)-3-((5-bromopyrimidin-2-yl)amino)cyclohexyl)isoindolin-1-one in Step 3. LCMS calculated for $C_{25}H_{29}F_3N_9O$ $(M+H)^+$: m/z=528.2; found: 528.2.

Example 110. (R)-1-(4-(3-(3-((5-(Trifluoromethyl)pyrimidin-2-yl)amino)piperidin-1-yl)imidazo[1,5-a]pyrazin-8-yl)piperidin-1-yl)prop-2-en-1-one Step 1. tert-Butyl (R)-4-(3-(3-((5-(trifluoromethyl)pyrimidin-2-yl)amino)piperidin-1-yl)imidazo[1,5-a]pyrazin-8-yl)-3,6-dihydropyridine-1(2H)-carboxylate This compound was prepared according to the procedures described in Example 108, with tert-butyl 4-(4,4,5,5-tetramethyl-1,3,2-dioxaborolan-2-yl)-3,6-dihydropyridine-1(2H)-carboxylate replacing tert-butyl 6-(4,4,5,5-tetramethyl-1,3,2-dioxaborolan-2-yl)-3,4-dihydropyridine-1(2H)-carboxylate in Step 1. LCMS calculated for $C_{26}H_{32}F_3N_8O_2$ $(M+H)^+$: m/z=545.3; found: 545.3.

Step 2. (R)—N-(1-(8-(Piperidin-4-yl)imidazo[1,5-a] pyrazin-3-yl)piperidin-3-yl)-5-(trifluoromethyl)py-rimidin-2-amine This compound was prepared according to the procedures described in Example 108, with tert-butyl (R)-4-(3-(3-((5-(trifluoromethyl)pyrimidin-2-yl)amino)piperidin-1-yl)imidazo[1,5-a]pyrazin-8-yl)-3,6-dihydropyridine-1(2H)-carboxylate replacing tert-butyl (R)-6-(3-(3-((5-(trifluoromethyl)pyrimidin-2-yl)amino)piperidin-1-yl)imidazo[1,5-a]pyrazin-8-yl)-3,4-dihydropyridine-1(2H)-carboxylate in Step 2. LCMS calculated for $C_{21}H_{26}F_3N_8$ (M+H)$^+$: m/z=447.2; found: 447.2.

Step 3. (R)-1-(4-(3-(3-((5-(Trifluoromethyl)pyrimi-din-2-yl)amino)piperidin-1-yl)imidazo[1,5-a] pyrazin-8-yl)piperidin-1-yl)prop-2-en-1-one This compound was prepared according to the procedures described in Example 68, with (R)—N-(1-(8-(piperidin-4-yl)imidazo[1,5-a]pyrazin-3-yl)piperidin-3-yl)-5-(trifluoromethyl)pyrimidin-2-amine replacing 6-amino-2-((1S,3R)-3-((5-bromopyrimidin-2-yl)amino)cyclohexyl)isoindolin-1-one in Step 3. LCMS calculated for $C_{24}H_{28}F_3N_8O$ (M+H)$^+$: m/z=501.2; found: 501.2. $^1$H NMR (500 MHz, DMSO) δ 8.73-8.61 (m, 2H), 8.22 (d, J=7.5 Hz, 1H), 8.14 (s, 1H), 7.84 (d, J=5.3 Hz, 1H), 7.42 (d, J=5.3 Hz, 1H), 6.86 (dd, J=16.7, 10.5 Hz, 1H), 6.13 (dd, J=16.7, 2.5 Hz, 1H), 5.70 (dd, J=10.5, 2.4 Hz, 1H), 4.59 (d, J=12.9 Hz, 1H), 4.25-4.19 (m, 1H), 4.22-4.10 (m, 1H), 3.64 (dd, J=12.1, 3.8 Hz, 1H), 3.56-3.48 (m, 1H), 3.41 (d, J=12.2 Hz, 1H), 3.25 (t, J=13.0 Hz, 1H), 3.00-2.89 (m, 2H), 2.82 (t, J=12.7 Hz, 1H), 2.03 (dd, J=12.9, 4.3 Hz, 1H), 1.96-1.88 (m, 3H), 1.86-1.70 (m, 3H), 1.69-1.58 (m, 1H).

Example 111. N-(2-((3R,5R)-3-Methoxy-5-((5-(trif-luoromethyl)pyrimidin-2-yl)amino)piperidin-1-yl)-1, 6-dimethyl-1H-benzo[d]imidazol-5-yl)acrylamide

336

Step 1. tert-Butyl (3R,5R)-3-(1,3-dioxoisoindolin-2-yl)-5-hydroxypiperidine-1-carboxylate To a reaction vial containing tert-butyl (3R,5R)-3-amino-5-hydroxypiperidine-1-carboxylate (72 mg, 0.33 mmol) in toluene (2 mL) was added phthalic anhydride (50 mg, 0.33 mmol) and triethylamine (136 μL, 0.99 mmol). The reaction mixture was stirred at reflux for 12 h. The reaction mixture was allowed to cool to r.t. before washed with water. The product was extracted with EtOAc, and the organic layer was subsequently washed with water and brine, dried over sodium sulfate, filtered, and the solvents were evaporated in vacuo. The crude material was purified by Biotage Isolera to give the product as a white solid. LCMS calculated for $C_{11}H_{23}N_2O_5$ (M+H)$^+$: m/z=347.2; found 347.2.

Step 2. tert-Butyl (3R,5R)-3-(1,3-dioxoisoindolin-2-yl)-5-methoxypiperidine-1-carboxylate To a reaction vial containing tert-butyl (3R,5R)-3-(1,3-dioxoisoindolin-2-yl)-5-hydroxypiperidine-1-carboxylate (110 mg, 0.32 mmol) was added THF (1 mL). The reaction mixture was stirred at 0° C. for 10 min before sodium hydride (38 mg, 0.985 mmol, 60% in mineral oil) was added. The reaction mixture was stirred at 0° C. for 10 min before iodomethane (30 μL, 0.48 mmol) was added. The reaction mixture was stirred at r.t. for 30 min, then quenched with water. The mixture was extracted with EtOAc and the organic layer was subsequently washed with water and brine, dried over sodium sulfate, filtered, and the solvents were evaporated in vacuo. The crude material was purified by Biotage Isolera to give the product. LCMS calculated for $C_{19}H_{25}N_2O_5$ (M+H)$^+$: m/z=361.2; found 361.2.

Step 3. 2-((3R,5R)-5-Methoxypiperidin-3-yl)isoin-doline-1,3-dione

This compound was prepared according to the procedures described in Example 94, with 2-((3R,5R)-5-methoxypip-eridin-3-yl)isoindoline-1,3-dione replacing tert-butyl (3R, 5R)-3-(((benzyloxy)carbonyl)amino)-5-hydroxypiperidine-1-carboxylate in Step 2. LCMS calculated for $C_{14}H_{17}N_2O_3$ (M+H)$^+$: m/z=261.1; found 261.1.

Step 4. 2-((3R,5R)-1-(1,6-Dimethyl-5-nitro-1H-benzo[d]imidazol-2-yl)-5-methoxypiperidin-3-yl)isoindoline-1,3-dione This compound was prepared according to the procedures described in Example 100, with 2-((3R,5R)-5-methoxypip-eridin-3-yl)isoindoline-1,3-dione replacing tert-butyl ((3R, 5R)-5-fluoropiperidin-3-yl)carbamate in Step 4. LCMS calculated for $C_{23}H_{24}N_5O_5$ (M+H)$^+$: m/z=450.2; found 450.2.

Step 5. (3R,5R)-1-(1,6-Dimethyl-5-nitro-1H-benzo[d]imidazol-2-yl)-5-methoxypiperidin-3-amine To a reaction vial of 2-((3R,5R)-1-(1,6-dimethyl-5-nitro-1H-benzo[d]imidazol-2-yl)-5-methoxypiperidin-3-yl)isoindoline-1,3-dione (114 mg, 0.254 mmol) in methanol (1 mL) was added hydrazine hydrate (80%, 12 μL, 0.381 mmol). The reaction mixture was stirred at reflux for 1 h. The reaction mixture was allowed to cool to r.t. before washed with 40% NaOH solution and extract with diethyl ether. The organic layer was subsequently washed with water and brine, dried over sodium sulfate, filtered, and the solvents were evaporated in vacuo. The crude material was purified by Biotage Isolera to give the product. LCMS calculated for $C_{15}H_{22}N_5O_3$ (M+H)$^+$: m/z=320.2; found 320.2.

Step 6. N-(2-((3R,5R)-3-Methoxy-5-((5-(trifluorom-ethyl)pyrimidin-2-yl)amino)piperidin-1-yl)-1,6-dim-ethyl-1H-benzo[d]imidazol-5-yl)acrylamide This compound was prepared according to the procedures described in Example 100 (Step 6-Step 8), with (3R,5R)-1-(1,6-dimethyl-5-nitro-1H-benzo[d]imidazol-2-yl)-5-methoxypiperidin-3-amine replacing (3R,5R)-1-(1,6-dim-ethyl-5-nitro-1H-benzo[d]imidazol-2-yl)-5-fluoropiperidin-3-amine. LCMS calculated for $C_{23}H_{27}F_3N_7O_2$ (M+H)$^+$: m/z=490.2; found: 490.2.

Example 112. (E)-N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)-4-hy-droxy-4-methylpent-2-enamide

Step 1. N-(2-((3R,5R)-3-Fluoro-5-((5-(trifluorom-ethyl)pyrimidin-2-yl)amino)piperidin-1-yl)-1,6-dim-ethyl-1H-benzo[d]imidazol-5-yl)-4-methylpent-3-enamide This compound was prepared according to the procedures described in Example 106 (Step 2), with 2-((3R,5R)-3-fluoro-5-((5-(trifluoromethyl)pyrimidin-2-yl)amino)piperi-din-1-yl)-1,6-dimethyl-1H-benzo[d]imidazol-5-amine replacing N-((3R,5R)-1-(8-(((1S,4S)-2,5-diazabicyclo[2.2.1]

heptan-2-yl)imidazo[1,5-a]pyrazin-3-yl)-5-fluoropiperidin-3-yl)-5-(trifluoromethyl)pyrimidin-2-amine and 4-methyl-pent-3-enoic acid replacing but-2-ynoic acid. LCMS calculated for $C_{25}H_{30}F_4N_7O$ $(M+H)^+$: m/z=520.2; found: 520.3.

Step 2. 2-(3,3-Dimethyloxiran-2-yl)-N-(2-((3R,5R)-3-fluoro-5-((5-(trifluoromethyl)pyrimidin-2-yl)amino)piperidin-1-yl)-1,6-dimethyl-1H-benzo[d]imidazol-5-yl)acetamide To a reaction vial containing N-(2-((3R,5R)-3-fluoro-5-((5-(trifluoromethyl)pyrimidin-2-yl)amino)piperidin-1-yl)-1,6-dimethyl-1H-benzo[d]imidazol-5-yl)-4-methylpent-3-enamide (12 mg, 0.023 mmol) was added DCM (0.5 mL). The reaction mixture was stirred at 0° C. for 10 min before 3-chloroperbenzoic acid (24 mg, 0.139 mmol) in DCM (0.5 mL) was added slowly. The reaction mixture was stirred at r.t. overnight before quenched with water. The mixture was extracted with DCM and the organic layer was subsequently washed with water and brine, dried over sodium sulfate, filtered, and the solvents were evaporated in vacuo. The crude material was purified by Biotage Isolera to give the product. LCMS calculated for $C_{25}H_{30}F_4N_7O_2$ $(M+H)^+$: m/z=536.2; found 536.2.

Step 3. (E)-N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)-4-hydroxy-4-methylpent-2-enamide To a reaction vial containing 2-(3,3-dimethyloxiran-2-yl)-N-(2-((3R,5R)-3-fluoro-5-((5-(trifluoromethyl)pyrimidin-2-yl)amino)piperidin-1-yl)-1,6-dimethyl-1H-benzo[d]imidazol-5-yl)acetamide (12 mg, 0.023 mmol) was added THF (0.2 mL). The reaction mixture was stirred at 0° C. for 10 min before lithium diisopropylamide solution in THF (35 µL, 0.069 mmol, 2.0 M) was added slowly. The reaction mixture was stirred at r.t. for 4 h before quenched with water. The mixture was extracted with EtOAc and the organic layer was subsequently washed with water and brine, dried over sodium sulfate, filtered, and the solvents were evaporated in vacuo. The crude material was purified by Biotage Isolera to give the product. LCMS calculated for $C_{25}H_{30}F_4N_7O_2$ $(M+H)^+$: m/z=536.2; found 536.2. $^1$H NMR (600 MHz, DMSO-d$_6$) δ 9.48 (s, 1H), 8.72 (d, J=9.8 Hz, 2H), 8.36 (d, J=7.7 Hz, 1H), 7.72 (s, 1H), 7.49 (s, 1H), 6.86 (d, J=15.3 Hz, 1H), 6.40 (d, J=15.3 Hz, 1H), 5.22 (d, J=46.2 Hz, 1H), 4.45 (m, 1H), 4.00 (d, J=11.0 Hz, 2H), 3.76 (s, 3H), 3.55 (dd, J=36.2, 14.1 Hz, 1H), 2.39-2.36 (m, 1H), 2.35 (s, 3H), 2.08-1.93 (m, 1H), 1.27 (s, 6H).

Example 113. N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)-4-hydroxy-4-methylpent-2-ynamide This compound was prepared according to the procedures described in Example 106 (Step 2), with 2-((3R,5R)-3-fluoro-5-((5-(trifluoromethyl)pyrimidin-2-yl)amino)piperidin-1-yl)-1,6-dimethyl-1H-benzo[d]imidazol-5-amine replacing N-((3R,5R)-1-(8-((1S,4S)-2,5-diazabicyclo[2.2.1]heptan-2-yl)imidazo[1,5-a]pyrazin-3-yl)-5-fluoropiperidin-3-yl)-5-(trifluoromethyl)pyrimidin-2-amine and 4-hydroxy-4-methylpent-2-ynoic acid replacing but-2-ynoic acid. LCMS calculated for $C_{25}H_{28}F_4N_7O_2$ $(M+H)^+$: m/z=534.2; found: 534.3.

Example 114. N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)-4-methoxy-but-2-ynamide This compound was prepared according to the procedures described in Example 106 (Step 2), with 2-((3R,5R)-3-fluoro-5-((5-(trifluoromethyl)pyrimidin-2-yl)amino)piperidin-1-yl)-1,6-dimethyl-1H-benzo[d]imidazol-5-amine replacing N-((3R,5R)-1-(8-((1S,4S)-2,5-diazabicyclo[2.2.1]heptan-2-yl)imidazo[1,5-a]pyrazin-3-yl)-5-fluoropiperidin-3-yl)-5-(trifluoromethyl)pyrimidin-2-amine and 4-methoxy-but-2-ynoic acid replacing but-2-ynoic acid. LCMS calculated for $C_{24}H_{26}F_4N_7O_2$ $(M+H)^+$: m/z=520.2; found: 520.2.

Example 115. N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)-4-hydroxybut-2-ynamide Example 117. 2-Fluoro-N-(2-((3R,5R)-3-fluoro-5-((5-(trifluoromethyl)pyrimidin-2-yl)amino)piperidin-1-yl)-1,6-dimethyl-1H-benzo[d]imidazol-5-yl)acrylamide This compound was prepared according to the procedures described in Example 106 (Step 2), with 2-((3R,5R)-3-fluoro-5-((5-(trifluoromethyl)pyrimidin-2-yl)amino)piperidin-1-yl)-1,6-dimethyl-1H-benzo[d]imidazol-5-amine replacing N-((3R,5R)-1-(8-((1S,4S)-2,5-diazabicyclo[2.2.1]heptan-2-yl)imidazo[1,5-a]pyrazin-3-yl)-5-fluoropiperidin-3-yl)-5-(trifluoromethyl)pyrimidin-2-amine and 4-hydroxybut-2-ynoic acid replacing but-2-ynoic acid. LCMS calculated for $C_{23}H_{24}F_4N_7O_2$ (M+H)$^+$: m/z=506.2; found: 506.2.

Example 116. N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)but-2-ynamide This compound was prepared according to the procedures described in Example 106 (Step 2), with 2-((3R,5R)-3-fluoro-5-((5-(trifluoromethyl)pyrimidin-2-yl)amino)piperidin-1-yl)-1,6-dimethyl-1H-benzo[d]imidazol-5-amine replacing N-((3R,5R)-1-(8-((1S,4S)-2,5-diazabicyclo[2.2.1]heptan-2-yl)imidazo[1,5-a]pyrazin-3-yl)-5-fluoropiperidin-3-yl)-5-(trifluoromethyl)pyrimidin-2-amine and but-2-ynoic acid replacing but-2-ynoic acid. LCMS calculated for $C_{23}H_{24}F_4N_7O$ (M+H)$^+$: m/z=490.2; found: 490.2.

This compound was prepared according to the procedures described in Example 106 (Step 2), with 2-((3R,5R)-3-fluoro-5-((5-(trifluoromethyl)pyrimidin-2-yl)amino)piperidin-1-yl)-1,6-dimethyl-1H-benzo[d]imidazol-5-amine replacing N-((3R,5R)-1-(8-((1S,4S)-2,5-diazabicyclo[2.2.1]heptan-2-yl)imidazo[1,5-a]pyrazin-3-yl)-5-fluoropiperidin-3-yl)-5-(trifluoromethyl)pyrimidin-2-amine and 2-fluoroacrylic acid replacing but-2-ynoic acid. LCMS calculated for $C_{22}H_{23}F_5N_7O$ (M+H)$^+$: m/z=496.2; found: 496.2.

Example 118. (E)-N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)-4-(piperidin-1-yl)but-2-enamide This compound was prepared according to the procedures described in Example 106 (Step 2), with 2-((3R,5R)-3-fluoro-5-((5-(trifluoromethyl)pyrimidin-2-yl)amino)piperidin-1-yl)-1,6-dimethyl-1H-benzo[d]imidazol-5-amine replacing N-((3R,5R)-1-(8-((1S,4S)-2,5-diazabicyclo[2.2.1]heptan-2-yl)imidazo[1,5-a]pyrazin-3-yl)-5-fluoropiperidin-3-yl)-5-(trifluoromethyl)pyrimidin-2-amine and (E)-4-(piperidin-1-yl)but-2-enoic acid replacing but-2-ynoic acid. LCMS calculated for $C_{28}H_{35}F_4N_8O$ (M+H)$^+$: m/z=575.3; found: 575.3.

Example 119. (Z)-4-(Dimethylamino)-N-(2-((3R, 5R)-3-fluoro-5-((5-(trifluoromethyl)pyrimidin-2-yl) amino)piperidin-1-yl)-1,6-dimethyl-1H-benzo[d] imidazol-5-yl)but-2-enamide This compound was prepared according to the procedures described in Example 106 (Step 2), with 2-((3R,5R)-3-fluoro-5-((5-(trifluoromethyl)pyrimidin-2-yl)amino)piperi-din-1-yl)-1,6-dimethyl-1H-benzo[d]imidazol-5-amine replacing N-((3R,5R)-1-(8-((1S,4S)-2,5-diazabicyclo[2.2.1] heptan-2-yl)imidazo[1,5-a]pyrazin-3-yl)-5-fluoropiperidin-3-yl)-5-(trifluoromethyl)pyrimidin-2-amine and (Z)-4-(dim-ethylamino)but-2-enoic acid replacing but-2-ynoic acid. LCMS calculated for $C_{25}H_{31}F_4N_8O$ (M+H)$^+$: m/z=535.3; found: 535.3.

Example 120. (E)-4-(Dimethylamino)-N-(2-((3R, 5R)-3-fluoro-5-((5-(trifluoromethyl)pyrimidin-2-yl) amino)piperidin-1-yl)-1,6-dimethyl-1H-benzo[d] imidazol-5-yl)but-2-enamide This compound was prepared according to the procedures described in Example 106 (Step 2), with 2-((3R,5R)-3-fluoro-5-((5-(trifluoromethyl)pyrimidin-2-yl)amino)piperi-din-1-yl)-1,6-dimethyl-1H-benzo[d]imidazol-5-amine replacing N-((3R,5R)-1-(8-((1S,4S)-2,5-diazabicyclo[2.2.1] heptan-2-yl)imidazo[1,5-a]pyrazin-3-yl)-5-fluoropiperidin-3-yl)-5-(trifluoromethyl)pyrimidin-2-amine and (E)-4-(dimethylamino)but-2-enoic acid replacing but-2-ynoic acid. LCMS calculated for $C_{25}H_{31}F_4N_8O$ (M+H)$^+$: m/z=535.3; found: 535.3.

Example 121. (E)-N-(2-((3R,5R)-3-Fluoro-5-((5-(trifluoromethyl)pyrimidin-2-yl)amino)piperidin-1-yl)-1,6-dimethyl-1H-benzo[d]imidazol-5-yl)-4-methoxybut-2-enamide This compound was prepared according to the procedures described in Example 106 (Step 2), with 2-((3R,5R)-3-fluoro-5-((5-(trifluoromethyl)pyrimidin-2-yl)amino)piperi-din-1-yl)-1,6-dimethyl-1H-benzo[d]imidazol-5-amine replacing N-((3R,5R)-1-(8-((1S,4S)-2,5-diazabicyclo[2.2.1] heptan-2-yl)imidazo[1,5-a]pyrazin-3-yl)-5-fluoropiperidin-3-yl)-5-(trifluoromethyl)pyrimidin-2-amine and (E)-4-methoxybut-2-enoic acid replacing but-2-ynoic acid. LCMS calculated for $C_{24}H_{28}F_4N_7O_2$ (M+H)$^+$: m/z=522.2; found: 522.2.

Example 122. N-(2-((3R,5R)-3-((5-Cyanopyrimidin-2-yl)amino)-5-hydroxypiperidin-1-yl)-1-methyl-1H-benzo[d]imidazol-5-yl)acrylamide This compound was prepared according to the procedures described in Example 88 (Step 2-4), with 2-chloropyrimi-dine-5-carbonitrile replacing 2-chloro-5-(trifluoromethyl) pyrimidine. LCMS calculated for $C_{21}H_{23}N_8O_2$ (M+H)$^+$: m/z=419.2; found: 419.2.

Example 123. (R)—N-(1-Methyl-2-(3-((5-(trifluo-romethyl)pyrimidin-2-yl)amino)piperidin-1-yl)-1H-benzo[d]imidazol-5-yl)acrylamide Step 1. (R)—N-(1-(1-Methyl-5-nitro-1H-benzo[d]imidazol-2-yl)piperidin-3-yl)-5-(trifluoromethyl)pyrimidin-2-amine This compound was prepared according to the procedures described in Example 37, with 2-chloro-5-(trifluoromethyl)pyrimidine replacing 2-chloro-4-methoxypyrimidine-5-carbonitrile in Step 2. LCMS calculated for $C_{18}H_{19}F_3N_7O_2$ (M+H)$^+$: m/z=422.1; found 422.1.

Step 2. (R)-1-Methyl-2-(3-((5-(trifluoromethyl)pyrimidin-2-yl)amino)piperidin-1-yl)-1H-benzo[d]imidazol-5-amine This compound was prepared according to the procedures described in Example 47, with (R)—N-(1-(1-methyl-5-nitro-1H-benzo[d]imidazol-2-yl)piperidin-3-yl)-5-(trifluoromethyl)pyrimidin-2-amine replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{18}H_{21}F_3N_7$ (M+H)$^+$: m/z=392.2; found 392.1.

Step 3. (R)—N-(1-Methyl-2-(3-((5-(trifluoromethyl)pyrimidin-2-yl)amino)piperidin-1-yl)-1H-benzo[d]imidazol-5-yl)acrylamide This compound was prepared according to the procedures described in Example 68, with (R)-1-methyl-2-(3-((5-(trifluoromethyl)pyrimidin-2-yl)amino)piperidin-1-yl)-1H-benzo[d]imidazol-5-amine replacing 6-amino-2-((1S,3R)-3-((5-bromopyrimidin-2-yl)amino)cyclohexyl)isoindolin-1-one in Step 3. LCMS calculated for $C_{21}H_{23}F_3N_7O$ (M+H)$^+$: m/z=446.2; found: 446.2. $^1$H NMR (500 MHz, DMSO) δ 10.43 (s, 1H), 8.69 (d, J=8.8 Hz, 2H), 8.33 (d, J=7.3 Hz, 1H), 8.11 (d, J=1.9 Hz, 1H), 7.58 (d, J=8.8 Hz, 1H), 7.51 (dd, J=8.8, 1.9 Hz, 1H), 6.47 (dd, J=16.9, 10.1 Hz, 1H), 6.29 (dd, J=16.9, 1.9 Hz, 1H), 5.79 (dd, J=10.1, 1.9 Hz, 1H), 4.16 (m, 1H), 3.97 (dd, J=12.5, 3.9 Hz, 1H), 3.75 (s, 3H), 3.71 (m, 1H), 3.37 (m, 1H), 3.25 (dd, J=12.5, 8.8 Hz, 1H), 2.07-1.94 (m, 2H), 1.87-1.70 (m, 2H).

Example 124. (R)—N-(2-(3,3-Difluoro-5-((5-(trifluoromethyl)pyrimidin-2-yl)amino)piperidin-1-yl)-1-methyl-1H-benzo[d]imidazol-5-yl)acrylamide This compound was prepared according to the procedures described in Example 88 (Step 1-4), with tert-butyl (R)-(5,5-difluoropiperidin-3-yl)carbamate replacing tert-butyl ((3R,5R)-5-hydroxypiperidin-3-yl)carbamate. LCMS calculated for $C_{21}H_{21}F_5N_7O$ (M+H)$^+$: m/z=482.2; found: 482.2.

Example 125. N-(2-((3S,4R)-3-((5-Cyanopyrimidin-2-yl)amino)-4-fluoropiperidin-1-yl)-1-methyl-1H-benzo[d]imidazol-5-yl)acrylamide This compound was prepared according to the procedures described in Example 90, with 2-chloropyrimidine-5-carbonitrile replacing 2-chloro-5-(trifluoromethyl)pyrimidine. LCMS calculated for $C_{21}H_{22}FN_8O$ (M+H)$^+$: m/z=421.2; found: 421.2.

Example 126. N-(2-((3S,4S)-3-((5-Cyanopyrimidin-2-yl)amino)-4-fluoropiperidin-1-yl)-1-methyl-1H-benzo[d]imidazol-5-yl)acrylamide This compound was prepared according to the procedures described in Example 91, with 2-chloropyrimidine-5-carbonitrile replacing 2-chloro-5-(trifluoromethyl)pyrimidine. LCMS calculated for $C_{21}H_{22}FN_8O$ (M+H)$^+$: m/z=421.2; found: 421.2.

Example 127. (S)—N-(2-(3-((5-Cyanopyrimidin-2-yl)amino)-4,4-difluoropiperidin-1-yl)-1-methyl-1H-benzo[d]imidazol-5-yl)acrylamide This compound was prepared according to the procedures described in Example 92, with 2-chloropyrimidine-5-carbonitrile replacing 2-chloro-5-(trifluoromethyl)pyrimidine. LCMS calculated for $C_{21}H_{21}F_2N_8O$ (M+H)$^+$: m/z=439.2; found: 439.2.

Example 128. (R)-1-(4-(1-Methyl-2-(3-((5-(trifluoromethyl)pyrimidin-2-yl)amino)piperidin-1-yl)-1H-benzo[d]imidazol-5-yl)piperazin-1-yl)prop-2-en-1-one

348

Step 1. (R)—N-(1-(5-Bromo-1-methyl-1H-benzo[d]imidazol-2-yl)piperidin-3-yl)-5-(trifluoromethyl)pyrimidin-2-amine This compound was prepared according to the procedures described in Example 100 (Step 4-6), with 5-bromo-2-chloro-1-methyl-1H-benzo[d]imidazole replacing 2-chloro-1-methyl-5-nitro-1H-benzo[d]imidazole and tert-butyl (R)-piperidin-3-ylcarbamate replacing tert-butyl ((3R,5R)-5-fluoropiperidin-3-yl)carbamate. LCMS calculated for $C_{18}H_{19}BrF_3N_6$ (M+H)$^+$: m/z=455.1; found: 455.2.

Step 2. tert-Butyl (R)-4-(1-methyl-2-(3-((5-(trifluoromethyl)pyrimidin-2-yl)amino)piperidin-1-yl)-1H-benzo[d]imidazol-5-yl)piperazine-1-carboxylate A reaction vial containing (R)—N-(1-(5-bromo-1-methyl-1H-benzo[d]imidazol-2-yl)piperidin-3-yl)-5-(trifluoromethyl)pyrimidin-2-amine (15 mg, 0.033 mmol), tert-butyl piperazine-1-carboxylate (62 mg, 0.33 mmol), cesium carbonate (27 mg, 0.082 mmol), tris(dibenzylideneacetone)dipalladium(0) (6 mg, 0.007 mmol) and 2-(dicyclohexylphosphino)3,6-dimethoxy-2',4',6'-triisopropyl-1,1'-biphenyl (7 mg, 0.013 mmol) was evacuated and backfilled with nitrogen. 1,4-Dioxane (1 mL) was added to the reaction mixture, which was then stirred at 100° C. for 2 h. The reaction mixture was cooled to r.t and was diluted with EtOAc. The organic layer was subsequently washed with water and brine, dried over sodium sulfate, filtered, and the solvents were evaporated in vacuo. The crude material was purified by Biotage Isolera. LCMS calculated for $C_{27}H_{36}F_3N_8O_2$ (M+H)$^+$: m/z=561.3; found 561.3.

Step 3. (R)-1-(4-(1-Methyl-2-(3-((5-(trifluoromethyl)pyrimidin-2-yl)amino)piperidin-1-yl)-1H-benzo[d]imidazol-5-yl)piperazin-1-yl)prop-2-en-1-one This compound was prepared according to the procedures described in Example 87 (Step 5), with tert-butyl (R)-4-(1-methyl-2-(3-((5-(trifluoromethyl)pyrimidin-2-yl)amino)piperidin-1-yl)-1H-benzo[d]imidazol-5-yl)piperazine-1-carboxylate replacing tert-butyl 2-(2-((3R,5R)-3-hydroxy-5-((5-(trifluoromethyl)pyrimidin-2-yl)amino)piperidin-1-yl)-1-methyl-1H-benzo[d]imidazol-5-yl)piperidine-1-carboxylate. LCMS calculated for $C_{25}H_{30}F_3N_8O$ (M+H)$^+$: m/z=515.2; found: 515.2.

Example 129. (R)—N-(2-(3-((5-Cyanothiazol-2-yl)amino)piperidin-1-yl)-1-methyl-1H-benzo[d]imidazol-5-yl)acrylamide

Step 1. (R)-2-((1-(1-Methyl-5-nitro-1H-benzo[d]imidazol-2-yl)piperidin-3-yl)amino)thiazole-5-carbonitrile To a mixture of 2-chlorothiazole-5-carbonitrile (28 mg, 0.195 mmol) and (R)-1-(1-methyl-5-nitro-1H-benzo[d]imidazol-2-yl)piperidin-3-amine (21 mg, 0.078 mmol) in DMF (1 mL) was added N,N-diisopropylethylamine (68 μL, 0.39 mmol). The reaction mixture was heated to 130° C. for 2 h and then cooled to r.t. The reaction mixture was diluted with EtOAc and the organic phase was washed with brine. It was then dried over sodium sulfate and filtered. Solvents were evaporated in vacuo and the crude material was purified by Biotage Isolera to give the product. LCMS calculated for $C_{17}H_{18}N_7O_2S$ (M+H)$^+$: m/z=384.1; found 384.2.

Step 2. (R)—N-(2-(3-((5-Cyanothiazol-2-yl)amino)piperidin-1-yl)-1-methyl-1H-benzo[d]imidazol-5-yl)acrylamide This compound was prepared according to the procedures described in Example 100 (Step 7-8), with (R)-2-((1-(1-methyl-5-nitro-1H-benzo[d]imidazol-2-yl)piperidin-3-yl)amino)thiazole-5-carbonitrile replacing N-((3R,5R)-1-(1,6- dimethyl-5-nitro-1H-benzo[d]imidazol-2-yl)-5-fluoropiperidin-3-yl)-5-(trifluoromethyl)pyrimidin-2-amine. LCMS calculated for $C_{20}H_{22}N_7OS$ (M+H)$^+$: m/z=408.2; found: 408.2. $^1$H NMR (600 MHz, DMSO-d$_6$) δ 10.40 (s, 1H), 8.91 (d, J=6.9 Hz, 1H), 8.13 (d, J=2.0 Hz, 1H), 7.96 (s, 1H), 7.58 (d, J=8.8 Hz, 1H), 7.49 (dd, J=8.9, 1.9 Hz, 1H), 6.46 (dd, J=16.9, 10.2 Hz, 1H), 6.29 (dd, J=17.0, 1.9 Hz, 1H), 5.79 (dd, J=10.1, 1.9 Hz, 1H), 4.05 (m, 1H), 3.91 (dd, J=12.6, 3.6 Hz, 1H), 3.71 (s, 3H), 3.67-3.58 (m, 1H), 3.48-3.35 (m, 2H), 2.05 (m, 1H), 1.95 (m, 1H), 1.76 (m, 2H).

Example 130. (R)—N-(1-Methyl-2-(3-((5-(trifluoromethyl)thiazol-2-yl)amino)piperidin-1-yl)-1H-benzo[d]imidazol-5-yl)acrylamide This compound was prepared according to the procedures described in Example 129, with 2-chloro-5-(trifluoromethyl)thiazole replacing 2-chlorothiazole-5-carbonitrile. LCMS calculated for $C_{20}H_{22}F_3N_6OS$ (M+H)$^+$: m/z=451.1; found: 451.1.

Example 131. N-(6-Ethyl-2-((3R,5R)-3-fluoro-5-((5-(trifluoromethyl)pyrimidin-2-yl)amino)piperidin-1-yl)-1-methyl-1H-benzo[d]imidazol-5-yl)acrylamide This compound was prepared according to the procedures described in Example 101, with 4,4,5,5-tetramethyl-2-vinyl-1,3,2-dioxaborolane replacing 4,4,5,5-tetramethyl-2-(isopropenyl)-1,3,2-dioxaborolane in Step 2. LCMS calculated for $C_{23}H_{26}F_4N_7O$ (M+H)$^+$: m/z=492.2; found: 492.2.

Example 132. N-(6-Fluoro-2-((3R,5R)-3-fluoro-5-((5-(trifluoromethyl)pyrimidin-2-yl)amino)piperidin-1-yl)-1-methyl-1H-benzo[d]imidazol-5-yl)acrylamide This compound was prepared according to the procedures described in Example 88, with tert-butyl ((3R,5R)-5-fluoropiperidin-3-yl)carbamate replacing tert-butyl ((3R,5R)-5-hydroxypiperidin-3-yl)carbamate and 2-chloro-6-fluoro-1-methyl-5-nitro-1H-benzo[d]imidazole replacing 2-chloro-1-methyl-5-nitro-1H-benzo[d]imidazole in Step 1. LCMS calculated for $C_{21}H_{21}F_5N_7O$ (M+H)$^+$: m/z=482.2; found: 482.2.

Example 133. N-(2-((3R,5R)-3-Fluoro-5-((5-(trifluoromethyl)pyrimidin-2-yl)amino)piperidin-1-yl)-6-(methoxymethyl)-1-methyl-1H-benzo[d]imidazol-5-yl)acrylamide Step 1. N-((3R,5R)-5-Fluoro-1-(6-(methoxymethyl)-1-methyl-5-nitro-1H-benzo[d]imidazol-2-yl)piperidin-3-yl)-5-(trifluoromethyl)pyrimidin-2-amine To a mixture of N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine (25 mg, 0.05 mmol), tributyl(methoxymethyl)stannane (30 μL, 0.10 mmol) was added triphenylphosphine palladium chloride (3 mg, 5 mol) and HMPA (0.25 ml). The reaction mixture was heated to 100° C. for 3 h and then cooled to r.t. The reaction mixture was poured into water and treated with aqueous potassium fluoride. The organic layer was extracted with ethyl acetate and dried over sodium sulfate. The crude material was used in the next step without further purification. LCMS calculated for $C_{20}H_{22}F_4N_7O_3$ (M+H)$^+$: m/z=484.2; found: 484.2.

Step 2. N-(2-((3R,5R)-3-Fluoro-5-((5-(trifluoromethyl)pyrimidin-2-yl)amino)piperidin-1-yl)-6-(methoxymethyl)-1-methyl-1H-benzo[d]imidazol-5-yl)acrylamide This compound was prepared according to the procedures described in Example 141, Steps 3-4 with N-((3R,5R)-5-fluoro-1-(6-(methoxymethyl)-1-methyl-5-nitro-1H-benzo [d]imidazol-2-yl)piperidin-3-yl)-5-(trifluoromethyl)pyrimidin-2-amine replacing N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine in Step 3. LCMS calculated for $C_{23}H_{26}F_4N_7O_2$ (M+H)$^+$: m/z=508.2; found: 508.2.

Example 134. N-(6-Chloro-2-((3R,5R)-3-fluoro-5-((5-(trifluoromethyl)pyrimidin-2-yl)amino)piperidin-1-yl)-1-methyl-1H-benzo[d]imidazol-5-yl)acrylamide

354

Step 1. N-((3R,5R)-1-(6-Chloro-1-methyl-5-nitro-1H-benzo[d]imidazol-2-yl)-5-fluoropiperidin-3-yl)-5-(trifluoromethyl)pyrimidin-2-amine Example 135. N-(2-((3R,5R)-3-Fluoro-5-((5-(trifluoromethyl)pyrimidin-2-yl)amino)piperidin-1-yl)-1-methyl-6-(methyl-d3)-1H-benzo[d]imidazol-5-yl)acrylamide To a microwave vial containing a solution of N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine (40 mg, 0.08 mmol), in DMF (0.77 ml) was added nickel (II) chloride (20 mg, 0.154 mmol). The microwave vial was sealed and heated to 170° C. under microwave irradiation for 1 h and then cooled to r.t. The reaction mixture was filtered and the solvent was removed in vacuo. The crude material was used in the next step without further purification. LCMS calculated for $C_{11}H_{17}ClF_4N_7O_2$ (M+H)$^+$: m/z=474.1; found: 474.1.

Step 2. N-(6-Chloro-2-((3R,5R)-3-fluoro-5-((5-(trifluoromethyl)pyrimidin-2-yl)amino)piperidin-1-yl)-1-methyl-1H-benzo[d]imidazol-5-yl)acrylamide This compound was prepared according to the procedures described in Example 141, Steps 3-4 with N-((3R,5R)-1-(6-chloro-1-methyl-5-nitro-1H-benzo[d]imidazol-2-yl)-5-fluoropiperidin-3-yl)-5-(trifluoromethyl)pyrimidin-2-amine replacing N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine in Step 3. LCMS calculated for $C_{21}H_{21}ClF_4N_7O$ (M+H)$^+$: m/z=498.1; found: 498.1.

This compound was prepared according to the procedures described in Example 101, with potassium trifluoro(methyl-d3)borate replacing 4,4,5,5-tetramethyl-2-(isopropenyl)-1,3,2-dioxaborolane in Step 2. LCMS calculated for $C_{22}H_{21}D_3F_4N_7O$ (M+H)$^+$: m/z=481.2; found: 481.2.

Example 136. N-(2-((3R,5R)-3-Fluoro-5-((5-(trifluoromethyl)pyrimidin-2-yl)amino)piperidin-1-yl)-1-methyl-6-(pyrrolidin-1-yl)-1H-benzo[d]imidazol-5-yl)acrylamide Step 1. N-((3R,5R)-5-Fluoro-1-(1-methyl-5-nitro-6-(pyrrolidin-1-yl)-1H-benzo[d]imidazol-2-yl)piperidin-3-yl)-5-(trifluoromethyl)pyrimidin-2-amine To a mixture of N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine (25 mg, 0.05 mmol) and pyrrolidine (3.4 mg, 0.05 mmol) was added potassium hydroxide (7 mg, 0.12 mmol) and DMF (1.0 ml). The reaction mixture was heated to 100° C. for 24 h and then cooled to r.t. The solvent was evaporated in vacuo and the crude material was used in the next step without further purification. LCMS calculated for $C_{22}H_{25}F_4N_8O_2$ (M+H)$^+$: m/z=509.2; found: 509.2.

Step 2. N-(2-((3R,5R)-3-Fluoro-5-((5-(trifluoromethyl)pyrimidin-2-yl)amino)piperidin-1-yl)-1-methyl-6-(pyrrolidin-1-yl)-1H-benzo[d]imidazol-5-yl)acrylamide This compound was prepared according to the procedures described in Example 141, Steps 3-4 with N-((3R,5R)-5-fluoro-1-(1-methyl-5-nitro-6-(pyrrolidin-1-yl)-1H-benzo[d]imidazol-2-yl)piperidin-3-yl)-5-(trifluoromethyl)pyrimidin-2-amine replacing N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine in Step 3. LCMS calculated for $C_{25}H_{29}F_4N_8O$ (M+H)$^+$: m/z=533.2; found: 533.2.

Example 137. N-(2-((3R,5R)-3-Fluoro-5-((5-(trifluoromethyl)pyrimidin-2-yl)amino)piperidin-1-yl)-1-methyl-6-(morpholine-4-carbonyl)-1H-benzo[d]imidazol-5-yl)acrylamide Step 1. (2-((3R,5R)-3-Fluoro-5-((5-(trifluoromethyl)pyrimidin-2-yl)amino)piperidin-1-yl)-1-methyl-5-nitro-1H-benzo[d]imidazol-6-yl)(morpholino)methanone A mixture of N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine (28 mg, 0.054 mmol) and triphenylphosphine palladium chloride (4 mg, 5.4 mol) in DMF (0.5 mL) was purged with carbon monoxide for 2 minutes, sealed, and heated to 90° C. for 16 h and then cooled to r.t. The mixture was filtered and the solvent was evaporated in vacuo. The crude material was dissolved in acetonitrile (2 mL) and N-ethyl-N-isopropylpropan-2-amine (22 μL, 0.124 mmol), morpholine (11 μL, 0.124 mmol), and 2,4,6-tripropyl-1,3,5,2,4,6-trioxatriphosphinane 2,4,6-trioxide (99 μL, 0.166 mmol, 50% wt in EtOAc) was added to this solution. The reaction mixture was allowed to stir at 22° C. for 1 h, after which the solvent was evaporated in vacuo and the crude material was used in the next step without further purification. LCMS calculated for $C_{23}H_{25}F_4N_8O_4$ (M+H)$^+$: m/z=553.2; found: 553.2.

Step 2. N-(2-((3R,5R)-3-Fluoro-5-((5-(trifluoromethyl)pyrimidin-2-yl)amino)piperidin-1-yl)-1-methyl-6-(morpholine-4-carbonyl)-1H-benzo[d]imidazol-5-yl)acrylamide This compound was prepared according to the procedures described in Example 141, Steps 3-4 with (2-((3R,5R)-3-fluoro-5-((5-(trifluoromethyl)pyrimidin-2-yl)amino)piperidin-1-yl)-1-methyl-5-nitro-1H-benzo[d]imidazol-6-yl)(morpholino)methanone replacing N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine in Step 3. LCMS calculated for $C_{26}H_{29}F_4N_8O_3$ (M+H)$^+$: m/z=577.2; found: 577.2.

Example 138. N-(2-((3R,5R)-3-Fluoro-5-((5-(trif-luoromethyl)pyrimidin-2-yl)amino)piperidin-1-yl)-1-methyl-6-(pyrrolidine-1-carbonyl)-1H-benzo[d]imi-dazol-5-yl)acrylamide This compound was prepared according to the procedures described in Example 137, with pyrrolidine replacing morpholine in Step 1. LCMS calculated for $C_{26}H_{29}F_4N_8O_2$ (M+H)$^+$: m/z=561.2; found: 561.2.

Example 139. N-(2-((3R,5R)-3-Fluoro-5-((5-(trif-luoromethyl)pyrimidin-2-yl)amino)piperidin-1-yl)-1-methyl-6-morpholino-1H-benzo[d]imidazol-5-yl) acrylamide This compound was prepared according to the procedures described in Example 136, with morpholine replacing pyrrolidine in Step 1. LCMS calculated for $C_{25}H_{29}F_4N_8O_2$ (M+H)$^+$: m/z=549.2; found: 549.2.

Example 140. N-(6-Cyano-2-((3R,5R)-3-fluoro-5-((5-(trifluoromethyl)pyrimidin-2-yl)amino)piperidin-1-yl)-1-methyl-1H-benzo[d]imidazol-5-yl)acrylam-ide Step 1. 2-((3R,5R)-3-Fluoro-5-((5-(trifluoromethyl) pyrimidin-2-yl)amino)piperidin-1-yl)-1-methyl-5-nitro-1H-benzo[d]imidazole-6-carbonitrile To a mixture of N-((3R,5R)-1-(6-bromo-1-methyl-5-ni-tro-1H-benzo[d]imidazol-2-yl)-5-fluoropiperidin-3-yl)-5-(trifluoromethyl)pyrimidin-2-amine (20 mg, 0.04 mmol), zinc cyanide (9 mg, 0.08 mmol), and Xantphos Pd G3 (4 mg, 3.8 mol) was added DMA (1.0 ml). The reaction mixture was evacuated and refilled with nitrogen, then heated to 85° C. for 18 h and then cooled to r.t. The reaction was filtered and the solvent was evaporated in vacuo. The crude material was used in the next step without further purification. LCMS calculated for $C_{19}H_{17}F_4N_8O_2$ (M+H)$^+$: m/z=465.1; found: 465.1.

Step 2. N-(6-Cyano-2-((3R,5R)-3-fluoro-5-((5-(trif-luoromethyl)pyrimidin-2-yl)amino)piperidin-1-yl)-1-methyl-1H-benzo[d]imidazol-5-yl)acrylamide This compound was prepared according to the procedures described in Example 141, Steps 3-4 with 2-((3R,5R)-3-fluoro-5-((5-(trifluoromethyl)pyrimidin-2-yl)amino)piperi-din-1-yl)-1-methyl-5-nitro-1H-benzo[d]imidazole-6-carbo-nitrile replacing N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine in Step 3. LCMS calculated for $C_{22}H_{21}F_4N_8O$ (M+H)$^+$: m/z=489.2; found: 489.2.

Example 141. N-(6-Bromo-2-((3R,5R)-3-fluoro-5-((5-(trifluoromethyl)pyrimidin-2-yl)amino)piperidin-1-yl)-1-methyl-1H-benzo[d]imidazol-5-yl)acrylam-ide Step 1. (3R,5R)-1-(6-Bromo-1-methyl-5-nitro-1H-benzo[d]imidazol-2-yl)-5-fluoropiperidin-3-amine To a mixture of 6-bromo-2-chloro-1-methyl-5-nitro-1H-benzo[d]imidazole, prepared as described in Step 1 of Example 95 (356 mg, 1.22 mmol) and tert-butyl ((3R,5R)-5-fluoropiperidin-3-yl)carbamate (267 mg, 1.224 mmol) in DMF (12.2 ml) was added N,N-diisopropylethylamine (641 μl, 3.67 mmol). The reaction mixture was heated to 100° C. for 1 h and then cooled to r.t. The reaction mixture was diluted with EtOAc and the organic phase was washed with 10% aqueous lithium chloride and brine, and was then dried over sodium sulfate. Solvents were evaporated in vacuo and the crude material was treated with a solution of 4:1 DCM/TFA (10 ml), and stirred at r.t. for 4 h. The solvents were evaporated in vacuo and the crude material was used in the next step without further purification. LCMS calculated for $C_{13}H_{16}BrFN_5O_2$ (M+H)$^+$: m/z=372.1; found 372.1.

Step 2. N-((3R,5R)-1-(6-Bromo-1-methyl-5-nitro-1H-benzo[d]imidazol-2-yl)-5-fluoropiperidin-3-yl)-5-(trifluoromethyl)pyrimidin-2-amine To a mixture of 2-chloro-5-(trifluoromethyl)pyrimidine (266 mg, 1.46 mmol) and (3R,5R)-1-(6-bromo-1-methyl-5-nitro-1H-benzo[d]imidazol-2-yl)-5-fluoropiperidin-3-amine (362 mg, 0.97 mmol) was added N,N-diisopropylethylamine (510 μl, 2.9 mmol) and DMF (5 ml). The reaction mixture was heated to 100° C. for 1 h and then cooled to r.t. Solvent was removed in vacuo and crude material was used in the next step without further purification. LCMS calculated for $C_{18}H_{17}BrF_4N_7O_2$ (M+H)$^+$: m/z=518.1; found: 518.1.

Step 3. 6-Bromo-2-((3R,5R)-3-fluoro-5-((5-(trifluoromethyl)pyrimidin-2-yl)amino)piperidin-1-yl)-1-methyl-1H-benzo[d]imidazol-5-amine

Example 142. N-(2-((R)-3-((5-cyano-4-((R)-3-(dimethylamino)pyrrolidin-1-yl)pyrimidin-2-yl)amino)piperidin-1-yl)-1-methyl-1H-benzo[d]imidazol-5-yl)acrylamide

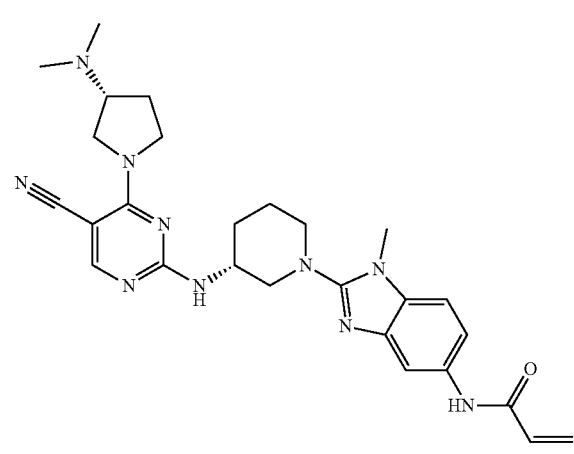 [SMILES: C=CC(=O)Nc1ccc2c(c1)nc(N1CCC[C@@H](Nc3ncc(C#N)c(N4CC[C@@H](N(C)C)C4)n3)C1)n2C]

To a reaction vial containing N-((3R,5R)-1-(6-bromo-1-methyl-5-nitro-1H-benzo[d]imidazol-2-yl)-5-fluoropiperidin-3-yl)-5-(trifluoromethyl)pyrimidin-2-amine (25 mg, 0.048 mmol), ammonium chloride (26 mg, 0.482 mmol) and zinc powder (32 mg, 0.482 mmol) was added THF (4 mL) and water (2 mL). The reaction mixture was heated to 40° C. for 1 h and then cooled to r.t. The reaction mixture was diluted with EtOAc and filtered through celite pad.

The organic layer was subsequently washed with water and brine, dried over sodium sulfate, filtered, and the solvents were evaporated in vacuo. The crude material was purified by Biotage Isolera to give the product. LCMS calculated for $C_{18}H_{19}BrF_4N_7$ (M+H)$^+$: m/z=488.1; found 488.1.

Step 4. N-(6-Bromo-2-((3R,5R)-3-fluoro-5-((5-(trifluoromethyl)pyrimidin-2-yl)amino)piperidin-1-yl)-1-methyl-1H-benzo[d]imidazol-5-yl)acrylamide To a solution of 6-bromo-2-((3R,5R)-3-fluoro-5-((5-(trifluoromethyl)pyrimidin-2-yl)amino)piperidin-1-yl)-1-methyl-1H-benzo[d]imidazol-5-amine (23 mg, 0.048 mmol) in DCM (4 ml) at 0° C. was added N,N-diisopropylethylamine (25 µl, 0.145 mmol) and acryloyl chloride (6 µl, 0.072 mmol). The reaction was allowed to stir at 0° C. for 10 min, then quenched with MeOH (2 ml) and solvents were evaporated in vacuo. The crude material was diluted with MeCN and purified by prep-LCMS (XBridge C18 column, eluting with a gradient of acetonitrile/water containing 0.1% TFA, at flow rate of 60 mL/min. LCMS calculated for $C_{21}H_{21}BrF_4N_7O$ (M+H)$^+$: m/z=542.1; found: 542.1.

Step 1. 4-((R)-3-(Dimethylamino)pyrrolidin-1-yl)-2-(((R)-1-(1-methyl-5-nitro-1H-benzo[d]imidazol-2-yl)piperidin-3-yl)amino)pyrimidine-5-carbonitrile To a mixture of 2,4-dichloropyrimidine-5-carbonitrile (51 mg, 0.30 mmol) and (R)-1-(1-methyl-5-nitro-1H-benzo[d]imidazol-2-yl)piperidin-3-amine as prepared in Step 1 of Example 37 (81 mg, 0.30 mmol) in DMF (4 mL) was added N,N-diisopropylethylamine (155 µL, 0.90 mmol). The reaction mixture was heated to 100° C. for 1 h and then cooled to r.t. Then (R)—N,N-dimethylpyrrolidin-3-amine (56 µL, 0.3 mmol) was added to the reaction mixture which was heated to 100° C. for 1 h and then cooled to r.t. The reaction mixture was diluted with EtOAc and the organic phase was washed with 10% aqueous lithium chloride and brine, and was then dried over sodium sulfate and filtered. Solvents were evaporated in vacuo and the crude material was used in the next step without further purification LCMS calculated for $C_{24}H_{31}N_{10}O_2$ (M+H)$^+$: m/z=491.3; found 491.3.

Step 2. N-(2-((R)-3-((5-Cyano-4-((R)-3-(dimethyl-amino)pyrrolidin-1-yl)pyrimidin-2-yl)amino)piperi-din-1-yl)-1-methyl-1H-benzo[d]imidazol-5-yl)acryl-amide This compound was prepared according to the procedures described in Example 37, Steps 3 and 4, with 4-((R)-3-(dimethylamino)pyrrolidin-1-yl)-2-(((R)-1-(1-methyl-5-ni-tro-1H-benzo[d]imidazol-2-yl)piperidin-3-yl)amino)py-rimidine-5-carbonitrile, as prepared in Step 1 of Example 142 replacing (R)-4-methoxy-2-((1-(1-methyl-5-nitro-1H-benzo[d]imidazol-2-yl)piperidin-3-yl)amino)pyrimidine-5-carbonitrile in Step 3. LCMS calculated for $C_{27}H_{35}N_{10}O$ $(M+H)^+$: m/z=515.3; found: 515.3.

Example 143. (R)—N-(2-(3-((5-Cyanopyrimidin-2-yl)amino)piperidin-1-yl)-1-methyl-1H-benzo[d]imi-dazol-5-yl)acrylamide This compound was prepared according to the procedures described in Example 37, with 2-chloropyrimidine-5-carbo-nitrile replacing 2-chloro-4-methoxypyrimidine-5-carboni-trile in Step 1. LCMS calculated for $C_{21}H_{23}N_8O$ $(M+H)^+$: m/z=403.2; found: 403.2.

Example 144. N-(2-((3R,5R)-3-Fluoro-5-((5-(trif-luoromethyl)pyrimidin-2-yl)amino)piperidin-1-yl)-1,4,6-trimethyl-1H-benzo[d]imidazol-5-yl)acrylamide Step 1. tert-Butyl ((3R,5R)-1-(5-amino-1,6-dim-ethyl-1H-benzo[d]imidazol-2-yl)-5-fluoropiperidin-3-yl)carbamate This compound was prepared according to the procedures described in Example 100 (Step 7), with tert-butyl ((3R,5R)-1-(1,6-dimethyl-5-nitro-1H-benzo[d]imidazol-2-yl)-5-fluoropiperidin-3-yl)carbamate replacing N-((3R,5R)-1-(1,6-dimethyl-5-nitro-1H-benzo[d]imidazol-2-yl)-5-fluoropiperidin-3-yl)-5-(trifluoromethyl)pyrimidin-2-amine. LCMS calculated for $C_{19}H_{29}FN_5O_2$ $(M+H)^+$: m/z=378.2; found: 378.2.

Step 2. tert-Butyl ((3R,5R)-1-(5-amino-4-bromo-1,6-dimethyl-1H-benzo[d]imidazol-2-yl)-5-fluoropip-eridin-3-yl)carbamate To a reaction vial containing tert-butyl ((3R,5R)-1-(5-amino-1,6-dimethyl-1H-benzo[d]imidazol-2-yl)-5-fluoropiperidin-3-yl)carbamate (385 mg, 1.02 mmol) in acetic acid (3 mL) was added bromine (163 mg, 1.02 mmol) in acetic acid (0.5 mL) slowly. The reaction mixture was stirred at r.t. for 10 min. The solvents were evaporated in vacuo. The crude material was purified by Biotage Isolera to give the desired product. LCMS calculated for $C_{19}H_{28}BrFN_5O_2$ $(M+H)^+$: m/z=456.1; found 456.2.

Step 3. tert-Butyl ((3R,5R)-1-(5-amino-1,4,6-trimethyl-1H-benzo[d]imidazol-2-yl)-5-fluoropiperidin-3-yl)carbamate The reaction vial containing tert-butyl ((3R,5R)-1-(5-amino-4-bromo-1,6-dimethyl-1H-benzo[d]imidazol-2-yl)-5-fluoropiperidin-3-yl)carbamate (70 mg, 0.153 mmol), trimethylboroxine (39 mg, 0.307 mmol), cesium carbonate (150 mg, 0.46 mmol) and [1,1'-bis(diphenylphosphino)ferrocene]-dichloropalladium(II) (22 mg, 0.031 mmol) was evacuated and backfilled with nitrogen. 1,4-Dioxane (2 mL) and water (0.4 mL) were added to the reaction mixture, which was then stirred at 100° C. for 3 h. The reaction mixture was cooled to r.t and was diluted with EtOAc. The organic layer was subsequently washed with water and brine, dried over sodium sulfate, filtered, and the solvents were evaporated in vacuo. The crude material was purified by Biotage Isolera. LCMS calculated for $C_{20}H_{31}FN_5O_2$ $(M+H)^+$: m/z=392.2; found 392.2.

Step 4. N-(2-((3R,5R)-3-Fluoro-5-((5-(trifluoromethyl)pyrimidin-2-yl)amino)piperidin-1-yl)-1,4,6-trimethyl-1H-benzo[d]imidazol-5-yl)acrylamide This compound was prepared according to the procedures described in Example 100 (Step 5-6, 8), with tert-butyl ((3R,5R)-1-(5-amino-1,4,6-trimethyl-1H-benzo[d]imidazol-2-yl)-5-fluoropiperidin-3-yl)carbamate replacing (3R,5R)-1-(1,6-dimethyl-5-nitro-1H-benzo[d]imidazol-2-yl)-5-fluoropiperidin-3-amine. LCMS calculated for $C_{23}H_{26}F_4N_7O$ $(M+H)^+$: m/z=492.2; found: 492.2.

Example 145. N-(4-Bromo-2-((3R,5R)-3-((5-cyano-pyrimidin-2-yl)amino)-5-fluoropiperidin-1-yl)-1,6-dimethyl-1H-benzo[d]imidazol-5-yl)acrylamide This compound was prepared according to the procedures described in Example 100 (Step 5-6, 8), with tert-butyl ((3R,5R)-1-(5-amino-4-bromo-1,6-dimethyl-1H-benzo[d] imidazol-2-yl)-5-fluoropiperidin-3-yl)carbamate replacing (3R,5R)-1-(1,6-dimethyl-5-nitro-1H-benzo[d]imidazol-2-yl)-5-fluoropiperidin-3-amine and 2-chloropyrimidine-5-carbonitrile replacing 2-chloro-5-(trifluoromethyl)pyrimidine. LCMS calculated for $C_{22}H_{23}BrFN_8O$ $(M+H)^+$: m/z=513.1; found: 513.1.

Example 146. N-(4-Bromo-2-((3R,5R)-3-fluoro-5-((5-(trifluoromethyl)pyrimidin-2-yl)amino)piperidin-1-yl)-1,6-dimethyl-1H-benzo[d]imidazol-5-yl)acrylamide This compound was prepared according to the procedures described in Example 100 (Step 5-6, 8), with tert-butyl ((3R,5R)-1-(5-amino-4-bromo-1,6-dimethyl-1H-benzo[d] imidazol-2-yl)-5-fluoropiperidin-3-yl)carbamate replacing (3R,5R)-1-(1,6-dimethyl-5-nitro-1H-benzo[d]imidazol-2-yl)-5-fluoropiperidin-3-amine. LCMS calculated for $C_{22}H_{23}BrF_4N_7O$ $(M+H)^+$: m/z=556.1; found: 556.1.

Example 147. N-(2-((3R,5R)-3-((5-Cyanopyrimidin-2-yl)amino)-5-hydroxypiperidin-1-yl)-1,6-dimethyl-1H-benzo[d]imidazol-5-yl)acrylamide This compound was prepared according to the procedures described in Example 94, with 2-chloropyrimidine-5-carbonitrile replacing 2-chloro-5-(trifluoromethyl)pyrimidine. LCMS calculated for $C_{22}H_{25}N_8O_2$ (M+H)$^+$: m/z=433.2; found: 433.2. $^1$H NMR (500 MHz, DMSO-$d_6$) $\delta$ 9.57 (s, 1H), 8.79 (d, J=3.0 Hz, 1H), 8.73 (d, J=3.0 Hz, 1H), 8.52 (d, J=7.7 Hz, 1H), 7.71 (s, 1H), 7.50 (s, 1H), 6.58 (dd, J=17.0, 10.2 Hz, 1H), 6.27 (dd, J=17.0, 2.0 Hz, 1H), 5.78 (dd, J=10.2, 2.0 Hz, 1H), 4.50 (m, 1H), 4.14 (m, 1H), 3.89 (dd, J=12.8, 4.0 Hz, 1H), 3.77 (s, 3H), 3.64 (dd, J=13.2, 4.3 Hz, 1H), 3.50 (dd, J=13.4, 2.3 Hz, 1H), 3.26 (dd, J=12.6, 9.2 Hz, 1H), 2.35 (s, 3H), 2.01 (m, 1H), 1.90 (m, 1H).

Example 148. N-(2-((3S,4R)-4-Hydroxy-3-((5-(trifluoromethyl)pyrimidin-2-yl)amino)piperidin-1-yl)-1,6-dimethyl-1H-benzo[d]imidazol-5-yl)acrylamide This compound was prepared according to the procedures described in Example 100 (Steps 4-8), with tert-butyl ((3S,4R)-4-hydroxypiperidin-3-yl)carbamate replacing tert-butyl ((3R,5R)-5-fluoropiperidin-3-yl)carbamate. LCMS calculated for $C_{22}H_{25}F_3N_7O_2$ (M+H)$^+$: m/z=476.2; found: 476.2.

Example 149. N-(2-((3S,4S)-4-Hydroxy-3-((5-(trifluoromethyl)pyrimidin-2-yl)amino)piperidin-1-yl)-1,6-dimethyl-1H-benzo[d]imidazol-5-yl)acrylamide This compound was prepared according to the procedures described in Example 100 (Steps 4-8), with tert-butyl ((3S,4S)-4-hydroxypiperidin-3-yl)carbamate replacing tert-butyl ((3R,5R)-5-fluoropiperidin-3-yl)carbamate. LCMS calculated for $C_{22}H_{25}F_3N_7O_2$ (M+H)$^+$: m/z=476.2; found: 476.2.

Example 150. (R)—N-(6-Cyclopropyl-1-methyl-2-(3-((5-(trifluoromethyl)pyrimidin-2-yl)amino)piperidin-1-yl)-1H-benzo[d]imidazol-5-yl)acrylamide This compound was prepared according to the procedures described in Example 95, with tert-butyl (R)-piperidin-3-ylcarbamate replacing tert-butyl ((3R,5R)-5-fluoropiperidin-3-yl)carbamate. LCMS calculated for $C_{24}H_{27}F_3N_7O$ (M+H)$^+$: m/z=486.2; found: 486.2.

Example 151. (R)—N-(2-(3-((5-Cyano-4-methoxy-pyridin-2-yl)amino)piperidin-1-yl)-1-methyl-1H-benzo[d]imidazol-5-yl)acrylamide Step 1. (R)-4-Methoxy-6-((1-(1-methyl-5-nitro-1H-benzo[d]imidazol-2-yl)piperidin-3-yl)amino)nicotinonitrile This compound was prepared according to the procedures described in Example 37, with 6-chloro-4-methoxynicotinonitrile replacing 2-chloro-4-methoxypyrimidine-5-carbonitrile in Step 2. LCMS calculated for $C_{20}H_{22}N_7O_3$ (M+H)$^+$: m/z=408.1; found 408.1.

Step 2. (R)-6-((1-(5-Amino-1-methyl-1H-benzo[d]imidazol-2-yl)piperidin-3-yl)amino)-4-methoxynicotinonitrile This compound was prepared according to the procedures described in Example 47, with (R)-4-methoxy-6-((1-(1-methyl-5-nitro-1H-benzo[d]imidazol-2-yl)piperidin-3-yl)amino)nicotinonitrile replacing 2-(2-((1S,3R)-3-((5-cyano-4-methoxypyrimidin-2-yl)amino)cyclohexyl)-5-nitro-1H-benzo[d]imidazol-1-yl)ethyl acetate in Step 5. LCMS calculated for $C_{20}H_{24}N_7O$ (M+H)$^+$: m/z=378.2; found 378.1.

Step 3. (R)—N-(2-(3-((5-Cyano-4-methoxypyridin-2-yl)amino)piperidin-1-yl)-1-methyl-1H-benzo[d]imidazol-5-yl)acrylamide This compound was prepared according to the procedures described in Example 68, with (R)-6-((1-(5-amino-1-methyl-1H-benzo[d]imidazol-2-yl)piperidin-3-yl)amino)-4-methoxynicotinonitrile replacing 6-amino-2-((1S,3R)-3-((5-bromopyrimidin-2-yl)amino)cyclohexyl)isoindolin-1-one in Step 3. LCMS calculated for $C_{23}H_{26}N_7O_2$ (M+H)$^+$: m/z=432.2; found: 432.2.

Example 152. (R)—N-(1-Methyl-2-(3-((4-(4-methylpiperazin-1-yl)-5-(trifluoromethyl)pyrimidin-2-yl)amino)piperidin-1-yl)-1H-benzo[d]imidazol-5-yl)acrylamide Step 1. (R)—N-(1-(1-Methyl-5-nitro-1H-benzo[d]imidazol-2-yl)piperidin-3-yl)-4-(4-methylpiperazin-1-yl)-5-(trifluoromethyl)pyrimidin-2-amine To a vial containing (R)-1-(1-methyl-5-nitro-1H-benzo[d]imidazol-2-yl)piperidin-3-amine (100 mg, 0.36 mmol (Example 37, Step 1)), DIPEA (190 μl, 1.09 mmol) in EtOH (2.4 ml) at 0° C. was added 2,4-dichloro-5-(trifluoromethyl)pyrimidine (87 mg, 0.40 mmol). After stirring at 0° C. for 30 min, 1-methylpiperazine (73 mg, 0.73 mmol) was added to the reaction mixture. The reaction mixture was heated to 80° C. for 1 h and then cooled to r.t. The reaction mixture was diluted with $CH_2Cl_2$ (10 mL) and the organic phase was washed with aqueous saturated sodium bicarbonate solution and extracted with $CH_2Cl_2$. The organic phase was washed with brine, dried over $MgSO_4$ and concentrated in vacuo. The obtained crude product was purified by Biotage Isolera to give the desired product as pale yellow oil. LCMS calculated for $C_{23}H_{29}F_3N_9O_2$ (M+H)$^+$: m/z=520.2; found 520.2.

Step 2. (R)-1-Methyl-2-(3-((4-(4-methylpiperazin-1-yl)-5-(trifluoromethyl)pyrimidin-2-yl)amino)piperidin-1-yl)-1H-benzo[d]imidazol-5-amine This compound was prepared according to the procedures described in Example 47, with (R)—N-(1-(1-methyl-5-nitro-1H-benzo[d]imidazol-2-yl)piperidin-3-yl)-4-(4-methylpiperazin-1-yl)-5-(trifluoromethyl)pyrimidin-2-amine replacing 2-(2-((1S,3R)-3-((5-cyano-4-methoxypyrimidin-2-yl)amino)cyclohexyl)-5-nitro-1H-benzo[d]imidazol-1-yl) ethyl acetate in Step 5. LCMS calculated for $C_{23}H_{31}F_3N_9$ (M+H)$^+$: m/z=490.3; found 490.2.

Step 3. (R)—N-(1-Methyl-2-(3-((4-(4-methylpiperazin-1-yl)-5-(trifluoromethyl)pyrimidin-2-yl)amino)piperidin-1-yl)-1H-benzo[d]imidazol-5-yl)acrylamide This compound was prepared according to the procedures described in Example 68, with (R)-1-methyl-2-(3-((4-(4-methylpiperazin-1-yl)-5-(trifluoromethyl)pyrimidin-2-yl)amino)piperidin-1-yl)-1H-benzo[d]imidazol-5-amine replacing 6-amino-2-((1S,3R)-3-((5-bromopyrimidin-2-yl)amino)cyclohexyl)isoindolin-1-one in Step 3. LCMS calculated for $C_{26}H_{33}F_3N_9O$ (M+H)$^+$: m/z=544.3; found: 544.3.

Example 153. (R)—N-(6-Ethyl-1-methyl-2-(3-((5-(trifluoromethyl)pyrimidin-2-yl)amino)piperidin-1-yl)-1H-benzo[d]imidazol-5-yl)acrylamide

Step 1. tert-Butyl (R)-(1-(1-methyl-5-nitro-6-vinyl-1H-benzo[d]imidazol-2-yl)piperidin-3-yl)carbamate A reaction vial containing tert-butyl (R)-(1-(6-bromo-1-methyl-5-nitro-1H-benzo[d]imidazol-2-yl)piperidin-3-yl) carbamate (150 mg, 0.33 mmol), vinylboronic acid pinacol ester (102 mg, 0.66 mmol), cesium carbonate (323 mg, 0.99 mmol) and [1,1'-bis(diphenylphosphino)ferrocene]-dichloropalladium(II) (24 mg, 0.033 mmol) was evacuated and backfilled with nitrogen. 1,4-Dioxane (2.5 mL) and water (0.5 mL) were added to the reaction mixture, which was then stirred at 100° C. for 3 h. The reaction mixture was cooled to r.t and was diluted with EtOAc. The organic layer was subsequently washed with water and brine, dried over sodium sulfate, filtered, and the solvents were evaporated in vacuo. The crude material was purified by Biotage Isolera. LCMS calculated for $C_{20}H_{28}N_5O_4$ (M+H)$^+$: m/z=402.2; found 402.2.

Step 2. tert-Butyl (R)-(1-(5-amino-6-ethyl-1-methyl-1H-benzo[d]imidazol-2-yl)piperidin-3-yl) carbamate To a solution tert-butyl (R)-(1-(1-methyl-5-nitro-6-vinyl-1H-benzo[d]imidazol-2-yl)piperidin-3-yl)carbamate (53 mg, 0.132 mmol) in MeOH (1 mL) and EtOAc (1 mL) was added 10% palladium on carbon (28 mg, 0.026 mmol). The reaction mixture was stirred under an atmosphere of hydrogen for 1 h. The reaction mixture was diluted with Et$_2$O and filtered through a plug of celite and the solvent was evaporated in vacuo. The crude material was used in the next step without further purification. LCMS calculated for $C_{20}H_{32}N_5O_2$ (M+H)$^+$: m/z=374.3; found 374.3.

Step 3. (R)—N-(6-Ethyl-1-methyl-2-(3-((5-(trifluoromethyl)pyrimidin-2-yl)amino)piperidin-1-yl)-1H-benzo[d]imidazol-5-yl)acrylamide This compound was prepared according to the procedures described in Example 100 (Steps 5-6 and 8), with tert-butyl (R)-(1-(5-amino-6-ethyl-1-methyl-1H-benzo[d]imidazol-2-yl)piperidin-3-yl)carbamate replacing tert-butyl ((3R,5R)-1-(1,6-dimethyl-5-nitro-1H-benzo[d]imidazol-2-yl)-5-fluoropiperidin-3-yl)carbamate. LCMS calculated for $C_{23}H_{27}F_3N_7O$ (M+H)$^+$: m/z=474.2; found: 474.2.

Example 154. (R)—N-(6-Isopropyl-1-methyl-2-(3-((5-(trifluoromethyl)pyrimidin-2-yl)amino)piperidin-1-yl)-1H-benzo[d]imidazol-5-yl)acrylamide This compound was prepared according to the procedures described in Example 101, with tert-butyl (R)-piperidin-3-ylcarbamate replacing tert-butyl ((3R,5R)-5-fluoropiperidin-3-yl)carbamate. LCMS calculated for $C_{24}H_{29}F_3N_7O$ (M+H)$^+$: m/z=488.2; found: 488.2.

Example 155. (R)—N-(6-Isopropyl-1,4-dimethyl-2-(3-((5-(trifluoromethyl)pyrimidin-2-yl)amino)piperidin-1-yl)-1H-benzo[d]imidazol-5-yl)acrylamide

Step 1. (R)-1,4-Dimethyl-6-(prop-1-en-2-yl)-2-(3-((5-(trifluoromethyl)pyrimidin-2-yl)amino)piperidin-1-yl)-1H-benzo[d]imidazol-5-amine A reaction vial containing (R)-6-bromo-1,4-dimethyl-2-(3-((5-(trifluoromethyl)pyrimidin-2-yl)amino)piperidin-1-yl)-1H-benzo[d]imidazol-5-amine (20 mg, 0.041 mmol, Example 103, Step 4), 4,4,5,5-tetramethyl-2-(isopropenyl)-1,3,2-dioxaborolane (14 mg, 0.083 mmol), cesium carbonate (40 mg, 0.124 mmol), [1,1'-bis(diphenylphosphino)ferrocene]dichloropalladium(II) (3 mg, 0.004 mmol) was evacuated and backfilled with nitrogen. 1,4-Dioxane (0.3 mL) and water (0.06 mL) were added to the reaction mixture, which was then stirred at 100° C. for 2 h. The reaction mixture was cooled to r.t and was diluted with EtOAc. The organic layer was subsequently washed with water and brine, dried over sodium sulfate, filtered, and the solvents were evaporated in vacuo. The crude material was purified by Biotage Isolera. LCMS calculated for $C_{22}H_{27}F_3N_7$ (M+H)$^+$: m/z=446.2; found 446.2.

Step 2. (R)-6-Isopropyl-1,4-dimethyl-2-(3-((5-(trifluoromethyl)pyrimidin-2-yl)amino)piperidin-1-yl)-1H-benzo[d]imidazol-5-amine To a solution of (R)-1,4-dimethyl-6-(prop-1-en-2-yl)-2-(3-((5-(trifluoromethyl)pyrimidin-2-yl)amino)piperidin-1-yl)-1H-benzo[d]imidazol-5-amine (7 mg, 0.016 mmol) in MeOH (0.5 mL) and EtOAc (0.5 mL) was added 10% palladium on carbon (8 mg, 0.007 mmol). The reaction mixture was stirred under an atmosphere of hydrogen for 1 h. The reaction mixture was diluted with Et$_2$O and filtered through a plug of celite and the solvent was evaporated in vacuo. The crude material was used in the next step without further purification. LCMS calculated for $C_{22}H_{29}F_3N_7$ (M+H)$^+$: m/z=448.2; found 448.2.

Step 3. (R)—N-(6-Isopropyl-1,4-dimethyl-2-(3-((5-(trifluoromethyl)pyrimidin-2-yl)amino)piperidin-1-yl)-1H-benzo[d]imidazol-5-yl)acrylamide This compound was prepared according to the procedures described in Example 100, (R)-6-isopropyl-1,4-dimethyl-2-(3-((5-(trifluoromethyl)pyrimidin-2-yl)amino)piperidin-1-yl)-1H-benzo[d]imidazol-5-amine replacing 2-((3R,5R)-3-fluoro-5-((5-(trifluoromethyl)-pyrimidin-2-yl)amino)piperidin-1-yl)-1,6-dimethyl-1H-benzo[d]imidazol-5-amine in Step 8. LCMS calculated for $C_{25}H_{31}F_3N_7O$ (M+H)$^+$: m/z=502.3; found: 502.3.

Example 156. (R)—N-(1,4-Dimethyl-2-(3-((5-(trif-luoromethyl)pyrimidin-2-yl)amino)piperidin-1-yl)-1H-benzo[d]imidazol-5-yl)acrylamide This compound was prepared according to the procedures described in Example 100, with (R)-1,4-dimethyl-2-(3-((5-(trifluoromethyl)pyrimidin-2-yl)amino)piperidin-1-yl)-1H-benzo[d]imidazol-5-amine (Example 103, Step 3) replacing 2-((3R,5R)-3-fluoro-5-((5-(trifluoromethyl)-pyrimidin-2-yl)amino)piperidin-1-yl)-1,6-dimethyl-1H-benzo[d]imida-zol-5-amine in Step 8. LCMS calculated for $C_{22}H_{25}F_3N_7O$ (M+H)$^+$: m/z=460.2; found: 460.2.

Example 157. N-(2-((3R,5R)-3-((5-Cyano-4-(dim-ethylamino)pyrimidin-2-yl)amino)-5-fluoropiperi-din-1-yl)-1,6-dimethyl-1H-benzo[d]imidazol-5-yl)acrylamide Step 1. 4-Chloro-2-(((3R,5R)-1-(1,6-dimethyl-5-nitro-1H-benzo[d]imidazol-2-yl)-5-fluoropiperidin-3-yl)amino)pyrimidine-5-carbonitrile A vial containing mixture of 2,4-dichloropyrimidine-5-carbonitrile (100 mg, 0.58 mmol) in tert-butanol (1 mL) and DCE (1 mL) under nitrogen was cooled to 0° C. To this a 0.5M solution of zinc(II) chloride (1.4 mL, 0.69 mmol) in diethyl ether was added and the resulting mixture was purged with nitrogen and stirred at 0° C. for 1 hour. To the reaction mixture was then added (3R,5R)-1-(1,6-dimethyl-5-nitro-1H-benzo[d]imidazol-2-yl)-5-fluoropiperidin-3-amine (177 mg, 0.58 mmol, Example 100, Step 5), followed by dropwise addition of a solution of N,N-diisopropyleth-ylamine (150 µl, 0.862 mmol). The reaction mixture was then allowed to warm to r.t. before heating to 60° C. overnight. Upon completion, the reaction mixture was concentrated in vacuo, and the crude material was purified by Biotage Isolera to give the desired product. LCMS calculated for $C_{19}H_{19}ClFN_8O_2$ (M+H)$^+$: m/z=445.1; found 445.1.

Step 2. 2-(((3R,5R)-1-(1,6-Dimethyl-5-nitro-1H-benzo[d]imidazol-2-yl)-5-fluoropiperidin-3-yl)amino)-4-(dimethylamino)pyrimidine-5-carbonitrile To a vial was added 4-chloro-2-(((3R,5R)-1-(1,6-dim-ethyl-5-nitro-1H-benzo[d]imidazol-2-yl)-5-fluoropiperidin-3-yl)amino)pyrimidine-5-carbonitrile (50 mg, 0.11 mmol), N,N-diisopropylethylamine (40 uL, 0.23 mmol), dimethyl-amine (2 M in THF, 84 µL, 0.17 mmol) and NMP (0.5 mL). This was heated to 100° C. for 1 h. Upon completion, the reaction was cooled to 0° C. and 5 mL of ice cold water was added. This was left to stir at 0° C. for 20 min, subsequently the mixture was filtered, and the resulting precipitate was washed with hexane, collected and used directly for the following step without further purification. LCMS calculated for $C_{21}H_{25}FN_9O_2$ (M+H)$^+$: m/z=454.2; found 454.2.

Step 3. 2-(((3R,5R)-1-(5-Amino-1,6-dimethyl-1H-benzo[d]imidazol-2-yl)-5-fluoropiperidin-3-yl)amino)-4-(dimethylamino)pyrimidine-5-carbonitrile To a reaction vial containing 2-(((3R,5R)-1-(1,6-dimethyl-5-nitro-1H-benzo[d]imidazol-2-yl)-5-fluoropiperidin-3-yl)amino)-4-(dimethylamino)pyrimidine-5-carbonitrile (50 mg, 0.11 mmol), iron powder (25 mg, 0.44 mmol), and ammonium chloride (12 mg, 0.22 mmol) was added THF (0.5 mL) and ethanol (0.25 mL). The reaction mixture was heated to 60° C. for 1 h and then cooled to r.t. The reaction mixture was diluted with EtOAc and filtered through a Celite pad. The organic layer was subsequently washed with water and brine, dried over sodium sulfate, filtered, and the solvent was evaporated in vacuo. The crude material was used directly for the next step. LCMS calculated for $C_{21}H_{27}FN_9$ (M+H)+: m/z=424.2; found 424.2.

Step 4. N-(2-((3R,5R)-3-((5-Cyano-4-(dimethylamino)pyrimidin-2-yl)amino)-5-fluoropiperidin-1-yl)-1,6-dimethyl-1H-benzo[d]imidazol-5-yl)acrylamide To a 2-(((3R,5R)-1-(5-amino-1,6-dimethyl-1H-benzo[d]imidazol-2-yl)-5-fluoropiperidin-3-yl)amino)-4-(dimethylamino)pyrimidine-5-carbonitrile (20 mg, 0.05 mmol) in DCM (0.5 mL) at −20° C. was added N,N-diisopropylethylamine (20 μL, 0.115 mmol) and acryloyl chloride (5 μL, 0.07 mmol). The reaction mixture was allowed to stir at −20° C. for 10 min, then quenched with water. The reaction mixture was diluted with DCM and the organic layer was subsequently washed with water and brine, dried over sodium sulfate, filtered, and the solvents were evaporated in vacuo. The resulting material was diluted with MeCN and purified by prep-LCMS (XBridge C18 column, eluting with a gradient of acetonitrile/water containing 0.1% TFA, at flow rate of 60 mL/min. LCMS calculated for $C_{24}H_{29}FN_9O$ (M+H)+: m/z=478.2; found: 478.3.

Example 158. N-(2-((3R,5R)-3-((5-Cyano-4-(methylamino)pyrimidin-2-yl)amino)-5-fluoropiperidin-1-yl)-1,6-dimethyl-1H-benzo[d]imidazol-5-yl)acrylamide This compound was prepared according to the procedures described in Example 157, with methylamine (2 M in THF) replacing dimethylamine (2 M in THF) in Step 2. LCMS calculated for $C_{23}H_{27}FN_9O$ (M+H)+: m/z=464.2; found: 464.3.

Example 159. (N-(2-((3R,5R)-3-Fluoro-5-((5-(trifluoromethyl)pyridin-2-yl)amino)piperidin-1-yl)-1,6-dimethyl-1H-benzo[d]imidazol-5-yl)acrylamide This compound was prepared according to the procedures described in Example 100, with Step 6 heated to 120° C. and 2-chloro-5-(trifluoromethyl)pyridine replacing 2-chloro-5-(trifluoromethyl)pyrimidine in Step 6. LCMS calculated for $C_{23}H_{25}F_4N_6O$ (M+H)+: m/z=477.2; found: 477.2.

Example 160. N-(2-((3R,5R)-3-((5-(Difluoromethyl)pyrimidin-2-yl)amino)-5-fluoropiperidin-1-yl)-1,6-dimethyl-1H-benzo[d]imidazol-5-yl)acrylamide

Step 1. 2-Chloro-5-(difluoromethyl)pyrimidine

A vial containing 2-chloropyrimidine-5-carbaldehyde (200 mg, 1.4 mmol) and DCE (7 mL) was cooled to 0° C. To this DAST (0.37 mL, 2.8 mmol) was added dropwise and the reaction was left to stir at 0° C. for 20 min. Upon completion (determined by absence of starting aldehyde by TLC [7:3 hexanes:ethyl acetate]) the reaction mixture was concentrated in vacuo, this crude residue was used in the next step without further purification. Diagnostic crude NMR peaks: $^1$H NMR (400 MHz, Chloroform-d) δ 8.81 (s, 2H), 6.80 (t, J=55.1 Hz, 1H); $^{19}$F NMR (376 MHz, Chloroform-d) δ -114.31.

Step 2. N-(2-((3R,5R)-3-((5-(Difluoromethyl)pyrimidin-2-yl)amino)-5-fluoropiperidin-1-yl)-1,6-dimethyl-1H-benzo[d]imidazol-5-yl)acrylamide This compound was prepared according to the procedures described in Example 100, with Step 6 heated to 100° C. and 2-chloro-5-(difluoromethyl)pyrimidine replacing 2-chloro-5-(trifluoromethyl)pyrimidine in Step 6. LCMS calculated for $C_{22}H_{25}F_3N_7O$ (M+H)$^+$: m/z=460.2; found: 460.3.

Example 161. N-(2-((3R,5R)-3-((5-Cyano-4-ethylpyrimidin-2-yl)amino)-5-fluoropiperidin-1-yl)-1,6-dimethyl-1H-benzo[d]imidazol-5-yl)acrylamide

Step 1. 2-(((3R,5R)-1-(1,6-Dimethyl-5-nitro-1H-benzo[d]imidazol-2-yl)-5-fluoropiperidin-3-yl)amino)-4-vinylpyrimidine-5-carbonitrile To a vial was added 4-chloro-2-(((3R,5R)-1-(1,6-dimethyl-5-nitro-1H-benzo[d]imidazol-2-yl)-5-fluoropiperidin-3-yl)amino)pyrimidine-5-carbonitrile (100 mg, 0.23 mmol, Example 157, Step 1), PdXphos G2 (18 mg, 0.02 mmol), and $Na_2CO_3$ (72 mg, 0.67 mmol). This was evacuated and backfilled with nitrogen 3 times. Subsequently THF (0.5 mL), water (50 μL) and 4,4,5,5-tetramethyl-2-vinyl-1,3,2-dioxaborolane (57 μl, 0.38 mmol) were added. The vial was sealed and heated to 80° C. for 1 h. Upon completion, the reaction was diluted with DCM, filtered through Celite and concentrated in vacuo. The crude material was purified by Biotage Isolera to give the desired product. LCMS calculated for $C_{21}H_{22}FN_8O_2$ (M+H)$^+$: m/z=437.2; found 437.2.

Step 2. N-(2-((3R,5R)-3-((5-Cyano-4-ethylpyrimidin-2-yl)amino)-5-fluoropiperidin-1-yl)-1,6-dimethyl-1H-benzo[d]imidazol-5-yl)acrylamide This compound was prepared according to the procedures described in Example 157, Steps 3-4 with 2-(((3R,5R)-1-(1, 6-dimethyl-5-nitro-1H-benzo[d]imidazol-2-yl)-5-fluoropiperidin-3-yl)amino)-4-vinylpyrimidine-5-carbonitrile replacing 2-(((3R,5R)-1-(1,6-dimethyl-5-nitro-1H-benzo[d]imidazol-2-yl)-5-fluoropiperidin-3-yl)amino)-4-(dimethylamino)pyrimidine-5-carbonitrile in Step 3. Note: the vinyl group was reduced in Step 3. LCMS calculated for $C_{24}H_{28}FN_8O$ (M+H)$^+$: m/z=463.2; found: 463.3. $^1$H NMR (600 MHz, DMSO-d$_6$, 343K) δ 9.35 (s, 1H), 8.64 (s, 1H), 8.26 (d, J=7.7 Hz, 1H), 7.60 (s, 1H), 7.37 (s, 1H), 6.54 (d, J=16.8 Hz, 1H), 6.26 (dd, J=17.0, 2.0 Hz, 1H), 5.74 (dd, J=10.3, 2.0 Hz, 1H), 5.18 (d, J=46.4 Hz, 1H), 4.51 (s, 1H), 3.95-3.84 (m, 2H), 3.72 (s, 3H), 3.51 (m, 1H), 3.13 (t, J=11.2 Hz, 1H), 2.81-2.70 (m, 2H), 2.34 (s, 3H), 2.10-1.94 (m, 1H), 1.25 (t, J=7.6 Hz, 3H).

Example 162. N-(2-((3R,5R)-3-((5-Cyanothiazol-2-yl)amino)-5-fluoropiperidin-1-yl)-1,6-dimethyl-1H-benzo[d]imidazol-5-yl)acrylamide This compound was prepared according to the procedures described in Example 100, with Step 6 heated to 100° C. and 2-chlorothiazole-5-carbonitrile replacing 2-chloro-5-(trifluoromethyl)pyrimidine in Step 6. LCMS calculated for $C_{21}H_{23}FN_7OS$ (M+H)$^+$: m/z=440.2; found: 440.2.

Example 163. N-(2-((3R,5R)-3-((5-Cyanopyridin-2-yl)amino)-5-fluoropiperidin-1-yl)-1,6-dimethyl-1H-benzo[d]imidazol-5-yl)acrylamide This compound was prepared according to the procedures described in Example 100, with Step 6 heated to 100° C. and 6-fluoronicotinonitrile replacing 2-chloro-5-(trifluoromethyl)pyrimidine in Step 6. LCMS calculated for $C_{23}H_{25}FN_7O$ (M+H)$^+$: m/z=434.2; found: 434.2.

Example 164. N-(2-((3R,5R)-3-((5-Cyano-4-methylpyrimidin-2-yl)amino)-5-fluoropiperidin-1-yl)-1,6-dimethyl-1H-benzo[d]imidazol-5-yl)acrylamide This compound was prepared according to the procedures described in Example 161, with trimethylboroxine replacing 4,4,5,5-tetramethyl-2-vinyl-1,3,2-dioxaborolane in Step 1. LCMS calculated for $C_{23}H_{26}FN_8O$ (M+H)$^+$: m/z=449.2; found: 449.2.

Example 165. N-(1-Methyl-2-((R)-3-((5-(trifluoromethyl)pyrimidin-2-yl)amino)piperidin-1-yl)-1H-benzo[d]imidazol-5-yl)-N-(tetrahydrofuran-3-yl)acrylamide

Step 1. tert-Butyl (R)-(1-(1-methyl-5-nitro-1H-benzo[d]imidazol-2-yl)piperidin-3-yl)carbamate To a vial containing tert-butyl (R)-piperidin-3-ylcarbamate (218 mg, 1.087 mmol) and 2-chloro-1-methyl-5-nitro-1H-benzo[d]imidazole (230 mg, 1.087 mmol) in DMSO (1.0 mL) was added DIPEA (230 μL, 1.30 mmol). The reaction mixture was heated to 100° C. for 1 h and then cooled to r.t. The reaction mixture was diluted with $CH_2Cl_2$ (10 mL) and the organic phase was washed with aqueous saturated sodium bicarbonate solution and extracted with $CH_2Cl_2$. The organic phase was washed with brine, dried over $MgSO_4$ and concentrated in vacuo. The obtained crude product was purified by Biotage Isolera to give the desired product as pale yellow oil. LCMS calculated for $C_{18}H_{26}N_5O_4$ (M+H)$^+$: m/z=376.2; found 376.2.

Step 2. tert-Butyl (R)-(1-(5-amino-1-methyl-1H-benzo[d]imidazol-2-yl)piperidin-3-yl)carbamate This compound was prepared according to the procedures described in Example 47, with tert-butyl (R)-(1-(1-methyl-5-nitro-1H-benzo[d]imidazol-2-yl)piperidin-3-yl)carbamate replacing 2-(2-((1S,3R)-3-((5-cyano-4-methoxypyrimidin-2-yl)amino)cyclohexyl)-5-nitro-1H-benzo[d]imidazol-1-yl) ethyl acetate in Step 5. LCMS calculated for $C_{11}H_{28}N_5O_2$ (M+H)$^+$: m/z=346.2; found: 346.1.

Step 3. tert-Butyl ((3R)-1-(1-methyl-5-((tetrahydrofuran-3-yl)amino)-1H-benzo[d]imidazol-2-yl)piperidin-3-yl)carbamate To a via containing tert-butyl (R)-(1-(5-amino-1-methyl-1H-benzo[d]imidazol-2-yl)piperidin-3-yl)carbamate (60 mg, 0.174 mmol) and dihydrofuran-3(2H)-one (30 mg, 0.347 mmol) in $CH_2Cl_2$ was added AcOH (1.0 μl, 0.017 mmol). After stirring at r.t. for 1 h, sodium cyanoborohydride (33 mg, 0.521 mmol) was added to the reaction mixture. After stirring at r.t. for 16 h, the reaction mixture was diluted with $CH_2Cl_2$ (3 mL) and the organic phase was washed with aqueous saturated sodium bicarbonate solution and extracted with $CH_2Cl_2$. The organic phase was washed with brine, dried over $MgSO_4$ and concentrated in vacuo. The obtained crude product was used in the next step without further purification. LCMS calculated for $C_{22}H_{34}N_5O_3$ (M+H)$^+$: m/z=416.3; found: 416.3.

Step 4. N-(2-((R)-3-Aminopiperidin-1-yl)-1-methyl-1H-benzo[d]imidazol-5-yl)-N-(tetrahydrofuran-3-yl) acrylamide This compound was prepared according to the procedures described in Intermediate D, with tert-butyl ((3R)-1-(1-methyl-5-((tetrahydrofuran-3-yl)amino)-1H-benzo[d]imidazol-2-yl)piperidin-3-yl)carbamate replacing tert-butyl ((1R, 3S)-3-(6-amino-1-oxoisoindolin-2-yl)cyclohexyl)carbamate in Step 3. LCMS calculated for $C_{20}H_{28}N_5O_2$ (M+H)$^+$: m/z=370.2; found: 370.2.

Step 5. N-(1-Methyl-2-((R)-3-((5-(trifluoromethyl) pyrimidin-2-yl)amino)piperidin-1-yl)-1H-benzo[d] imidazol-5-yl)-N-(tetrahydrofuran-3-yl)acrylamide To a vial containing 2-((R)-3-aminopiperidin-1-yl)-1-methyl-1H-benzo[d]imidazol-5-yl)-N-(tetrahydrofuran-3-yl)acrylamide (30 mg, 0.081 mmol) and DIPEA (43 μL, 0.244 mmol) in EtOH (0.5 mL) was added 2-chloro-5-(trifluoromethyl)pyrimidine (16 mg, 0.089 mmol). After stirring at 40° C. for 1 h, the reaction mixture was diluted with CH$_3$CN and water and purified by prep-LCMS (XBridge C18 column, eluting with a gradient of acetonitrile/water containing 0.1% TFA, at flow rate of 60 mL/min). LCMS calculated for $C_{25}H_{29}F_3N_7O_2$ (M+H)$^+$: m/z=516.2; found: 516.2.

Example 166. (R)—N-(6-Methoxy-1-methyl-2-(3-((5-(trifluoromethyl)pyrimidin-2-yl)amino)piperidin-1-yl)-1H-benzo[d]imidazol-5-yl)acrylamide

Step 1. 4-Bromo-5-methoxy-N$^1$-methylbenzene-1,2-diamine

To a vial containing 1-bromo-4-fluoro-2-methoxy-5-nitrobenzene (500 mg, 2.0 mmol) and potassium carbonate (553 mg, 4.0 mmol) in acetonitrile (6.7 ml) was added methanamine solution (1.5 ml, 3.0 mmol, 2.0 M in THF). The reaction mixture was heated to 80° C. for 16 h and then cooled to r.t. The reaction mixture was diluted with acetonitrile and filtered through celite pad. The filtrate was concentrated in vacuo. To the obtained crude product in THF (4.0 mL) and water (2.0 mL) was added ammonia hydrochloride (1.07 g, 20.0 mmol) and zinc (1.31 g, 1.251 mmol). After heating at 40° C. for 1 h, the reaction mixture was filtered and washed with CH$_2$Cl$_2$. The organic phase was separated and washed with brine, dried over MgSO4, and concentrated in vacuo. The obtained crude product was used in the next step without further purification. LCMS calculated for $C_8H_{12}BrN_2O$ (M+H)$^+$: m/z=231.0/233.0; found 231.1/233.0.

Step 2. 5-Bromo-6-methoxy-1-methyl-1,3-dihydro-2H-benzo[d]imidazol-2-one

This compound was prepared according to the procedures described in Example 100, with 4-bromo-5-methoxy-N$^1$-methylbenzene-1,2-diamine replacing N$^1$,5-dimethyl-4-nitrobenzene-1,2-diamine in Step 2. LCMS calculated for $C_9H_{10}BrN_2O_2$ (M+H)$^+$: m/z=257.0/259.0; found 257.0/259.1.

Step 3. 5-Bromo-2-chloro-6-methoxy-1-methyl-1H-benzo[d]imidazole

This compound was prepared according to the procedures described in Example 100, with 5-bromo-6-methoxy-1-methyl-1,3-dihydro-2H-benzo[d]imidazol-2-one replacing 1,6-dimethyl-5-nitro-1,3-dihydro-2H-benzo[d]imidazol-2-one in Step 3. LCMS calculated for $C_9H_9BrClN_2O$ (M+H)$^+$: m/z=276.9; found 277.0.

Step 4. (R)-1-(5-Bromo-6-methoxy-1-methyl-1H-benzo[d]imidazol-2-yl)piperidin-3-amine To a vial containing 5-bromo-2-chloro-6-methoxy-1-methyl-1H-benzo[d]imidazole (210 mg, 0.76 mmol) and tert-butyl (R)-piperidin-3-ylcarbamate (183 mg, 0.92 mmol) in DMSO (0.76 ml) was added DIPEA (400 µl, 2.29 mmol). The reaction mixture was heated to 130° C. for 16 h and then cooled to r.t. The reaction mixture was diluted with CH$_2$Cl$_2$ (10 mL) and the organic phase was washed with aqueous saturated sodium bicarbonate solution and extracted with CH$_2$Cl$_2$. The organic phase was washed with brine, dried over MgSO$_4$ and concentrated in vacuo. The obtained crude product was redissolved in CH$_2$Cl$_2$ (1.0 mL) and TFA (1.0 mL). After stirring at 40° C. for 1 h, the reaction mixture was concentrated in vacuo. The crude material was redissolved in CH$_2$Cl$_2$ (5 mL) and the pH of the mixture was adjusted to ~10 with ammonia aqueous solution and then extracted into CH$_2$Cl$_2$. The organic phase was washed with brine, dried over MgSO$_4$, and concentrated in vacuo. The obtained crude product was used in the next step without further purification. LCMS calculated for C$_{14}$H$_{20}$BrN$_4$O (M+H)$^+$: m/z=339.1/341.1; found: 339.1/341.1.

Step 5. (R)—N-(1-(5-Bromo-6-methoxy-1-methyl-1H-benzo[d]imidazol-2-yl)piperidin-3-yl)-5-(trifluoromethyl)pyrimidin-2-amine This compound was prepared according to the procedures described in Example 72, with (R)-1-(5-bromo-6-methoxy-1-methyl-1H-benzo[d]imidazol-2-yl)piperidin-3-amine replacing (1R,3S)-3-(5-bromo-1-methyl-1H-benzo[d]imidazol-2-yl)cyclohexan-1-amine in Step 3. LCMS calculated for C$_{19}$H$_{21}$BrF$_3$N$_6$O (M+H)$^+$: m/z=485.1/487.1; found: 485.1/487.1.

Step 6. (R)-6-Methoxy-1-methyl-2-(3-((5-(trifluoromethyl)pyrimidin-2-yl)amino)piperidin-1-yl)-1H-benzo[d]imidazol-5-amine This compound was prepared according to the procedures described in Example 69, with (R)—N-(1-(5-bromo-6-methoxy-1-methyl-1H-benzo[d]imidazol-2-yl)piperidin-3-yl)-5-(trifluoromethyl)pyrimidin-2-amine replacing 2-(((1R,3S)-3-(4-bromo-1H-benzo[d]imidazol-1-yl)cyclohexyl)amino)pyrimidine-5-carbonitrile in Step 6. LCMS calculated for C$_{19}$H$_{23}$F$_3$N$_7$O (M+H)$^+$: m/z=422.2; found: 422.2.

Step 7. (R)—N-(6-Methoxy-1-methyl-2-(3-((5-(trifluoromethyl)pyrimidin-2-yl)amino)piperidin-1-yl)-1H-benzo[d]imidazol-5-yl)acrylamide This compound was prepared according to the procedures described in Example 68, with (R)-6-methoxy-1-methyl-2-(3-((5-(trifluoromethyl)pyrimidin-2-yl)amino)piperidin-1-yl)-1H-benzo[d]imidazol-5-amine replacing 6-amino-2-((1S,3R)-3-((5-bromopyrimidin-2-yl)amino)cyclohexyl)isoindolin-1-one in Step 3. LCMS calculated for C$_{22}$H$_{25}$F$_3$N$_7$O$_2$ (M+H)$^+$: m/z=476.2; found: 476.2.

Example A1. CDK Enzymatic Assays

The following activity of the CDK enzymes in complex with their respective cyclins we assayed: CDK1 complexed with Cyclin B1; CDK2 complexed with Cyclin E1; CDK4 complexed with Cyclin D1; CDK6 complexed with Cyclin D1; CDK6 complexed with Cyclin D3; CDK9 complexed with Cyclin T1; CDK7 complexed with Cyclin H/MAT1; CDK2 complexed with Cyclin A2; CDK5 complexed with p35; CDK12 complexed with Cyclin K; CDK13 complexed with Cyclin K. These in vitro enzyme activity are assayed using homogeneous time-resolved energy transfer (HTRF), which measures phosphorylation of a peptide substrate. The LANCER Ultra kinase assay (PerkinElmer) uses a ULight™-labeled EIF4E-binding protein 1 (THR37/46) peptide (DYSTTPGGTLFSTTPGTRI (SEQ ID NO: 1)) substrate and a Europium-labeled anti-phospho-4E-BP1 antibody (CDK2, CDK1, CDK4, CDK6, CDK9, CDK12, CDK13) or ULight™-labeled Myelin Basic Protein peptide (VTPRTPPP (SEQ ID NO: 2)) substrate and a Europium-labeled anti-phospho-MBP antibody (CDK7). Each CDK enzyme activity assays utilized human CDK co-expressed as N-terminal GST-tagged protein with its full length cyclin partner using a baculovirus expression system.

Enzyme was pre-incubated with compounds for 30 minutes (CDK1,2,4,6,9) or 60 minutes (CDK7, CDK12, CDK13) prior to addition of ATP and Ulight-peptide (1 mM and 50 nM final, respectively), in assay buffer containing 50 mM HEPES pH 7.5, 1 mM EGTA, 10 mM MgCl$_2$, 2 mM DTT, 0.05 mg/mL BSA, and 0.01% Tween 20. The reaction was then incubated for 60-90 minutes at room temperature. The reactions were stopped by the addition of EDTA and Europium labeled antibody, for a final concentration of 15 mM and 1.0-1.5 nM, respectively. HTRF signals were read after 15-120 minutes. A ratio of fluorescence transferred to the labeled substrate (665 nm) relative to fluorescence of the Europium donor (620 nm) represents the extent of phosphorylation. Ratios for treated wells were normalized to DMSO only (100% activity) and no enzyme (0% activity) controls. Normalized data was analyzed using a three or four parameter dose response curve to determine $IC_{50}$ for each compound and are shown in Table A. Control reference inhibitors were included on each plate.

TABLE A

| Ex. No. | CDK12 $IC_{50}$ (nM) |
|---|---|
| 1 | + |
| 2 | + |
| 3 | + |
| 4 | +++ |
| 5 | + |
| 6 | + |
| 7 | + |
| 8 | +++ |
| 9 | + |
| 10 | + |
| 11 | ++ |
| 12 | + |
| 13 | ++ |
| 14 | + |
| 15 | +++ |
| 16 | ++ |
| 17 | + |
| 18 | + |
| 19 | + |
| 20 | ++ |
| 21 | ++ |
| 22 | + |
| 23 | + |
| 24 | + |
| 25 | ++ |
| 26 | +++ |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | +++ |
| 40 | + |
| 41 | + |
| 42 | ++ |
| 43 | + |
| 44 | + |
| 45 | + |
| 46 | + |
| 47 | + |
| 48 | + |
| 49 | + |
| 50 | + |
| 51 | ++ |
| 52 | + |
| 53 | ++ |
| 54 | ++ |
| 55 | + |
| 56 | ++ |
| 57 | ++ |
| 58 | + |

TABLE A-continued

| Ex. No. | CDK12 $IC_{50}$ (nM) |
|---|---|
| 59 | + |
| 60 | ++ |
| 61 | + |
| 62 | + |
| 63 | + |
| 64 | +++ |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | ++ |
| 85 | + |
| 88 | + |
| 89 | + |
| 90 | + |
| 91 | + |
| 92 | + |
| 93 | + |
| 95 | + |
| 97 | + |
| 98 | + |
| 99 | + |
| 101 | + |
| 103 | + |
| 109 | + |

+ refers to $IC_{50}$ of <50 nM
++ refers to $IC_{50}$ of ≥50 nM to ≤500 nM
+++ refers to >500 nM Example A2. Alternative CDK Enzymatic Assays The following activity of the CDK enzymes in complex with their respective cyclins we assayed: CDK1 complexed with Cyclin B1; CDK2 complexed with Cyclin E1; CDK4 complexed with Cyclin D1; CDK6 complexed with Cyclin D1; CDK6 complexed with Cyclin D3; CDK9 complexed with Cyclin T1; CDK7 complexed with Cyclin H/MAT1; CDK2 complexed with Cyclin A2; CDK5 complexed with p35; CDK12 complexed with Cyclin K; CDK13 complexed with Cyclin K. These in vitro enzyme activity are assayed using homogeneous time-resolved energy transfer (HTRF), which measures phosphorylation of a peptide substrate. The LANCER Ultra kinase assay (PerkinElmer) uses a ULight™-labeled EIF4E-binding protein 1 (THR37/46) peptide (DYSTTPGGTLFSTTPGTRI (SEQ ID NO: 1)) substrate and a Europium-labeled anti-phospho-4E-BP1 antibody (CDK2, CDK1, CDK4, CDK6, CDK9, CDK12, CDK13) or ULight™-labeled Myelin Basic Protein peptide (VTPRTPPP (SEQ ID NO: 2)) substrate and a Europium-labeled anti-phospho-MBP antibody (CDK7). Each CDK enzyme activity assays utilized human CDK co-expressed as N-terminal GST-tagged protein with its full length cyclin partner using a baculovirus expression system.

Enzyme was pre-incubated with compounds and 1 mM ATP for 60 minutes (CDK 1, 2, 4, 6, 9, 7, 12, 13) prior to the addition of ATP and Ulight-peptide (1 mM and 50 nM final, respectively), in assay buffer containing 50 mM HEPES pH 7.5, 1 mM EGTA, 10 mM MgCl$_2$, 2 mM DTT, 0.05 mg/mL BSA, and 0.01% Tween 20. The reaction was then incubated for 120 minutes at 25° C. incubator. The reactions were stopped by the addition of EDTA and Europium labeled antibody, for a final concentration of 15 mM and 0.5-1.5 nM, respectively. HTRF signals were read after 15-120 minutes. A ratio of fluorescence transferred to the labeled substrate (665 nm) relative to fluorescence of the Europium donor (620 nm) represents the extent of phosphorylation. Ratios for treated wells were normalized to DMSO only (100% activity) and no enzyme (0% activity) controls. Normalized data was analyzed using a three or four parameter dose response curve to determine IC$_{50}$ for each compound and are shown in Table B. Control reference inhibitors were included on each plate.

TABLE B

| Ex. No. | CDK12 IC$_{50}$ (nM) |
|---|---|
| 86 | ++ |
| 87 | ++ |
| 94 | ++ |
| 96 | ++ |
| 100 | + |
| 102 | + |
| 104 | ++ |
| 105 | + |
| 106 | ++ |
| 107 | ++ |
| 108 | ++ |
| 110 | ++ |
| 111 | ++ |
| 112 | +++ |
| 113 | + |
| 114 | + |
| 115 | + |
| 116 | ++ |
| 117 | ++ |
| 118 | +++ |
| 119 | +++ |
| 120 | +++ |
| 121 | ++ |
| 122 | + |
| 123 | + |
| 124 | + |
| 125 | + |
| 126 | + |
| 127 | + |
| 128 | ++ |
| 129 | + |
| 130 | + |
| 131 | ++ |
| 132 | + |
| 133 | + |
| 134 | + |
| 135 | + |
| 136 | + |
| 137 | ++ |
| 138 | ++ |
| 139 | ++ |
| 140 | + |
| 141 | + |
| 142 | + |
| 143 | + |
| 144 | +++ |
| 145 | ++ |
| 146 | ++ |
| 147 | ++ |
| 148 | +++ |
| 149 | +++ |
| 150 | + |
| 151 | + |
| 152 | + |

TABLE B-continued

| Ex. No. | CDK12 IC$_{50}$ (nM) |
|---|---|
| 153 | + |
| 154 | + |
| 155 | + |
| 156 | + |
| 157 | ++ |
| 158 | + |
| 159 | ++ |
| 160 | ++ |
| 161 | + |
| 162 | ++ |
| 163 | ++ |
| 164 | ++ |
| 165 | + |
| 166 | + |

+ refers to IC$_{50}$ of <50 nM

++ refers to IC$_{50}$ of ≥50 nM to ≤500 nM

+++ refers to >500 nM

Example B. CDK Cellular Activity Assays

A. HTRF Assay

The following signals were detected using an HTRF assay from Cisbio: CDK12/13 activity (RNA POL II pser2 HTRF assay in multiple cell lines); CDK2 activity (pRbS780 HTRF assay in COV318 cells); CDK4 (pRbS780 HTRF assay in JEKO-1 cells); CDK6 activity (pRbS780 HTRF assay in MV4-11 cells); CDK12 specific activity (RNA POL II pser2 in CDK13$^{-/-}$ isogenic THP1 cells); CDK13 specific activity (RNA POL II pser2 in CDK12$^{-/-}$ isogenic THP1 cells); Gamma H2AX for DNA damage (HTRF assay in multiple cell lines).

All HTRF assays were performed following the following standard protocol. First, cells were plated in a 96 well plate and treated with 3 fold dilution series of compound for 6 hours (CDK2, CDK4, CDK6, CDK12, CDK13) or 48 hours (Gamma H2AX). Then, 4× Cisbio lysis buffer was diluted 4 fold with distilled water supplemented with 100× blocking buffer and a 1:10,000 dilution of Benzonase Nuclease (Sigma Cat #E1014-5KU). Next, 50 µL of the prepared 1× Cisbio lysis buffer was added to each well of cells. The plates were gently shaken at room temperature for 30-45 minutes to lyse. The lysates were then used immediately or stored at −80° C. and processed at a later date. To process, the 96 well plates were centrifuged at 1400 rpm for 5 minutes at 4° C. Then, acceptor D2 and donor K antibody mixes were made up as follows: 50 µL of antibody+950 µL detection buffer per one 384 plate (equal to 4×96 well plates). 2 µL acceptor D2 and 2 µL of donor K antibody mixes were added to enough wells of a 384 well Greiner white plate (Greiner cat #784075) to accommodate the number of cell samples from the 96 well plate. Lastly, 16 µL of each cell lysate from the 96 well plate was transferred to the wells in the 384 well plate containing the 4 µL of acceptor D2+donor K antibody mixes (final volume of 20 µL per well). The 384 well plate was then incubated overnight at room temperature covered in foil. HTRF signal was measured on the Pherastar microplate reader the next morning.

B. In Cell Western Blotting Assay

The following signals were detected using an in cell western blotting assay: CDK1 activity (pNPM-T199 signal); CDK7 activity (RNA POL II pser5 signal).

Cells were plated at 25,000 cells per well in a 96 well plate at 37° C. and allowed to attach overnight. The next day, cells were treated with a 3 fold dilution series of compound for 6 hours. Next, media was removed and the cells were washed once with 140 μL/well of 1×PBS. The cells were then fixed with freshly diluted 3.7% paraformaldehyde/PBS for 20 minutes at room temperature. The fixing solution was removed and the cells were washed 3 times with 1×PBS containing 0.1% TX-100 for 5-10 minutes per wash with gentle shaking for permeabilization. Next, the plates were blocked by adding 50 μL/well of Odyssey blocking buffer with 0.1% TX-100 followed by rocking gently for 1 hour at room temperature. The blocking buffer was then removed from Pierce (Cat #23225) and equal amounts of protein were then run on a 4 to 12% NuPAGE gel (Cat #NP0322). Expression as analyzed following standard western blotting procedure. Briefly, membranes were blocked with 5% milk in TBST for 1 hour and then incubated with primary antibody (GET CAT #) at 1:2000 overnight. Membranes were then washed 3 times with TBST and incubated (1:4000 dilution) with secondary antibody (Cell Signaling Cat #7074). For imaging, membranes were in incubated in HRP substrate and imaged on a gel-doc imager.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

```
                        SEQUENCE LISTING

Sequence total quantity: 2
    SEQ ID NO: 1           moltype = AA  length = 19
    FEATURE                Location/Qualifiers
    source                 1..19
                           mol_type = protein
                           organism = synthetic construct
    SEQUENCE: 1
    DYSTTPGGTL FSTTPGTRI                                        19

SEQ ID NO: 2           moltype = AA  length = 8
    FEATURE                Location/Qualifiers
    source                 1..8
                           mol_type = protein
                           organism = synthetic construct
    SEQUENCE: 2
    VTPRTPPP                                                    8
``` and replaced with 40 μL/well of primary antibody diluted in Odyssey blocking buffer (1:200-1:500) with 0.1% TX-100 and the plates were incubated overnight with moderate shaking at 4° C. Next, the primary antibody was removed and the plates were washed 3 times with 140 μL of 1×PBS containing 0.1% Tween-20 for 10 minutes per wash with gentle shaking. Then 40 L/well of secondary antibody (IRDye® 800CW Goat anti-Rabbit, 1:2000) and CellTag 700 (1:600) in Odyssey blocking buffer with 0.1% TX-100 was added and the plates were covered in foil and rocked gently for 2 hours at room temperature. Next, secondary antibody was removed and washed 3 times with 140 μL of 1×PBS containing 0.1% Tween-20 for 10 minutes per wash with gentle shaking. The plates were protected from light during washing. After the final wash, the washing solution was completely removed from wells and the bottom plate surface and the scanning bed were cleaned with lint-free paper. The plate was scanned with detection in both 700 and 800 nm channels using an Odyssey CLx. (scanning parameters: Odyssey CLx 169 μm resolution at 3.5 mm focus offset).

C. Standard Western Blotting

The following signal was detected using standard western blotting: CDK5 activity (pFAKT732); CDK9 activity (MCL-1 protein level).

Cells were plated overnight in a 6 well plate and treated with a 3 fold dilution of compound. Cells were then washed with ice cold PBS and then lysed using the standard Cell Signaling Lysis Protocol (Cat #9803). Cell lysates were then quantified using the standard BCA protein assay protocol

What is claimed is:

1. A compound of Formula (I):

(I)

or a pharmaceutical acceptable salt thereof, wherein:

each ---- is independently a single or a double bond;

k is 1 or 2;

n is 0, 1, or 2;

p is 0, 1, 2, 3, 4, 5, 6, 7, 8, 9, or 10;

X is CH or N;

Y is $CR^4$ or N; and W is $CR^2$; or

Y is $NR^4$, O or S; and W is absent;

| 393 | 394 |

Ring A is a monocyclic 5-6 membered heteroaryl ring; the moiety is selected from:

wherein Ring B is optionally substituted with 1 or 2 independently selected R substituents; and wherein Ring C is optionally substituted with 1 or 2 independently selected R⁶ substituents;

each R^W, attached to the B ring or the C ring, is independently:

each L¹ is -L-NHC(O)—, wherein L is a bond and L¹ is attached to Ring C through the bond L;

each L² is -L-, -L-NHC(O)—, -L-N(tetrahydrofuran)C(O)—, or -L-N(CH₃)C(O)—, wherein L is a bond and L² is attached to Ring C through the bond L;

each L⁶ is NHC(O) or C(O);

each Ring D is independently a 4-12 membered heterocycloalkyl, $C_{3-12}$ cycloalkyl, $C_{6-10}$ aryl, or a 5-10 membered heteroaryl, each of which is optionally substituted with 1, 2, 3, or 4 independently selected $C_{1-6}$ alkyl groups;

each X¹ is independently O or NR⁹;

each R⁸¹, R⁸², and R⁸³ are independently selected from H, D, halo, NO₂, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a8}$, $SR^{a8}$, $NHOR^{a8}$, $C(O)R^{b8}$, $C(O)NR^{c8}R^{d8}$, $C(O)NR^{c8}(OR^{a8})$, $C(O)OR^{a8}$, $OC(O)R^{b8}$, $OC(O)NR^{c8}R^{d8}$, $NR^{c8}R^{d8}$, $NR^{c8}NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NR^{e8})NR^{c8}R^{d8}$, $NR^{c8}C(=NR^{e8})NR^{c8}R^{d8}$, $NR^{c8}C(=NR^{e8})R^{b8}$, $NR^{c8}S(O)NR^{c8}R^{d8}$, $NR^{c8}S(O)R^{b8}$, $NR^{c8}S(O)_2R^{b8}$, $NR^{c8}S(O)(=NR^{e8})R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$, $OS(O)(=NR^{e8})R^{b8}$, $OS(O)_2R^{b8}$, $S(O)(=NR^{e8})R^{b8}$, $SF_5$, $P(O)R^{f8}R^{g8}$, $OP(O)(OR^{h8})(OR^{i8})$, $P(O)(OR^{h8})(OR^{i8})$, and $BR^{j8}R^{k8}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ substituents;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^G$ substituents;

or, any $R^{c8}$ and $R^{d8}$ attached to the same N atom, together with the N atom to which they are attached, form a 4-10 membered heterocycloalkyl group, which is optionally substituted with 1, 2, 3, or 4 independently selected $R^G$ substituents;

each $R^{b8}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^G$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f8}$ and $R^{g8}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h8}$ and $R^{i8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j8}$ and $R^{k8}$ is independently selected from OH, $C_{1-6}$ alkoxy, and $C_{1-6}$ haloalkoxy;

or any $R^{j8}$ and $R^{k8}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

or any two $R^{81}$ and $R^{82}$ together with the atoms to which they are attached, form $C_{3-7}$ cycloalkyl, 4-7 membered heterocycloalkyl, phenyl, or 5-6-membered heteroaryl ring, each of which is optionally substituted with 1, 2, 3, or 4 independently selected $R^G$ substituents;

each $R^{84}$ is independently H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, or 5-10 membered heteroaryl-$C_{1-4}$ alkyl, wherein said $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, or 5-10 membered heteroaryl-$C_{1-4}$ alkyl are optionally substituted by 1, 2, 3, or 4 independently selected $R^G$ substituents;

each $R^{85}$ is independently H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, or $C_{3-10}$ cycloalkyl-$C_{1-4}$ alkyl, wherein said $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl are each optionally substituted by 1, 2, 3, or 4 independently selected $R^G$ substituents;

each $R^9$ is independently selected from H, halo, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $C(=NR^{e9})R^{b9}$, $C(=NR^{e9})NR^{c9}R^{d9}$, $NR^{c9}C(=NR^{e9})NR^{c9}R^{d9}$, $NR^{c9}C(=NR^{e9})R^{b9}$, $NR^{c9}S(O)NR^{c9}R^{d9}$, $NR^{c9}S(O)R^{b9}$, $NR^{c9}S(O)_2R^{b9}$, $NR^{c9}S(O)(=NR^{e9})R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $OS(O)(=NR^{e9})R^{b9}$, $OS(O)_2R^{b9}$, and $S(O)(=NR^{e9})R^{b9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

or, any $R^{c9}$ and $R^{d9}$ attached to the same N atom, together with the N atom to which they are attached, form a 4-10 membered heterocycloalkyl group, which is optionally substituted with 1, 2, 3, or 4 independently selected $R^{9A}$ substituents;

each $R^{b9}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{9A}$ substituents;

each $R^{e9}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, $NR^{c91}C(O)NR^{c91}R^{d91}$, $C(=NR^{e91})R^{b91}$, $C(=NR^{e91})NR^{c91}R^{d91}$, $NR^{c91}C(=NR^{e91})NR^{c91}R^{d91}$, $NR^{c91}C(=NR^{e91})R^{b91}$, $NR^{c91}S(O)NR^{c91}R^{d91}$, $NR^{c91}S(O)R^{d91}$, $NR^{c91}S(O)_2R^{b91}$, $NR^{c91}S(O)(=NR^{e91})R^{b91}$, $NR^{c91}S(O)_2NR^{c91}R^{d91}$, $S(O)R^{b91}$, $S(O)NR^{c91}R^{d91}$, $S(O)_2R^{b91}$, $S(O)_2NR^{c91}R^{d91}$, $OS(O)(=NR^{e91})R^{b91}$, $OS(O)_2R^{b91}$, $S(O)(=NR^{e91})R^{b91}$, $SF_5$, $P(O)R^{f91}R^{g91}$, $OP(O)(OR^{h91})(OR^{i91})$, $P(O)(OR^{h91})(OR^{i91})$, and $BR^{j91}R^{k91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

or, any $R^{c91}$ and $R^{d91}$ attached to the same N atom, together with the N atom to which they are attached, form a 4-7 membered heterocycloalkyl group, which is optionally substituted with 1, 2, 3, or 4 independently selected $R^{9B}$ substituents;

each $R^{b91}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f91}$ and $R^{g91}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h91}$ and $R^{i91}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j91}$ and $R^{k91}$ is independently selected from OH, $C_{1-6}$ alkoxy, and $C_{1-6}$ haloalkoxy;

or any $R^{j91}$ and $R^{k91}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, $NR^{c92}C(O)NR^{c92}R^{d92}$, $C(=NR^{e92})R^{b92}$, $C(=NR^{e92})NR^{c92}R^{d92}$, $NR^{c92}C(=NR^{e92})NR^{c92}R^{d92}$, $NR^{c92}C(=NR^{e92})R^{d92}$, $NR^{c92}S(O)NR^{c92}R^{d92}$, $NR^{c92}S(O)R^{b92}$, $NR^{c92}S(O)_2R^{b92}$, $NR^{c92}S(O)(=NR^{e92})R^{b92}$, $NR^{c92}S(O)_2NR^{c92}R^{d92}$, $S(O)R^{b92}$, $S(O)NR^{c92}R^{d92}$, $S(O)_2R^{b92}$, $S(O)_2NR^{c92}R^{d92}$, $OS(O)(=NR^{e92})R^{b92}$, $OS(O)_2R^{b92}$, $S(O)(=NR^{e92})R^{b92}$, $SF_5$, $P(O)R^{f92}R^{d92}$, $OP(O)(OR^{h92})(OR^{i92})$, $P(O)(OR^{h92})(OR^{i92})$ and $BR^{j92}R^{k92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents;

or, any $R^{c92}$ and $R^{d92}$ attached to the same N atom, together with the N atom to which they are attached, form a 4-7 membered heterocycloalkyl group, which is optionally substituted with 1, 2, 3, or 4 independently selected $R^{G}$ substituents;

each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e92}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f92}$ and $R^{g92}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h92}$ and $R^{i92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j92}$ and $R^{k92}$ is independently selected from OH, $C_{1-6}$ alkoxy, and $C_{1-6}$ haloalkoxy;

or any $R^{j92}$ and $R^{k92}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, 4-10 membered heterocycloalkyl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, are each optionally substituted with 1, 2, 3, or 4 independently selected $R^{1A}$ substituents;

or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl, which are each optionally substituted with 1, 2, 3, or 4 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{f1}$ and $R^{g1}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)NR^{c11}R^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, $OS(O)_2R^{b11}$, $S(O)(=NR^{e11})R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

or, any $R^{c11}$ and $R^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f11}$ and $R^{g11}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $R^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)NR^{c12}R^{d12}$, $NR^{c12}S(O)R^{b12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, $OS(O)_2R^{b12}$, $S(O)(=NR^{e12})R^{b12}$, $SF_5$, $P(O)R^{f12}R^{g12}$, $OP(O)(OR^{h12})(OR^{i12})$, $P(O)(OR^{h12})(OR^{i12})$, and $BR^{j12}R^{k12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1C}$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1C}$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1C}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f12}$ and $R^{g12}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h12}$ and $R^{i12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j12}$ and $R^{k12}$ is independently selected from OH, $C_{1-6}$ alkoxy, and $C_{1-6}$ haloalkoxy;

or any $R^{j12}$ and $R^{k12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1C}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $R^{a13}$, $SR^{a13}$, $NHOR^{a13}$, $C(O)R^{b13}$, $C(O)NR^{c13}R^{d13}$, $C(O)NR^{c13}(OR^{a13})$, $C(O)OR^{a13}$, $OC(O)R^{b13}$, $OC(O)NR^{c13}R^{d13}$, $NR^{c13}R^{d13}$, $NR^{c13}NR^{c13}R^{d13}$, $NR^{c13}C(O)R^{b13}$, $NR^{c13}C(O)OR^{a13}$, $NR^{c13}C(O)$ $NR^{c13}R^{d13}$, $C(=NR^{e13})R^{b13}$, $C(=NR^{e13})NR^{c13}R^{d13}$, $NR^{c13}C(=NR^{e13})NR^{c13}R^{d13}$, $NR^{c13}C(=NR^{e13})R^{b13}$, $NR^{c13}S(O)NR^{c13}R^{d13}$, $NR^{c13}S(O)R^{b13}$, $NR^{c13}S(O)_2$ $R^{b13}$, $NR^{c13}S(O)(=NR^{e13})R^{b13}$, $NR^{c13}S(O)_2$ $NR^{c13}R^{d13}$, $S(O)R^{b13}$, $S(O)NR^{c13}R^{d13}$, $S(O)_2R^{b13}$, $S(O)_2NR^{c13}R^{d13}$, $OS(O)(=NR^{e13})R^{b13}$, $OS(O)_2R^{b13}$, $S(O)(=NR^{e13})R^{b13}$, $SF_5$, $P(O)R^{f13}R^{g13}$, $OP(O)$ $(OR^{h13})(OR^{i13})$, $P(O)(OR^{h13})(OR^{i13})$, and $BR^{j13}R^{k13}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a13}$, $R^{c13}$, and $R^{d13}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-}t$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c13}$ and $R^{d13}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b13}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e13}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f13}$ and $R^{g13}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h13}$ and $R^{i13}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j13}$ and $R^{k13}$ is independently selected from OH, $C_{1-6}$ alkoxy, and $C_{1-6}$ haloalkoxy;

or any $R^{j13}$ and $R^{k13}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^2$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)$ $NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)$ $R^{b2}$, $NR^{c2}C(O)OR^{a2}$, $NR^{c2}C(O)NR^{c2}R^{d2}$, $C(=NR^{e2})$ $R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)$ $R^{b2}$, $NR^{c2}S(O)_2R^{b2}$, $NR^{c2}S(O)(=NR^{e2})R^{b2}$, $NR^{c2}S$ $(O)_2NR^{c2}R^{d2}$, $S(O)R^{b2}$, $S(O)NR^{c2}R^{d2}$, $S(O)_2R^{b2}$, $S(O)_2$ $NR^{c2}R^{d2}$, $OS(O)(=NR^{e2})R^{b2}$, $OS(O)_2R^{b2}$, $S(O)$ $(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heteroaryl-$C_{1-4}$ alkyl, and 5-10 membered heteroaryl-$C_{1-4}$ alkyl are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f2}$ and $R^{g2}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{2A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, $OS(O)_2R^{b21}$, $S(O)(=NR^{e21})R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c21}$ and $R^{d21}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b21}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f21}$ and $R^{g21}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^3$ is H, D, $CH_3$, or $CD_3$;

$R^4$ is H, D, halo, CN, $C_{1-6}$ alkyl, $C_{1-6}$ haloalkyl, $C_{1-3}$ alkoxy, $C_{1-3}$ haloalkoxy, cyano-$C_{1-6}$ alkyl, HO—$C_{1-6}$ alkyl, $C_{1-3}$ alkoxy-$C_{1-6}$ alkyl, or $C_{3-6}$ cycloalkyl;

$R^{4y}$ is H, $C_{1-4}$ alkyl, $C_{1-4}$ haloalkyl, cyano-$C_{1-4}$ alkyl, HO—$C_{1-4}$ alkyl, $C_{1-3}$ alkoxy-$C_{1-4}$ alkyl, or $C_{3-4}$ cycloalkyl;

each $R^5$ is independently selected from oxo, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)NR^{c5}R^{d5}$, $NR^{c5}S(O)R^{b5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $S(O)(=NR^{e5})R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f5}$ and $R^{g5}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j5}$ and $R^{k5}$ is independently selected from OH, $C_6$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)NR^{c51}$ $(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})$ $R^{b51}$, $C(=NR^{e51})NR^{c51}R^{d51}$, $NR^{c51}C(=NR^{e51})$ $NR^{c51}R^{d51}$, $NR^{c51}C(=NR^{e51})R^{b51}$, $NR^{c51}S(O)$ $NR^{c51}R^{d51}$, $NR^{c51}S(O)R^{b51}$, $NR^{c51}S(O)_2R^{b51}$, $NR^{c51}S$ $(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)$ $(=NR^{e51})R^{b51}$, $OS(O)_2R^{b51}$, $S(O)(=NR^{e51})R^{b51}$, $SF_5$, $P(O)R^{f51}R^{g51}$, $OP(O)(OR^{h51})(OR^{i51})$, $P(O)(OR^{h51})$ $(OR^{i51})$, and $BR^{j51}R^{k51}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

or, any $R^{c51}$ and $R^{d51}$ attached to the same N atom, together with the N atom to which they are attached, form a 4-7 membered heterocycloalkyl group, which is optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f51}$ and $R^{g51}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h51}$ and $R^{i51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j51}$ and $R^{k51}$ is independently selected from OH, $C_{1-6}$ alkoxy, and $C_{1-6}$ haloalkoxy;

or any $R^{j51}$ and $R^{k51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{c52}C(=NR^{e52})NR^{c52}R^{d52}$, $NR^{c52}C(=NR^{e52})R^{b52}$, $NR^{c52}S(O)NR^{c52}R^{d52}$, $NR^{c52}S(O)R^{b52}$, $NR^{c52}S(O)_2R^{b52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, $OS(O)_2R^{b52}$, $S(O)(=NR^{e52})R^{b52}$, $SF_5$, $P(O)R^{f52}R^{g52}$, $OP(O)(OR^{h52})(OR^{i52})$, $P(O)(OR^{h52})(OR^{i52})$, and $BR^{j52}R^{k52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c52}$ and $R^{d52}$ attached to the same N atom, together with the N atom to which they are attached, form a 4-7 membered heterocycloalkyl group, which is optionally substituted with 1, 2, 3, or 4 independently selected $R^G$ substituents;

each $R^{d52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e52}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f52}$ and $R^{g52}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h52}$ and $R^{i12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j52}$ and $R^{k52}$ is independently selected from OH, $C_{1-6}$ alkoxy, and $C_{1-6}$ haloalkoxy;

or any $R^{j52}$ and $R^{k52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^6$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)NR^{c6}R^{d6}$, $NR^{c6}S(O)R^{b6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $S(O)(=NR^{e6})R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{64}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{64}$ substituents;

or, any $R^{c6}$ and $R^{d6}$ attached to the same N atom, together with the N atom to which they are attached, form a 4-10 membered heterocycloalkyl group, which is optionally substituted with 1, 2, 3, or 4 independently selected $R^{64}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-C$_{1-4}$ alkyl, and 5-10 membered heteroaryl-C$_{1-4}$ alkyl, which are each optionally substituted with 1, 2, 3, or 4 independently selected R$^{6A}$ substituents;

each R$^{e6}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{f6}$ and R$^{g6}$ are independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{h6}$ and R$^{i6}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{j6}$ and R$^{k6}$ is independently selected from OH, C$_{1-6}$ alkoxy, and C$_{1-6}$ haloalkoxy;

or any R$^{j6}$ and R$^{k6}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{6A}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, 5-10 membered heteroaryl-C$_{1-4}$ alkyl, OR$^{a61}$, SR$^{a61}$, NHOR$^{a61}$, C(O)R$^{b61}$, C(O)NR$^{c61}$R$^{d61}$, C(O)NR$^{c61}$(OR$^{a61}$), C(O)OR$^{a61}$, OC(O)R$^{b61}$, OC(O)NR$^{c61}$R$^{d61}$, NR$^{c61}$R$^{d61}$, NR$^{c61}$NR$^{c61}$R$^{d61}$, NR$^{c61}$C(O)R$^{b61}$, NR$^{c61}$C(O)OR$^{a61}$, NR$^{c61}$C(O)NR$^{c61}$R$^{d61}$, C(=NR$^{e61}$)R$^{b61}$, C(=NR$^{e61}$)NR$^{c61}$R$^{d61}$, NR$^{c61}$C(=NR$^{e61}$)NR$^{c61}$R$^{d61}$, NR$^{c61}$C(=NR$^{e61}$)R$^{b61}$, NR$^{c61}$S(O)NR$^{c61}$R$^{d61}$, NR$^{c61}$S(O)R$^{b61}$, NR$^{c61}$S(O)$_2$R$^{b61}$, NR$^{c61}$S(O)(=NR$^{e61}$)R$^{b61}$, NR$^{c61}$S(O)$_2$NR$^{c61}$R$^{d61}$, S(O)R$^{b61}$, S(O)NR$^{c61}$R$^{d61}$, S(O)$_2$R$^{b61}$, S(O)$_2$NR$^{c61}$R$^{d61}$, OS(O)(=NR$^{e61}$)R$^{b61}$, OS(O)$_2$R$^{b61}$, S(O)(=NR$^{e61}$)R$^{b61}$, SF$_5$, P(O)R$^{f61}$R$^{g61}$, OP(O)(OR$^{h61}$)(OR$^{i61}$), P(O)(OR$^{h61}$)(OR$^{i61}$), and BR$^{j61}$R$^{k61}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{6B}$ substituents;

each R$^{a61}$, R$^{c61}$, and R$^{d61}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{6B}$ substituents;

or, any R$^{c61}$ and R$^{d61}$ attached to the same N atom, together with the N atom to which they are attached, form a 4-7 membered heterocycloalkyl group, which is optionally substituted with 1, 2, 3, or 4 independently selected R$^{6B}$ substituents;

each R$^{b61}$ is independently selected from C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, which are each optionally substituted with 1, 2, 3, or 4 independently selected R$^{6B}$ substituents;

each R$^{e61}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{f61}$ and R$^{g61}$ are independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{h61}$ and R$^{i61}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{j61}$ and R$^{k61}$ is independently selected from OH, C$_{1-6}$ alkoxy, and C$_{1-6}$ haloalkoxy;

or any R$^{j61}$ and R$^{k61}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{6B}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a62}$, SR$^{a62}$, NHOR$^{a62}$, C(O)R$^{b62}$, C(O)NR$^{c62}$R$^{d62}$, C(O)NR$^{c62}$(OR$^{a62}$), C(O)OR$^{a62}$, OC(O)R$^{b62}$, OC(O)NR$^{c62}$R$^{d62}$, NR$^{c62}$R$^{d62}$, NR$^{c62}$NR$^{c62}$R$^{d62}$, NR$^{c62}$C(O)R$^{b62}$, NR$^{c62}$C(O)OR$^{a62}$, NR$^{c62}$C(O)NR$^{c62}$R$^{d62}$, C(=NR$^{e62}$)R$^{b62}$, C(=NR$^{e62}$)NR$^{c62}$R$^{d62}$, NR$^{c62}$C(=NR$^{e62}$)NR$^{c62}$R$^{d62}$, NR$^{c62}$C(=NR$^{e62}$)R$^{b62}$, NR$^{c62}$S(O)NR$^{c62}$R$^{d62}$, NR$^{c62}$S(O)R$^{b62}$, NR$^{c62}$S(O)$_2$R$^{b62}$, NR$^{c62}$S(O)(=NR$^{e62}$)R$^{b62}$, NR$^{c62}$S(O)$_2$NR$^{c62}$R$^{d62}$, S(O)R$^{b62}$, S(O)NR$^{c62}$R$^{d62}$, S(O)$_2$R$^{b62}$, S(O)$_2$NR$^{c62}$R$^{d62}$, OS(O)(=NR$^{e62}$)R$^{b62}$, OS(O)$_2$R$^{b62}$, S(O)(=NR$^{e62}$)R$^{b62}$, SF$_5$, P(O)R$^{f62}$R$^{g62}$, OP(O)(OR$^{h62}$)(OR$^{i62}$), P(O)(OR$^{h62}$)(OR$^{i62}$), and BR$^{j62}$R$^{k62}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a62}$, $R^{c62}$, and $R^{d62}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c62}$ and $R^{d62}$ attached to the same N atom, together with the N atom to which they are attached, form a 4-7 membered heterocycloalkyl group, which is optionally substituted with 1, 2, 3, or 4 independently selected $R^G$ substituents;

each $R^{b62}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e62}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f62}$ and $R^{g62}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h62}$ and $R^{i62}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j62}$ and $R^{k62}$ is independently selected from OH, $C_{1-6}$ alkoxy, and $C_{1-6}$ haloalkoxy;

or any $R^{j62}$ and $R^{k62}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^7$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)NR^{c7}R^{d7}$, $NR^{c7}S(O)R^{b7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $S(O)(=NR^{e7})R^{b7}$, $SF_5$, $P(O)R^{f7}R^{g7}$, $OP(O)(OR^{h7})(OR^{i7})$, $P(O)(OR^{h7})(OR^{i7})$, and $BR^{f7}R^{k7}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{74}$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{74}$ substituents;

or, any $R^{c7}$ and $R^{d7}$ attached to the same N atom, together with the N atom to which they are attached, form a 4-10 membered heterocycloalkyl group, which is optionally substituted with 1, 2, 3, or 4 independently selected $R^{74}$ substituents;

each $R^{b7}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{74}$ substituents;

each $R^{e7}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f7}$ and $R^{g7}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j7}$ and $R^{k7}$ is independently selected from OH, $C_{1-6}$ alkoxy, and $C_{1-6}$ haloalkoxy;

or any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a71}$, $SR^{a71}$, $NHOR^{a71}$, $C(O)R^{b71}$, $C(O)NR^{c71}R^{d71}$, $C(O)NR^{c71}$ $(OR^{a71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c71}C(O)R^{b71}$, $NR^{c71}C(O)OR^{a71}$, $NR^{c71}C(O)NR^{c71}R^{d71}$, $C(=NR^{e71})$ $R^{b71}$, $C(=NR^{e71})NR^{c71}R^{d71}$, $NR^{c71}C(=NR^{e71})$ $NR^{c71}R^{d71}$, $NR^{c71}C(=NR^{e71})R^{b71}$, $NR^{c71}S(O)$ $NR^{c71}R^{d71}$, $NR^{c71}S(O)R^{b71}$, $NR^{c71}S(O)_2R^{b71}$, $NR^{c71}S$ $(O)(=NR^{e71})R^{b71}$, $NR^{c71}S(O)_2NR^{c71}R^{d71}$, $S(O)R^{b71}$, $S(O)NR^{c71}R^{d71}$, $S(O)_2R^{b71}$, $S(O)_2NR^{c71}R^{d71}$, $OS(O)$ $(=NR^{e71})R^{b71}$, $OS(O)_2R^{b71}$, $S(O)(=NR^{e71})R^{b71}$, $SF_5$, $P(O)R^{f71}R^{g71}$, $OP(O)(OR^{h71})(OR^{i71})$, $P(O)(OR^{h71})$ $(OR^{i71})$, and $BR^{j71}R^{k71}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7B}$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{7B}$ substituents;

or, any $R^{c71}$ and $R^{d71}$ attached to the same N atom, together with the N atom to which they are attached, form a 4-7 membered heterocycloalkyl group, which is optionally substituted with 1, 2, 3, or 4 independently selected $R^{7B}$ substituents;

each $R^{b71}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{7B}$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f71}$ and $R^{g71}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h71}$ and $R^{i71}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j71}$ and $R^{k71}$ is independently selected from OH, $C_6$ alkoxy, and $C_{1-6}$ haloalkoxy;

or any $R^{j71}$ and $R^{k71}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{7B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a72}$, $SR^{a72}$, $NHOR^{a72}$, $C(O)R^{b72}$, $C(O)$ $NR^{c72}R^{d72}$, $C(O)NR^{c72}(OR^{a72})$, $C(O)OR^{a72}$, $OC(O)$ $R^{b72}$, $OC(O)NR^{c72}R^{d72}$, $NR^{c72}R^{d72}$, $NR^{c72}NR^{c72}R^{d72}$, $NR^{c72}C(O)R^{b72}$, $NR^{c72}C(O)OR^{a72}$, $NR^{c72}C(O)$ $NR^{c72}R^{d72}$, $C(=NR^{e72})R^{b72}$, $C(=NR^{e72})NR^{c72}R^{d72}$, $NR^{c72}C(=NR^{e72})NR^{c72}R^{b72}$, $NR^{c72}C(=NR^{e72})R^{b72}$, $NR^{c72}S(O)NR^{c72}R^{d72}$, $NR^{c72}S(O)R^{b72}$, $NR^{c72}S(O)_2$ $R^{b72}$, $NR^{c72}S(O)(=NR^{e72})R^{b72}$, $NR^{c72}S(O)_2$ $NR^{c72}R^{d72}$, $S(O)R^{b72}$, $S(O)NR^{c72}R^{d72}$, $S(O)_2R^{b72}$, $S(O)_2NR^{c72}R^{d72}$, $OS(O)(=NR^{e72})R^{b72}$, $OS(O)_2R^{b72}$, $S(O)(=NR^{e72})R^{b72}$, $SF_5$, $P(O)R^{f72}R^{g72}$, $OP(O)$ $(OR^{h72})(OR^{i72})$, $P(O)(OR^{h72})(OR^{i72})$ and $BR^{j72}R^{k72}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c72}$ and $R^{d72}$ attached to the same N atom, together with the N atom to which they are attached, form a 4-7 membered heterocycloalkyl group, which is optionally substituted with 1, 2, 3, or 4 independently selected $R^G$ substituents;

each $R^{b72}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e72}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f72}$ and $R^{g72}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h72}$ and $R^{i72}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j72}$ and $R^{k72}$ is independently selected from OH, $C_{1-6}$ alkoxy, and $C_{1-6}$ haloalkoxy;

or any $R^{j72}$ and $R^{k72}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^G$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

2. The compound of claim 1, or a pharmaceutically acceptable salt thereof, wherein:

each $R^W$, attached to the C ring, is independently:

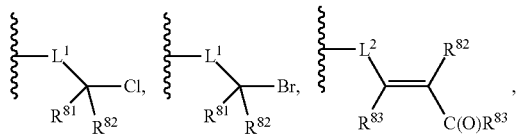

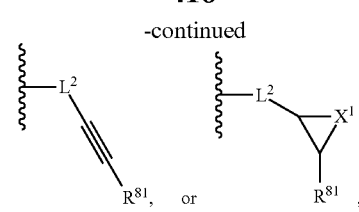

each $L^1$ is -L-NHC(O)—, wherein L is a bond and $L^1$ is attached to Ring C through the bond L; and each $L^2$ is -L-, -L-NHC(O)—, -L-N(tetrahydrofuran)C (O)—, or -L-N($CH_3$)C(O)—, wherein L is a bond and $L^2$ is attached to Ring C through the bond L.

3. The compound of claim 1, or a pharmaceutically acceptable salt thereof, wherein W is $CR^2$.

4. The compound of claim 1, or a pharmaceutically acceptable salt thereof, wherein:

$R^2$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, and $OS(O)_2R^{b2}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{2A}$ substituents; and each $R^{b2}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2A}$ substituents.

5. The compound of claim 1, or a pharmaceutically acceptable salt thereof, wherein $R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl, 4-6 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, and 5-6 membered heteroaryl are each optionally substituted with 1, 2, 3, or 4 independently selected $R^{2A}$ substituents.

6. The compound of claim 1, or a pharmaceutically acceptable salt thereof, wherein:

each $R^{2A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b21}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

7. The compound of claim 1, or a pharmaceutically acceptable salt thereof, wherein:

each $R^{2A}$ is independently selected from D, halo, CN, $C_{1-6}$ alkyl, $C_{2-6}$ alkenyl, $C_{2-6}$ alkynyl, $C_{1-6}$ haloalkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$;

each $R^{a21}$, $R^{c21}$, and $R^{b21}$ is independently selected from H, $C_{1-6}$ alkyl, and $C_{1-6}$ haloalkyl; and each $R^{b21}$ is independently selected from $C_{1-6}$ alkyl and $C_{1-6}$ haloalkyl.

8. The compound of claim 1, or a pharmaceutically acceptable salt thereof, wherein each $R^{2A}$ is independently selected from $CH_3$ and $OCH_3$.

9. The compound of claim 1, or a pharmaceutically acceptable salt thereof, wherein Y is N.

10. The compound of claim 1, or a pharmaceutically acceptable salt thereof, wherein Y is $CR^4$.

11. The compound of claim 1, or a pharmaceutically acceptable salt thereof, wherein $R^4$ is H.

12. The compound of claim 1, or a pharmaceutically acceptable salt thereof, wherein W is absent.

13. The compound of claim 1, or a pharmaceutically acceptable salt thereof, wherein Y is S.

14. The compound of claim 1, or a pharmaceutically acceptable salt thereof, wherein:

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $C_{3-7}$ cycloalkyl-$C_{1-4}$ alkyl, 4-7 membered heterocycloalkyl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, and $OS(O)_2R^{b1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $C_{3-7}$ cycloalkyl-$C_{1-4}$ alkyl, and 4-7 membered heterocycloalkyl-$C_{1-4}$ alkyl, are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, $C_{3-7}$ cycloalkyl-$C_{1-4}$ alkyl, and 4-7 membered heterocycloalkyl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $C_{3-7}$ cycloalkyl-$C_{1-4}$ alkyl, and 4-7 membered heterocycloalkyl-$C_{1-4}$ alkyl, are each optionally substituted with 1, 2, 3, or 4 independently selected $R^{1A}$ substituents;

or, any $R^{c1}$ and $R^{d1}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1A}$ substituents; and each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, $C_{3-7}$ cycloalkyl-$C_{1-4}$ alkyl, and 4-7 membered heterocycloalkyl-$C_{1-4}$ alkyl, which are each optionally substituted with 1, 2, 3, or 4 independently selected $R^{1A}$ substituents.

15. The compound of claim 1, or a pharmaceutically acceptable salt thereof, wherein:

each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$;

each $R^{a12}$, $R^{c12}$, and $R^{d12}$ is independently selected from H, $C_{1-6}$ alkyl, $C_{1-6}$ haloalkyl, $C_{2-6}$ alkenyl, and $C_{2-6}$ alkynyl; and each $R^{b12}$ is independently selected from $C_{1-6}$ alkyl, $C_{1-6}$ haloalkyl, $C_{2-6}$ alkenyl, and $C_{2-6}$ alkynyl.

16. The compound of claim 1, or a pharmaceutically acceptable salt thereof, wherein:

each $R^{14}$ is independently selected from D, halo, CN, $C_{1-6}$ alkyl, $C_{2-6}$ alkenyl, $C_{2-6}$ alkynyl, $C_{1-6}$ haloalkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$;

each $R^{a11}$, $R^{c11}$, and $R^{d11}$ is independently selected from H, $C_{1-6}$ alkyl, and $C_{1-6}$ haloalkyl; and each $R^{b11}$ is independently selected from $C_{1-6}$ alkyl and $C_{1-6}$ haloalkyl.

17. The compound of claim 1, or a pharmaceutically acceptable salt thereof, wherein $R^3$ is H or $CH_3$.

18. The compound of claim 1, or a pharmaceutically acceptable salt thereof, wherein X is N.

19. The compound of claim 1, or a pharmaceutically acceptable salt thereof, wherein X is CH.

20. The compound of claim 1, or a pharmaceutically acceptable salt thereof, wherein n is 0 or 1.

21. The compound of claim 1, or a pharmaceutically acceptable salt thereof, wherein p is 0, 1, or 2.

22. The compound of claim 1, or a pharmaceutically acceptable salt thereof, wherein each $R^7$ is independently selected from D, OH, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

23. The compound of claim 1, or a pharmaceutically acceptable salt thereof, wherein:

each $R^5$ is independently selected from oxo, D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $OS(O)_2R^5$; wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents; and each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5A}$ substituents.

24. The compound of claim 1, or a pharmaceutically acceptable salt thereof, wherein:

each $R^5$ is independently selected from oxo, D, halo, CN, $C_{1-6}$ alkyl, $C_{2-6}$ alkenyl, $C_{2-6}$ alkynyl, $C_{1-6}$ haloalkyl, $C_{3-6}$ cycloalkyl, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2$$R^{b5}$, $S(O)_2NR^{c5}R^{d5}$, and $OS(O)_2R^{b5}$; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{5A}$ substituents; and each $R^{b5}$ is independently selected from $C_{1-6}$ alkyl, $C_{1-6}$ haloalkyl, $C_{2-6}$ alkenyl, $C_{2-6}$ alkynyl, and $C_{3-4}$ cycloalkyl, which are each optionally substituted with 1, 2, 3, or 4 independently selected $R^{5A}$ substituents.

25. The compound of claim 1, or a pharmaceutically acceptable salt thereof, wherein:

each $R^{5A}$ is independently selected from D, halo, CN, $C_{1-6}$ alkyl, $C_{2-6}$ alkenyl, $C_{2-6}$ alkynyl, $C_{1-6}$ haloalkyl, $OR^{a51}$, $SR^{a51}$, $NHOR^{a51}$, $C(O)R^{b51}$, $C(O)NR^{c51}R^{d51}$, $C(O)$$OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)$$NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl; and each $R^{b51}$ is independently selected from $C_{1-6}$ alkyl and $C_{1-6}$ haloalkyl.

26. The compound of claim 1, or a pharmaceutically acceptable salt thereof, wherein:

each $R^6$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a6}$, $SR^{a6}$, $NHOR^{a6}$, $C(O)R^{b6}$, $C(O)NR^{c6}R^{d6}$, $C(O)$$OR^{a6}$, $OC(O)R^{b6}$, $OC(O)NR^{c6}R^{d6}$, $NR^{c6}R^{d6}$, $NR^{c6}C$$(O)R^{b6}$, $NR^{c6}C(O)OR^{a6}$, $NR^{c6}C(O)NR^{c6}R^{d6}$, $NR^{c6}S$$(O)NR^{c6}R^{d6}$, $NR^{c6}S(O)R^{b6}$, $NR^{c6}S(O)_2R^{b6}$, $NR^{c6}S$$(O)_2$ $NR^{c6}R^{d6}$, $S(O)R^{b6}$, $S(O)NR^{c6}R^{d6}$, $S(O)_2R^{b6}$, $S(O)_2$ $NR^{c6}R^{d6}$, and $OS(O)_2R^{b6}$; wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{6A}$ substituents;

or, any $R^{c6}$ and $R^{d6}$ attached to the same N atom, together with the N atom to which they are attached, form a 4-7 membered heterocycloalkyl group, which is optionally substituted with 1, 2, 3, or 4 independently selected $R^{6A}$ substituents; and each $R^{b6}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{6A}$ substituents.

27. The compound of claim 1, or a pharmaceutically acceptable salt thereof, wherein:

each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, 4-7 membered heterocycloalkyl, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)$$OR^{a6}$, $NR^{c6}C(O)NR^{c6}R^{d6}$, $NR^{c6}S(O)NR^{c6}R^{d6}$, $NR^{c6}S$$(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, and $OS(O)_2$ $R^{b6}$; wherein said $C_{1-6}$ alkyl, $C_{2-6}$ alkenyl, $C_{2-6}$ alkynyl, $C_{1-6}$ haloalkyl, $C_{3-4}$ cycloalkyl, and 4-7 membered heterocycloalkyl are each optionally substituted by 1, 2, 3, or 4 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, and $C_{3-4}$ cycloalkyl, wherein said $C_{1-6}$ alkyl, $C_{1-6}$ haloalkyl, $C_{2-6}$ alkenyl, $C_{2-6}$ alkynyl, and $C_{3-4}$ cycloalkyl are each optionally substituted with 1, 2, 3, or 4 independently selected $R^{6A}$ substituents; and each $R^{b6}$ is independently selected from $C_{1-6}$ alkyl, $C_{1-6}$ haloalkyl, $C_{2-6}$ alkenyl, $C_{2-6}$ alkynyl, $C_{3-4}$ cycloalkyl, and 4-7 membered heterocycloalkyl, which are each optionally substituted with 1, 2, 3, or 4 independently selected $R^{6A}$ substituents.

28. The compound of claim 1, or a pharmaceutically acceptable salt thereof, wherein:

each $R^{6A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $OR^{a61}$, $SR^{a61}$, $NHOR^{a61}$, $C(O)R^{b61}$, $C(O)$$NR^{c61}R^{d61}$, $C(O)OR^{a61}$, $OC(O)R^{b61}$, $OC(O)$$NR^{c61}R^{d61}$, $NR^{c61}R^{d61}$, $NR^{c61}C(O)R^{b61}$, $NR^{c61}C(O)$$OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2$$NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl; and each $R^{b61}$ is independently selected from $C_{1-6}$ alkyl and $C_{1-6}$ haloalkyl.

29. The compound of claim 1, or a pharmaceutically acceptable salt thereof, wherein k is 1.

30. The compound of claim 1, or a pharmaceutically acceptable salt thereof, wherein:

each $R^9$ is independently selected from H, halo, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(O)$ $R^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O)NR$^{c9}$R$^{d9}$, NR$^{c9}$S(O)NR$^{c9}$R$^{d9}$, NR$^{c9}$S(O)R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, and S(O)$_2$NR$^{c9}$R$^{d9}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^{9A}$ substituents;

each R$^{a9}$, R$^{c9}$, and R$^{d9}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{9A}$ substituents; and each R$^{b9}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^{9A}$ substituents.

31. The compound of claim 1, or a pharmaceutically acceptable salt thereof, wherein:
each R$^{9A}$ is independently selected from D, halo, CN, C$_{1-6}$ alkyl, C$_{2-6}$ alkenyl, C$_{2-6}$ alkynyl, C$_{1-6}$ haloalkyl, OR$^{a91}$, SR$^{a91}$, NHOR$^{a91}$, C(O)R$^{b91}$, C(O)NR$^{c91}$R$^{d91}$, C(O)OR$^{a91}$, OC(O)R$^{b91}$, OC(O)NR$^{c91}$R$^{d91}$, NR$^{c91}$R$^{d91}$, NR$^{c91}$C(O)R$^{b91}$, NR$^{c91}$C(O)OR$^{a91}$, NR$^{c91}$C(O)NR$^{c91}$R$^{d91}$, NR$^{c91}$S(O)NR$^{c91}$R$^{d91}$, NR$^{c91}$S(O)R$^{b91}$, NR$^{c91}$S(O)$_2$R$^{b91}$, NR$^{c91}$S(O)$_2$NR$^{c91}$R$^{d91}$, S(O)R$^{b91}$, S(O)NR$^{c91}$R$^{d91}$, S(O)$_2$R$^{b91}$, and S(O)$_2$NR$^{c91}$R$^{d91}$;
each R$^{a91}$, R$^{c91}$, and R$^{d91}$ is independently selected from H, C$_{1-6}$ alkyl, and C$_{1-6}$ haloalkyl; and
each R$^{b91}$ is independently selected from C$_{1-6}$ alkyl and C$_{1-6}$ haloalkyl.

32. The compound of claim 1, or a pharmaceutically acceptable salt thereof, wherein:
each R$^{81}$, R$^{82}$, and R$^{83}$ are independently selected from H, D, halo, CN, OR$^{a8}$, C(O)OR$^{a8}$, C$_{1-6}$ alkyl, C$_{2-6}$ alkenyl, C$_{2-6}$ alkynyl, C$_{1-6}$ haloalkyl, C$_{3-4}$ cycloalkyl, and 4-7 membered heterocycloalkyl-C$_{1-4}$ alkyl; wherein said C$_{1-6}$ alkyl, C$_{2-6}$ alkenyl, C$_{2-6}$ alkynyl, C$_{1-6}$ haloalkyl, C$_{3-4}$ cycloalkyl, and 4-7 membered heterocycloalkyl-C$_{1-4}$ alkyl are each optionally substituted by 1, 2, 3, or 4 independently selected R$^{G}$ substituents;
each R$^{a8}$ is independently selected from H, C$_{1-6}$ alkyl, C$_{1-6}$ haloalkyl, C$_{2-6}$ alkenyl, and C$_{2-6}$ alkynyl, wherein said C$_{1-6}$ alkyl, C$_{2-6}$ alkenyl, C$_{2-6}$ alkynyl, and C$_{1-6}$ haloalkyl are each optionally substituted with 1, 2, 3, or 4 independently selected R$^{G}$ substituents.

33. The compound of claim 1, or a pharmaceutically acceptable salt thereof, wherein X$^1$ is O.

34. The compound of claim 1, wherein each Ring D is independently a 4-8 membered heterocycloalkyl, C$_{3-7}$ cycloalkyl, phenyl, or a 5-6 membered heteroaryl, each of which is optionally substituted with 1, 2, 3, or 4 independently selected C$_{1-6}$ alkyl groups.

35. The compound of claim 1, wherein each Ring D is independently a monocyclic 4-7 membered heterocycloalkyl, bicyclic 7-10 membered heterocycloalkyl, or a spirocyclic 7-10 membered heterocycloalkyl, each of which is optionally substituted by 1 or 2 independently selected C$_{1-6}$ alkyl groups.

36. The compound of claim 1, or a pharmaceutically acceptable salt thereof, wherein:
each ---- is independently a single or a double bond;
k is 1 or 2;
n is 0 or 1;
p is 0, 1, or 2;
X is CH or N;
Y is CR$^4$ or N; and W is CR$^2$; or
Y is NR$^{4y}$, O or S; and W is absent;
Ring A is a monocyclic 5-6 membered heteroaryl ring;
each X$^1$ is independently O or NR$^9$;
each Ring D is independently a 4-8 membered heterocycloalkyl, C$_{3-7}$ cycloalkyl, phenyl, or a 5-6 membered heteroaryl, each of which is optionally substituted with 1, 2, 3, or 4 independently selected C$_{1-6}$ alkyl groups;
each R$^{81}$, R$^{82}$, and R$^{83}$ are independently selected from H, D, halo, CN, OR$^{a8}$, C(O)OR$^{a8}$, C$_{1-6}$ alkyl, C$_{2-6}$ alkenyl, C$_{2-6}$ alkynyl, C$_{1-6}$ haloalkyl, C$_{3-4}$ cycloalkyl, and 4-7 membered heterocycloalkyl-C$_{1-4}$ alkyl; wherein said C$_{1-6}$ alkyl, C$_{2-6}$ alkenyl, C$_{2-6}$ alkynyl, C$_{1-6}$ haloalkyl, C$_{3-4}$ cycloalkyl, and 4-7 membered heterocycloalkyl-C$_{1-4}$ alkyl are each optionally substituted by 1, 2, 3, or 4 independently selected R$^{G}$ substituents;
each R$^{a8}$ is independently selected from H, C$_{1-6}$ alkyl, C$_{1-6}$ haloalkyl, C$_{2-6}$ alkenyl, and C$_{2-6}$ alkynyl, wherein said C$_{1-6}$ alkyl, C$_{2-6}$ alkenyl, C$_{2-6}$ alkynyl, and C$_{1-6}$ haloalkyl are each optionally substituted with 1, 2, 3, or 4 independently selected R$^{G}$ substituents;
each R$^{84}$ is independently H, D, halo, CN, OH, C$_{1-3}$ alkoxy, C$_{1-3}$ haloalkoxy, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, or 5-10 membered heteroaryl-C$_{1-4}$ alkyl, each of which is optionally substituted by 1, 2, 3, or 4 independently selected R$^{G}$ substituents;
each R$^9$ is independently selected from H, halo, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O)NR$^{c9}$R$^{d9}$, NR$^{c9}$S(O)NR$^{c9}$R$^{d9}$, NR$^{c9}$S(O)R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, and S(O)$_2$NR$^{c9}$R$^{d9}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents;

each $R^{b9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9A}$ substituents;

each $R^{9A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{b91}$, and $S(O)_2NR^{c91}R^{d91}$;

each $R^{a91}$, $R^{c91}$, and $R^{d91}$ is independently selected from H, $C_{1-6}$ alkyl, and $C_{1-6}$ haloalkyl;

each $R^{b91}$ is independently selected from $C_{1-6}$ alkyl and $C_{1-6}$ haloalkyl;

$R^1$ is selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, $OR^{a1}$, and $NR^{c1}R^{d1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, and 4-7 membered heterocycloalkyl are each optionally substituted with 1, 2, 3, or 4 independently selected $R^{14}$ substituents;

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{14}$ substituents;

each $R^{14}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from D, halo, CN, $C_{1-6}$ alkyl, $C_{2-6}$ alkenyl, $C_{2-6}$ alkynyl, $C_{1-6}$ haloalkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$;

each $R^{a12}$, $R^{c12}$, and $R^{d12}$ is independently selected from H, $C_{1-6}$ alkyl, $C_{1-6}$ haloalkyl, $C_{2-6}$ alkenyl, and $C_{2-6}$ alkynyl;

each $R^{b12}$ is independently selected from $C_{1-6}$ alkyl, $C_{1-6}$ haloalkyl, $C_{2-6}$ alkenyl, and $C_{2-6}$ alkynyl;

$R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl, 4-6 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, and 5-6 membered heteroaryl are each optionally substituted with 1, 2, 3, or 4 independently selected $R^{2A}$ substituents;

each $R^{2A}$ is independently selected from D, halo, CN, $C_{1-6}$ alkyl, $C_{2-6}$ alkenyl, $C_{2-6}$ alkynyl, $C_{1-6}$ haloalkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$;

each $R^{a21}$, $R^{c21}$, and $R^{d21}$ is independently selected from H, $C_{1-6}$ alkyl, and $C_{1-6}$ haloalkyl;

each $R^{b21}$ is independently selected from $C_{1-6}$ alkyl and $C_{1-6}$ haloalkyl;

$R^3$ is H or $CH_3$;

$R^4$ is H, D, halo, CN, or $C_{1-6}$ alkyl;

$R^{4y}$ is H, $C_{1-4}$ alkyl, or $C_{1-4}$ haloalkyl;

each $R^5$ is independently selected from oxo, D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a5}$, $SR^{a5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S$ (O)NR$^{c5}$R$^{d5}$, NR$^{c5}$S(O)R$^{b5}$, NR$^{c5}$S(O)$_2$R$^{b5}$, NR$^{c5}$S(O)$_2$ NR$^{c5}$R$^{d5}$, S(O)R$^{b5}$, S(O)NR$^{c5}$R$^{d5}$, S(O)$_2$R$^{b5}$, S(O)$_2$ NR$^{c5}$R$^{d5}$, and OS(O)$_2$R$^{b5}$; wherein said C$_{1-6}$ alkyl, C$_{2-6}$ alkenyl, C$_{2-6}$ alkynyl, C$_{1-6}$ haloalkyl, and C$_{3-4}$ cycloalkyl are each optionally substituted by 1, 2, 3, or 4 independently selected R$^{5A}$ substituents;

each R$^{a5}$, R$^{c5}$, and R$^{d5}$ is independently selected from H, C$_{1-6}$ alkyl, C$_{1-6}$ haloalkyl, C$_{2-6}$ alkenyl, C$_{2-6}$ alkynyl, and C$_{3-4}$ cycloalkyl, wherein said C$_{1-6}$ alkyl, C$_{1-6}$ haloalkyl, C$_{2-6}$ alkenyl, C$_{2-6}$ alkynyl, and C$_{3-4}$ cycloalkyl are each optionally substituted with 1, 2, 3, or 4 independently selected R$^{5A}$ substituents;

each R$^{b5}$ is independently selected from C$_{1-6}$ alkyl, C$_{1-6}$ haloalkyl, C$_{2-6}$ alkenyl, C$_{2-6}$ alkynyl, and C$_{3-4}$ cycloalkyl, which are each optionally substituted with 1, 2, 3, or 4 independently selected R$^{5A}$ substituents;

each R$^{5A}$ is independently selected from D, halo, CN, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a51}$, SR$^{a51}$, NHOR$^{a51}$, C(O)R$^{b51}$, C(O)NR$^{c51}$R$^{d51}$, C(O)OR$^{a51}$, OC(O)R$^{b51}$, OC(O)NR$^{c51}$R$^{d51}$, NR$^{c51}$R$^{d51}$, NR$^{c51}$C(O)R$^{b51}$, NR$^{c51}$C(O)OR$^{a51}$, NR$^{c51}$C(O)NR$^{c51}$R$^{d51}$, NR$^{c51}$S(O)NR$^{c51}$R$^{d51}$, NR$^{c51}$S(O)R$^{b51}$, NR$^{c51}$S(O)$_2$R$^{b51}$, NR$^{c51}$S(O)$_2$NR$^{c51}$R$^{d51}$, S(O)R$^{b51}$, S(O)NR$^{c51}$R$^{d51}$, S(O)$_2$R$^{b51}$, and S(O)$_2$NR$^{c51}$R$^{d51}$;

each R$^{a51}$, R$^{c51}$, and R$^{d51}$ is independently selected from H, C$_{1-6}$ alkyl, and C$_{1-6}$ haloalkyl;

each R$^{b51}$ is independently selected from C$_{1-6}$ alkyl and C$_{1-6}$ haloalkyl;

each R$^6$ is independently selected from D, halo, CN, C$_{1-6}$ alkyl, C$_{2-6}$ alkenyl, C$_{2-6}$ alkynyl, C$_{1-6}$ haloalkyl, C$_{3-4}$ cycloalkyl, 4-7 membered heterocycloalkyl, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, NR$^{c6}$C(O)NR$^{c6}$R$^{d6}$, NR$^{c6}$S(O)NR$^{c6}$R$^{d6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, and OS(O)$_2$R$^{b6}$; wherein said C$_{1-6}$ alkyl, C$_{2-6}$ alkenyl, C$_{2-6}$ alkynyl, C$_{1-6}$ haloalkyl, C$_{3-4}$ cycloalkyl, and 4-7 membered heterocycloalkyl, are each optionally substituted by 1, 2, 3, or 4 independently selected R$^{6A}$ substituents;

each R$^{a6}$, R$^{c6}$, and R$^{d6}$ is independently selected from H, C$_{1-6}$ alkyl, C$_{1-6}$ haloalkyl, C$_{2-6}$ alkenyl, C$_{2-6}$ alkynyl, and C$_{3-4}$ cycloalkyl, wherein said C$_{1-6}$ alkyl, C$_{1-6}$ haloalkyl, C$_{2-6}$ alkenyl, C$_{2-6}$ alkynyl, and C$_{3-4}$ cycloalkyl are each optionally substituted with 1, 2, 3, or 4 independently selected R$^{6A}$ substituents;

each R$^{b6}$ is independently selected from C$_{1-6}$ alkyl, C$_{1-6}$ haloalkyl, C$_{2-6}$ alkenyl, C$_{2-6}$ alkynyl, C$_{3-4}$ cycloalkyl, and 4-7 membered heterocycloalkyl, which are each optionally substituted with 1, 2, 3, or 4 independently selected R$^{6A}$ substituents;

each R$^{6A}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a61}$, SR$^{a61}$, NHOR$^{a61}$, C(O)R$^{b61}$, C(O)NR$^{c61}$R$^{d61}$, C(O)OR$^{a61}$, OC(O)R$^{b61}$, OC(O)NR$^{c61}$R$^{d61}$, NR$^{c61}$R$^{d61}$, NR$^{c61}$C(O)R$^{b61}$, NR$^{c61}$C(O)OR$^{a61}$, NR$^{c61}$C(O)NR$^{c61}$R$^{d61}$, NR$^{c61}$S(O)NR$^{c61}$R$^{d61}$, NR$^{c61}$S(O)R$^{b61}$, NR$^{c61}$S(O)$_2$R$^{b61}$, NR$^{c61}$S(O)$_2$NR$^{c61}$R$^{d61}$, S(O)R$^{b61}$, S(O)NR$^{c61}$R$^{d61}$, S(O)$_2$R$^{b61}$, and S(O)$_2$NR$^{c61}$R$^{d61}$;

each R$^{a61}$, R$^{c61}$, and R$^{d61}$ is independently selected from H, C$_{1-6}$ alkyl, and C$_{1-6}$ haloalkyl;

each R$^{b61}$ is independently selected from C$_{1-6}$ alkyl and C$_{1-6}$ haloalkyl;

each R$^7$ is independently selected from D, halo, NO$_2$, CN, C$_{1-6}$ alkyl, C$_{2-6}$ alkenyl, C$_{2-6}$ alkynyl, C$_{1-6}$ haloalkyl, OR$^{a7}$, SR$^{a7}$, NHOR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, NR$^{c7}$S(O)NR$^{c7}$R$^{d7}$, NR$^{c7}$S(O)R$^{b7}$, NR$^{c7}$S(O)$_2$R$^{b7}$, NR$^{c7}$S(O)$_2$ NR$^{c7}$R$^{d7}$, S(O)R$^{b7}$, S(O)NR$^{c7}$R$^{d7}$, S(O)$_2$R$^{b7}$, S(O)$_2$ NR$^{c7}$R$^{d7}$, and OS(O)$_2$R$^{b7}$, wherein said C$_{1-6}$ alkyl, C$_{2-6}$ alkenyl, C$_{2-6}$ alkynyl, and C$_{1-6}$ haloalkyl are each optionally substituted by 1, 2, 3, or 4 independently selected R$^{7A}$ substituents;

each R$^{a7}$, R$^{c7}$, and R$^{d7}$ is independently selected from H, C$_{1-6}$ alkyl, C$_{1-6}$ haloalkyl, C$_{2-6}$ alkenyl, and C$_{2-6}$ alkynyl, wherein said C$_{1-6}$ alkyl, C$_{2-6}$ alkenyl, C$_{2-6}$ alkynyl, and C$_{1-6}$ haloalkyl, are each optionally substituted with 1, 2, 3, or 4 independently selected R$^{7A}$ substituents;

each R$^{b7}$ is independently selected from C$_{1-6}$ alkyl, C$_{1-6}$ haloalkyl, C$_{2-6}$ alkenyl, and C$_{2-6}$ alkynyl, which are each optionally substituted with 1, 2, 3, or 4 independently selected R$^{7A}$ substituents;

each R$^{7A}$ is independently selected from D, halo, CN, C$_{1-6}$ alkyl, C$_{2-6}$ alkenyl, C$_{2-6}$ alkynyl, C$_{1-6}$ haloalkyl, OR$^{a71}$, SR$^{a71}$, NHOR$^{a71}$, C(O)R$^{b71}$, C(O)NR$^{c71}$R$^{d71}$, C(O)OR$^{a71}$, OC(O)R$^{b71}$, OC(O)NR$^{c71}$R$^{d71}$, NR$^{c71}$R$^{d71}$, NR$^{c71}$C(O)R$^{b71}$, NR$^{c71}$C(O)OR$^{a71}$, NR$^{c71}$C(O)NR$^{c71}$R$^{d71}$, NR$^{c71}$S(O)NR$^{c71}$R$^{d71}$, NR$^{c71}$S(O)R$^{b71}$, NR$^{c71}$S(O)$_2$R$^{b71}$, NR$^{c71}$S(O)$_2$NR$^{c71}$R$^{d71}$, S(O)R$^{b71}$, S(O)NR$^{c71}$R$^{d71}$, S(O)$_2$R$^{b71}$, and S(O)$_2$NR$^{c71}$R$^{d71}$;

each R$^{a71}$, R$^{c71}$, and R$^{d71}$ is independently selected from H, C$_{1-6}$ alkyl, and C$_{1-6}$ haloalkyl;

each R$^{b71}$ is independently selected from C$_{1-6}$ alkyl and C$_{1-6}$ haloalkyl; and each R$^G$ is independently selected from D, OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-3}$ alkoxycarbonyl, C$_{1-3}$ alkylcarbonyloxy, C$_{1-3}$ alkylcarbonylamino, C$_{1-3}$ alkoxycarbonylamino, C$_{1-3}$ alkylaminocarbonyloxy, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino.

37. The compound of claim 1, or a pharmaceutically acceptable salt thereof, wherein:

each ---- is independently a single or a double bond;

k is 1 or 2;

n is 0 or 1;

p is 0, 1, or 2;

X is CH or N;

Y is CR$^4$ or N; and W is CR$^2$; or

Y is NR$^{4y}$, O or S; and W is absent;

Ring A is a monocyclic 5-6 membered heteroaryl ring;

each $X^1$ is O;

each Ring D is independently a monocyclic 4-7 membered heterocycloalkyl, bicyclic 7-10 membered heterocycloalkyl, or a spirocyclic 7-10 membered heterocycloalkyl, each of which is optionally substituted by 1 or 2 independently selected $C_{1-6}$ alkyl groups;

each $R^{81}$, $R^{82}$, and $R^{83}$ are independently selected from H, D, halo, CN, $OR^{a8}$, $C(O)OR^{a8}$, $C_{1-6}$ alkyl, $C_{2-6}$ alkenyl, $C_{2-6}$ alkynyl, $C_{1-6}$ haloalkyl, and 4-7 membered heterocycloalkyl-$C_{1-4}$ alkyl; wherein said $C_{1-6}$ alkyl, $C_{2-6}$ alkenyl, $C_{2-6}$ alkynyl, $C_{1-6}$ haloalkyl, and 4-7 membered heterocycloalkyl-$C_{1-4}$ alkyl are each optionally substituted by 1, 2, 3, or 4 independently selected $R^G$ substituents;

each $R^{a8}$ is independently selected from H, $C_{1-6}$ alkyl, $C_{1-6}$ haloalkyl, $C_{2-6}$ alkenyl, and $C_{2-6}$ alkynyl;

$R^1$ is selected from H, D, halo, CN, $C_{1-6}$ alkyl, $C_{1-6}$ haloalkyl, 4-7 membered heterocycloalkyl, $OR^{a1}$, and $NR^{c1}R^{d1}$, wherein said $C_{1-6}$ alkyl, $C_{1-6}$ haloalkyl, and 4-7 membered heterocycloalkyl are each optionally substituted with 1, 2, 3, or 4 independently selected $R^{1A}$ substituents;

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{1A}$ substituents;

each $R^{1A}$ is independently selected from D, halo, CN, $C_{1-6}$ alkyl, $C_{2-6}$ alkenyl, $C_{2-6}$ alkynyl, $C_{1-6}$ haloalkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$;

each $R^{a11}$, $R^{c11}$, and $R^{d11}$ is independently selected from H, $C_{1-6}$ alkyl, and $C_{1-6}$ haloalkyl;

each $R^{b11}$ is independently selected from $C_{1-6}$ alkyl and $C_{1-6}$ haloalkyl;

$R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl, 4-6 membered heterocycloalkyl, and 5-6 membered heteroaryl, wherein said Cut alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, and 5-6 membered heteroaryl are each optionally substituted with 1 or 2 independently selected $R^{2A}$ substituents;

each $R^{2A}$ is independently selected from D, halo, CN, $C_{1-6}$ alkyl, $C_{2-6}$ alkenyl, $C_{2-6}$ alkynyl, $C_{1-6}$ haloalkyl, $OR^{a21}$, $SR^{a21}$, $NHOR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)NR^{c21}R^{d21}$, $NR^{c21}S(O)R^{b21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, and $S(O)_2NR^{c21}R^{d21}$;

each $R^{a21}$, $R^{c21}$, and $R^{d21}$ is independently selected from H, $C_{1-6}$ alkyl, and $C_{1-6}$ haloalkyl;

each $R^{b21}$ is independently selected from $C_{1-6}$ alkyl and $C_{1-6}$ haloalkyl;

$R^3$ is H or $CH_3$;

$R^4$ is H, D, halo, CN, or $C_{1-6}$ alkyl;

$R^{4y}$ is H, $C_{1-4}$ alkyl, or $C_{1-4}$ haloalkyl;

each $R^{5A}$ is independently selected from oxo, D, halo, CN, $C_{1-6}$ alkyl, $C_{2-6}$ alkenyl, $C_{2-6}$ alkynyl, $C_{1-6}$ haloalkyl, $OR^{a5}$, and $NR^{c5}R^{d5}$; wherein said $C_{1-6}$ alkyl, $C_{2-6}$ alkenyl, $C_{2-6}$ alkynyl, and $C_{1-6}$ haloalkyl are each optionally substituted by 1 or 2 independently selected $R^{5A}$ substituents;

each $R^{a5}$, $R^{c5}$, and $R^{d5}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{5A}$ substituents;

each $R^{5A}$ is independently selected from D, halo, CN, $C_{1-6}$ alkyl, $C_{2-6}$ alkenyl, $C_{2-6}$ alkynyl, $C_{1-6}$ haloalkyl, $OR^{a51}$, $SR^{a51}$, $NHOR^{a51}$, $C(O)R^{b51}$, $C(O)NR^{c51}R^{d51}$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$;

each $R^{a51}$, $R^{c51}$, and $R^{d51}$ is independently selected from H, $C_{1-6}$ alkyl, and $C_{1-6}$ haloalkyl;

each $R^{b51}$ is independently selected from $C_{1-6}$ alkyl and $C_{1-6}$ haloalkyl;

each $R^6$ is independently selected from D, halo, CN, $C_{1-6}$ alkyl, $C_{2-6}$ alkenyl, $C_{2-6}$ alkynyl, $C_{1-6}$ haloalkyl, $C_{3-6}$ cycloalkyl, 4-7 membered heterocycloalkyl, $OR^{a6}$, $C(O)R^{b6}$, and $NR^{c6}R^{d6}$; wherein said $C_{1-6}$ alkyl, $C_{2-6}$ alkenyl, $C_{2-6}$ alkynyl, $C_{1-6}$ haloalkyl, $C_{3-6}$ cycloalkyl, and 4-7 membered heterocycloalkyl, are each optionally substituted by 1, 2, or 3 independently selected $R^{6A}$ substituents;

each $R^{a6}$, $R^{c6}$, and $R^{d6}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1 or 2 independently selected $R^{6A}$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{3-4}$ cycloalkyl, and 4-7 membered heterocycloalkyl, which are each optionally substituted with 1 or 2 independently selected $R^{6A}$ substituents;

each $R^4$ is independently selected from D, halo, CN, $NO_2$, $C_{1-6}$ alkyl, $C_{2-6}$ alkenyl, $C_{2-6}$ alkynyl, $C_{1-6}$ haloalkyl, $OR^{a61}$, $SR^{a61}$, $NHOR^{a61}$, $C(O)R^{b61}$, $C(O)NR^{c61}R^{d61}$, $C(O)OR^{a61}$, $OC(O)R^{b61}$, $OC(O)NR^{c61}R^{d61}$, $NR^{c61}R^{d61}$, $NR^{c61}C(O)R^{b61}$, $NR^{c61}C(O)OR^{a61}$, $NR^{c61}C(O)NR^{c61}R^{d61}$, $NR^{c61}S(O)NR^{c61}R^{d61}$, $NR^{c61}S(O)R^{b61}$, $NR^{c61}S(O)_2R^{b61}$, $NR^{c61}S(O)_2NR^{c61}R^{d61}$, $S(O)R^{b61}$, $S(O)NR^{c61}R^{d61}$, $S(O)_2R^{b61}$, and $S(O)_2NR^{c61}R^{d61}$;

each $R^{a61}$, $R^{c61}$, and $R^{d61}$ is independently selected from H, $C_{1-6}$ alkyl, and $C_{1-6}$ haloalkyl;

each $R^{b61}$ is independently selected from $C_{1-6}$ alkyl and $C_{1-6}$ haloalkyl;

each $R^7$ is independently selected from D, OH, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino; and each $R^G$ is independently selected from D, OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

38. The compound of claim 1, or a pharmaceutically acceptable salt thereof, wherein:

each ---- is independently a single or a double bond;

k is 1;

n is 0 or 1;

p is 0, 1, or 2;

X is CH or N;

Y is CH or N; and W is $CR^2$; or

Y is S; and W is absent;

Ring A is a monocyclic 5-6 membered heteroaryl ring;

each $X^1$ is O;

each Ring D is independently a monocyclic 4-7 membered heterocycloalkyl, bicyclic 7-10 membered heterocycloalkyl, or a spirocyclic 7-10 membered heterocycloalkyl, each of which is optionally substituted by 1 or 2 independently selected $C_{1-6}$ alkyl groups;

each $R^{81}$, $R^{82}$, and $R^{83}$ are independently selected from H, halo, $OR^{a8}$, $C(O)OR^{a8}$, $C_{1-6}$ alkyl, $C_{1-6}$ haloalkyl, and 4-7 membered heterocycloalkyl-$C_{1-4}$ alkyl; wherein said $C_{1-6}$ alkyl, is optionally substituted by 1, 2, or 3 independently selected $R^G$ substituents;

each $R^{a8}$ is independently selected from H and $C_{1-6}$ alkyl;

$R^1$ is selected from H, CN, $C_{1-6}$ alkyl, $C_{1-6}$ haloalkyl, 4-7 membered heterocycloalkyl, $OR^{a1}$, and $NR^{c1}R^{d1}$, wherein said $C_{1-6}$ alkyl, $C_{1-6}$ haloalkyl, and 4-7 membered heterocycloalkyl are each optionally substituted with 1, 2, 3, or 4 independently selected $R^{1A}$ substituents;

each $R^{a1}$, $R^{c1}$, and $R^{d1}$ is independently selected from H and $C_{1-6}$ alkyl, wherein said $C_{1-6}$ alkyl is optionally substituted with 1, 2, or 3 independently selected $R^{1A}$ substituents;

each $R^{1A}$ is independently selected from $C_{1-6}$ alkyl, $OR^{a11}$, and $NR^{c11}R^{d11}$;

each $R^{a11}$, $R^{c11}$, and $R^{d11}$ is independently selected from H and $C_{1-6}$ alkyl;

$R^2$ is selected from H, halo, CN, $C_{1-6}$ alkyl, $C_{2-6}$ alkenyl, $C_{2-6}$ alkynyl, $C_{1-6}$ haloalkyl, $C_{1-6}$ haloalkoxy, $C_{3-6}$ cycloalkyl, phenyl and 5-6 membered heteroaryl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, and 5-6 membered heteroaryl are each optionally substituted with 1 or 2 independently selected $R^{2A}$ substituents;

each $R^{2A}$ is independently selected from $OR^{a21}$ and $NR^{c21}R^{d21}$;

each $R^{a21}$, $R^{c21}$, and $R^{d21}$ is independently selected from H and $C_{1-6}$ alkyl;

$R^3$ is H or $CH_3$;

$R^4$ is H;

each $R^5$ is independently selected from oxo, halo, CN, $C_{1-6}$ alkyl, and $C_{1-6}$ haloalkyl; wherein said $C_{1-6}$ alkyl is optionally substituted by 1 or 2 independently selected $R^{5A}$ substituents;

each $R^{5A}$ is independently selected from $OR^{a51}$ and $NR^{c51}R^{d51}$;

each $R^{a51}$, $R^{c51}$, and $R^{d51}$ is independently selected from H and $C_{1-6}$ alkyl;

each $R^6$ is independently selected from D, halo, CN, $C_{1-6}$ alkyl, $C_{1-6}$ haloalkyl, $C_{3-4}$ cycloalkyl, 4-7 membered heterocycloalkyl, $OR^{a6}$, and $C(O)R^{b6}$; wherein said $C_{1-6}$ alkyl, $C_{1-6}$ haloalkyl, $C_{3-4}$ cycloalkyl, and 4-7 membered heterocycloalkyl, are each optionally substituted by 1, 2, or 3 independently selected $R^{6A}$ substituents;

each $R^{a6}$ is independently selected from H and $C_{1-6}$ alkyl, wherein said $C_{1-6}$ alkyl is optionally substituted with 1 or 2 independently selected $R^{6A}$ substituents;

each $R^{b6}$ is independently selected from $C_{1-6}$ alkyl, $C_{1-6}$ haloalkyl, and 4-7 membered heterocycloalkyl;

each $R^{6A}$ is independently selected from D, $OR^{a61}$, and $NR^{c61}R^{d61}$;

each $R^{a61}$, $R^{c61}$, and $R^{d61}$ is independently selected from H, and $C_{1-6}$ alkyl;

each $R^7$ is independently selected from OH, CN, halo, $C_{1-3}$ alkoxy, and $C_{1-3}$ haloalkoxy; and each $R^G$ is independently selected from D, OH, CN, halo, $C_{1-3}$ alkyl, $C_{1-3}$ haloalkyl, $C_{1-3}$ alkoxy, $C_{1-3}$ haloalkoxy, amino, and $C_{1-3}$ alkylamino, di($C_{1-3}$ alkyl)amino.

39. The compound of claim 1, or a pharmaceutically acceptable salt thereof, wherein:

(a) $R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 8-10 membered heterocycloalkyl, $C_{3-10}$ cycloalkyl-$C_{1-4}$ alkyl, 4-10 membered heterocycloalkyl-$C_{1-4}$ alkyl, $OR^{m1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)$ $R^{b1}$, $NR^{c1}C(O)OR^{a1}$, $NR^{c1}C(O)NR^{c1}R^{d1}$, $C(=NR^{e1})$ $R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}S(O)NR^{c1}R^{d1}$, $NR^{c1}S(O)$ $R^{b1}$, $NR^{c1}S(O)_2R^{b1}$, $NR^{c1}S(O)(=NR^{e1})R^{b1}$, $NR^{c1}S$ $(O)_2NR^{c1}R^{d1}$, $S(O)R^{b1}$, $S(O)NR^{c1}R^{d1}$, $S(O)_2R^{b1}$, $S(O)_2 NR^{c1}R^{d1}$, $OS(O)(=NR^{e1})R^{b1}$, $OS(O)_2R^{b1}$, $S(O)$ $(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl are each optionally substituted with 1, 2, 3, or 4 independently selected $R^{1A}$ substituents; and each $R^{m1}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1A}$ substituents; or (b) $R^2$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 6-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C$ $(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S$ $(O)NR^{c2}R^{d2}$, $NR^{c2}S(O)R^{b2}$, $NR^{c2}S(O)_2R^{b2}$, $NR^{c2}S(O)$ $(=NR^{e2})R^{b2}$, $NR^{c2}S(O)_2NR^{c2}R^{d2}$, $S(O)R^{b2}$, $S(O)$ $NR^{c2}R^{d2}$, $S(O)_2R^{b2}$, $S(O)_2NR^{c2}R^{d2}$, $OS(O)(=NR^{e2})$ $R^{b2}$, $OS(O)_2R^{b2}$, $S(O)(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 6-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents; and each $R^{c2}$ and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents.

40. The compound of claim 1, or a pharmaceutically acceptable salt thereof, wherein:

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 8-10 membered heterocycloalkyl, $C_{3-10}$ cycloalkyl-$C_{1-4}$ alkyl, 4-10 membered heterocycloalkyl-$C_{1-4}$ alkyl, $OR^{m1}$, $SR^{a1}$, $NHOR^{a1}$, $C(O)R^{b1}$, $C(O)NR^{c1}R^{d1}$, $C(O)$ $NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)$ $OR^{a1}$, $NR^{c1}C(O)NR^{c1}R^{d1}$, $C(=NR^{e1})R^{b1}$, $C(=NR^{e1})$ $NR^{c1}R^{d1}$, $NR^{c1}C(=NR^{e1})NR^{c1}R^{d1}$, $NR^{c1}C(=NR^{e1})$ $R^{b1}$, $NR^{c1}S(O)NR^{c1}R^{d1}$, $NR^{c1}S(O)R^{b1}$, $NR^{c1}S(O)_2$ $R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})$ $(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{3-10}$ cycloalkyl-$C_{1-4}$ alkyl, and 4-10 membered heterocycloalkyl-$C_{1-4}$ alkyl are each optionally substituted with 1, 2, 3, or 4 independently selected $R^{1A}$ substituents;

each $R^{m1}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1A}$ substituents;

$R^2$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 6-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)$ $NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)$ $R^{b2}$, $NR^{c2}C(O)OR^{a2}$, $NR^{c2}C(O)NR^{c2}R^{d2}$, $C(=NR^{e2})$ $R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)$ $R^{b2}$, $NR^{c2}S(O)_2R^{b2}$, $NR^{c2}S(O)(=NR^{e2})R^{b2}$, $NR^{c2}S$ $(O)_2NR^{c2}R^{d2}$, $S(O)R^{b2}$, $S(O)NR^{c2}R^{d2}$, $S(O)_2R^{b2}$, $S(O)_2$ $NR^{c2}R^{d2}$, $OS(O)(=NR^{e2})R^{b2}$, $OS(O)_2R^{b2}$, $S(O)$ $(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 6-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents; and each $R^{c2}$ and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents.

41. The compound of claim 1, which is:

(a) a compound Formula (II):

(II)

or a pharmaceutically acceptable salt thereof; or (b) a compound of Formula (III):

(III)

or a pharmaceutically acceptable salt thereof; or (c) a compound of Formula (IV):

(IV)

or a pharmaceutically acceptable salt thereof; or (d) a compound of Formula (V):

(V)

or a pharmaceutically acceptable salt thereof,
(e) a compound of Formula (VI):

(VI)

or a pharmaceutically acceptable salt thereof; or
(f) a compound of Formula (VII):

(VII)

or a pharmaceutically acceptable salt thereof.

42. The compound of claim 1, selected from:

(R)—N-(6-(3-((5-cyano-4-methoxypyrimidin-2-yl)amino)piperidin-1-yl)-1-methyl-1H-pyrazolo[4,3-c]pyridin-3-yl)acrylamide;

(R)—N-(6-(3-((5-cyano-4-methoxypyrimidin-2-yl)amino)pyrrolidin-1-yl)-1-methyl-1H-pyrazolo[4,3-c]pyridin-3-yl)acrylamide;

(R)—N-(8-(3-((5-cyano-4-methoxypyrimidin-2-yl)amino)pyrrolidin-1-yl)-[1,2,4]triazolo[1,5-a]pyrazin-2-yl)acrylamide;

N-(2-((1S,3R)-3-((5-(4-methoxyphenyl)pyrimidin-2-yl)amino)cyclohexyl)-3-oxoisoindolin-5-yl)acrylamide;

N-(2-((1S,3R)-3-((5-methyl-4-(trifluoromethyl)pyrimidin-2-yl)amino)cyclohexyl)-3-oxoisoindolin-5-yl)acrylamide;

N-(2-((1S,3R)-3-((5-(difluoromethoxy)pyrimidin-2-yl)amino)cyclohexyl)-3-oxoisoindolin-5-yl)acrylamide;

N-(3-oxo-2-((1S,3R)-3-((5-vinylpyrimidin-2-yl)amino)cyclohexyl)isoindolin-5-yl)acrylamide;

N-(2-((1S,3R)-3-((5-(1-methyl-1H-pyrazol-4-yl)pyrimidin-2-yl)amino)cyclohexyl)-3-oxoisoindolin-5-yl)acrylamide;

N-(2-((1S,3R)-3-((5-cyano-4-methylpyrimidin-2-yl)amino)cyclohexyl)-3-oxoisoindolin-5-yl)acrylamide;

N-(2-((1S,3R)-3-((5-ethylpyrimidin-2-yl)amino)cyclohexyl)-3-oxoisoindolin-5-yl)acrylamide;

N-(2-((1S,3R)-3-((5-cyclopropylpyrimidin-2-yl)amino)cyclohexyl)-3-oxoisoindolin-5-yl)acrylamide;

N-(2-((1S,3R)-3-((5-isopropylpyrimidin-2-yl)amino)cyclohexyl)-3-oxoisoindolin-5-yl)acrylamide;

N-(2-((1S,3R)-3-((4-methoxy-5-methylpyrimidin-2-yl)amino)cyclohexyl)-3-oxoisoindolin-5-yl)acrylamide;

(R)—N-(8-(3-((5-cyano-4-methoxypyrimidin-2-yl)amino)piperidin-1-yl)-2-methylimidazo[1,2-a]pyrazin-3-yl)acrylamide;

N-(2-((1S,3R)-3-((5-cyano-6-methylpyridin-2-yl)amino)cyclohexyl)-3-oxoisoindolin-5-yl)acrylamide;

N-(2-((1S,3R)-3-((5-cyano-4-methylpyridin-2-yl)amino)cyclohexyl)-3-oxoisoindolin-5-yl)acrylamide;

N-(2-((1S,3R)-3-((5-ethynylpyrimidin-2-yl)amino)cyclohexyl)-3-oxoisoindolin-5-yl)acrylamide;

N-(2-((1S,3R)-3-((5-cyano-4-(trifluoromethyl)pyridin-2-yl)amino)cyclohexyl)-3-oxoisoindolin-5-yl)acrylamide;

N-(2-((1S,3R)-3-((4-cyano-5-(trifluoromethyl)pyridin-2-yl)amino)cyclohexyl)-3-oxoisoindolin-5-yl)acrylamide;

(R)—N-(7-(3-((5-cyanopyrimidin-2-yl)amino)pyrrolidin-1-yl)-1-methyl-1H-indazol-3-yl)acrylamide;

(R)—N-(6-(3-((5-cyano-4-methoxypyrimidin-2-yl)amino)pyrrolidin-1-yl)-1-methyl-1H-indazol-3-yl)acrylamide;

(R)—N-(5-(3-((5-cyano-4-methoxypyrimidin-2-yl)amino)piperidin-1-yl)-[1,2,4]triazolo[1,5-a]pyridin-2-yl)acrylamide;

(R)—N-(5-(3-((5-cyano-4-methoxypyrimidin-2-yl)amino)pyrrolidin-1-yl)-[1,2,4]triazolo[1,5-a]pyridin-2-yl)acrylamide;

N-(1-((1S,3R)-3-((5-cyano-4-methoxypyrimidin-2-yl)amino)cyclohexyl)-1H-indazol-4-yl)acrylamide;

N-(1-((1S,3R)-3-((5-cyano-4-methoxypyrimidin-2-yl)amino)cyclohexyl)-1H-indazol-5-yl)acrylamide;

N-(1-((1S,3R)-3-((5-cyano-4-methoxypyrimidin-2-yl)amino)cyclohexyl)-1H-indol-5-yl)acrylamide;

N-(1-((1S,3R)-3-((5-Cyano-4-methoxypyrimidin-2-yl)amino)cyclohexyl)-1H-benzo[d]imidazol-4-yl)acrylamide;

(R)—N-(3-(3-((5-cyano-4-methoxypyrimidin-2-yl)amino)piperidin-1-yl)benzo[d]isoxazol-7-yl)acrylamide;

N-(3-oxo-2-((1S,3R)-3-((5-(trifluoromethyl)thiazol-2-yl)amino)cyclohexyl)isoindolin-5-yl)acrylamide;

(R)—N-(6-(3-((5-cyano-4-methoxypyrimidin-2-yl)amino)piperidin-1-yl)-1-methyl-1H-pyrazolo[4,3-c]pyridin-3-yl)but-2-ynamide;

2-bromo-N-(6-((R)-3-((5-cyano-4-methoxypyrimidin-2-yl)amino)piperidin-1-yl)-1-methyl-1H-pyrazolo[4,3-c]pyridin-3-yl)butanamide;

2-bromo-N-(6-((R)-3-((5-cyano-4-methoxypyrimidin-2-yl)amino)piperidin-1-yl)-1-methyl-1H-pyrazolo[4,3-c]pyridin-3-yl)propanamide;

(R)-2-chloro-N-(6-(3-((5-cyano-4-methoxypyrimidin-2-yl)amino)piperidin-1-yl)-1-methyl-1H-pyrazolo[4,3-c]pyridin-3-yl)acetamide;

(R)—N-(8-(3-((5-cyano-4-methoxypyrimidin-2-yl)amino)piperidin-1-yl)imidazo[1,2-a]pyrazin-3-yl)acrylamide;

(R)—N-(3-(3-((5-cyano-4-methoxypyrimidin-2-yl)amino)piperidin-1-yl)-1-methyl-1H-indazol-7-yl)acrylamide;

(R)—N-(2-(3-((5-cyano-4-methoxypyrimidin-2-yl)amino)piperidin-1-yl)benzo[d]oxazol-5-yl)acrylamide;

(R)—N-(2-(3-((5-cyano-4-methoxypyrimidin-2-yl)
amino)piperidin-1-yl)-1-methyl-1H-benzo[d]imidazol-
5-yl)acrylamide;

(R)—N-(2-(3-((5-cyano-4-methoxypyrimidin-2-yl)
amino)piperidin-1-yl)-1-methyl-1H-indol-5-yl)acryl-
amide;

(R)—N-(2-(3-((5-cyano-4-methoxypyrimidin-2-yl)
amino)piperidin-1-yl)benzo[d]thiazol-5-yl)acrylamide;

(R)—N-(2-(3-((5-cyano-4-methoxypyrimidin-2-yl)
amino)pyrrolidin-1-yl)benzo[d]thiazol-5-yl)acrylam-
ide;

(R)—N-(3-(3-((5-cyano-4-methoxypyrimidin-2-yl)
amino)piperidin-1-yl)benzo[b]thiophen-6-yl)acrylam-
ide;

(R)—N-(3-(3-((5-cyano-4-methoxypyrimidin-2-yl)
amino)piperidin-1-yl)-1-methyl-1H-indazol-6-yl)acry-
lamide;

(R)—N-(2-(3-((5-cyano-4-methoxypyrimidin-2-yl)
amino)piperidin-1-yl)-[1,2,4]triazolo[1,5-a]pyridin-6-
yl)acrylamide;

(R)—N-(2-(3-((5-cyano-4-methoxypyrimidin-2-yl)
amino)pyrrolidin-1-yl)-[1,2,4]triazolo[1,5-a]pyridin-6-
yl)acrylamide;

(R)—N-(2-(3-((5-cyano-4-methoxypyrimidin-2-yl)
amino)piperidin-1-yl)benzo[d]thiazol-6-yl)acrylamide;

N-(2-((1S,3R)-3-((5-cyano-4-methoxypyrimidin-2-yl)
amino)cyclohexyl)-1-(2-hydroxyethyl)-1H-benzo[d]
imidazol-5-yl)acrylamide;

ethyl (E)-4-((2-((1S,3R)-3-((5-cyano-4-methoxypyrimi-
din-2-yl)amino)cyclohexyl)-1-methyl-1H-benzo[d]
imidazol-5-yl)amino)-4-oxobut-2-enoate;

2-bromo-N-(2-((1S,3R)-3-((5-cyano-4-methoxypyrimi-
din-2-yl)amino)cyclohexyl)-1-methyl-1H-benzo[d]
imidazol-5-yl)butanamide;

2-chloro-N-(2-((1S,3R)-3-((5-cyano-4-methoxypyrimi-
din-2-yl)amino)cyclohexyl)-1-methyl-1H-benzo[d]
imidazol-5-yl)acetamide;

3-((2-((1S,3R)-3-((5-cyano-4-methoxypyrimidin-2-yl)
amino)cyclohexyl)-1-methyl-1H-benzo[d]imidazol-5-
yl)carbamoyl)oxirane-2-carboxylic acid;

2-bromo-N-(2-((1S,3R)-3-((5-cyano-4-methoxypyrimi-
din-2-yl)amino)cyclohexyl)-1-methyl-1H-benzo[d]
imidazol-5-yl)propanamide;

N-(2-((1S,3R)-3-((5-cyano-4-methoxypyrimidin-2-yl)
amino)cyclohexyl)-1-methyl-1H-benzo[d]imidazol-5-
yl)-2-fluoroacrylamide;

N-(2-((1S,3R)-3-((5-cyano-4-methoxypyrimidin-2-yl)
amino)cyclohexyl)-1-methyl-1H-benzo[d]imidazol-5-
yl)but-2-ynamide;

2-bromo-N-(2-((1S,3R)-3-((5-cyano-4-methoxypyrimi-
din-2-yl)amino)cyclohexyl)-3-oxoisoindolin-5-yl)pro-
panamide;

N-(2-((1S,3R)-3-((5-cyano-4-methoxypyrimidin-2-yl)
amino)cyclohexyl)-3-oxoisoindolin-5-yl)-2-fluoro-
acrylamide;

(E)-N-(2-((1S,3R)-3-((5-cyano-4-methoxypyrimidin-2-
yl)amino)cyclohexyl)-3-oxoisoindolin-5-yl)-4-fluo-
robut-2-enamide;

2-bromo-N-(2-((1S,3R)-3-((5-cyano-4-methoxypyrimi-
din-2-yl)amino)cyclohexyl)-3-oxoisoindolin-5-yl)acet-
amide;

2-chloro-N-(2-((1S,3R)-3-((5-cyano-4-methoxypyrimi-
din-2-yl)amino)cyclohexyl)-3-oxoisoindolin-5-yl)acet-
amide;

N-(2-((1S,3R)-3-((5-cyano-4-methoxypyrimidin-2-yl)
amino)cyclohexyl)-3-oxoisoindolin-5-yl)but-2-yna-
mide;

N-(2-((1S,3R)-3-((4-methoxy-5-(trifluoromethyl)pyrimi-
din-2-yl)amino)cyclohexyl)-3-oxoisoindolin-5-yl)
acrylamide;

N-(2-((1S,3R)-3-((4-((R)-3-(dimethylamino)pyrrolidin-
1-yl)-5-(trifluoromethyl)pyrimidin-2-yl)amino)cyclo-
hexyl)-3-oxoisoindolin-5-yl)acrylamide;

(E)-N-(2-((1S,3R)-3-((5-cyano-4-methoxypyrimidin-2-
yl)amino)cyclohexyl)-3-oxoisoindolin-5-yl)-4-(dim-
ethylamino)but-2-enamide;

(E)-N-(2-((1S,3R)-3-((5-cyano-4-methoxypyrimidin-2-
yl)amino)cyclohexyl)-3-oxoisoindolin-5-yl)but-2-ena-
mide;

N-(2-((1S,3R)-3-((5-cyano-4-methoxypyrimidin-2-yl)
amino)cyclohexyl)-3-oxoisoindolin-5-yl)-N-methyl-
acrylamide;

N-(2-((1S,3R)-3-((5-cyano-4-((2-hydroxy-2-methylpro-
pyl)amino)pyrimidin-2-yl)amino)cyclohexyl)-3-oxoi-
soindolin-5-yl)acrylamide;

N-(2-((1S,3R)-3-((5-cyano-4-(methylamino)pyrimidin-2-
yl)amino)cyclohexyl)-3-oxoisoindolin-5-yl)acrylam-
ide;

N-(2-((1S,3R)-3-((5-bromopyrimidin-2-yl)amino)cyclo-
hexyl)-3-oxoisoindolin-5-yl)acrylamide;

N-(1-((1S,3R)-3-((5-cyanopyrimidin-2-yl)amino)cyclo-
hexyl)-1H-benzo[d]imidazol-4-yl)acrylamide;

N-(2-((1S,3R)-3-((5-cyanopyrimidin-2-yl)amino)cyclo-
pentyl)-1-methyl-1H-benzo[d]imidazol-5-yl)acrylam-
ide;

N-(1-((1S,3R)-3-((5-cyanopyrimidin-2-yl)amino)cyclo-
hexyl)-1H-benzo[d][1,2,3]triazol-5-yl)acrylamide;

N-(1-methyl-2-((1S,3R)-3-((5-(trifluoromethyl)pyrimi-
din-2-yl)amino)cyclohexyl)-1H-benzo[d]imidazol-5-
yl)acrylamide;

N-(2-((1S,3R)-3-((5-cyano-4-methoxypyrimidin-2-yl)
amino)cyclohexyl)-1-methyl-1H-benzo[d]imidazol-5-
yl)acrylamide;

N-(2-((1S,3R)-3-((5-cyanopyrimidin-2-yl)amino)cyclo-
hexyl)-1-methyl-1H-benzo[d]imidazol-5-yl)acrylam-
ide;

N-(2-((1S,3R)-3-((5-bromo-4-(trifluoromethyl)pyrimi-
din-2-yl)amino)cyclohexyl)-3-oxoisoindolin-5-yl)
acrylamide;

N-(2-((1S,3R)-3-((5-cyano-4-morpholinopyrimidin-2-yl)
amino)cyclohexyl)-3-oxoisoindolin-5-yl)acrylamide;

N-(2-((1S,3R)-3-((5-cyano-4-(dimethylamino)pyrimidin-
2-yl)amino)cyclohexyl)-3-oxoisoindolin-5-yl)acrylam-
ide;

N-(2-((1S,3R)-3-((4-(methylamino)-5-(trifluoromethyl)
pyrimidin-2-yl)amino)cyclohexyl)-3-oxoisoindolin-5-
yl)acrylamide;

N-(1-((1S,3R)-3-((5-cyano-4-methoxypyrimidin-2-yl)
amino)cyclohexyl)-1H-benzo[d]imidazol-5-yl)acryl-
amide;

2-chloro-N-(2-((1S,3R)-3-((5-cyano-4-methoxypyrimi-
din-2-yl)amino)cyclohexyl)-1-methyl-1H-benzo[d]
imidazol-5-yl)acrylamide;

N-(2-((1S,3R)-3-((5-chloro-4-methoxypyrimidin-2-yl)
amino)cyclohexyl)-3-oxoisoindolin-5-yl)acrylamide;

N-(2-((1S,3R)-3-((5-chloropyrimidin-2-yl)amino)cyclo-
hexyl)-3-oxoisoindolin-5-yl)acrylamide;

N-(2-((1S,3R)-3-((5-cyano-4-methoxypyrimidin-2-yl)
amino)cyclohexyl)-3-oxoisoindolin-5-yl)acrylamide;

N-(1-((1S,3R)-3-((5-cyanopyrimidin-2-yl)amino)cyclo-
hexyl)-2-(difluoromethyl)-1H-benzo[d]imidazol-5-yl)
acrylamide; and N-(3-oxo-2-((1S,3R)-3-((5-(trifluoromethyl)pyrimidin-2-
yl)amino)cyclohexyl)isoindolin-5-yl)acrylamide;

or a pharmaceutically acceptable salt thereof.

43. The compound of claim 1, selected from:

N—((R)-1-(3-((3R,5R)-3-Fluoro-5-((5-(trifluoromethyl) pyrimidin-2-yl)amino)piperidin-1-yl)imidazo[1,5-a] pyrazin-8-yl)pyrrolidin-3-yl)acrylamide;

1-(2-(2-((3R,5R)-3-Hydroxy-5-((5-(trifluoromethyl)py-rimidin-2-yl)amino)piperidin-1-yl)-1-methyl-1H-benzo[d]imidazol-5-yl)piperidin-1-yl)prop-2-en-1-one;

N-(2-((3R,5R)-3-Hydroxy-5-((5-(trifluoromethyl)pyrimi-din-2-yl)amino)piperidin-1-yl)-1-methyl-1H-benzo[d] imidazol-5-yl)acrylamide;

N-(2-((3R,5R)-3-((5-Cyanopyrimidin-2-yl)amino)-5-fluoropiperidin-1-yl)-1-methyl-1H-benzo[d]imidazol-5-yl)acrylamide;

N-(2-((3S,4R)-4-Fluoro-3-((5-(trifluoromethyl)pyrimi-din-2-yl)amino)piperidin-1-yl)-1-methyl-1H-benzo[d] imidazol-5-yl)acrylamide;

N-(2-((3S,4S)-4-Fluoro-3-((5-(trifluoromethyl)pyrimi-din-2-yl)amino)piperidin-1-yl)-1-methyl-1H-benzo[d] imidazol-5-yl)acrylamide;

(S)—N-(2-(4,4-Difluoro-3-((5-(trifluoromethyl)pyrimi-din-2-yl)amino)piperidin-1-yl)-1-methyl-1H-benzo[d] imidazol-5-yl)acrylamide;

N-(2-((3R,5R)-3-Fluoro-5-((5-(trifluoromethyl)pyrimi-din-2-yl)amino)piperidin-1-yl)-1-methyl-1H-benzo[d] imidazol-5-yl)acrylamide;

N-(2-((3R,5R)-3-Hydroxy-5-((5-(trifluoromethyl)pyrimi-din-2-yl)amino)piperi-dine-1-yl)-1,6-dimethyl-1H-benzo[d]imidazol-5-yl)acrylamide;

N-(6-Cyclopropyl-2-((3R,5R)-3-fluoro-5-((5-(trifluo-romethyl)pyrimidin-2-yl)amino)piperidin-1-yl)-1-methyl-1H-benzo[d]imidazol-5-yl)acrylamide;

N-(2-((3R,5R)-3-((5-cyanopyrimidin-2-yl)amino)-5-fluoropiperidin-1-yl)-1,6-dimethyl-1H-benzo[d]imida-zol-5-yl)acrylamide;

(S)—N-(2-(4,4-Difluoro-3-((5-(trifluoromethyl)pyrimi-din-2-yl)amino)piperidin-1-yl)-1,6-dimethyl-1H-benzo[d]imidazol-5-yl)acrylamide;

N-(2-((3S,4R)-4-Fluoro-3-((5-(trifluoromethyl)pyrimi-din-2-yl)amino)piperidin-1-yl)-1,6-dimethyl-1H-benzo[d]imidazol-5-yl)acrylamide;

N-(2-((3S,4S)-4-Fluoro-3-((5-(trifluoromethyl)pyrimi-din-2-yl)amino)piperidin-1-yl)-1,6-dimethyl-1H-benzo[d]imidazol-5-yl)acrylamide;

N-(2-((3R,5R)-3-fluoro-5-((5-(trifluoromethyl)pyrimi-din-2-yl)amino)piperidin-1-yl)-1,6-dimethyl-1H-benzo[d]imidazol-5-yl)acrylamide;

N-(2-((3R,5R)-3-Fluoro-5-((5-(trifluoromethyl)pyrimi-din-2-yl)amino)piperidin-1-yl)-6-isopropyl-1-methyl-1H-benzo[d]imidazol-5-yl)acrylamide;

(R)—N-(1,6-Dimethyl-2-(3-((5-(trifluoromethyl)pyrimi-din-2-yl)amino)piperidin-1-yl)-1H-benzo[d]imidazol-5-yl)acrylamide;

(R)—N-(6-Bromo-1,4-dimethyl-2-(3-((5-(trifluorom-ethyl)pyrimidin-2-yl)amino)piperidin-1-yl)-1H-benzo [d]imidazol-5-yl)acrylamide;

1-((2S,6R)-4-(3-((3R,5R)-3-Fluoro-5-((5-(trifluorom-ethyl)pyrimidin-2-yl)amino)piperidin-1-yl)imidazo[1, 5-a]pyrazin-8-yl)-2,6-dimethylpiperazin-1-yl)prop-2-en-1-one;

1-(6-(3-((3R,5R)-3-Fluoro-5-((5-(trifluoromethyl)py-rimidin-2-yl)amino)piperidin-1-yl)imidazo[1,5-a] pyrazin-8-yl)-1,6-diazaspiro[3.3]heptan-1-yl)prop-2-en-1-one;

1-((1S,4S)-5-(3-((3R,5R)-3-Fluoro-5-((5-(trifluorom-ethyl)pyrimidin-2-yl)amino)piperidin-1-yl)imidazo[1, 5-a]pyrazin-8-yl)-2,5-diazabicyclo[2.2.1]heptan-2-yl) but-2-yn-1-one;

1-((1S,4S)-5-(3-((3R,5R)-3-Fluoro-5-((5-(trifluorom-ethyl)pyrimidin-2-yl)amino)piperidin-1-yl)imidazo[1, 5-a]pyrazin-8-yl)-2,5-diazabicyclo[2.2.1]heptan-2-yl) prop-2-en-1-one;

1-(2-(3-((R)-3-((5-(Trifluoromethyl)pyrimidin-2-yl) amino)piperidin-1-yl)imidazo[1,5-a]pyrazin-8-yl)pip-eridin-1-yl)prop-2-en-1-one;

1-(3-(3-((R)-3-((5-(Trifluoromethyl)pyrimidin-2-yl) amino)piperidin-1-yl)imidazo[1,5-a]pyrazin-8-yl)-3,8-diazabicyclo[3.2.1]octan-8-yl)prop-2-en-1-one; and (R)-1-(4-(3-(3-((5-(Trifluoromethyl)pyrimidin-2-yl) amino)piperidin-1-yl)imidazo[1,5-a]pyrazin-8-yl)pip-eridin-1-yl)prop-2-en-1-one;

or a pharmaceutically acceptable salt thereof.

44. The compound of claim 1, selected from:

N-(2-((3R,5R)-3-methoxy-5-((5-(trifluoromethyl)pyrimi-din-2-yl)amino)piperidin-1-yl)-1,6-dimethyl-1H-benzo[d]imidazol-5-yl)acrylamide;

(E)-N-(2-((3R,5R)-3-fluoro-5-((5-(trifluoromethyl)py-rimidin-2-yl)amino)piperidin-1-yl)-1,6-dimethyl-1H-benzo[d]imidazol-5-yl)-4-hydroxy-4-methylpent-2-enamide;

N-(2-((3R,5R)-3-fluoro-5-((5-(trifluoromethyl)pyrimi-din-2-yl)amino)piperidin-1-yl)-1,6-dimethyl-1H-benzo[d]imidazol-5-yl)-4-hydroxy-4-methylpent-2-ynamide;

N-(2-((3R,5R)-3-fluoro-5-((5-(trifluoromethyl)pyrimi-din-2-yl)amino)piperidin-1-yl)-1,6-dimethyl-1H-benzo[d]imidazol-5-yl)-4-methoxybut-2-ynamide;

N-(2-((3R,5R)-3-fluoro-5-((5-(trifluoromethyl)pyrimi-din-2-yl)amino)piperidin-1-yl)-1,6-dimethyl-1H-benzo[d]imidazol-5-yl)-4-hydroxybut-2-ynamide;

N-(2-((3R,5R)-3-fluoro-5-((5-(trifluoromethyl)pyrimi-din-2-yl)amino)piperidin-1-yl)-1,6-dimethyl-1H-benzo[d]imidazol-5-yl)but-2-ynamide;

2-fluoro-N-(2-((3R,5R)-3-fluoro-5-((5-(trifluoromethyl) pyrimidin-2-yl)amino)piperidin-1-yl)-1,6-dimethyl-1H-benzo[d]imidazol-5-yl)acrylamide;

(E)-N-(2-((3R,5R)-3-fluoro-5-((5-(trifluoromethyl)py-rimidin-2-yl)amino)piperidin-1-yl)-1,6-dimethyl-1H-benzo[d]imidazol-5-yl)-4-(piperidin-1-yl)but-2-enam-ide;

(Z)-4-(dimethylamino)-N-(2-((3R,5R)-3-fluoro-5-((5-(trifluoromethyl)pyrimidin-2-yl)amino)piperidin-1-yl)-1,6-dimethyl-1H-benzo[d]imidazol-5-yl)but-2-ena-mide;

(E)-4-(dimethylamino)-N-(2-((3R,5R)-3-fluoro-5-((5-(trifluoromethyl)pyrimidin-2-yl)amino)piperidin-1-yl)-1,6-dimethyl-1H-benzo[d]imidazol-5-yl)but-2-ena-mide;

(E)-N-(2-((3R,5R)-3-fluoro-5-((5-(trifluoromethyl)py-rimidin-2-yl)amino)piperidin-1-yl)-1,6-dimethyl-1H-benzo[d]imidazol-5-yl)-4-methoxybut-2-enamide;

N-(2-((3R,5R)-3-((5-cyanopyrimidin-2-yl)amino)-5-hy-droxypiperidin-1-yl)-1-methyl-1H-benzo[d]imidazol-5-yl)acrylamide;

(R)—N-(1-methyl-2-(3-((5-(trifluoromethyl)pyrimidin-2-yl)amino)piperidin-1-yl)-1H-benzo[d]imidazol-5-yl) acrylamide;

(R)—N-(2-(3,3-difluoro-5-((5-(trifluoromethyl)pyrimi-din-2-yl)amino)piperidin-1-yl)-1-methyl-1H-benzo[d] imidazol-5-yl)acrylamide;

N-(2-((3S,4R)-3-((5-cyanopyrimidin-2-yl)amino)-4-fluoropiperidin-1-yl)-1-methyl-1H-benzo[d]imidazol-5-yl)acrylamide;

N-(2-((3S,4S)-3-((5-cyanopyrimidin-2-yl)amino)-4-fluoropiperidin-1-yl)-1-methyl-1H-benzo[d]imidazol-5-yl)acrylamide;

(S)—N-(2-(3-((5-cyanopyrimidin-2-yl)amino)-4,4-difluoropiperidin-1-yl)-1-methyl-1H-benzo[d]imidazol-5-yl)acrylamide;

(R)-1-(4-(1-methyl-2-(3-((5-(trifluoromethyl)pyrimidin-2-yl)amino)piperidin-1-yl)-1H-benzo[d]imidazol-5-yl)piperazin-1-yl)prop-2-en-1-one;

(R)—N-(2-(3-((5-cyanothiazol-2-yl)amino)piperidin-1-yl)-1-methyl-1H-benzo[d]imidazol-5-yl)acrylamide;

(R)—N-(1-methyl-2-(3-((5-(trifluoromethyl)thiazol-2-yl)amino)piperidin-1-yl)-1H-benzo[d]imidazol-5-yl)acrylamide;

N-(6-ethyl-2-((3R,5R)-3-fluoro-5-((5-(trifluoromethyl)pyrimidin-2-yl)amino)piperidin-1-yl)-1-methyl-1H-benzo[d]imidazol-5-yl)acrylamide;

N-(6-fluoro-2-((3R,5R)-3-fluoro-5-((5-(trifluoromethyl)pyrimidin-2-yl)amino)piperidin-1-yl)-1-methyl-1H-benzo[d]imidazol-5-yl)acrylamide;

N-(2-((3R,5R)-3-fluoro-5-((5-(trifluoromethyl)pyrimidin-2-yl)amino)piperidin-1-yl)-6-(methoxymethyl)-1-methyl-1H-benzo[d]imidazol-5-yl)acrylamide;

N-(6-chloro-2-((3R,5R)-3-fluoro-5-((5-(trifluoromethyl)pyrimidin-2-yl)amino)piperidin-1-yl)-1-methyl-1H-benzo[d]imidazol-5-yl)acrylamide;

N-(2-((3R,5R)-3-fluoro-5-((5-(trifluoromethyl)pyrimidin-2-yl)amino)piperidin-1-yl)-1-methyl-6-(methyl-d3)-1H-benzo[d]imidazol-5-yl)acrylamide;

N-(2-((3R,5R)-3-fluoro-5-((5-(trifluoromethyl)pyrimidin-2-yl)amino)piperidin-1-yl)-1-methyl-6-(pyrrolidin-1-yl)-1H-benzo[d]imidazol-5-yl)acrylamide;

N-(2-((3R,5R)-3-fluoro-5-((5-(trifluoromethyl)pyrimidin-2-yl)amino)piperidin-1-yl)-1-methyl-6-(morpholine-4-carbonyl)-1H-benzo[d]imidazol-5-yl)acrylamide;

N-(2-((3R,5R)-3-fluoro-5-((5-(trifluoromethyl)pyrimidin-2-yl)amino)piperidin-1-yl)-1-methyl-6-(pyrrolidine-1-carbonyl)-1H-benzo[d]imidazol-5-yl)acrylamide;

N-(2-((3R,5R)-3-fluoro-5-((5-(trifluoromethyl)pyrimidin-2-yl)amino)piperidin-1-yl)-1-methyl-6-morpholino-1H-benzo[d]imidazol-5-yl)acrylamide;

N-(6-cyano-2-((3R,5R)-3-fluoro-5-((5-(trifluoromethyl)pyrimidin-2-yl)amino)piperidin-1-yl)-1-methyl-1H-benzo[d]imidazol-5-yl)acrylamide;

N-(6-bromo-2-((3R,5R)-3-fluoro-5-((5-(trifluoromethyl)pyrimidin-2-yl)amino)piperidin-1-yl)-1-methyl-1H-benzo[d]imidazol-5-yl)acrylamide;

N-(2-((R)-3-((5-cyano-4-((R)-3-(dimethylamino)pyrrolidin-1-yl)pyrimidin-2-yl)amino)piperidin-1-yl)-1-methyl-1H-benzo[d]imidazol-5-yl)acrylamide;

(R)—N-(2-(3-((5-cyanopyrimidin-2-yl)amino)piperidin-1-yl)-1-methyl-1H-benzo[d]imidazol-5-yl)acrylamide;

N-(2-((3R,5R)-3-fluoro-5-((5-(trifluoromethyl)pyrimidin-2-yl)amino)piperidin-1-yl)-1,4,6-trimethyl-1H-benzo[d]imidazol-5-yl)acrylamide;

N-(4-bromo-2-((3R,5R)-3-((5-cyanopyrimidin-2-yl)amino)-5-fluoropiperidin-1-yl)-1,6-dimethyl-1H-benzo[d]imidazol-5-yl)acrylamide;

N-(4-bromo-2-((3R,5R)-3-fluoro-5-((5-(trifluoromethyl)pyrimidin-2-yl)amino)piperidin-1-yl)-1,6-dimethyl-1H-benzo[d]imidazol-5-yl)acrylamide;

N-(2-((3R,5R)-3-((5-cyanopyrimidin-2-yl)amino)-5-hydroxypiperidin-1-yl)-1,6-dimethyl-1H-benzo[d]imidazol-5-yl)acrylamide;

N-(2-((3S,4R)-4-hydroxy-3-((5-(trifluoromethyl)pyrimidin-2-yl)amino)piperidin-1-yl)-1,6-dimethyl-1H-benzo[d]imidazol-5-yl)acrylamide;

N-(2-((3S,4S)-4-hydroxy-3-((5-(trifluoromethyl)pyrimidin-2-yl)amino)piperidin-1-yl)-1,6-dimethyl-1H-benzo[d]imidazol-5-yl)acrylamide;

(R)—N-(6-cyclopropyl-1-methyl-2-(3-((5-(trifluoromethyl)pyrimidin-2-yl)amino)piperidin-1-yl)-1H-benzo[d]imidazol-5-yl)acrylamide;

(R)—N-(2-(3-((5-cyano-4-methoxypyridin-2-yl)amino)piperidin-1-yl)-1-methyl-1H-benzo[d]imidazol-5-yl)acrylamide;

(R)—N-(1-methyl-2-(3-((4-(4-methylpiperazin-1-yl)-5-(trifluoromethyl)pyrimidin-2-yl)amino)piperidin-1-yl)-1H-benzo[d]imidazol-5-yl)acrylamide;

(R)—N-(6-ethyl-1-methyl-2-(3-((5-(trifluoromethyl)pyrimidin-2-yl)amino)piperidin-1-yl)-1H-benzo[d]imidazol-5-yl)acrylamide;

(R)—N-(6-isopropyl-1-methyl-2-(3-((5-(trifluoromethyl)pyrimidin-2-yl)amino)piperidin-1-yl)-1H-benzo[d]imidazol-5-yl)acrylamide;

(R)—N-(6-isopropyl-1,4-dimethyl-2-(3-((5-(trifluoromethyl)pyrimidin-2-yl)amino)piperidin-1-yl)-1H-benzo[d]imidazol-5-yl)acrylamide;

(R)—N-(1,4-dimethyl-2-(3-((5-(trifluoromethyl)pyrimidin-2-yl)amino)piperidin-1-yl)-1H-benzo[d]imidazol-5-yl)acrylamide;

N-(2-((3R,5R)-3-((5-cyano-4-(dimethylamino)pyrimidin-2-yl)amino)-5-fluoropiperidin-1-yl)-1,6-dimethyl-1H-benzo[d]imidazol-5-yl)acrylamide;

N-(2-((3R,5R)-3-((5-cyano-4-(methylamino)pyrimidin-2-yl)amino)-5-fluoropiperidin-1-yl)-1,6-dimethyl-1H-benzo[d]imidazol-5-yl)acrylamide;

(N-(2-((3R,5R)-3-fluoro-5-((5-(trifluoromethyl)pyridin-2-yl)amino)piperidin-1-yl)-1,6-dimethyl-1H-benzo[d]imidazol-5-yl)acrylamide;

N-(2-((3R,5R)-3-((5-(difluoromethyl)pyrimidin-2-yl)amino)-5-fluoropiperidin-1-yl)-1,6-dimethyl-1H-benzo[d]imidazol-5-yl)acrylamide;

N-(2-((3R,5R)-3-((5-cyano-4-ethylpyrimidin-2-yl)amino)-5-fluoropiperidin-1-yl)-1,6-dimethyl-1H-benzo[d]imidazol-5-yl)acrylamide;

N-(2-((3R,5R)-3-((5-cyanothiazol-2-yl)amino)-5-fluoropiperidin-1-yl)-1,6-dimethyl-1H-benzo[d]imidazol-5-yl)acrylamide;

N-(2-((3R,5R)-3-((5-cyanopyridin-2-yl)amino)-5-fluoropiperidin-1-yl)-1,6-dimethyl-1H-benzo[d]imidazol-5-yl)acrylamide;

N-(2-((3R,5R)-3-((5-cyano-4-methylpyrimidin-2-yl)amino)-5-fluoropiperidin-1-yl)-1,6-dimethyl-1H-benzo[d]imidazol-5-yl)acrylamide;

N-(1-methyl-2-((R)-3-((5-(trifluoromethyl)pyrimidin-2-yl)amino)piperidin-1-yl)-1H-benzo[d]imidazol-5-yl)-N-(tetrahydrofuran-3-yl)acrylamide; and (R)—N-(6-methoxy-1-methyl-2-(3-((5-(trifluoromethyl)pyrimidin-2-yl)amino)piperidin-1-yl)-1H-benzo[d]imidazol-5-yl)acrylamide;

or a pharmaceutically acceptable salt thereof.

45. A pharmaceutical composition comprising the compound of claim 1, or a pharmaceutically acceptable salt thereof, and a pharmaceutically acceptable carrier.

46. A method of inhibiting CDK12, comprising contacting the CDK12 with the compound of claim 1, or a pharmaceutically acceptable salt thereof.

47. A method of inhibiting CDK12 in a patient, comprising administering to the patient the compound of claim 1, or a pharmaceutically acceptable salt thereof.

48. A method of treating a disease or disorder associated with CDK12 in a patient, comprising administering to the patient a therapeutically effective amount of the compound of claim 1, or pharmaceutically acceptable salt thereof.

49. The method of claim 48, wherein the disease or disorder is cancer.

50. The method of claim 48, wherein the disease or disorder is a cancer which has been previously identified as homologous recombination deficiency (HRD) high.

51. The method of claim 49, wherein the cancer is ovarian cancer, breast cancer, Ewing's sarcoma, osteosarcoma, liver cancer, hepatocellular carcinoma, or colorectal cancer.

52. The compound of claim 1, which is N-(2-((3R,5R)-3-fluoro-5-((5-(trifluoromethyl)pyrimidin-2-yl)amino)piperidin-1-yl)-1,6-dimethyl-1H-benzo[d]imidazol-5-yl)acrylamide, or a pharmaceutically acceptable salt thereof.

53. A compound, which is (R)—N-(2-(3-((5-cyano-4-methoxypyrimidin-2-yl)amino)pyrrolidin-1-yl)thiazolo[5,4-c]pyridin-7-yl)acrylamide, or a pharmaceutically acceptable salt thereof.

* * * * *